US012610730B2

(12) United States Patent
Chi et al.

(10) Patent No.: US 12,610,730 B2
(45) Date of Patent: Apr. 21, 2026

(54) METAL COMPLEX AND LIGHT EMITTING DEVICE

(71) Applicant: City University of Hong Kong, Kowloon (HK)

(72) Inventors: Yun Chi, Kowloon (HK); Jie Yan, Kowloon (HK)

(73) Assignee: City University of Hong Kong, Kowloon (HK)

( * ) Notice: Subject to any disclaimer, the term of this patent is extended or adjusted under 35 U.S.C. 154(b) by 806 days.

(21) Appl. No.: 17/892,250

(22) Filed: Aug. 22, 2022

(65) Prior Publication Data

US 2023/0006152 A1 Jan. 5, 2023

Related U.S. Application Data

(63) Continuation-in-part of application No. 17/743,543, filed on May 13, 2022.

(60) Provisional application No. 63/189,942, filed on May 18, 2021.

(51) Int. Cl.

| | |
|---|---|
| ***C07F 15/00*** | (2006.01) |
| ***C07D 473/00*** | (2006.01) |
| ***C07D 487/04*** | (2006.01) |
| ***C09K 11/06*** | (2006.01) |
| ***H01L 51/00*** | (2006.01) |
| ***H10K 85/30*** | (2023.01) |
| *H10K 50/11* | (2023.01) |
| *H10K 101/10* | (2023.01) |

(52) U.S. Cl.
CPC ......... *H10K 85/342* (2023.02); *C07D 473/00* (2013.01); *C07D 487/04* (2013.01); *C09K 11/06* (2013.01); *C07B 2200/09* (2013.01); *C09K 2211/1074* (2013.01); *C09K 2211/185* (2013.01); *H10K 50/11* (2023.02); *H10K 2101/10* (2023.02)

(58) Field of Classification Search
CPC ............................ C07F 15/0033; H10K 50/00
USPC ............. 548/103; 546/10; 544/225; 313/498
See application file for complete search history.

(56) References Cited

U.S. PATENT DOCUMENTS

| | | | | |
|---|---|---|---|---|
| 9,315,724 | B2 | 4/2016 | Metz et al. | |
| 10,418,569 | B2 | 9/2019 | Kwong et al. | |
| 2005/0258742 | A1* | 11/2005 | Tsai | H10K 85/342 313/504 |
| 2005/0260441 | A1* | 11/2005 | Thompson | H05B 33/14 549/3 |
| 2012/0228583 | A1* | 9/2012 | Wu | C07F 15/0033 546/4 |
| 2013/0032766 | A1* | 2/2013 | Molt | C07D 307/91 252/301.16 |
| 2016/0260914 | A1 | 9/2016 | Kamtekar et al. | |

FOREIGN PATENT DOCUMENTS

| | | |
|---|---|---|
| WO | 2011073149 | 6/2011 |
| WO | 2012121936 | 9/2012 |
| WO | 2014147006 | 9/2014 |
| WO | 2014147134 | 9/2014 |
| WO | 2015000955 | 1/2015 |
| WO | 2015014835 | 2/2015 |
| WO | 2015091716 | 6/2015 |
| WO | 2016193243 | 12/2016 |

* cited by examiner

*Primary Examiner* — Charanjit Aulakh

(74) *Attorney, Agent, or Firm* — Renner, Kenner, Greive, Bobak, Taylor & Weber

(57) ABSTRACT

A metal complex having at least one chelating N-heterocyclic carbene ligand. The metal complex provides a blue emission. This is useful for organic light emitting diode (OLED) components where blue emitters have trailed behind the advances of red and green emitters.

7 Claims, 26 Drawing Sheets

METAL COMPLEX AND LIGHT EMITTING DEVICE

TECHNICAL FIELD

The invention relates to a metal complex and a light emitting device, particularly a light emitting device including an emissive layer having a metal complex.

BACKGROUND

Organic light-emitting diodes (OLED) have already become a very important technology of the 21st century, e.g. for the display panel and lighting industries. Full-color OLED displays demand utilization of efficient and stable OLED emitters with all three elementary colors, namely: red, green and blue (RGB). Their success is due to the fast development of efficient luminescent materials and associated device architectures, for achieving nearly unitary external quantum efficiency. Despite remarkable progression within the field there is still a high demand within both the academic and industrial sectors for OLED emitters showing improved performance in all three RGB colors. A key requirement for OLED emitters is their capability to harvest both the electrically generated singlet and triplet excitons for lower power consumption and better performance. Meanwhile, the OLED should achieve longer operation lifespans, which could be, in part, solved by using more robust and durable emitters, together with achievement of balanced carrier transports within the devices.

Currently, both red and green emitters have been well developed, passing all stringent industrial assessment and being employed for commercial processes. However, blue emitters within an OLED remain a challenge for industrialization. Due to the higher emission energy of blue emitters compared to that of red and green counterparts, the associated devices tend to possess an inferior emission efficiency and poor stability during operation as a result of the facile thermal population to the upper lying quenching states and longer radiative lifetime of emitters.

Currently within the field of OLEDs there are two classes of highly efficient emitters, namely: thermally activated delayed fluorescence (TADF) emitters (e.g. pure organic TADF materials) and phosphorescent emitters (e.g. transition metal-based phosphors). These materials are competing for the future commercial applications. One reason is that both emitters can provide excellent luminescent properties, adequate thermal and chemical stabilities, and versatile color tunability, and especially very high internal quantum efficiency of 100% based on the theoretical prediction. Hence, those with better stability and reduced radiative lifetime upon excitation will be more suitable for future commercial applications.

As discussed above, there is a necessity for robust blue emitters, so that the thermally induced decomposition can be suppressed. This challenge may be solved by employment of both the phosphorescent sensitizer and TADF terminal emitters, to which the Forster resonance energy transfer (FRET) from the assistant phosphor to terminal emitter may eventually afford the efficient narrow bandwidth blue electroluminescence.

Iridium(III) metal complexes have been proposed as possible phosphors and integral components for OLED devices due to their remarkable stability and efficient green and red luminescence. Systematical design of the chromophoric chelates is essential to control and fine-tune their emission wavelengths. Some of the reported Ir(III) complexes involve functional cyclometalating bidentate chelates linked to a N-donor fragment (such as pyridine, pyrazole or imidazole) in the form of either the homoleptic or heteroleptic derivatives with formula $Ir(C^\wedge N)_3$ or $Ir(C^\wedge N)_2(L^\wedge X)$, where $C^\wedge N$ is N-containing aromatics and $L^\wedge X$ is anionic ancillary.

However, one problem that hampers the widespread adoption of OLED technology is the lack of efficient and stable blue phosphors. Due to the stronger ligand-centered $\pi\pi^*$ contribution of typical $C^\wedge N$ chelates upon excitation and poor ligand field strength exerted by the N-donor group, the corresponding blue emitters exhibit structured emission profile and multiple peak maxima, and relatively longer radiative lifetime and poor emission efficiency.

FIG. 1 shows the potential energy surface diagram of a hypothetical $Ir(C^\wedge N)_3$ or $Ir(C^\wedge N)_2(L^\wedge X)$ complex, as exemplified by sky-blue emissive bis[2-(4,6-difluorophenyl)pyridinato-$C^2$,N](picolinato)iridium(III) (FIrpic). It has been reported that the emissive $T_1$ state constituted a mixed metal-to-ligand charge transfer (MLCT) and ligand-centered $\pi\pi^*$ processes, while the metal-centered (MC) dd state is a $T_1$ state in geometry with metal-ligand distances lengthened, which is thermally activated from the $T_1$ state in geometry close to the ground state $S_0$. Thus, tuning emission from sky-blue FIrpic and analogues in giving a new blue emitter can be done by addition of electron-withdrawing (or donating) group at the HOMO (or LUMO) segment of the Ir(III) complexes, which gives a new $T_1'$ state. However, this manipulation is expected to reduce the $T_1'$-MC dd energy gap to the derivatized emitter, thus causing enhanced emission quenching. This means that the class of $Ir(C^\wedge N)_3$ or $Ir(C^\wedge N)_2(L^\wedge X)$ complex is not the desired and durable blue OLED emitter.

SUMMARY

It is an object of the invention to address the above needs, to overcome or substantially ameliorate the above disadvantages or, more generally, to provide blue phosphors with an improved emission efficiency as well as better stability against unwanted degradation of emitters during device operation.

It is also an object of the invention to provide phosphors which render increasing photoluminescence quantum yield, for example to a value higher than 60%, phosphorescence peak max. located in the region 450-490 nm, radiative lifetime lower than 2 microsecond, and a true blue color with Commission Internationale de l'Éclairage coordinates CIE (y)-corrected current efficiency maximum ($cd\cdot A^{-1}/y$)≥280, or CIE(y)=0.16 and below. Generally, these features will provide high-performance OLED devices.

In a first aspect, the present invention provides a metal complex comprising a structure of Formula (I):

$$ML^1_aL^2_bL^3_cL^4_dL^5_e \quad \text{Formula (I),}$$

where:

M is a transition metal;

$L^1$ is a bidentate ligand and a is an integer of 1 to 3;

$L^2$, $L^3$, $L^4$, and $L^5$ are independently a monodentate ligand, or two adjacent $L^2$, $L^3$, $L^4$, and $L^5$ is a bidentate ligand, and b, c, d, and e are independently an integer of 0 to 4;

a+b+c+d+e is 2, 3, 4, or 5; and $L^1$ has a structure of Formula (II):

Formula (II)

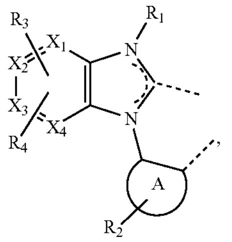

where:

A is a $C_{6-10}$ aryl ring or a 5 to 10 membered heteroaryl ring;

$R_1$ is selected from the group consisting of: $C_{1-6}$ alkyl, $C_{2-6}$ alkylether, $C_{1-6}$ alkoxy, $C_{1-6}$ fluoroalkyl, $C_{2-6}$ alkenyl, $C_{2-6}$ alkynyl, substituted or unsubstituted $C_{3-8}$ cycloalkyl, substituted or unsubstituted $C_{3-8}$ cycloalkenyl, substituted or unsubstituted 3 to 8 membered heterocycloalkyl, substituted or unsubstituted 3 to 8 membered heterocycloalkenyl, substituted or unsubstituted $C_{6-10}$ aryl, substituted or unsubstituted $C_{7-11}$ aralkyl, substituted or unsubstituted heteroaryl having 5 to 10 carbon atoms or heteroatoms, and substituted or unsubstituted heteroaralkyl having 6 to 11 carbon atoms or heteroatoms;

$R_2$, $R_3$, and $R_4$ are independently selected from the group consisting of: hydrogen, deuterium, fluorine, cyano, $C_{1-6}$ alkyl, $C_{1-6}$ alkoxy, $C_{1-6}$ fluoroalkyl, substituted or unsubstituted $C_{6-10}$ aryl, and substituted or unsubstituted heteroaryl having 5 to 10 carbon atoms or heteroatoms; and $X_1$, $X_2$, $X_3$, and $X_4$ are independently C or N.

M may be selected from the group consisting of: iridium, rhodium, platinum, palladium, gold, osmium, and ruthenium. Preferably, M is iridium.

Preferably, A is a phenyl ring.

Preferably, $R_1$ is selected from the group consisting of: $C_{1-6}$ alkyl, $C_{2-6}$ alkylether, $C_{1-6}$ alkoxy, $C_{1-6}$ fluoroalkyl, substituted or unsubstituted $C_{6-10}$ aryl, and substituted or unsubstituted $C_{7-11}$ aralkyl. More preferably, $R_1$ is methyl, ethyl, propyl, phenyl, p-methylphenyl, 2,6- and 3,5-dimethylphenyl, p-tert-butylphenyl, m-tert-butylphenyl, 1,1'-biphenyl, p-trifluoromethylphenyl, or the corresponding deuterated derivative thereof.

Preferably, $R_2$, $R_3$, and $R_4$ are independently selected from the group consisting of: hydrogen, deuterium, fluorine, cyano, $C_{1-6}$ alkyl, $C_{1-6}$ fluoroalkyl, and substituted, unsubstituted $C_{6-10}$ aryl, and the corresponding deuterated derivative thereof. More preferably, $R_2$ is hydrogen, methyl, tert-butyl, trifluoromethyl, or phenyl, and additionally or alternatively, $R_3$ and $R_4$ are independently hydrogen, tert-butyl, 2,6-dimethylphenyl, cyano, trifluoromethyl, or phenyl.

Optionally, when $X_1$ and $X_4$ are N, $X_1$ and $X_3$ are N, or $X_2$ and $X_4$ are N, $R_3$ and $R_4$ are different from each other. When $X_1$ and $X_4$ are N, one of $R_3$ and $R_4$ may be tert-butyl, while the other one of $R_3$ and $R_4$ may be hydrogen or trifluoromethyl.

Optionally, two of $X_1$, $X_2$, $X_3$, and $X_4$ are C, and the other two of $X_1$, $X_2$, $X_3$, and $X_4$ are N. When $X_1$ and $X_4$ are N, $X_1$ and $X_3$ are N, or $X_2$ and $X_4$ are N, $R_3$ and $R_4$ are different from each other. When $X_1$ and $X_4$ are N, one of $R_3$ and $R_4$ may be tert-butyl, while the other one of $R_3$ and $R_4$ may be hydrogen, trifluoromethyl, phenyl, or aryl group.

In a preferred embodiment, $R_1$ is phenyl, $R_2$ is hydrogen, methyl, or tert-butyl, and one of $R_3$ and $R_4$ is 2,6-dimethylphenyl.

Optionally, the metal complex is a homoleptic metal complex, where all ligands are identical. The homoleptic metal complex may have distinctive cyclometalating N-aryl groups, e.g., where two of three identical chelates are cyclometalating at the phenyl group while the other one is cyclometalating at the alternative p-tert-butyl phenyl group, vice versa, such as 75-fac and 76-fac.

Optionally, the metal complex is a tris-bidentate metal complex with two pairs of two adjacent $L^2$, $L^3$, $L^4$, and $L^5$ identical to $L^1$, or a tris-bidentate metal complex with only one pair of two adjacent $L^2$, $L^3$, $L^4$, and $L^5$ identical to $L^1$.

Optionally, the metal complex comprises a facial isomer or a meridional isomer.

Optionally, the metal complex is selected from one of the following:

1-fac

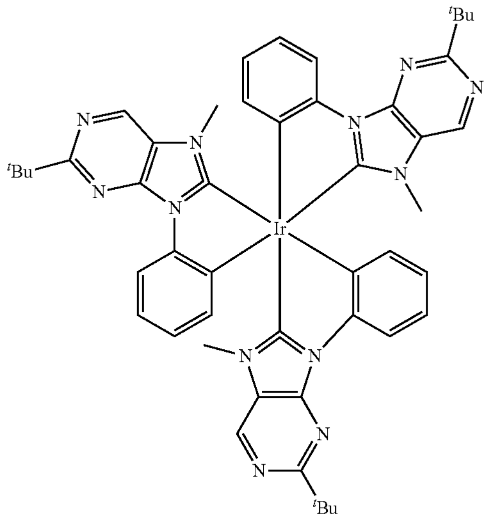

1-mer

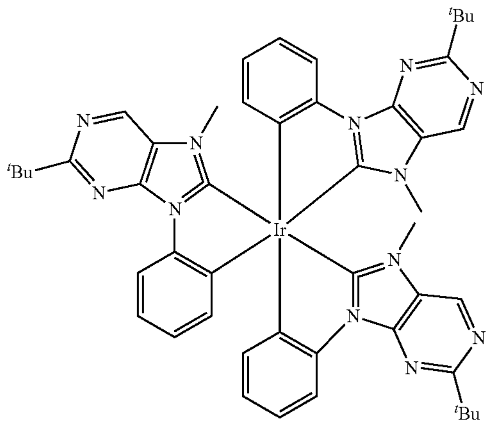

-continued
2-fac
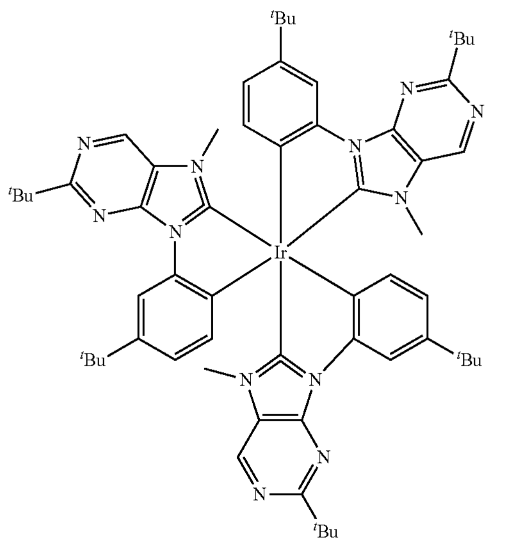
2-mer
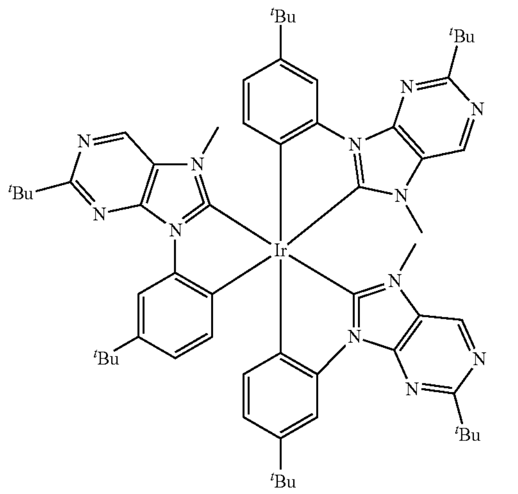
3-fac
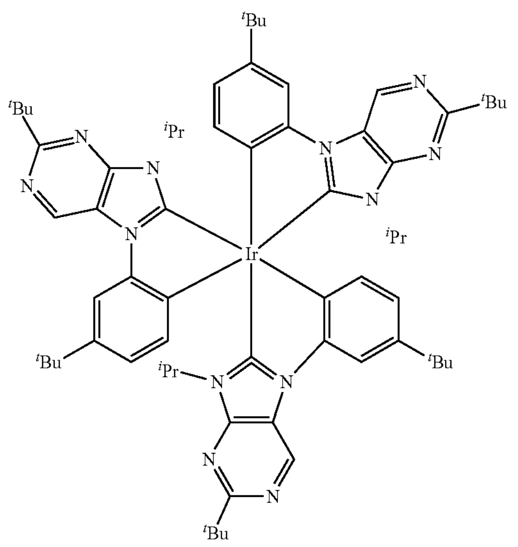
-continued
3-mer
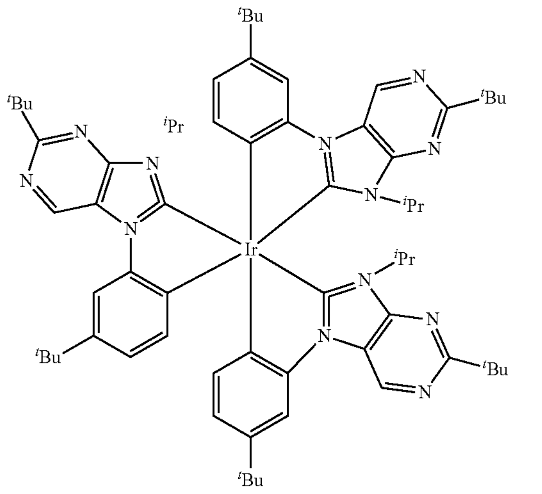
4-fac
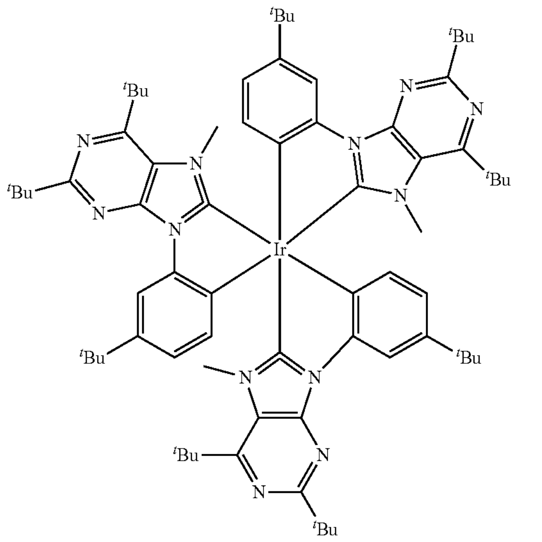
4-mer
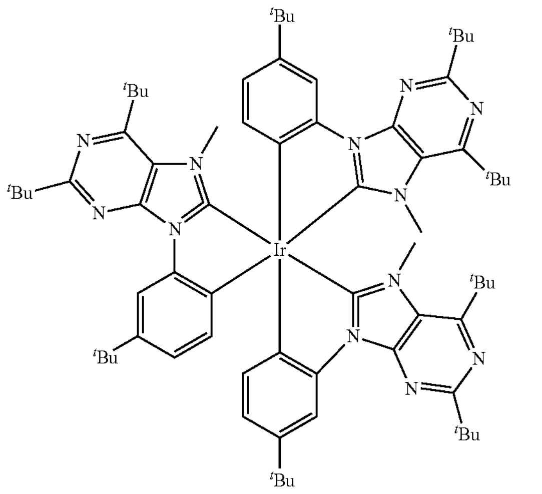

5-fac
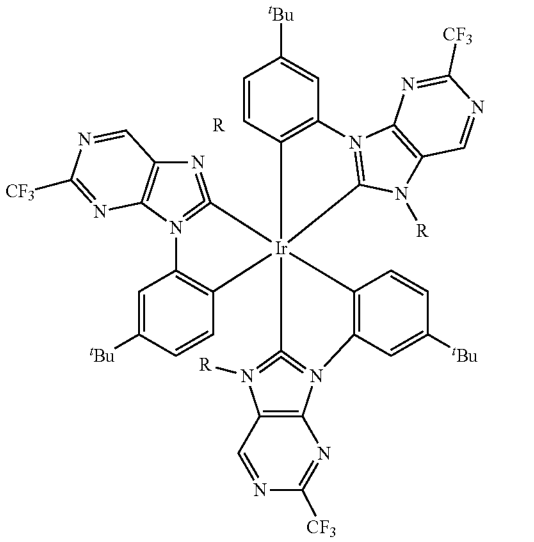
(R = $^{i}$Pr)
5-mer
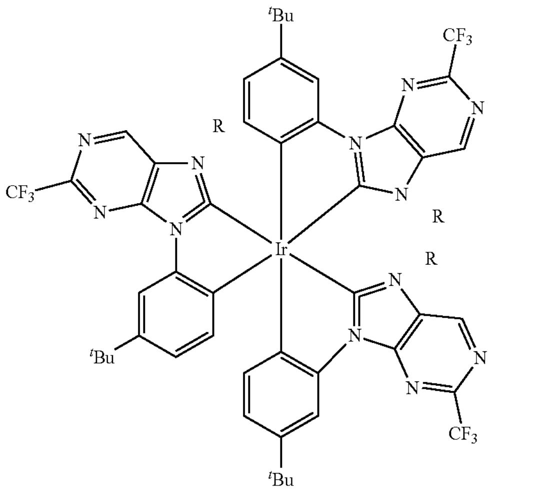
(R = $^{i}$Pr)
6-fac
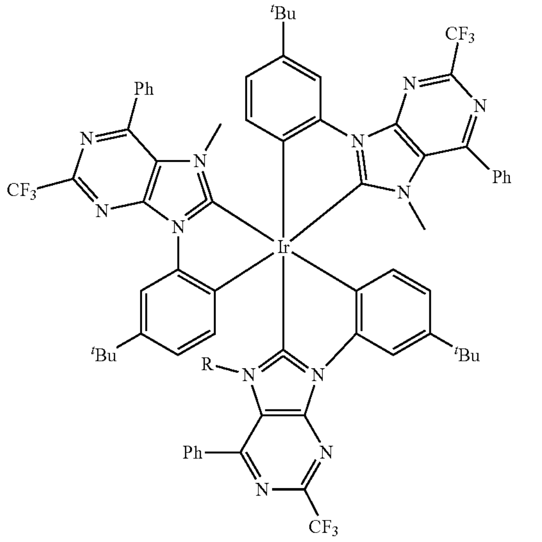
6-mer
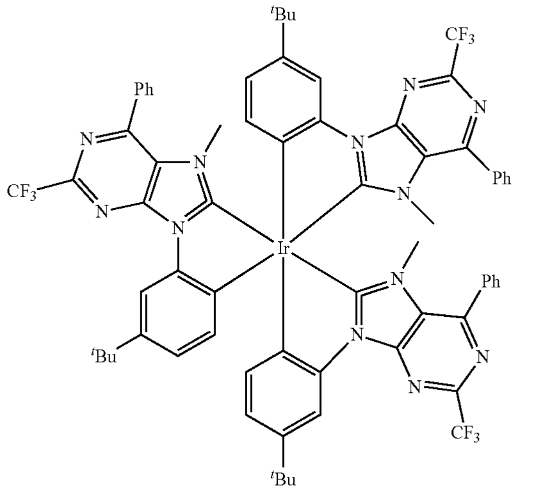
7-fac
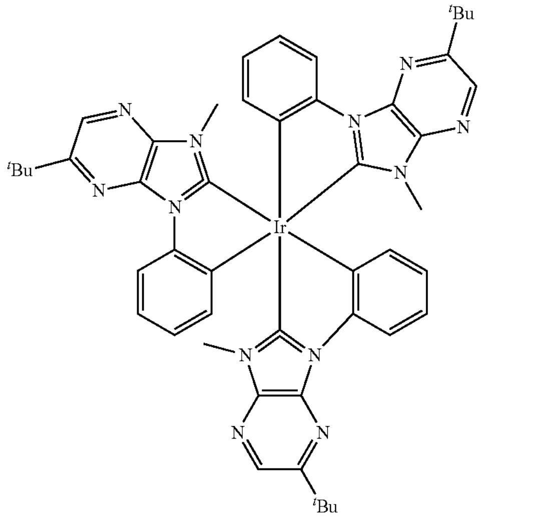

-continued
7-mer
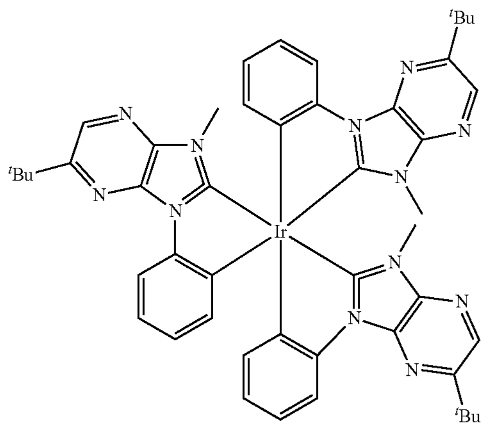
8-fac
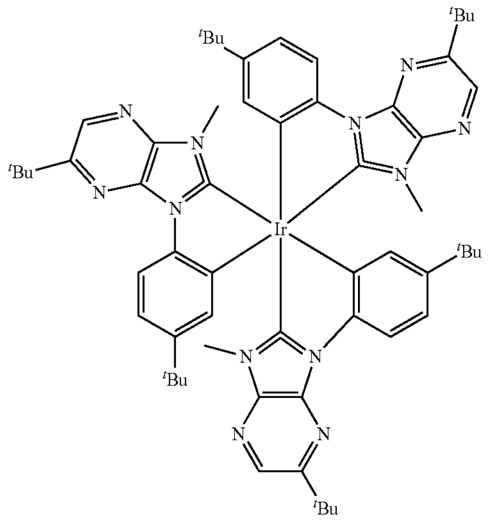
8-mer
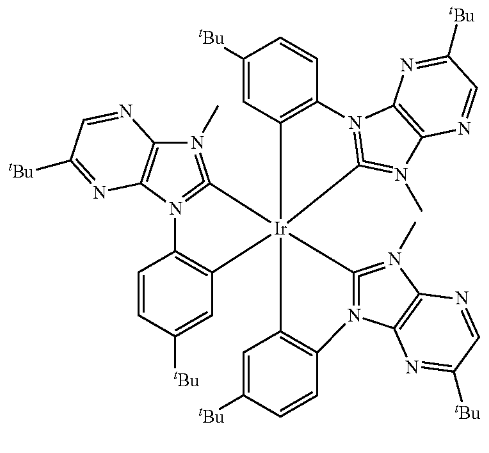
-continued
9-fac
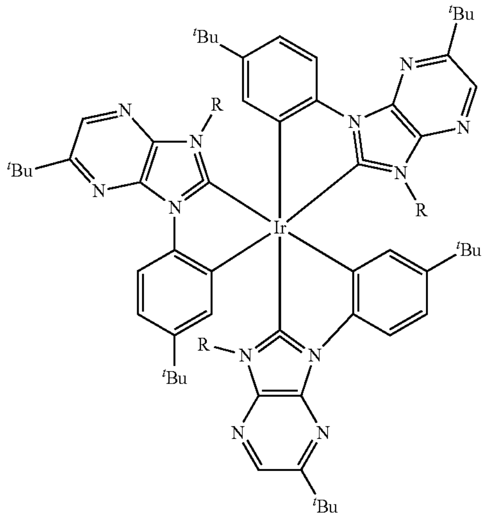
R = $C_2H_5$
9-mer
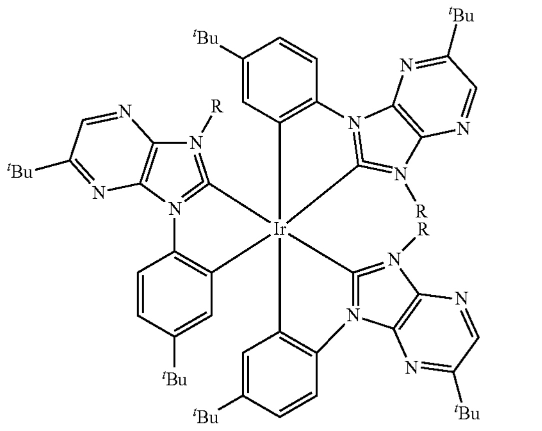
R = $C_2H_5$
10-fac
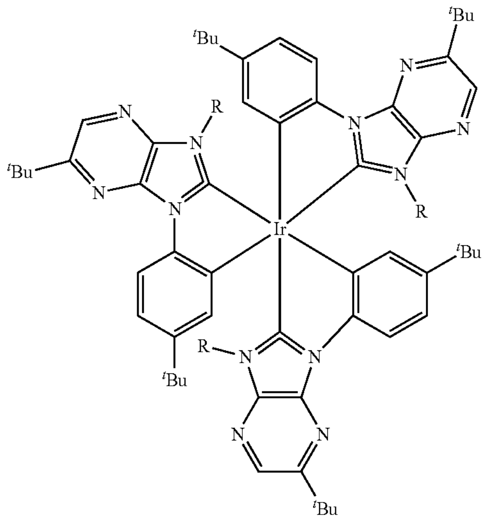
R = $C_6H_5$ -continued
11-fac
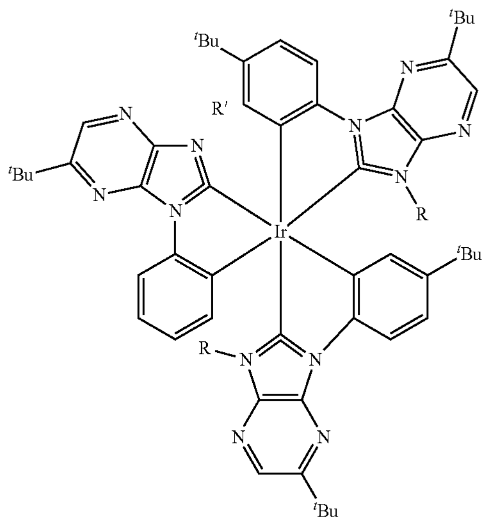
R = $C_6H_5$;
R′ = p-$C_6H_4$-$^t$Bu
12-fac
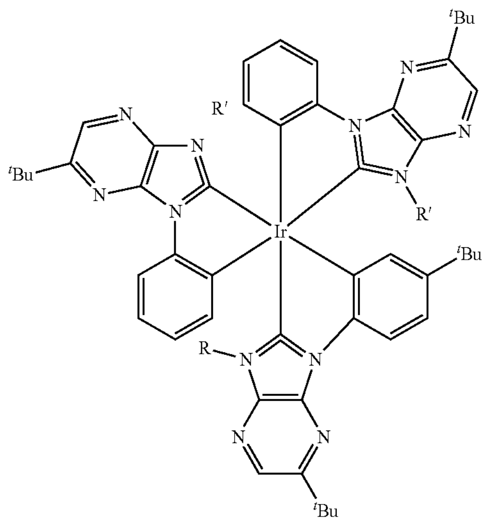
R = $C_6H_5$;
R′ = p-$C_6H_4$-$^t$Bu
-continued
13-fac
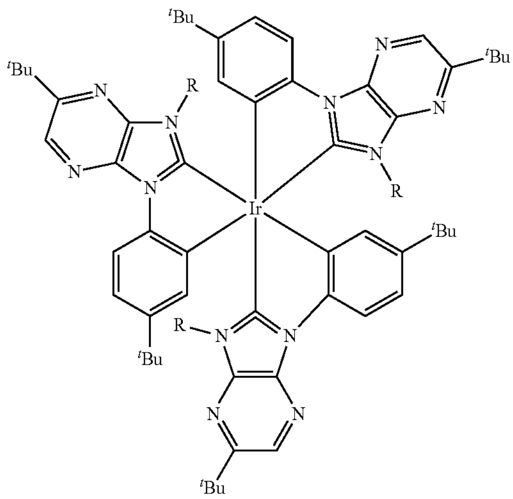
R = $C_6H_5$
14-fac
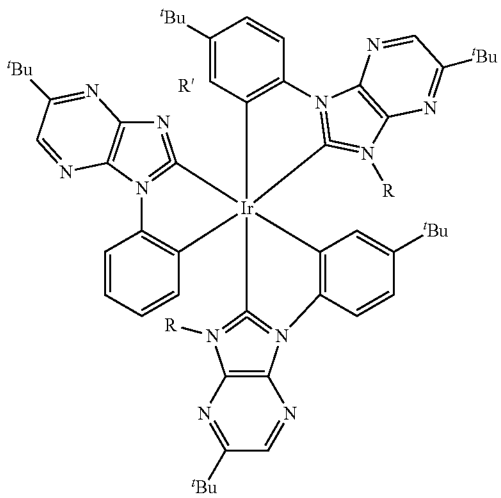
R = $C_6H_5$;
R′ = p-$C_6H_4$-$^t$Bu -continued
15-fac
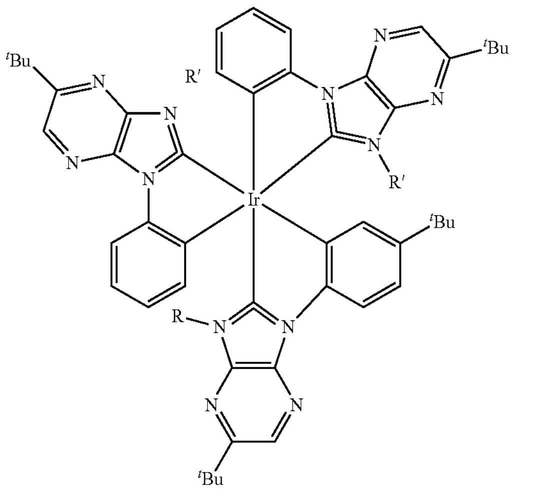
R = $C_6H_5$;
R′ = p-$C_6H_4$-$^t$Bu
16-fac
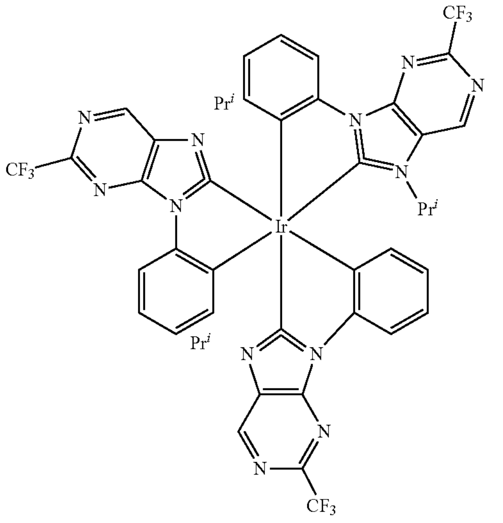
16-mer
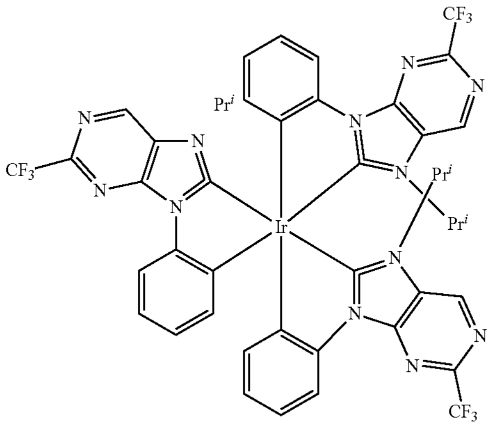
-continued
17-fac
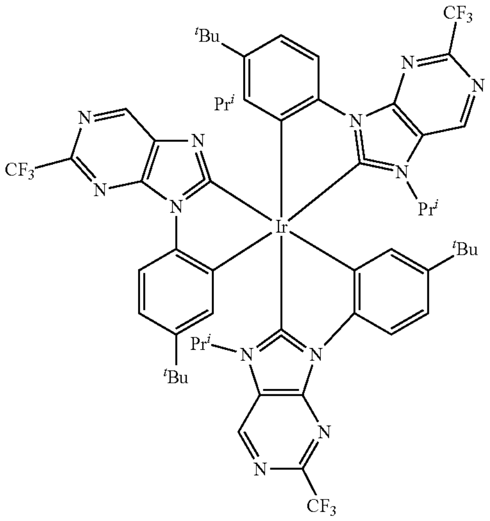
17-mer
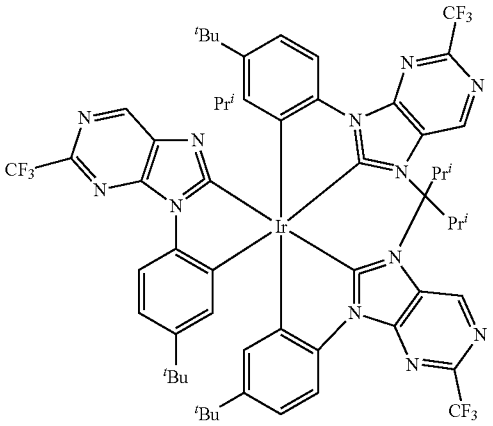
18-fac
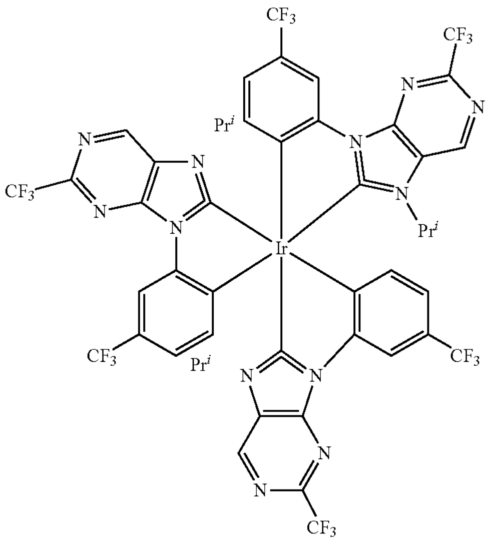

-continued
18-mer
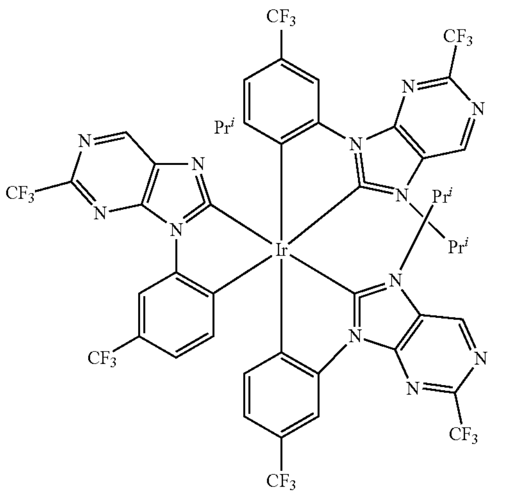
19-fac
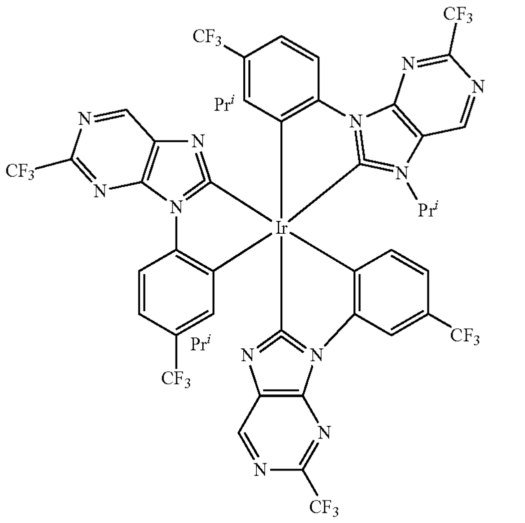
19-mer
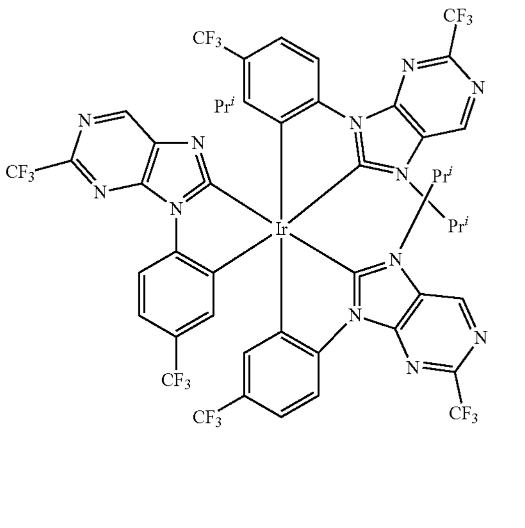
-continued
20-fac
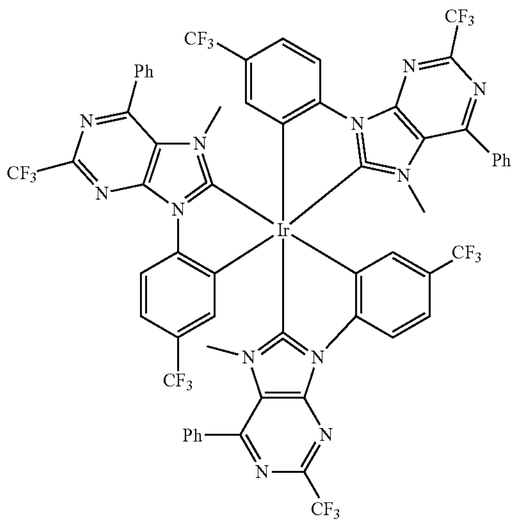
20-mer
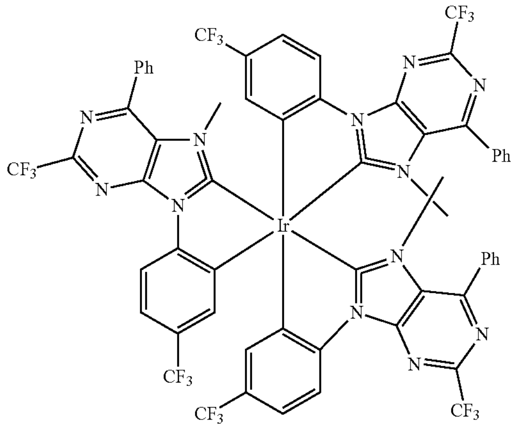
21-fac
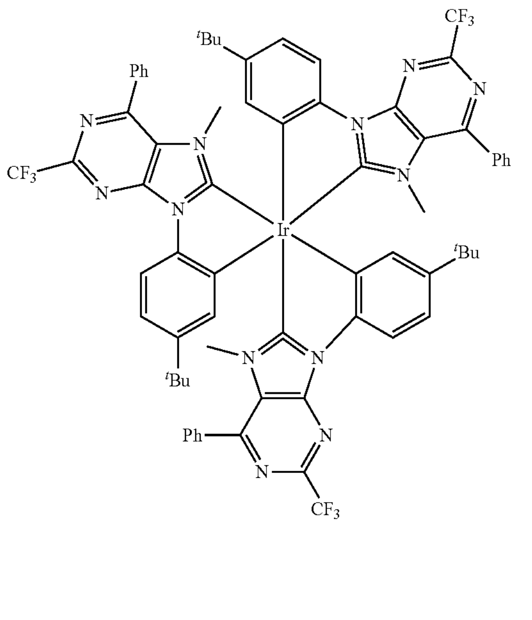

-continued
21-mer
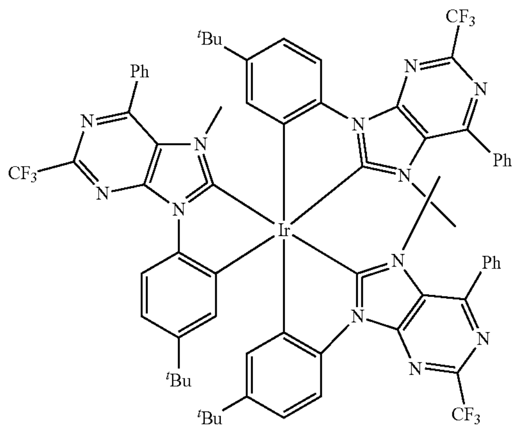
22-fac
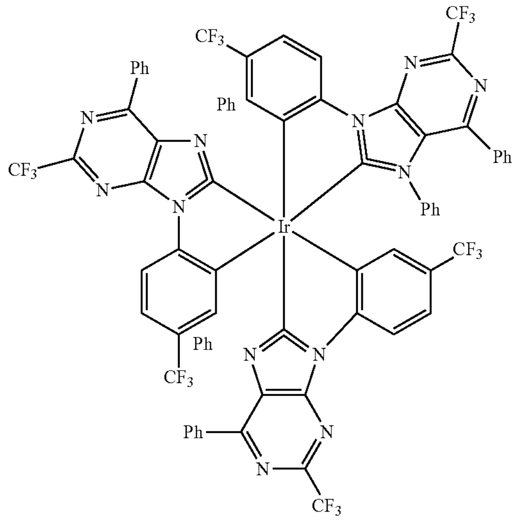
22-mer
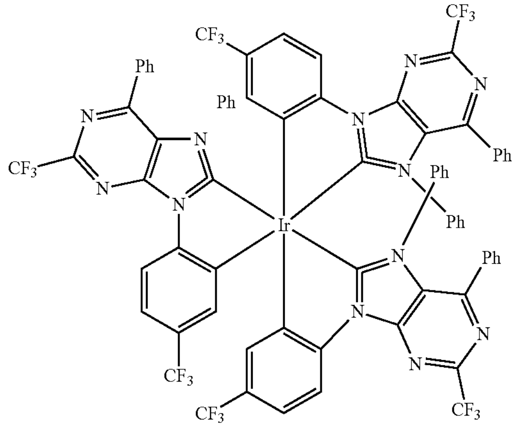
-continued
23-fac
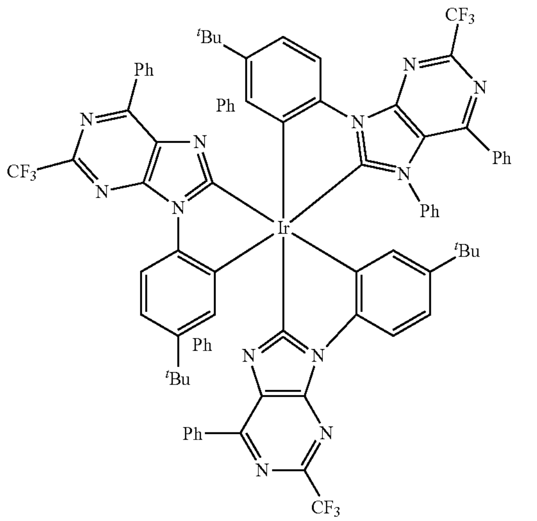
23-mer
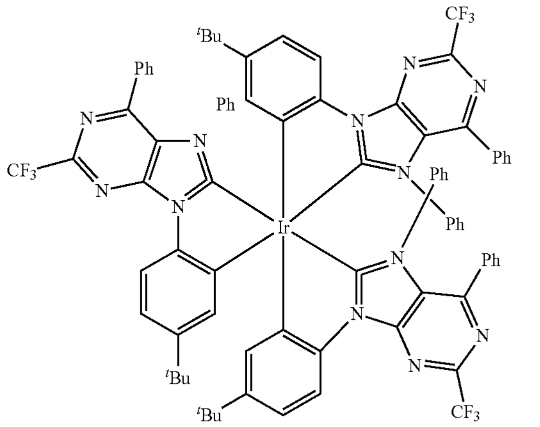
24-fac
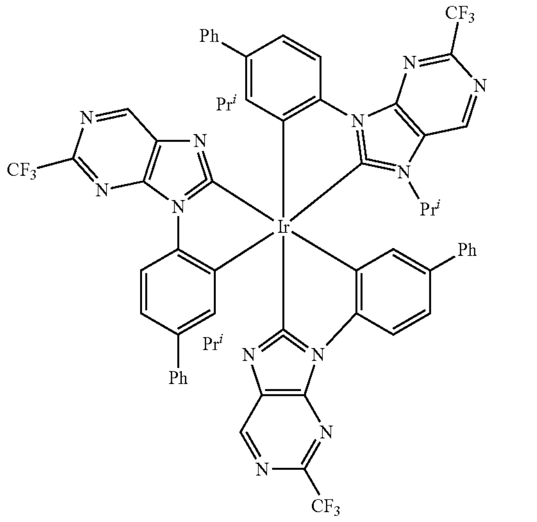

-continued
24-mer
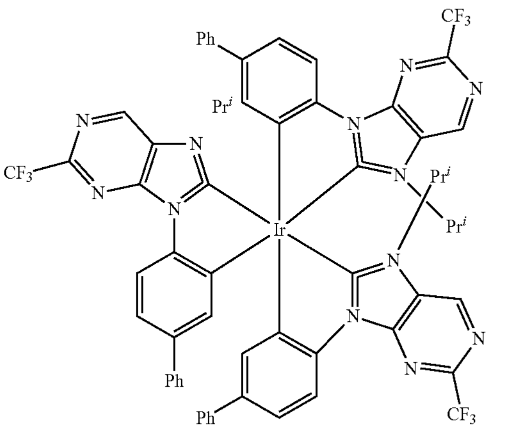
25-fac
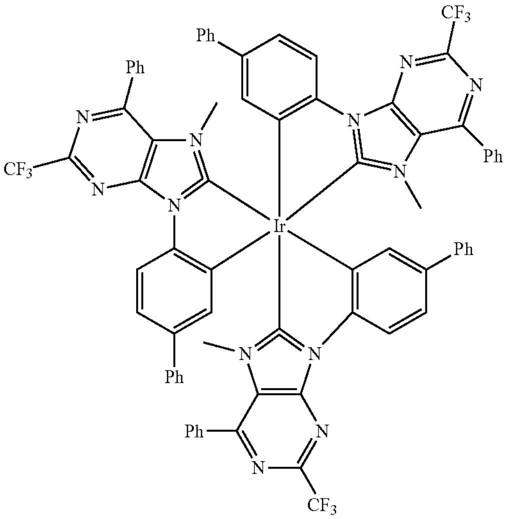
25-mer
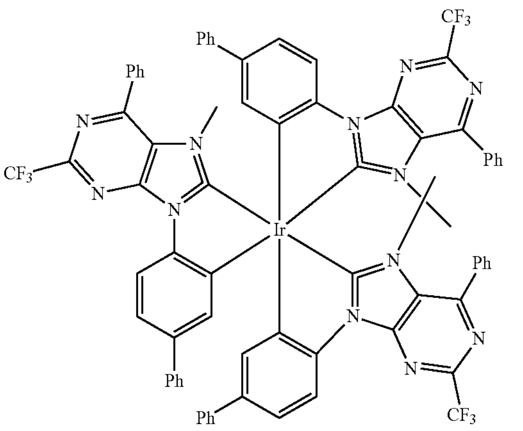
-continued
26-fac
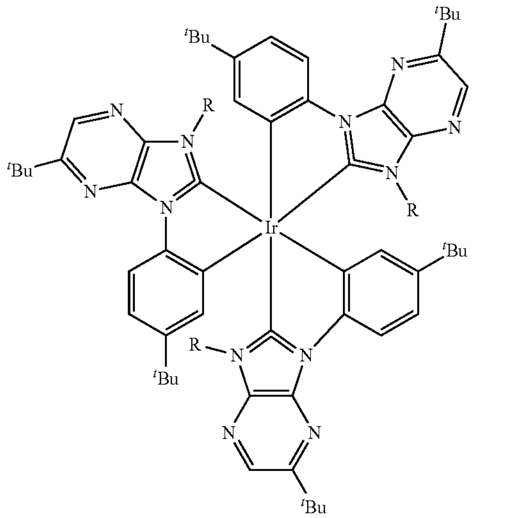
R = 1,1′-biphenyl
27-fac
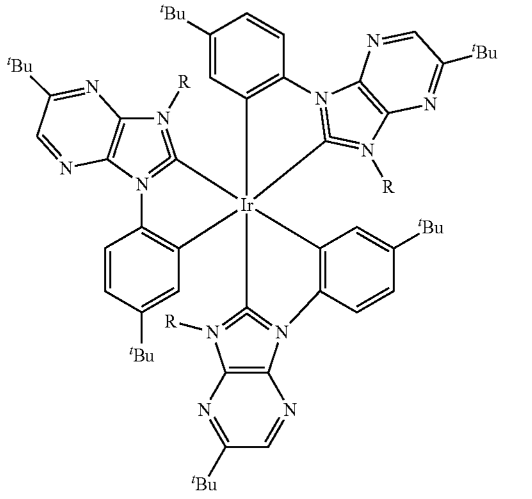
R = 1,1′-biphenyl -continued
28-fac
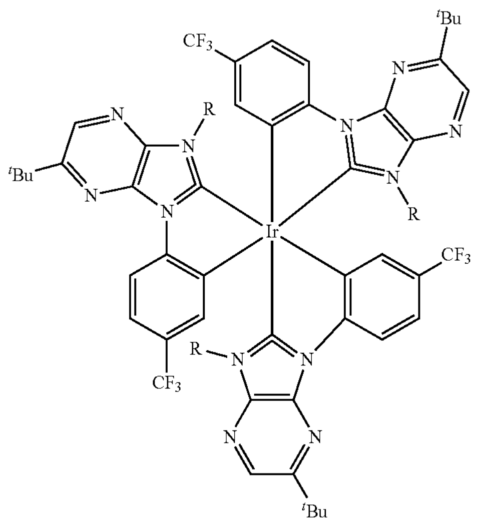
R = 1,1′-biphenyl
29-fac
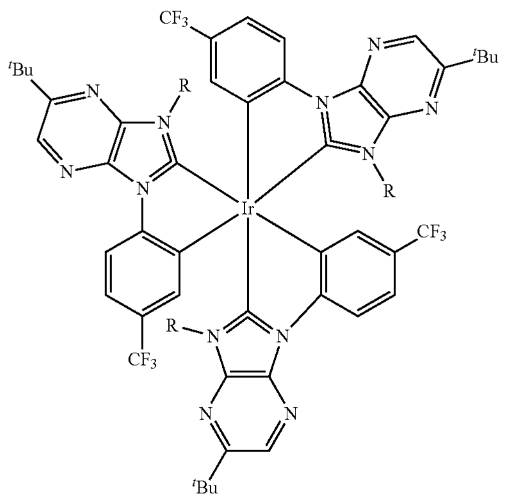
R = 1,1′-biphenyl
30-fac
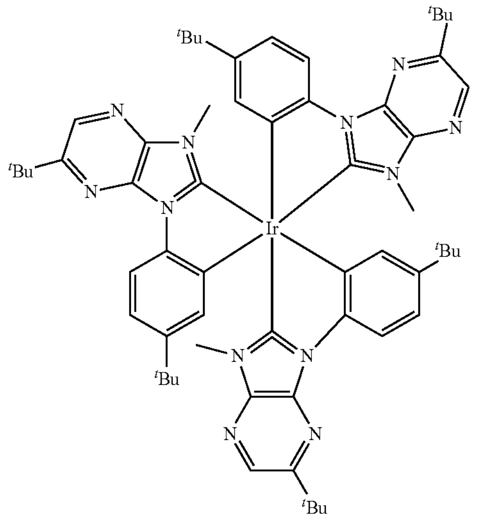
-continued
31-fac
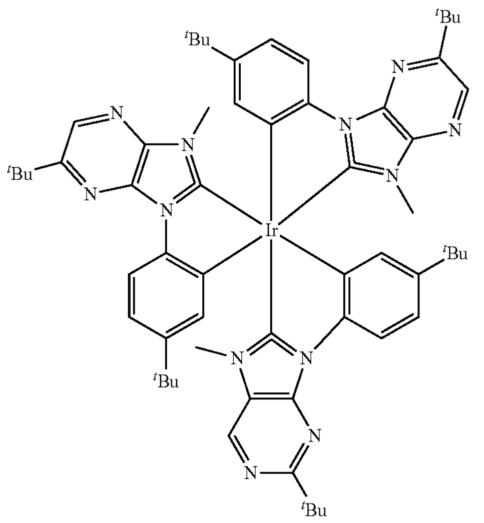
32-fac
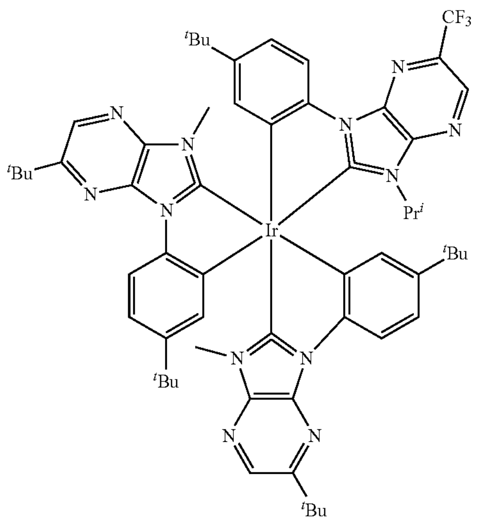
33-fac
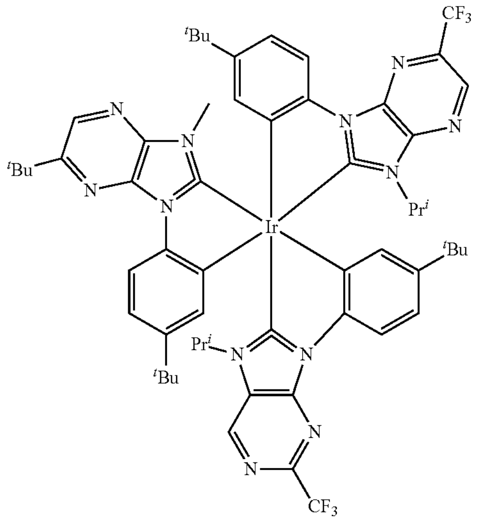

-continued
34-fac
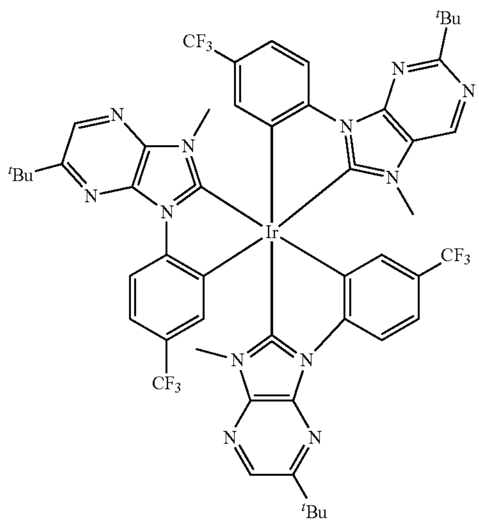
35-fac
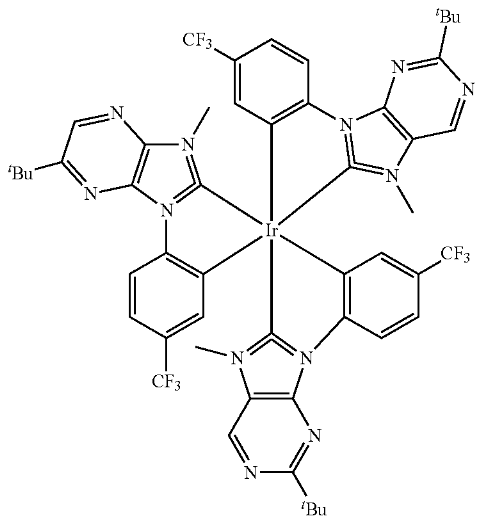
36-fac
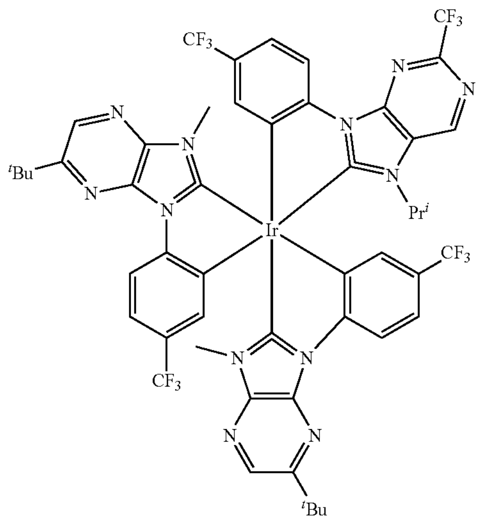
-continued
37-fac
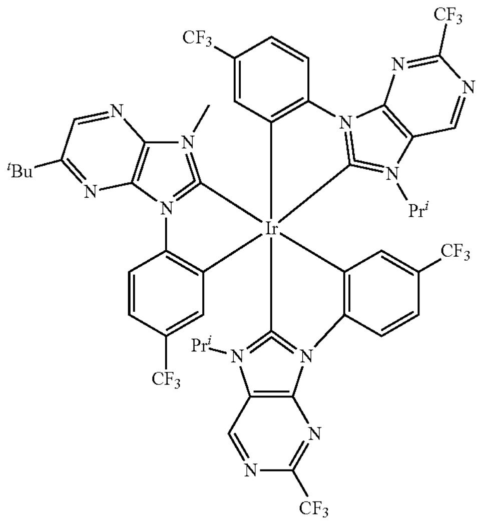
38-fac
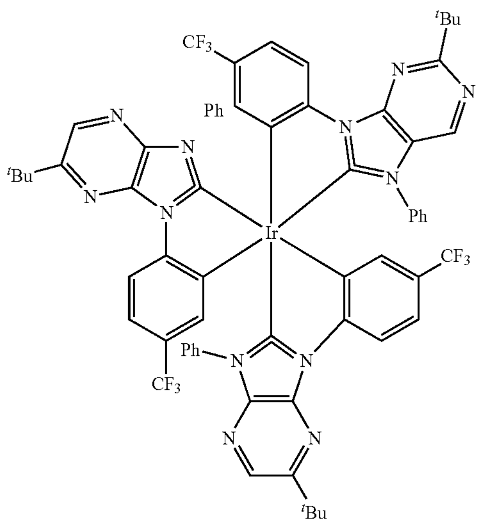
39-fac
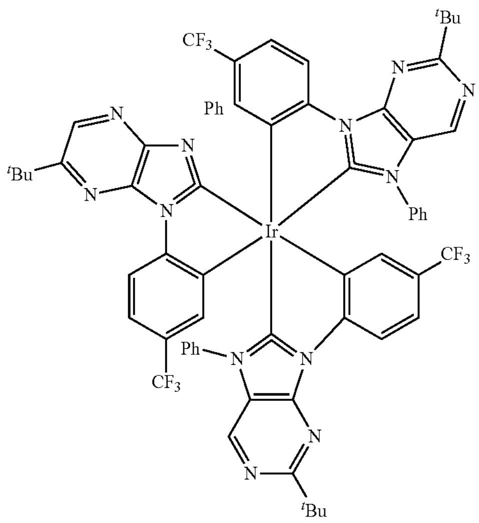

-continued
40-fac
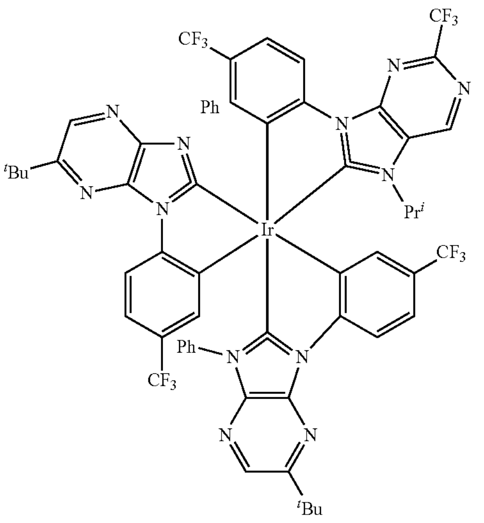
41-fac
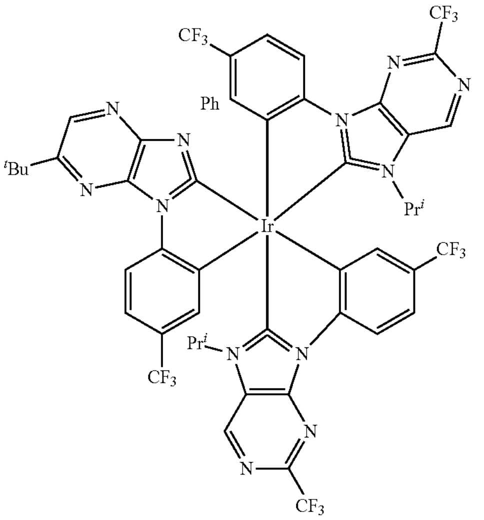
Optionally, the metal complex is selected from one of the following:
42-mer
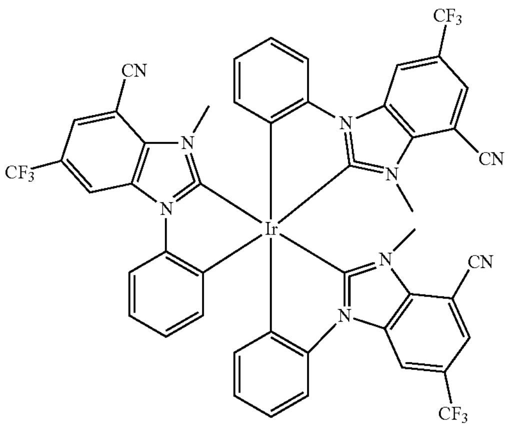
-continued
42-fac
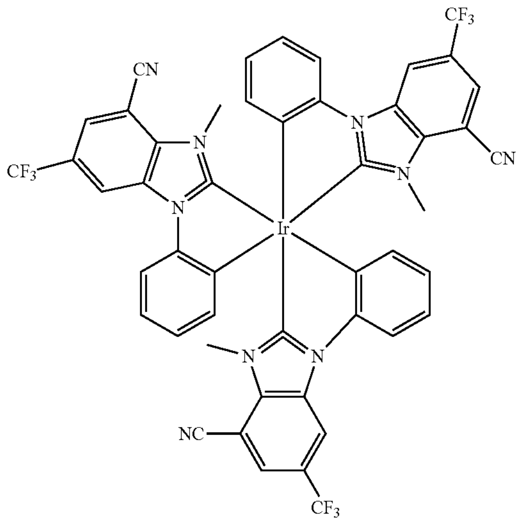
43-mer
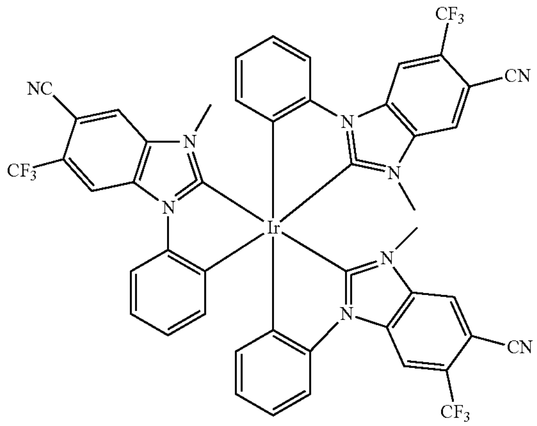
43-fac
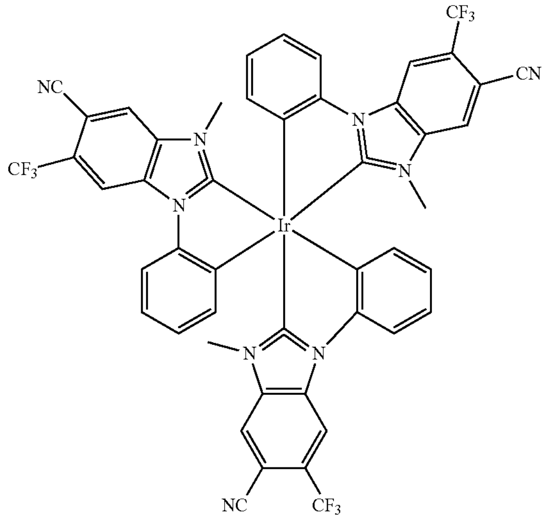

44-mer
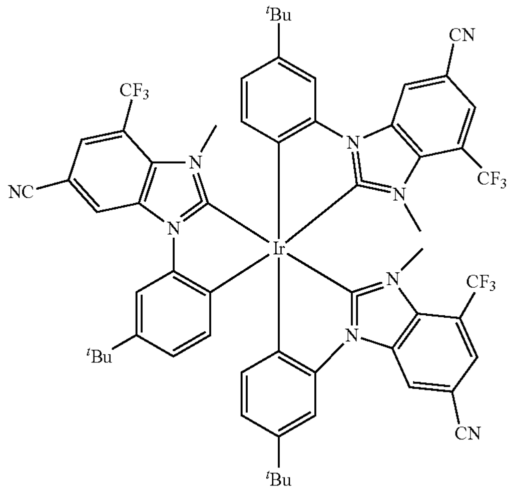
44-fac
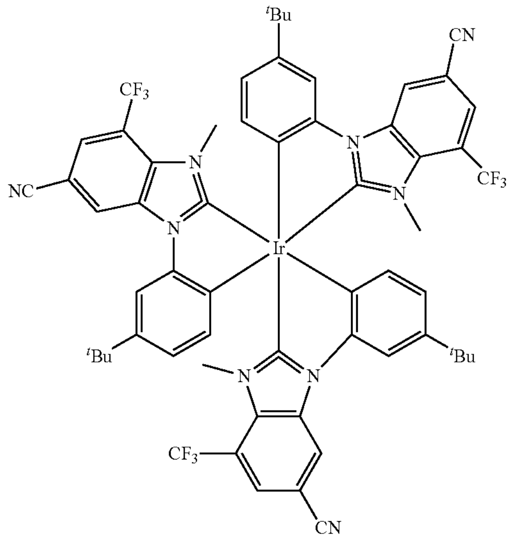
45-fac
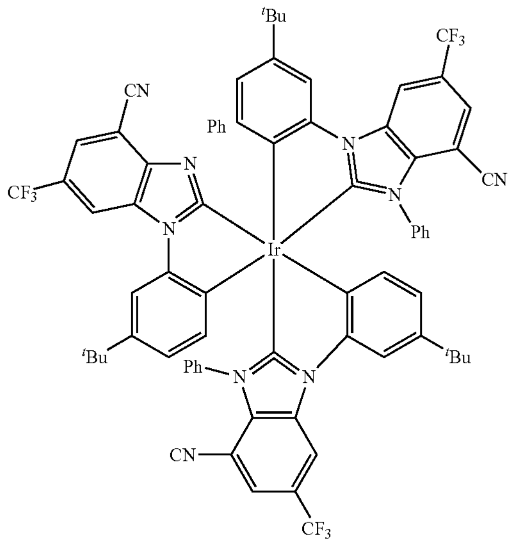
46-fac
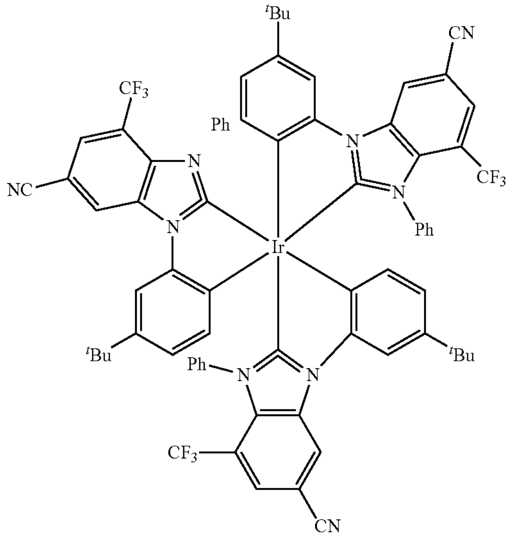
47-fac
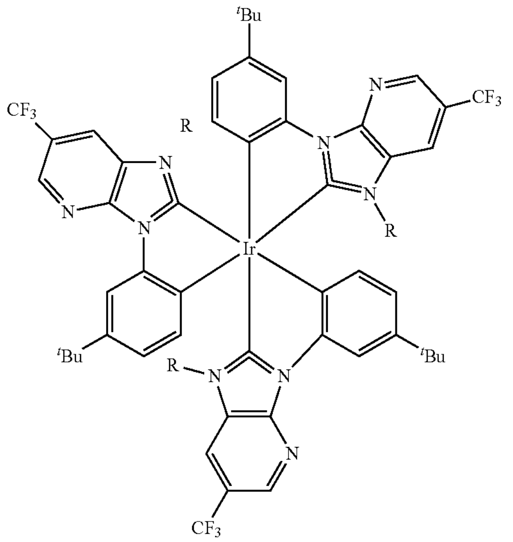
R = $C_6H_5$;

-continued
48-fac
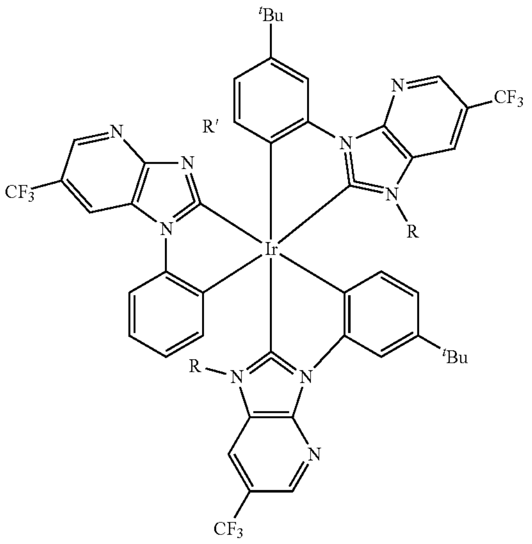
R = $C_6H_5$;
R′ = m-$C_6H_4{}^tBu$
49-fac
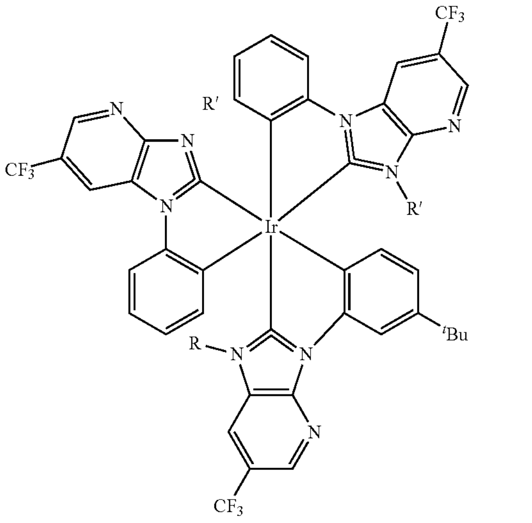
R = $C_6H_5$;
R′ = m-$C_6H_4{}^tBu$
-continued
50-fac
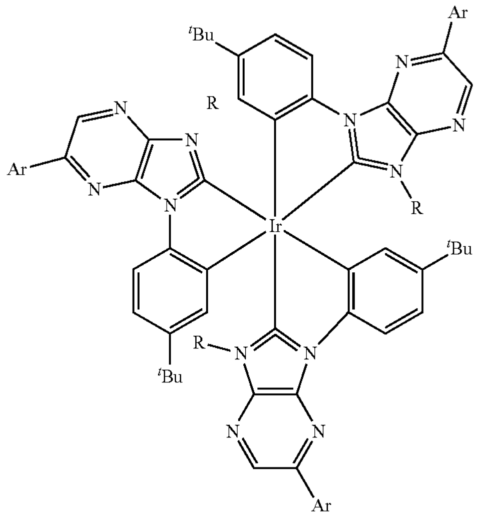
Ar = 2,6-$C_8H_3Me_2$
R = $C_6H_5$;
51-fac
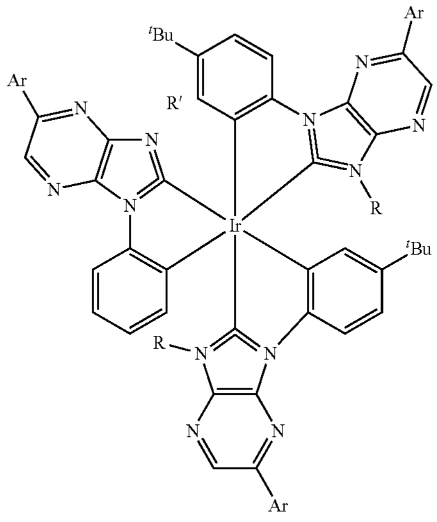
Ar = 2,6-$C_8H_3Me_2$
R = $C_6H_5$;
R′ = p-$C_6H_4{}^tBu$ -continued
52-fac
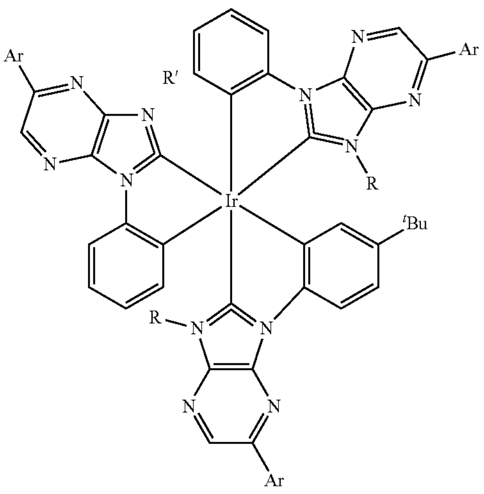
Ar = 2,6-$C_8H_3Me_2$
R = $C_6H_5$;
R′ = p-$C_8H_4{}^tBu$
53-fac
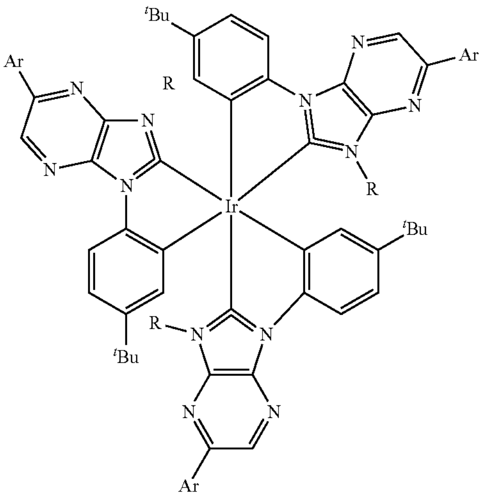
Ar = 2,6-$C_8H_3Me_2$
R = $C_6H_5$;
-continued
54-fac
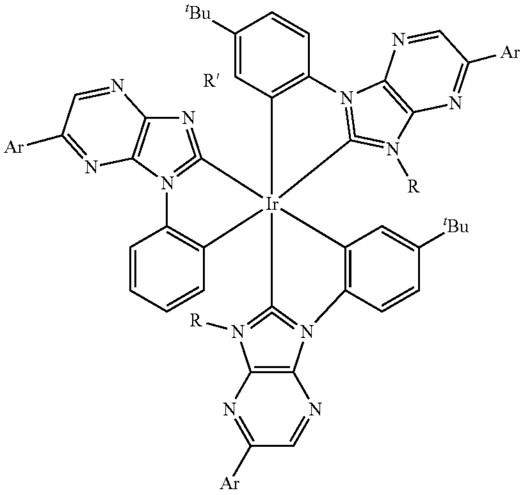
Ar = 2,6-$C_8H_3Me_2$
R = $C_6H_5$;
R′ = p-$C_6H_4{}^tBu$
55-fac
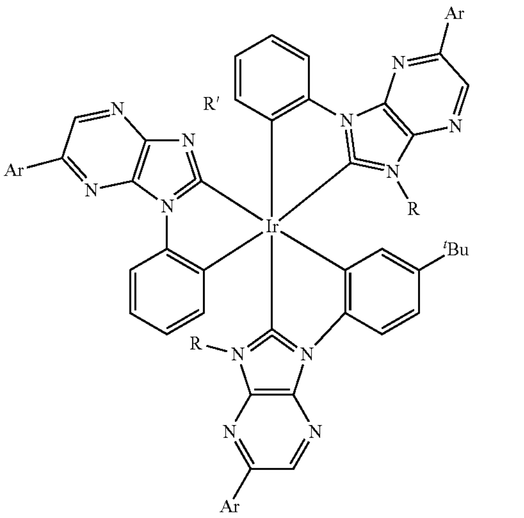
Ar = 2,6-$C_8H_3Me_2$
R = $C_6H_5$;
R′ = p-$C_6H_4{}^tBu$ -continued
56-fac
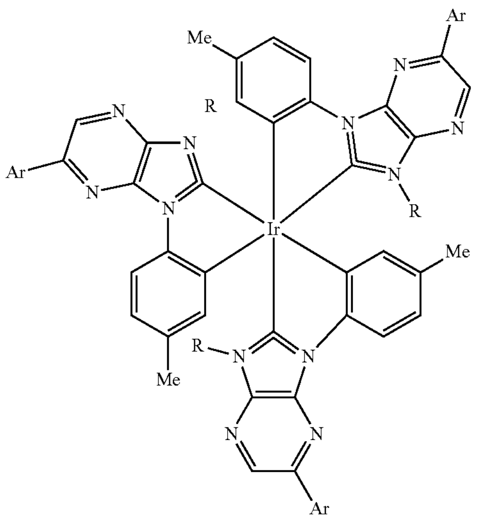
Ar = 2,6-$C_8H_3Me_2$
R = $C_6H_5$;
57-fac
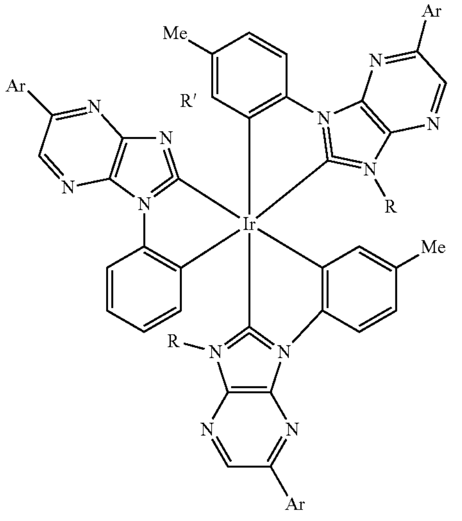
Ar = 2,6-$C_8H_3Me_2$
R = $C_6H_5$;
R′ = p-$C_6H_4Me$
-continued
58-fac
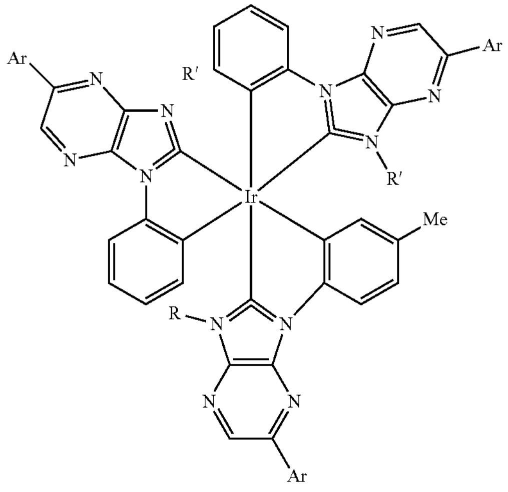
Ar = 2,6-$C_8H_3Me_2$
R = $C_6H_5$;
R′ = p-$C_6H_4Me$
59-fac
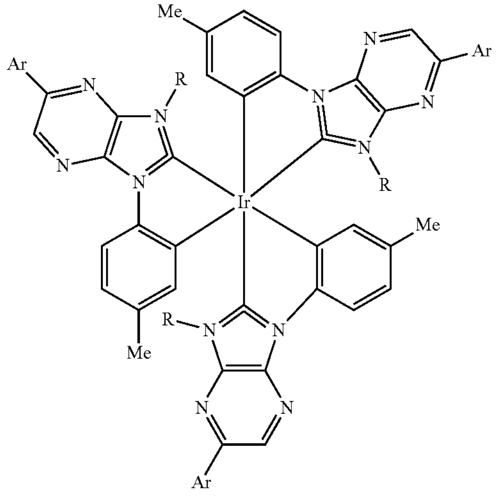
Ar = 2,6-$C_8H_3Me_2$
R = $C_6H_5$;

-continued
60-fac
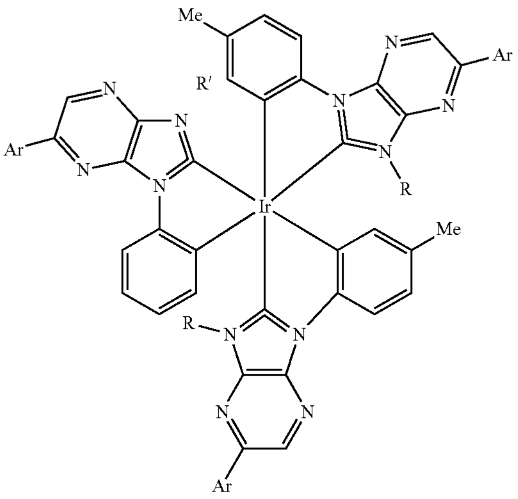
Ar = 2,6-$C_8H_3Me_2$
R = $C_6H_5$;
R′ = p-$C_6H_4Me$
61-fac
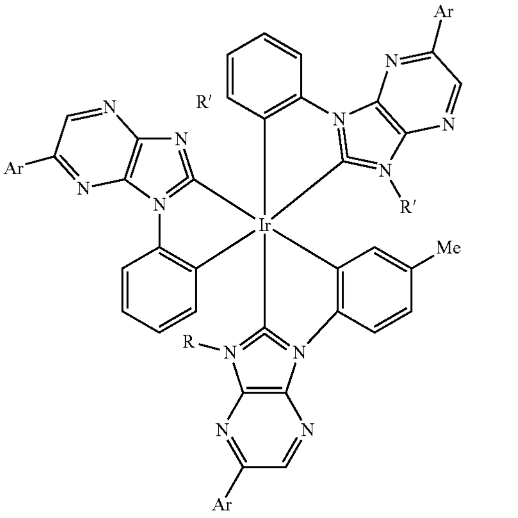
Ar = 2,6-$C_8H_3Me_2$
R = $C_6H_5$;
R′ = p-$C_6H_4Me$
-continued
62-fac
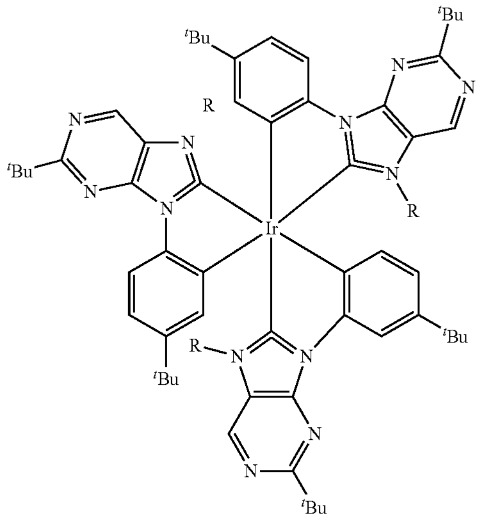
R = $C_6H_5$;
63-fac
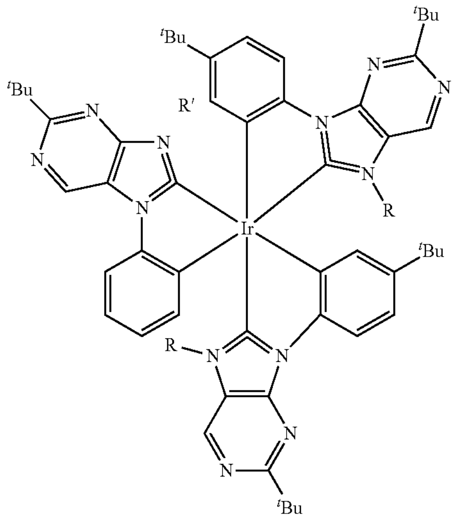
R = $C_6H_5$;
R′ = p-$C_6H_4{}^tBu$ -continued
64-fac
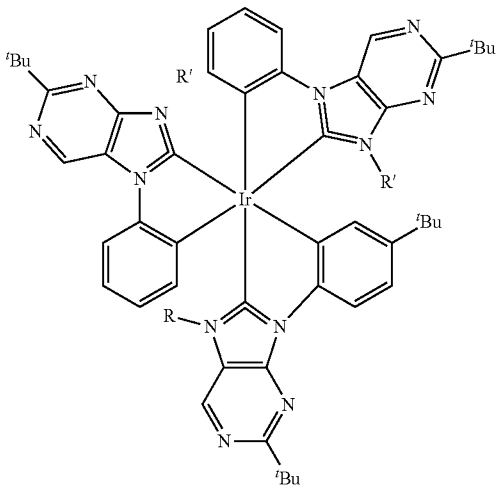
R = $C_6H_5$;
R′ = p-$C_6H_4{}^tBu$
-continued
66-fac
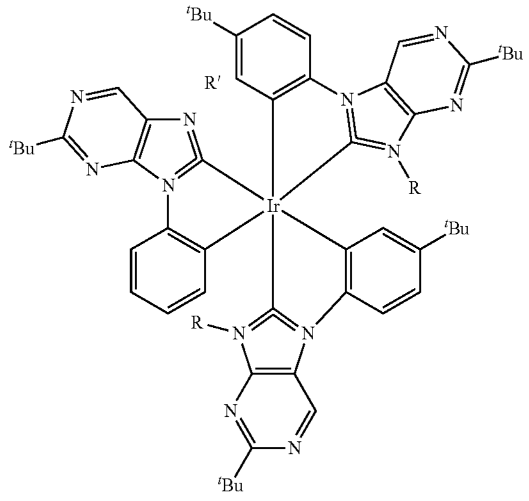
R = $C_6H_5$;
R′ = p-$C_6H_4{}^tBu$
65-fac
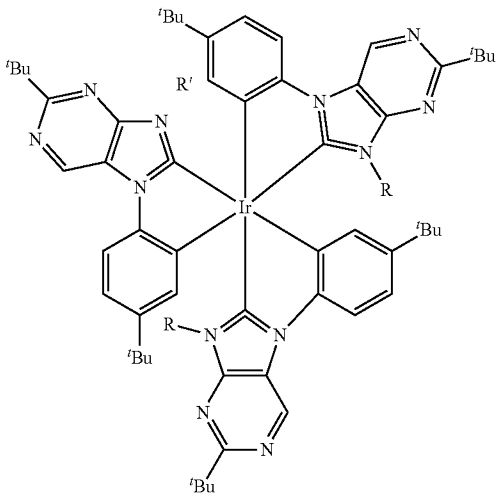
R = $C_6H_5$;
67-fac
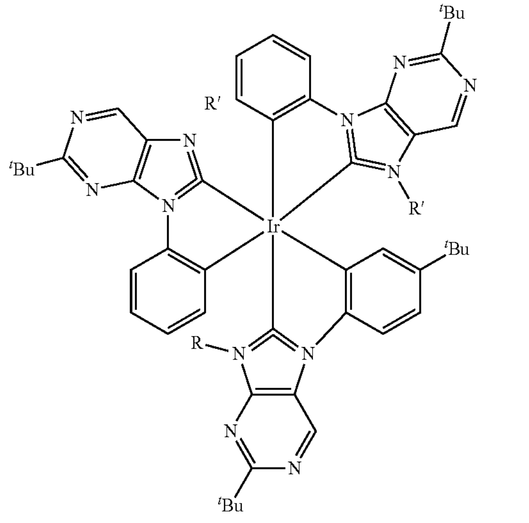
R = $C_6H_5$;
R′ = p-$C_6H_4{}^tBu$ -continued
68-fac
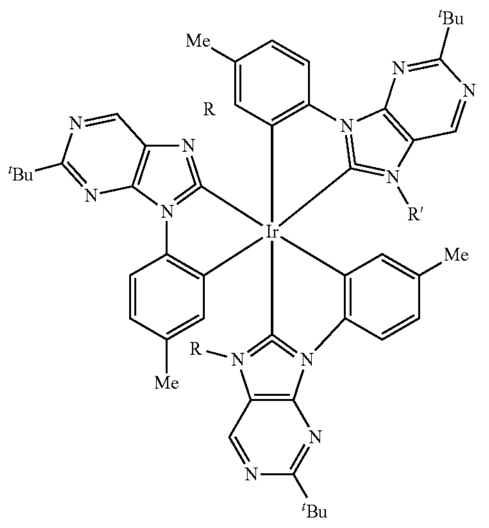
R = $C_6H_5$;
69-fac
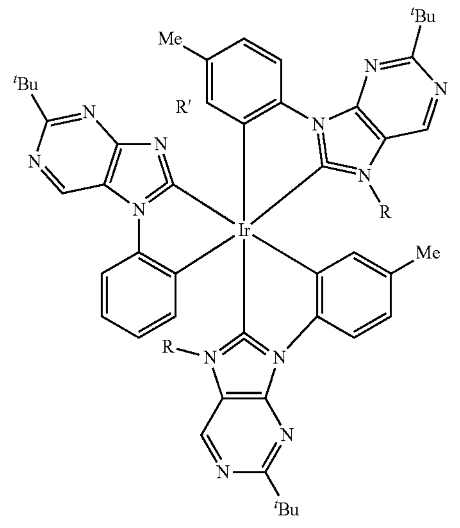
R = $C_6H_5$;
R′ = p-$C_6H_4Me$
-continued
70-fac
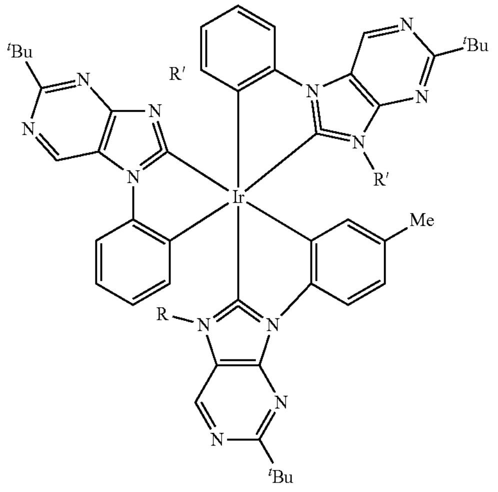
R = $C_6H_5$;
R′ = p-$C_6H_4Me$
71-fac
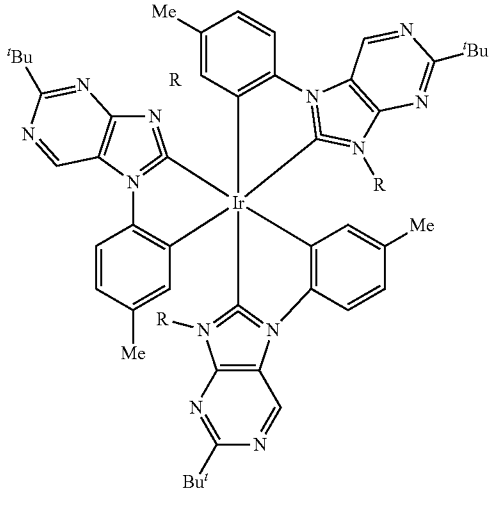
R = $C_6H_5$;

72-fac
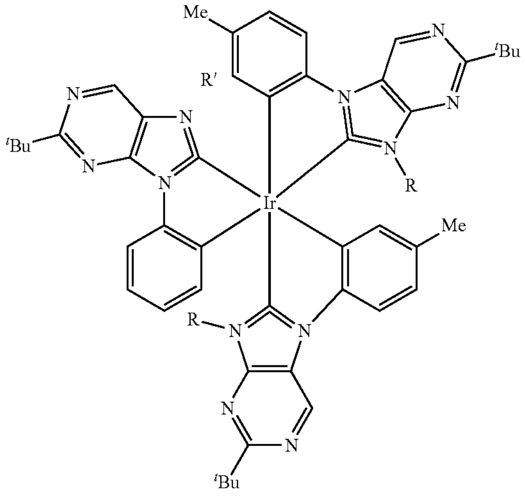
R = $C_6H_5$;
R′ = p-$C_6H_4Me$
74-fac
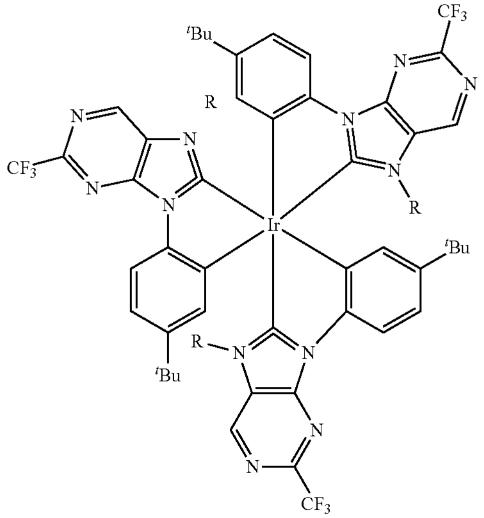
R = $C_6H_5$;
73-fac
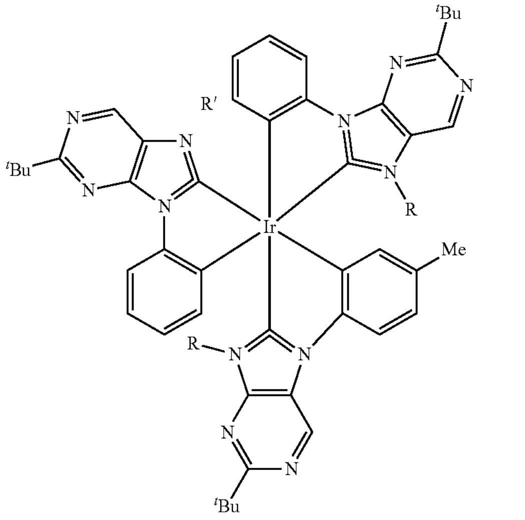
R = $C_6H_5$;
R′ = p-$C_6H_4Me$
75-fac
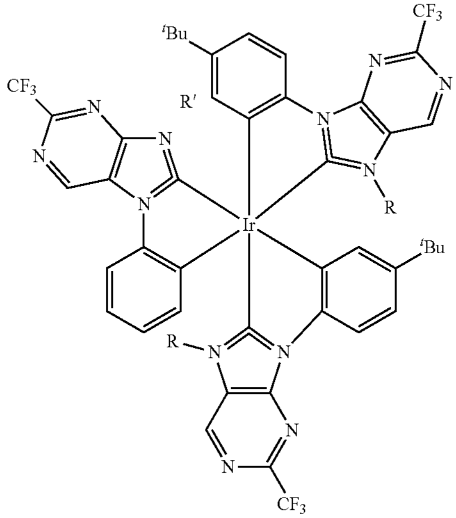
R = $C_6H_5$;
R′ = p-$C_6H_4{}^tBu$ -continued
76-fac
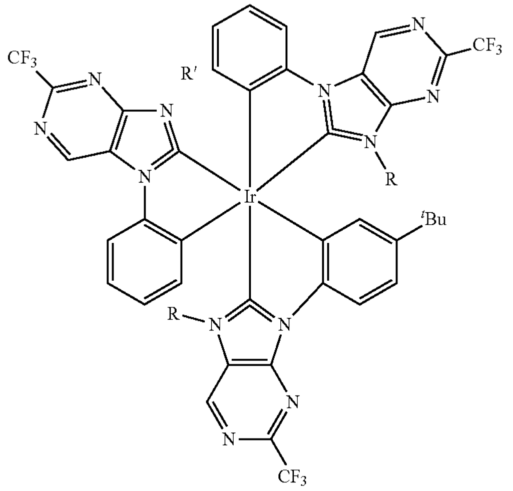
R = $C_6H_5$;
R′ = p-$C_6H_4{}^tBu$
77-fac
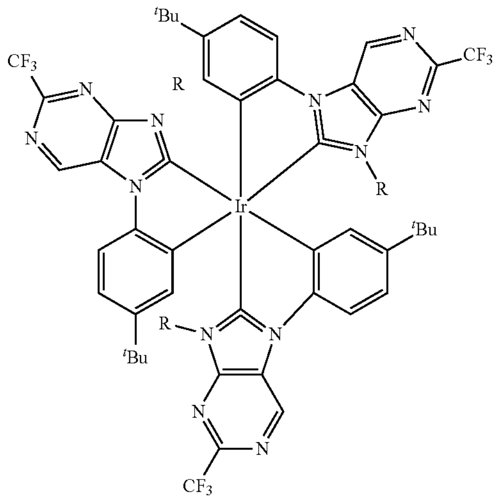
R = $C_6H_5$;
-continued
78-fac
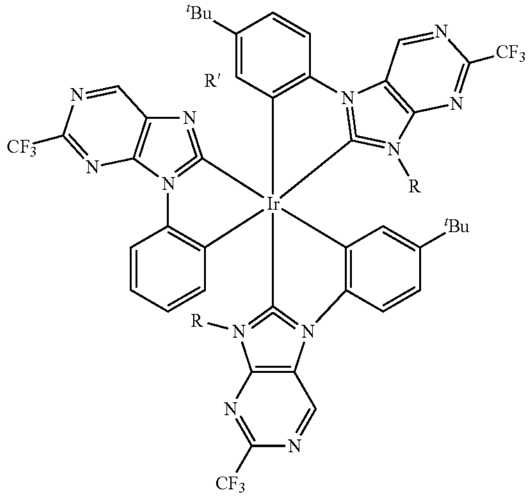
R = $C_6H_5$;
R′ = p-$C_6H_4{}^tBu$
79-fac
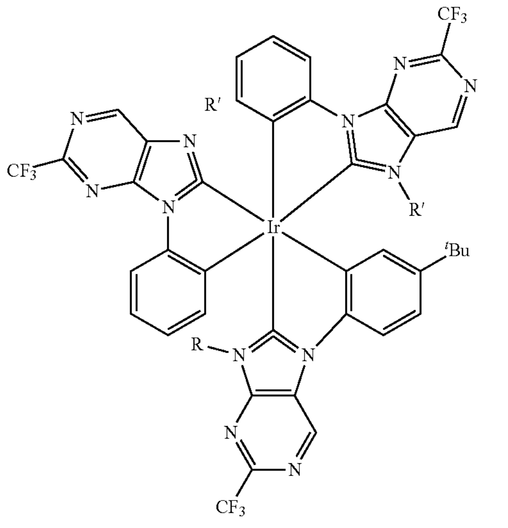
R = $C_6H_5$;
R′ = p-$C_6H_4{}^tBu$ -continued
80-fac
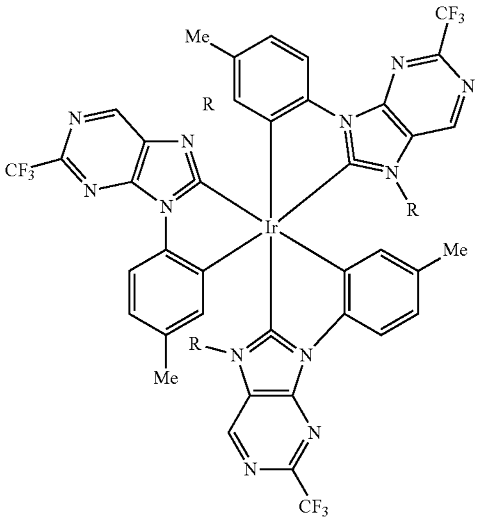
R = $C_6H_5$;
81-fac
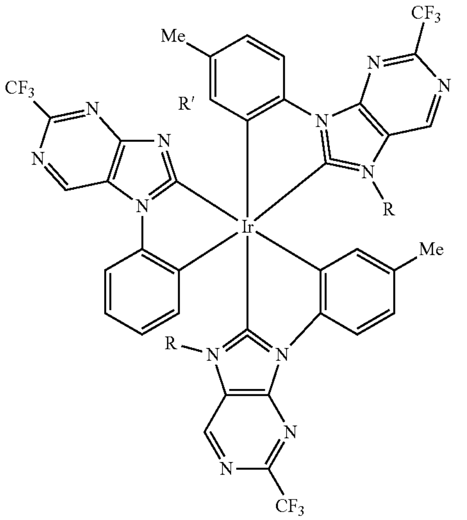
R = $C_6H_5$;
R′ = p-$C_6H_4$Me
-continued
82-fac
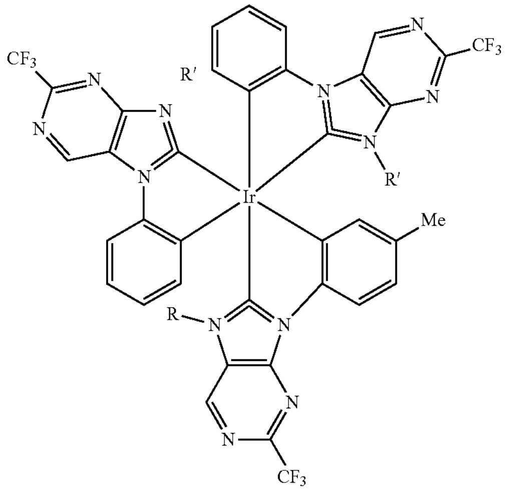
R = $C_6H_5$;
R′ = p-$C_6H_4$Me
83-fac
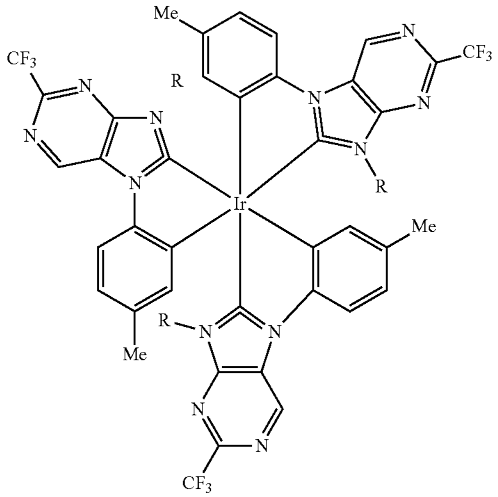
R = $C_6H_5$;

-continued
84-fac
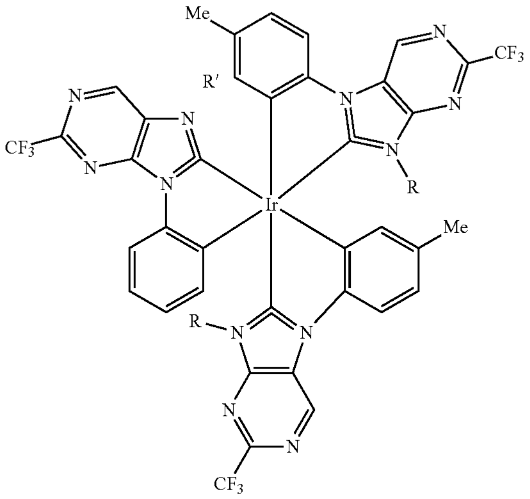
R = $C_6H_5$;
R′ = p-$C_6H_4Me$
86-fac
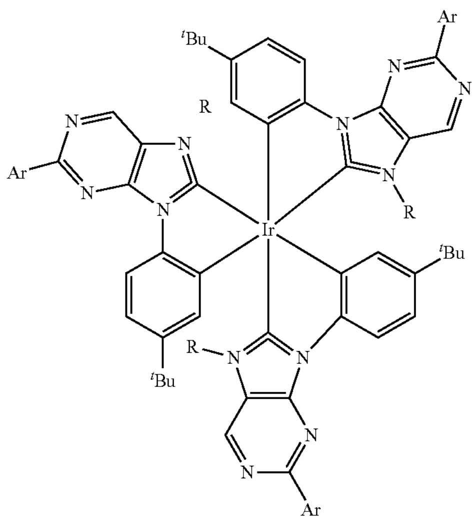
Ar = 2,6-$C_6H_3Me_2$
R = $C_6H_5$;
85-fac
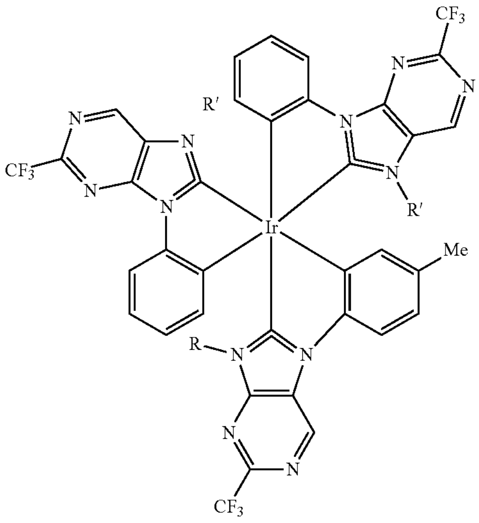
R = $C_6H_5$;
R′ = p-$C_6H_4Me$
87-fac
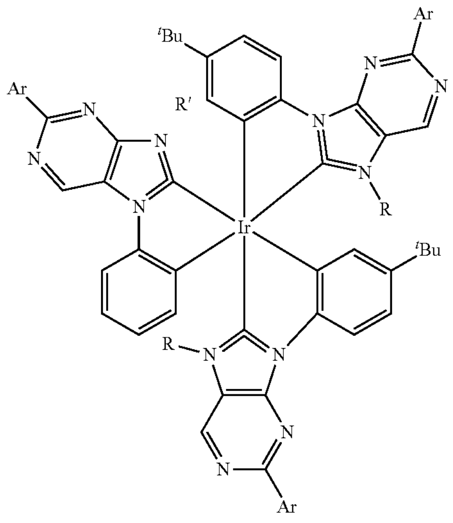
Ar = 2,6-$C_6H_3Me_2$
R = $C_6H_5$;
R′ = p-$C_6H_4{}^tBu$ -continued
88-fac
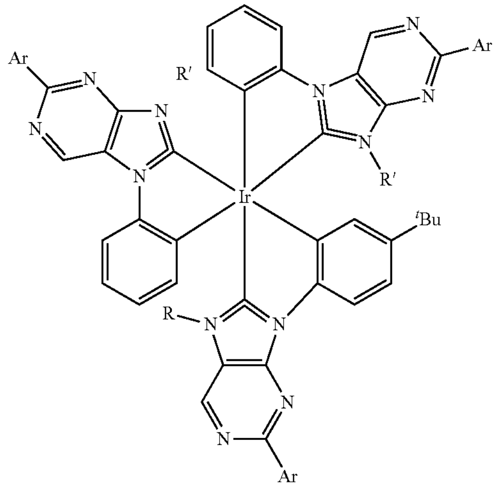
Ar = 2,6-$C_6H_3Me_2$
R = $C_6H_5$;
R′ = p-$C_6H_4{}^tBu$
89-fac
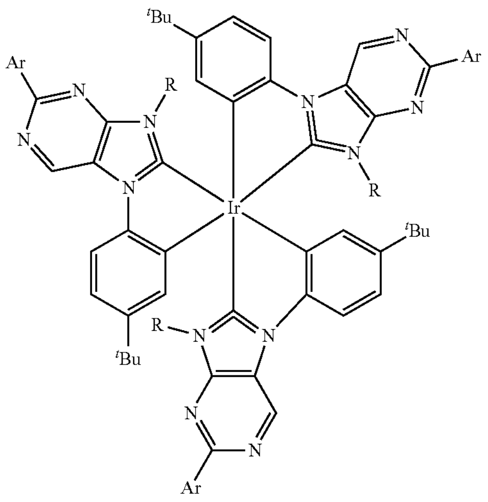
Ar = 2,6-$C_6H_3Me_2$
R = $C_6H_5$;
-continued
90-fac
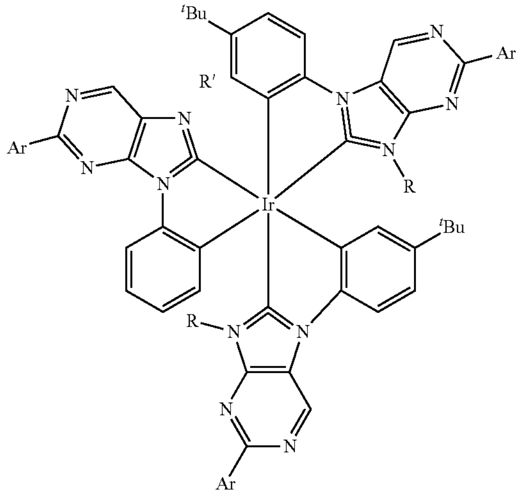
Ar = 2,6-$C_6H_3Me_2$
R = $C_6H_5$;
R′ = p-$C_6H_4$-${}^tBu$
91-fac
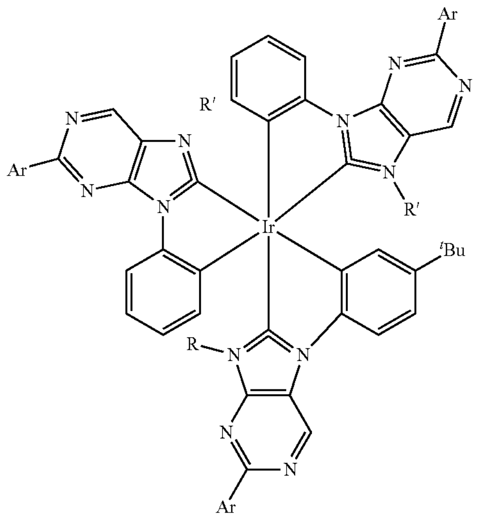
Ar = 2,6-$C_6H_3Me_2$
R = $C_6H_5$;
R′ = p-$C_6H_4$-${}^tBu$ -continued
92-fac
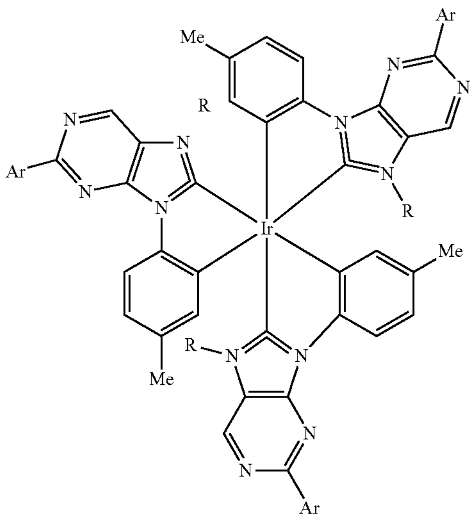
Ar = 2,6-$C_6H_3Me_2$
R = $C_6H_5$;
94-fac
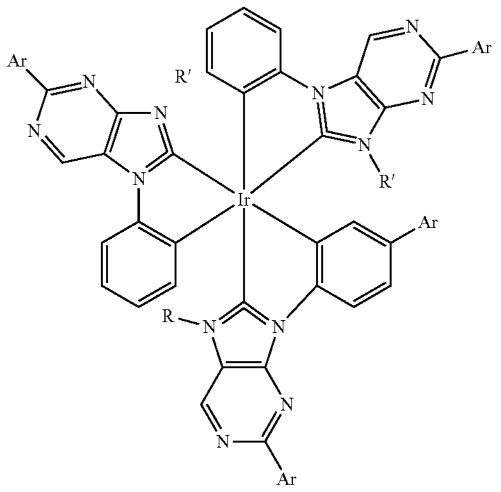
Ar = 2,6-$C_6H_3Me_2$
R = $C_6H_5$;
R′ = p-$C_6H_4Me$
93-fac
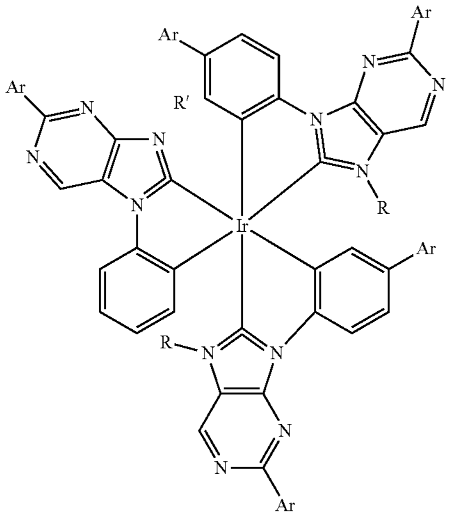
Ar = 2,6-$C_6H_3Me_2$
R = $C_6H_5$;
R′ = p-$C_6H_4Me$
95-fac
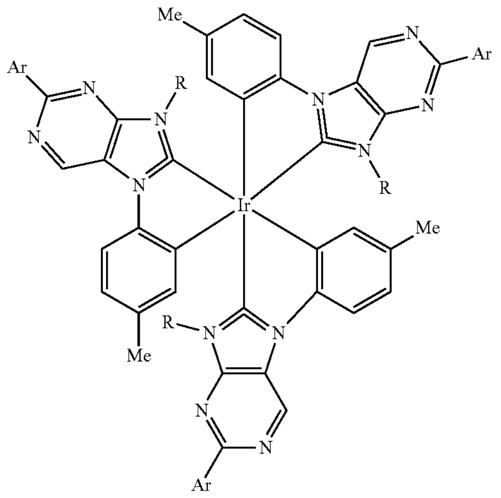
Ar = 2,6-$C_6H_3Me_2$
R = $C_6H_5$;

-continued
96-fac
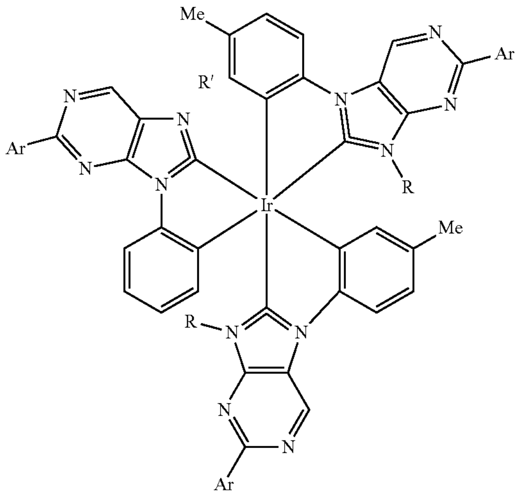
Ar = 2,6-$C_6H_3Me_2$
R = $C_6H_5$;
R′ = p-$C_6H_4Me$
98-fac
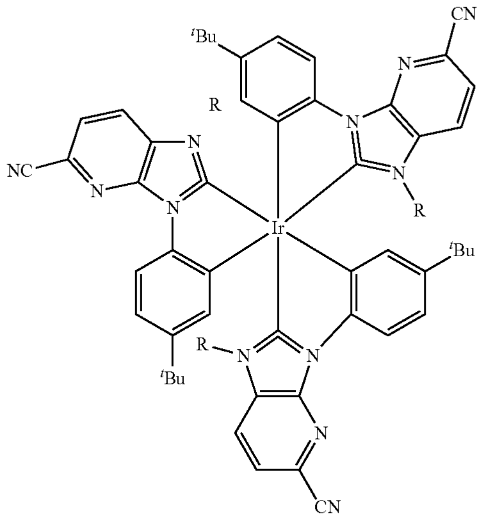
R = $C_6H_5$;
97-fac
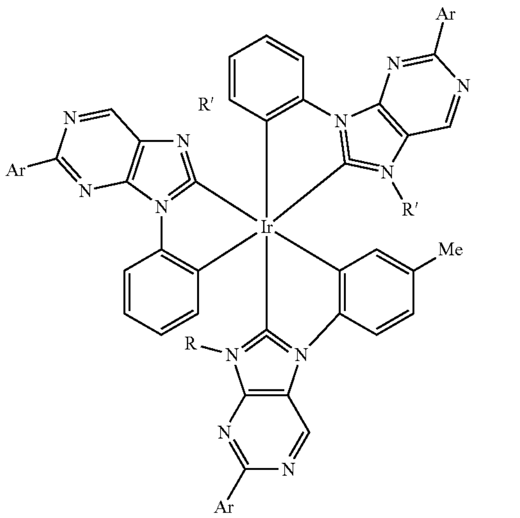
Ar = 2,6-$C_6H_3Me_2$
R = $C_6H_5$;
R′ = p-$C_6H_4Me$
99-fac
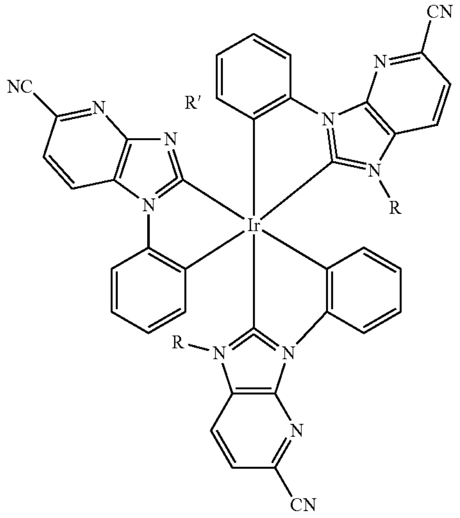
R = p-$C_6H_4{}^tBu$ -continued
100-mer
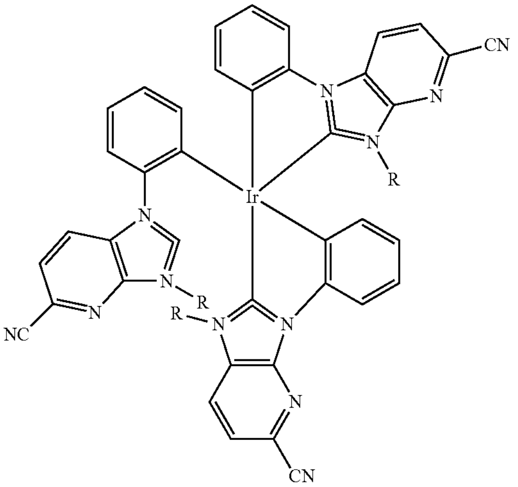
R = p-$C_6H_4{}^tBu$;
101-fac
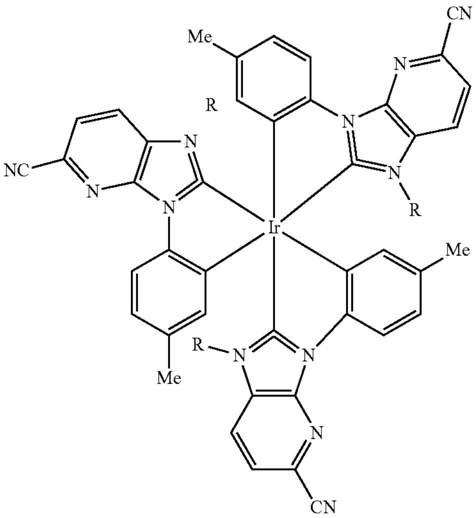
R = $C_6H_5$;
-continued
102-fac
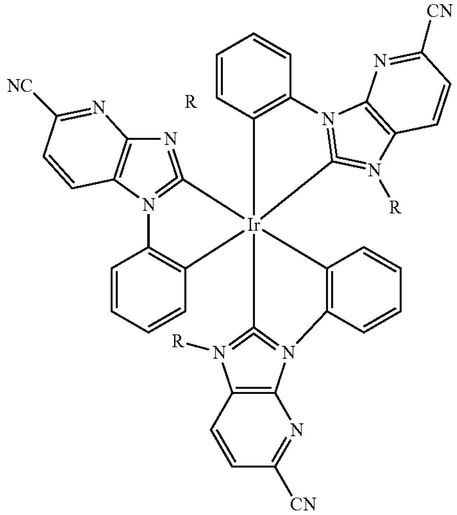
R = p-$C_6H_4Me$;
103-mer
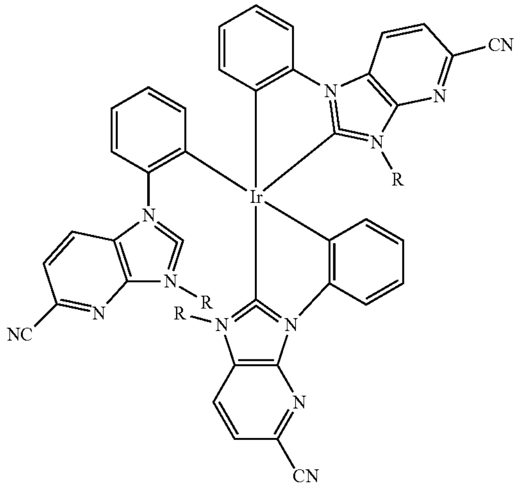
R = p-$C_6H_4Me$;

-continued
104-fac
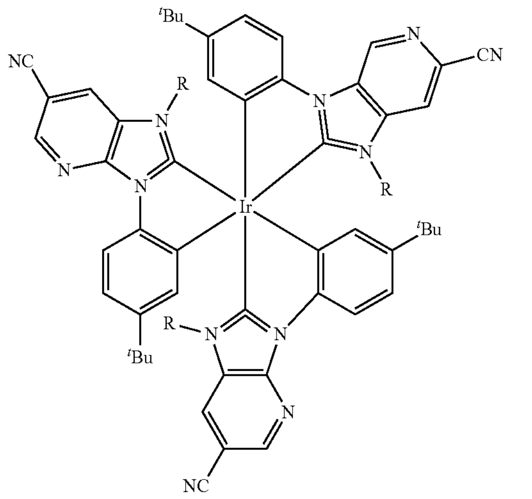
R = $C_6H_5$;
105-fac
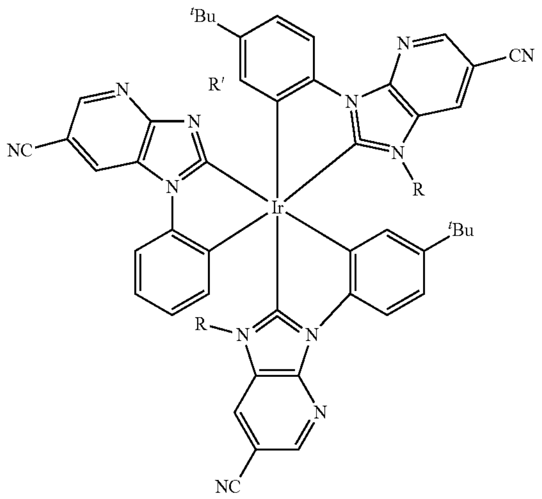
R = $C_6H_5$;
R′ = p-$C_6H_4{}^tBu$
-continued
106-fac
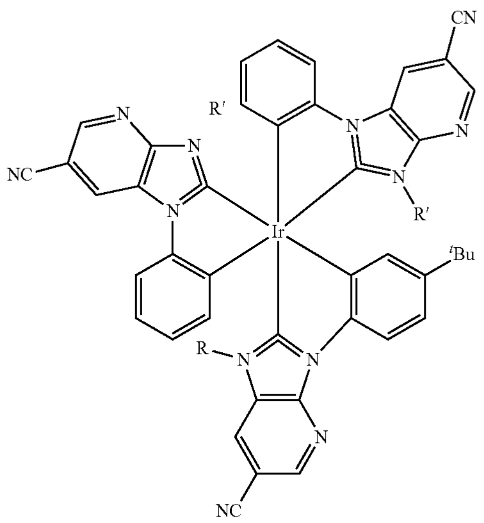
R = $C_6H_5$;
R′ = p-$C_6H_4{}^tBu$
107-fac
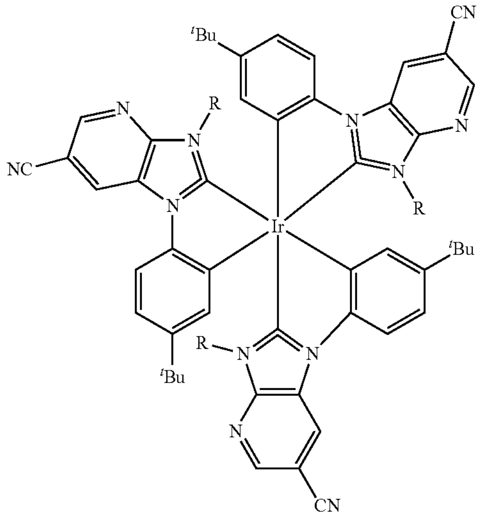
R = $C_6H_5$;

-continued
108-fac
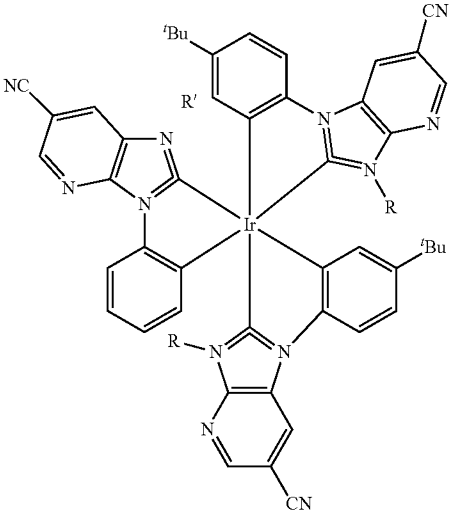
R = $C_6H_5$;
R' = p-$C_6H_4{}^tBu$
109-fac
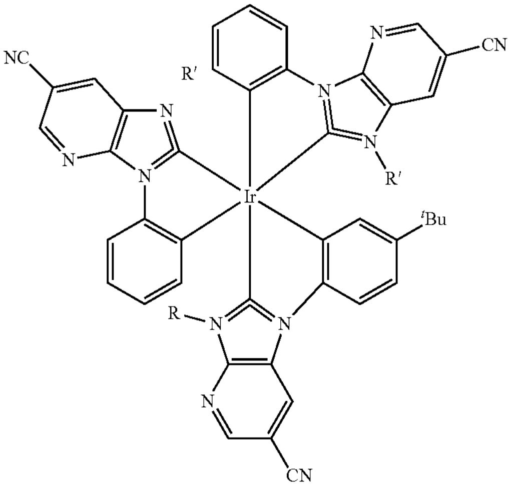
R = $C_6H_5$;
R' = p-$C_6H_4{}^tBu$
-continued
110-fac
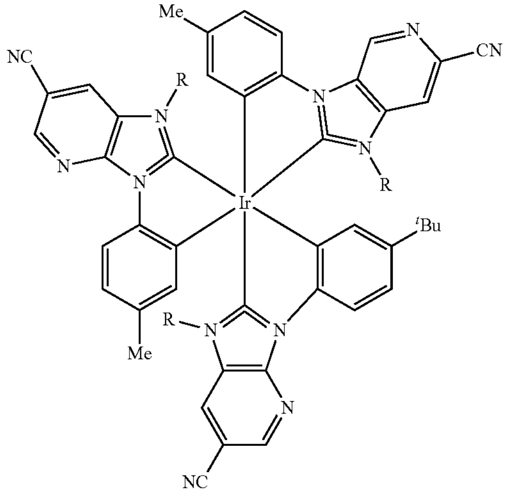
R = $C_6H_5$;
111-fac
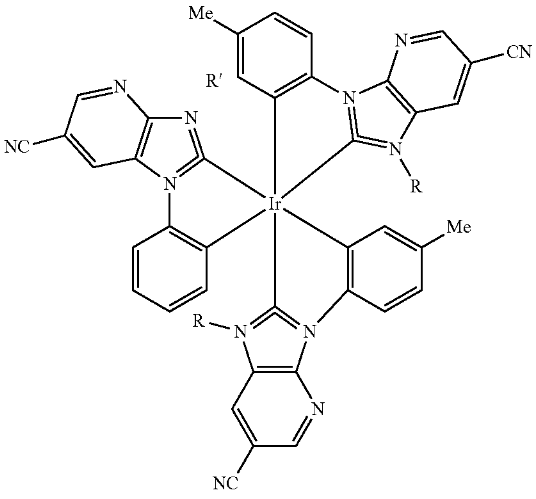
R = $C_6H_5$;
R' = p-$C_6H_4Me$ -continued
112-fac
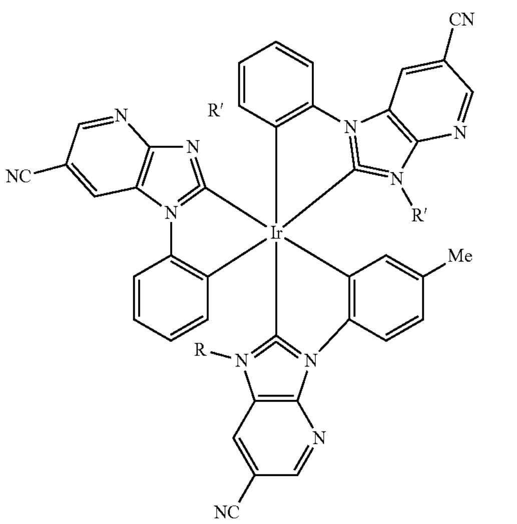
R = $C_6H_5$;
R′ = p-$C_6H_4$Me
114-fac
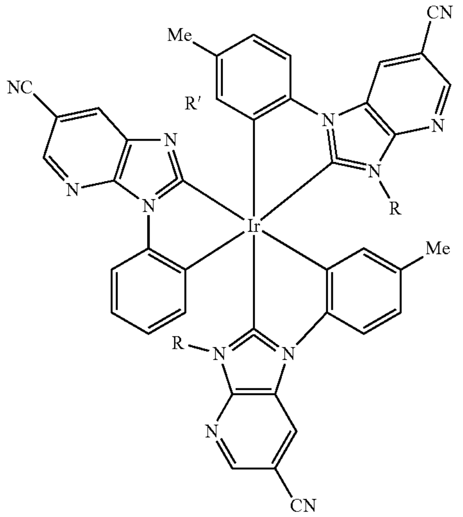
R = $C_6H_5$;
R′ = p-$C_6H_4$Me
113-fac
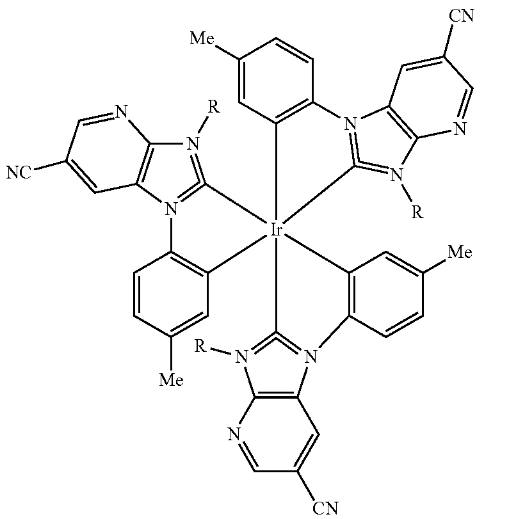
R = $C_6H_5$;
115-fac
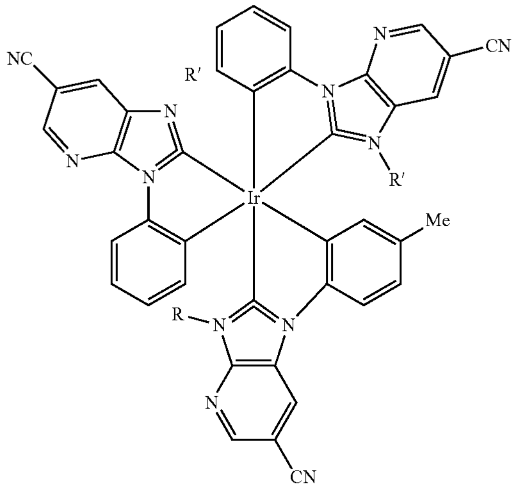
R = $C_6H_5$;
R′ = p-$C_6H_4$Me -continued 116-fac

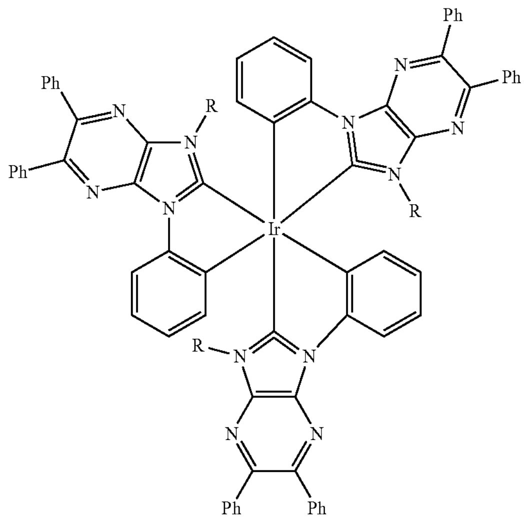

$R = C_6H_5$;

117-fac

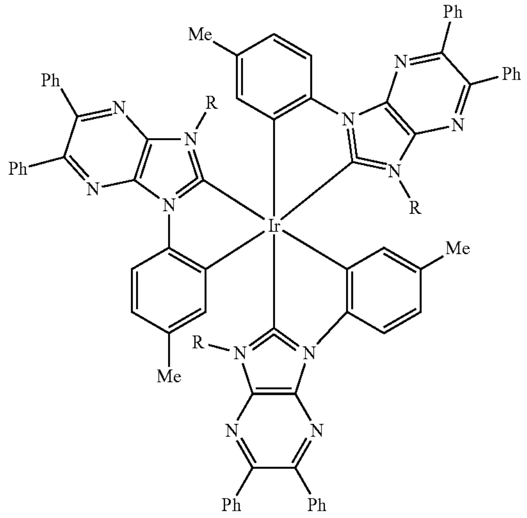

$R = p\text{-}C_6H_4Me$

-continued 118-fac

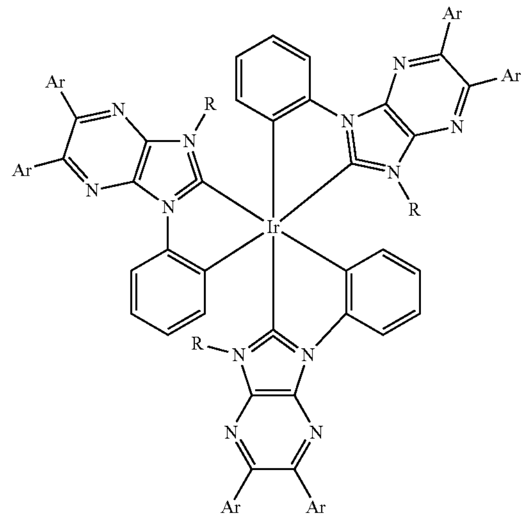

$Ar = p\text{-}C_6H_4Me$
$R = C_6H_5$

In a second aspect, the present invention provides a method of preparing a metal complex. The metal complex may be the metal complex in the first aspect. The method comprises the steps of: forming a chelating agent from a reagent selected from the group consisting of: a pyrimidone-based reagent, a pyrimidineamine-based reagent, a pyrimidinediol-based reagent, a pyrazinecarbonitrile-based, and a pyridineamine-based reagent, and mixing the chelating agent and a metal reagent to form the metal complex.

The chelating agent may be a functional 9H-purin-7-ium derivative, such as a tert-butyl-, a 2,6-dimethylphenyl- or a $CF_3$-substituted 9H-purin-7-ium derivative, or a functional imidazo[4,5-b]pyrazin-3-ium derivative, such as a tert-butyl- or a 2,6-dimethylphenyl-substituted imidazo[4,5-b]pyrazin-3-ium derivative, or a functional imidazo[4,5-b]pyridin-3-ium derivative, such as a $CF_3$- or a cyano-substituted imidazo[4,5-b]pyridin-3-ium derivative. The metal reagent may be $IrCl_3(tht)_3$.

In a third aspect, the present invention provides a light emitting device (e.g. a phosphorescent organic light-emitting diode) comprising an emissive layer having a metal complex. The metal complex may be the metal complex in the first aspect or a metal complex prepared using the method in the second aspect. The emissive layer may be arranged to emit light with a wavelength in the range of 420-565 nm, preferably in the range of 420-490 nm.

BRIEF DESCRIPTION OF THE DRAWINGS

Embodiments of the invention will now be described, by way of example, with reference to the accompanying drawings, in which.

DETAILED DESCRIPTION

Figure 1:
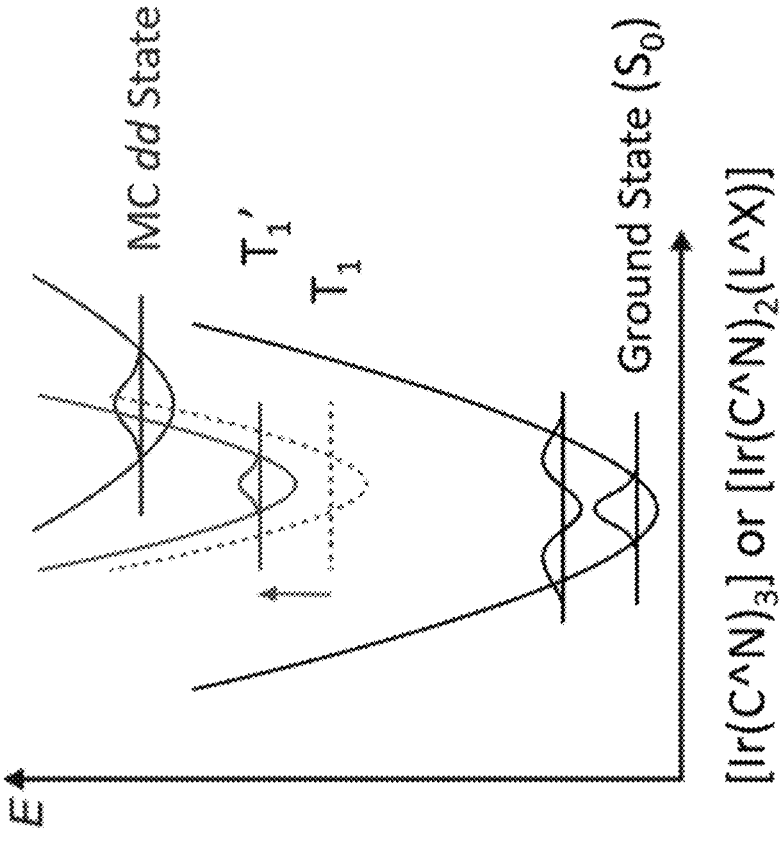
FIG. 1 shows the potential energy surface diagram of a hypothetical $Ir(C^\wedge N)_3$ or $Ir(C^\wedge N)_2(L^\wedge X)$ complex.

Before any embodiments of the invention are explained in detail, it is to be understood that the invention is capable of other embodiments and of being practiced or of being carried out in various ways. Also, it is to be understood that the phraseology and terminology used herein is for the purpose of description and should not be regarded as limiting. Terms of degree, such as “about” or “approximately” are understood by those of ordinary skill to refer to reasonable ranges outside of the given value, for example, general tolerances associated with manufacturing, assembly, testing, and use of the described embodiments.

The inventors have, through their own research, trials and experiments, devised that N-heterocyclic carbene-based (NHC-based) Ir(III) complexes constitute an optimal design for efficient blue phosphors for use in OLEDs.

The heavy atom effect of third-row transition-metal complexes (e.g. Ir(III) complexes) can often induce a fast spin-orbit coupling that, in turn, promotes facile and electro-generated singlet-to-triplet transition and efficient phosphorescence with shortened radiative lifetime, resulting in promising phosphors.

Emission color of Ir(III) complexes can be fine-tuned across all visible spectral region by: (i) introduction of greater (or reduced) π-conjugation on the chromophoric segment, which causes red (or blue) shifted emission, (ii) addition of electron-withdrawing (or donating) group on the segment that dominates the highest occupied molecular orbitals (HOMO) of molecule, which induces blue (or red) shifting, and (iii) functionalization of electron-withdrawing (or donating) group on the segment that dominates the lowest unoccupied molecular orbitals (LUMO), which offers red (or blue) shifting. Moreover, strong spin-orbital coupling facilitated by the iridium atom gives efficient intersystem crossing between the singlet and triplet excited states, facilitating nearly 100% internal conversion efficiency, which is beneficial for fabrication of efficient OLEDs.

NHCs are highly versatile ligands with unique features that are capable to engage into robust metal-ligand bonds, owing to their strong σ-donating and relatively weak π-accepting abilities. NHCs such as functional imidazolylidene and benzoimidazolylidene cyclometalates, can be used for the synthesis of higher energy (i.e., purple and blue) emitters, due to the strongly destabilized π*-orbitals of carbene (C^C) chelates. Further destabilization of π*-orbitals of these carbine (C^C) chelates can be achieved upon substitution of cyano, trifluoromethyl or both function functional groups to the carbene entity. These carbene complexes can involve either bidentate or tridentate pincer designs, to which their key function is to increase the crystal field strength of resulting metal complexes and to mitigate the thermal population to their upper lying MC dd excited states for achieving better luminescence.

Particularly, the class of homoleptic, tris-bidentate Ir(III) complexes $Ir(C^\wedge C)_3$ possess the following practical advantages, namely: (i) possession of the third-row transition metal ion at 3+ oxidation state, (ii) possession of six iridium-carbon (e.g.; both Ir—$C_{carbene}$ and Ir—$C_{aryl}$) bonds which could exert the strongest ligand field strength and notably destabilize the corresponding MC dd excited states, and (iii) adoption of higher lying LUMO orbital on the coordinative carbene fragments. Among these intrinsic properties, points (i) and (ii) are especially important for effective destabilization of MC dd excited states which reduces the relatively rate of nonradiative decay processes, thereby giving improved thermal and photo stabilities and thus emission efficiency. Point (iii) is essential for achieving the true blue and blue emission of the widened HOMO-LUMO energy gap. Hence, this coordination mode is expected to offer a sufficient large energy-gap between the emissive excited state ($T_1$ state) and upper lying MC dd excited state, giving a suppressed quenching process, even for blue emitters.

Figure 2:
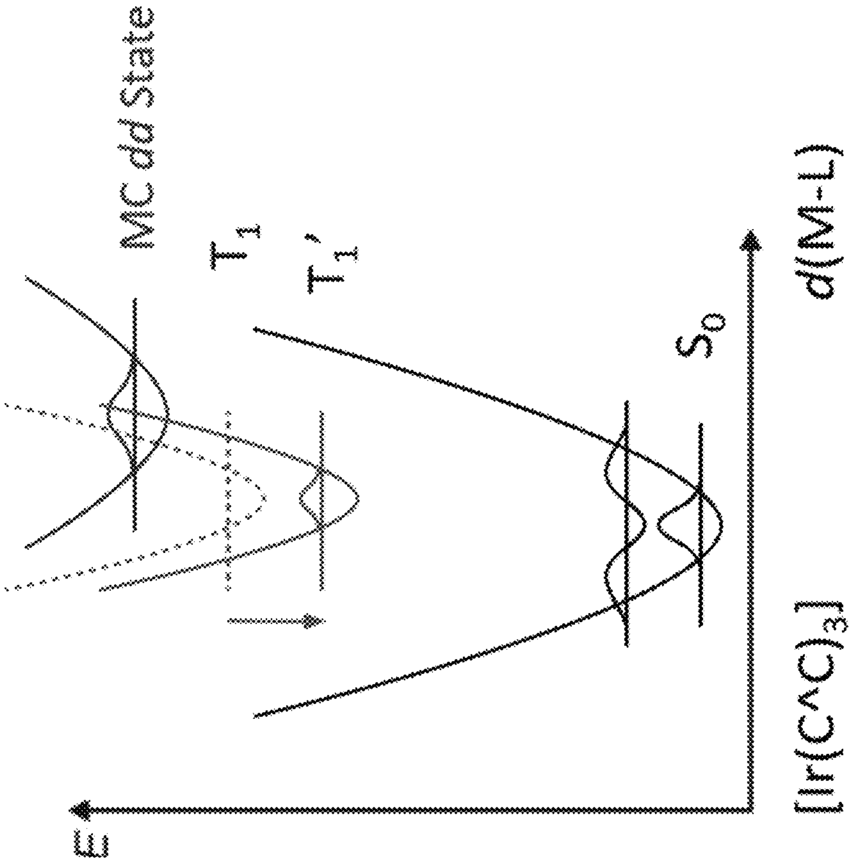
FIG. 2 shows the potential energy surface diagram of a hypothetical $Ir(C^\wedge C)_3$ complex.

FIG. 2 shows the potential energy surface diagram of a hypothetical $Ir(C^\wedge C)_3$ complex, as exemplified by purple emitting tris(1-phenyl-3-methylbenzimidazolin-2-ylidene-C,$C^{2'}$)iridium(III), $[Ir(pmb)_3]$. Comparing FIGS. 1 and 2, the lowest energy triplet excited state ($T_1$) and upper lying metal-centered (MC) dd quenching state of the hypothetical $Ir(C^\wedge C)_3$ complex are both of higher energy than those of the class of $Ir(C^\wedge N)_3$ or $Ir(C^\wedge N)_2(L^\wedge X)$ complexes. Different from that of the hypothetical complexes $Ir(C^\wedge N)_3$ or $Ir(C^\wedge N)_2(L^\wedge X)$ (FIG. 1), tuning emission from purple $[Ir(pmb)_3]$ and derivatives to a pure blue emitter required stabilization of the initial $T_1$ state in giving a new $T_1'$ state of lowered energy, by addition of electron-withdrawing (or donating) group at the LUMO (or HOMO) segment of the Ir(III) complexes. Hence, the enlarged $T_1'$-MC dd state separation would retard the thermally activated non-radiative decay. This offers an important advantage for blue emissive $[Ir(C^\wedge C)_3]$ complexes over that of $Ir(C^\wedge N)_3$ or $Ir(C^\wedge N)_2(L^\wedge X)$ complexes, if all other factors, such as inherent stability of chelate and metal-chelate bond strength, remain substantially the same. Moreover, Ir(III) emitters bearing the electron deficient carbene chelates with two N-aryl substituents are notably more stable than those with a single N-aryl and another N-alkyl substituent. Hence, the present embodiments aim to place special emphasis on these chelates in targeting the durable carbene based Ir(III) complexes and respective blue emissive OLED devices.

In one embodiment, the metal complex comprises a structure of Formula (I):

$$ML^1_aL^2_bL^3_cL^4_dL^5_e \qquad \text{Formula (I),}$$

where:

M is a transition metal;

$L^1$ is a bidentate ligand and a is an integer of 1 to 3;

$L^2$, $L^3$, $L^4$, and $L^5$ are independently a monodentate ligand, or two adjacent $L^2$, $L^3$, $L^4$, and $L^5$ is a bidentate ligand, and b, c, d, and e are independently an integer of 0 to 4;

a+b+c+d+e is 2, 3, 4, or 5; and $L^1$ has a structure of Formula (II):

Formula (II)

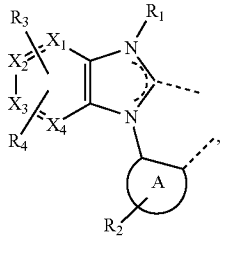

where:

A is a 5-membered or 6-membered carbocyclic or heterocyclic ring, $R_1$ is selected from the group consisting of: $C_{1-6}$ alkyl, $C_{2-6}$ alkylether, $C_{1-6}$ alkoxy, $C_{1-6}$ fluoroalkyl, $C_{2-6}$ alkenyl, $C_{2-6}$ alkynyl, substituted or unsubstituted $C_{3-8}$ cycloalkyl, substituted or unsubstituted $C_{3-8}$ cycloalkenyl, substituted or unsubstituted 3 to 8 membered heterocycloalkyl, substituted or unsubstituted 3 to 8 membered heterocycloalkenyl, substituted or unsubstituted $C_{6-10}$ aryl, substituted or unsubstituted $C_{7-11}$ aralkyl, substituted or unsubstituted heteroaryl having 5 to 10 carbon atoms or heteroatoms, and substituted or unsubstituted heteroaralkyl having 6 to 11 carbon atoms or heteroatoms, preferably methyl, ethyl, propyl, phenyl, p-methylphenyl, 2,6- and 3,5-dimethylphenyl, p-tert-butylphenyl, m-tert-butylphenyl, 1,1'-biphenyl, p-trifluoromethylphenyl, or the corresponding deuterated derivative thereof;

$R_2$, $R_3$, and $R_4$ are independently selected from the group consisting of: hydrogen, deuterium, fluorine, cyano, $C_{1-6}$ alkyl, $C_{1-6}$ alkoxy, $C_{1-6}$ fluoroalkyl, substituted or unsubstituted $C_{6-10}$ aryl, and substituted or unsubstituted heteroaryl having 5 to 10 carbon atoms or heteroatoms, preferably hydrogen, deuterium, fluorine, cyano, $C_{1-6}$ alkyl, $C_{1-6}$ fluoroalkyl, and substituted or unsubstituted $C_{6-10}$ aryl, or the corresponding deuterated derivative thereof, and $X_1$, $X_2$, $X_3$, and $X_4$ are independently C or N.

As used herein, "the corresponding deuterated derivative thereof" refers to any of the aforementioned functional groups with at least one hydrogen atom substituted by deuterium.

The metal complex is preferably a tris-bidentate metal complex. M is selected from the group consisting of: iridium, rhodium, platinum, palladium, gold, osmium, and ruthenium. Preferably, M is iridium, platinum, or gold. A is preferably a phenyl ring. $R_2$ is hydrogen, methyl, trifluoromethyl, phenyl or tert-butyl. $R_3$ and $R_4$ are independently hydrogen, tert-butyl, 2,6-dimethylphenyl, cyano, trifluoromethyl, or phenyl. In a preferred embodiment, $R_1$ is phenyl, $R_2$ is hydrogen, methyl, or tert-butyl, and one of $R_3$ and $R_4$ is 2,6-dimethylphenyl. In a preferred embodiment, when $X_1$ and $X_4$ are N, $X_1$ and $X_3$ are N, or $X_2$ and $X_4$ are N, $R_3$ and $R_4$ are different. In addition, when $R_3$ and $R_4$ are independently cyano or trifluoromethyl, $R_3$ and $R_4$ are at $X_1$ and $X_3$, or $X_2$ and $X_3$, and $R_3$ and $R_4$ are different from each other.

As will be known by the skilled person based on the above disclosure, when the metal complex is an Ir(III) complex, the ligands occupy an octahedral arrangement around the Ir(III) metal center. The three ligands of the same type can occupy either the corners of one face of the octahedron (facial isomer (fac-isomer)) or meridional positions, i.e. two of the three ligand bonding points are in trans positions relative to one another (meridional isomer (mer-isomer)). "f" and "fac-" and "m" and "mer-" are used interchangeably herein to refer to "facial" and "meridional" respectively. The metal complex may be predominantly or exclusively a single isomer, or it may be a mixture of isomers. Where the metal complex is a mixture of isomers, it may be any mixture.

In some embodiment, when the metal complex is a homoleptic Ir(III) carbene complex, it may include N-phenyl, N-methyl-imidazol-2-ylidene (pmi) or N-phenyl, N-methyl-benzimidazol-2-ylene (pmb) chelate. To red-shift emission, N-phenyl cyclometalating fragment can be replaced with aromatic entities with greater π-conjugation. However, this modification would unavoidably increase both the ligand-centered ππ* contribution and radiative lifetime at the excited states and, hence, is less desirable.

In contrast, to blue-shift emission, functional 7,9-dihydro-8H-purin-8-ylidene, imidazo[4,5-b]pyridin-2-ylidene (pmp) and imidazo[4,5-b]pyrazin-2-ylidene (pmpz, cb and tpz) chelates can be used to synthesize true-blue Ir(III) carbene complexes, among which the introduced nitrogen atom can effectively lower the LUMO energy level and maintain a higher degree of metal-to-ligand charge transfer (MLCT) characters. Notably, these homoleptic Ir(III) complexes exist as both the facial (fac) and meridional (mer) isomers, with fac-isomers always exhibit more blue shifted emission wavelength compared to mer-isomers. Hence, isomerization can also be employed for further widening the photophysical landscape. Despite the above advantages, the basic lone pair electron on the N atom of the N-aromatic groups (i.e., pyridine, pyrimidine or pyrazine) may interact with the electrophilic reagents, such as the positive polarons generated during OLED device operation, which may adversely induce instability to the OLED devices. Also, the emission of such OLED devices may occur at or beyond the violet region with a higher energy and, hence, may not be suitable for fabrication of OLED devices with emission spanning the visible region, i.e., from blue, green to red emission.

Additionally or alternatively, introduction of electron withdrawing groups, such as cyano and trifluoromethyl groups, at the benzimidazol-2-ylene based coordination fragment shifts the emission from purple to true blue due to the effective lowering of LUMO energy level of Ir(III) metal complexes, in a way similar to the substitution of pyridinyl, pyrimidinyl, pyrazinyl, or other N-heterocyclic groups in the above embodiments. Advantageously, cyano and trifluoromethyl substituents are considered relatively inert and, hence, will not be affected (or destabilized) by the positive polarons when being used in OLED devices. In particular, the lone pair on the N atom of the cyano group is less basic than the N atom of N-heteroaromatic fragments such as pyridine, pyrazine, and pyrimidine, leading to better emission quantum yield for the as-prepared Ir(III) emitters and longer lifespan for the fabricated OLED devices.

Therefore, in preferred embodiments, purin-8-ylidene and imidazo[4,5-b]pyrazin-2-ylidene are preferred over imidazolylidene, benzoimidazolylidene, and imidazo[4,5-b]pyridin-2-ylidene for reducing the respective LUMO energy level in achievement of the desired true blue emission and capability in fabrication of OLEDs. This is attributed to the presence of at least one (or two) additional electronegative N-atom(s) at the outer peripheral of respective chelating carbene entity.

Electron-withdrawing groups on the carbene fragment are also capable of offering the identical results in giving the true blue emission. In some embodiments, two electron withdrawing groups (i.e., a combination of N atom, $CF_3$ and cyano substituent) at the benzoimidazolylidene (or carbene) chelate is preferred over a single electron withdrawing group. As an example, a single cyano substituent or a single trifluoromethyl substituent may not be electron deficient enough to red-shift emission from the violet region to the true-blue region. Hence, with one N atom at the backbone, a second trifluoromethyl substituent or cyano substituent may be required to further red-shift emission to the true-blue region.

It is expected that, with proper adjustment of both the electronic and steric properties of the NHC chelates, the desired efficient true-blue emission, together with considerably shortened radiative lifetime to the microsecond and hundredth nanosecond region can be achieved. These photophysical characters are of particular importance as the shorter radiative lifetime, the less emission quenching would occur at the higher driving voltages during operation. Not to mentioned that, faster radiative decay would improve stability of emitters due to the reduced residence time at the highly energized excited states after excitation. Also, the employed carbene chelates are preferable to possess two structurally distinctive N-aryl substituents instead of one aryl and one alkyl substituent, due to both the improved chemical and physical stabilities for the associated Ir(III) metal complexes.

In the most preferred embodiment, the metal complex is selected from one of the following:

1-fac

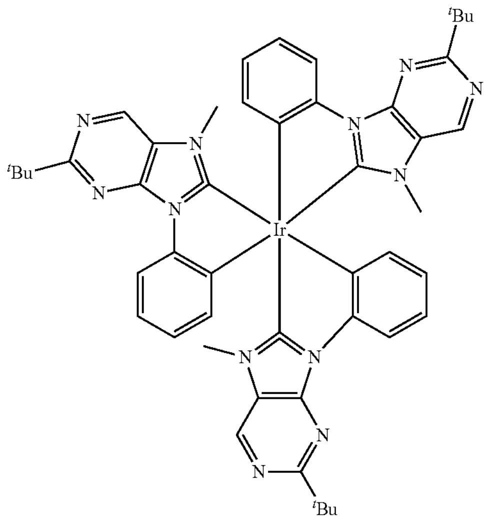

1-mer

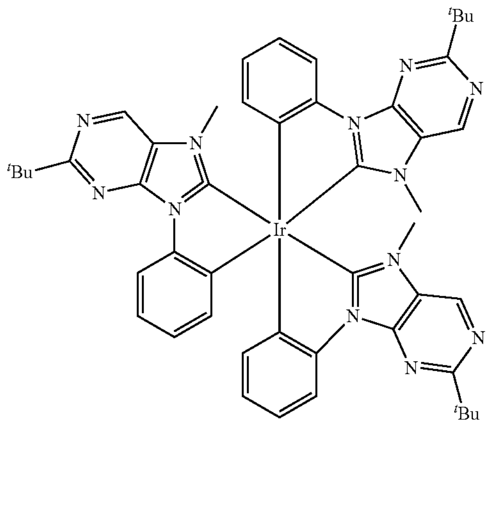

-continued
2-fac
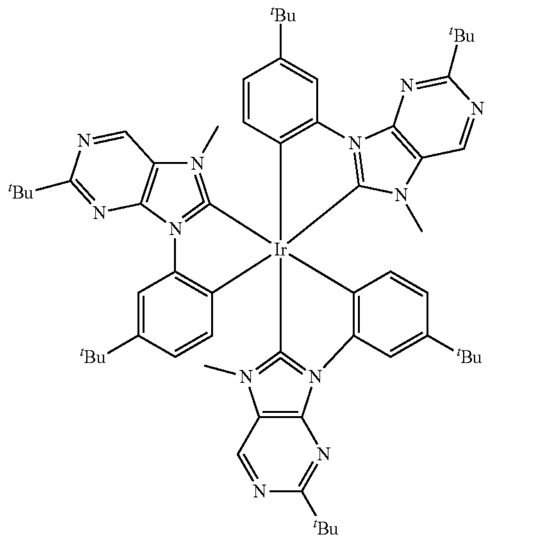
2-mer
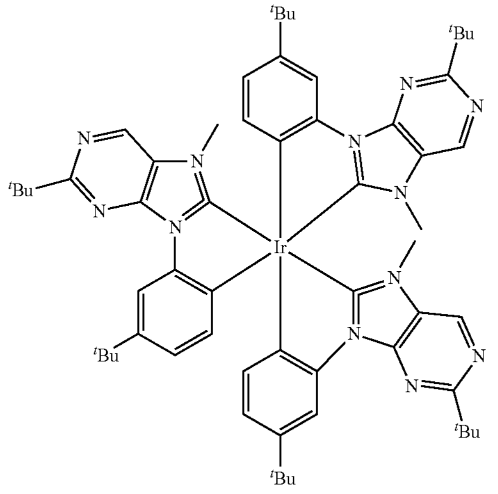
3-fac
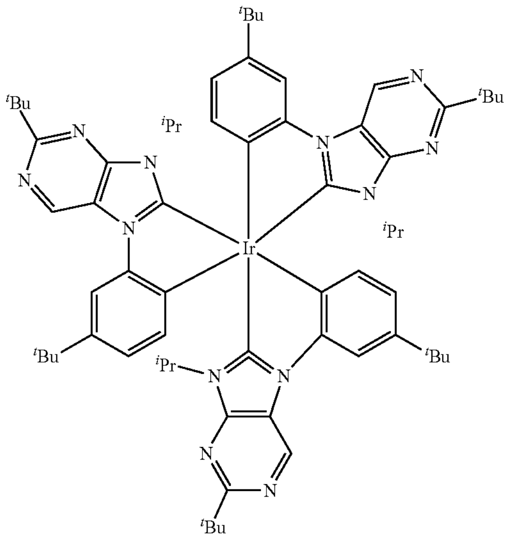
-continued
3-mer
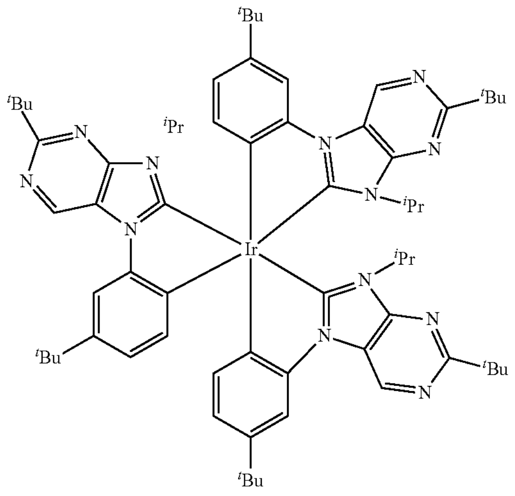
4-fac
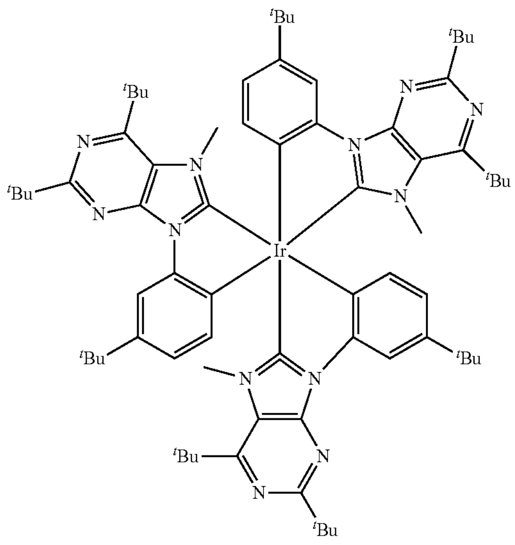
4-mer
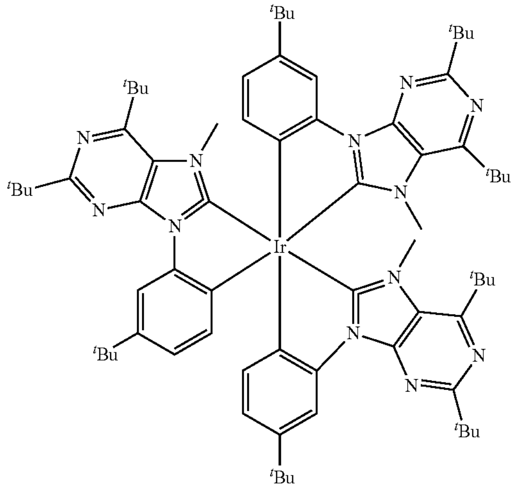

-continued
5-fac
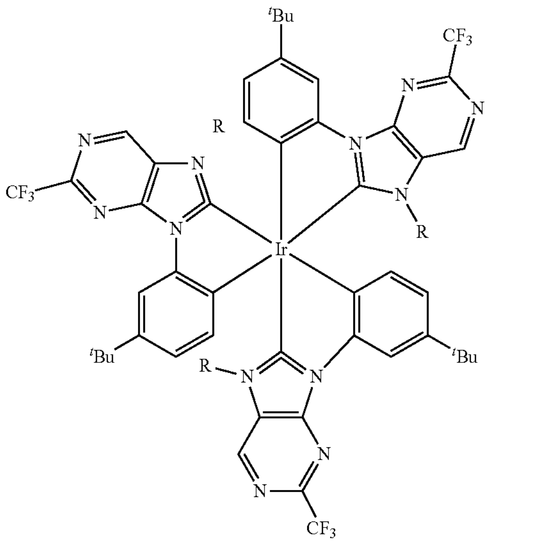
(R = $^{i}$Pr)
5-mer
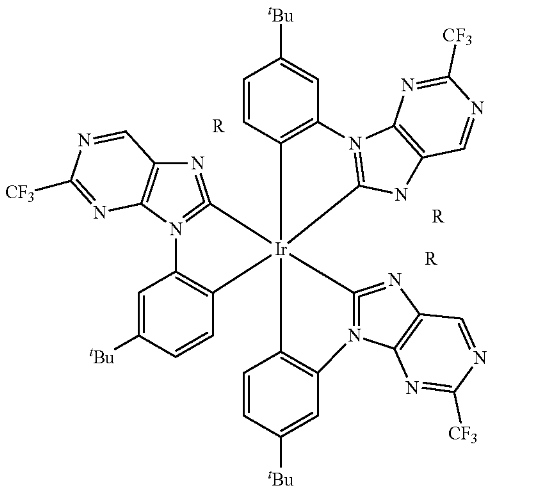
(R = $^{i}$Pr)
-continued
6-fac
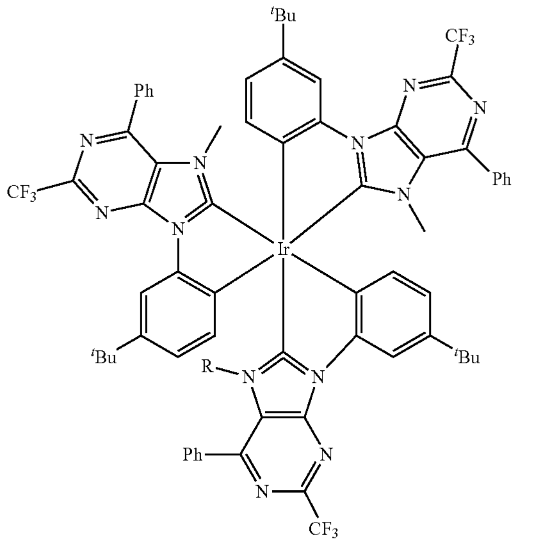
6-mer
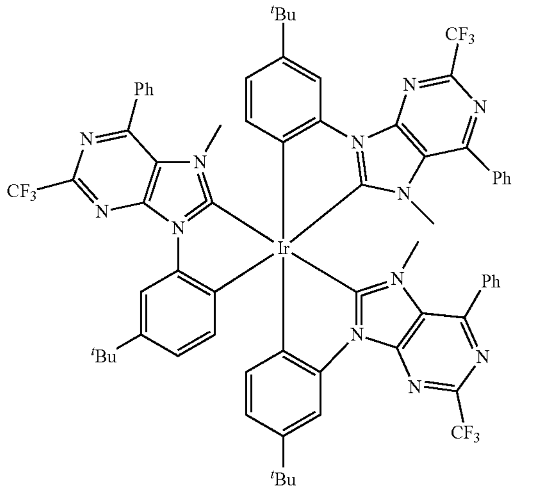
7-fac
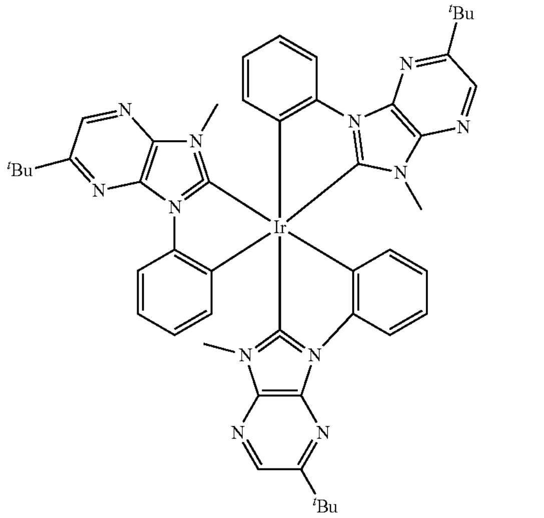

-continued
7-mer
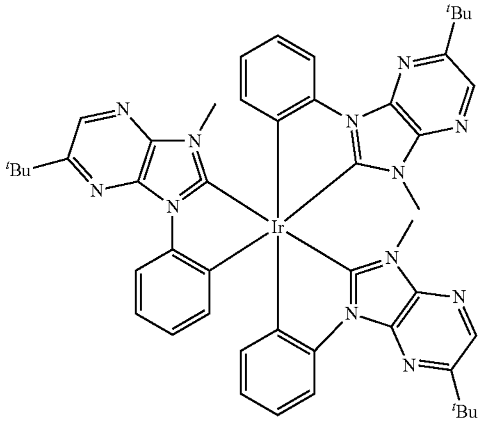
8-fac
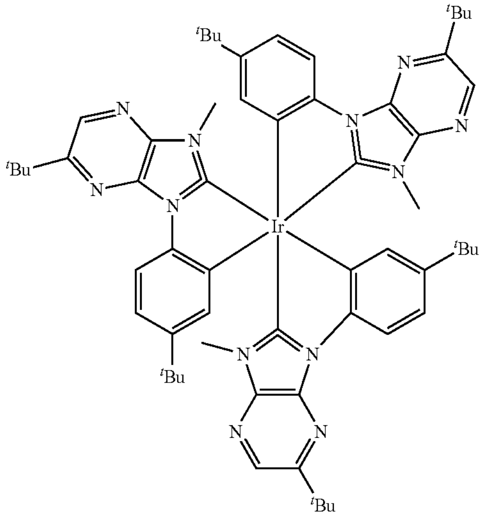
8-mer
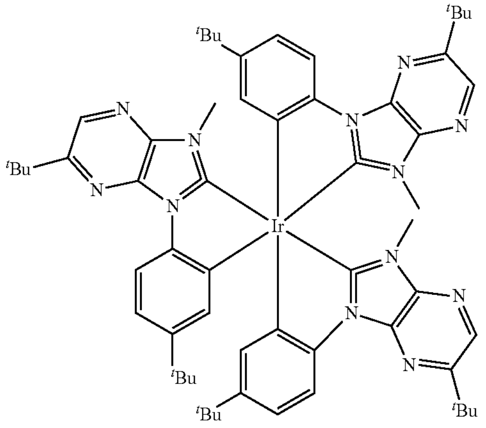
-continued
9-fac
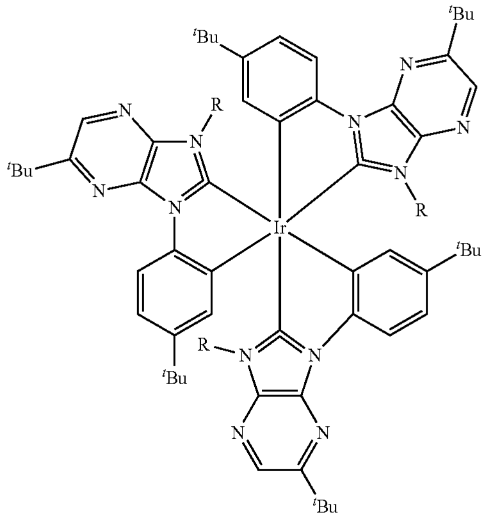
R = $C_2H_5$
9-mer
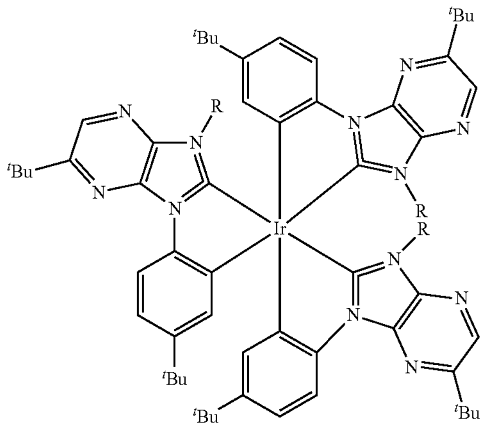
R = $C_2H_5$
10-fac
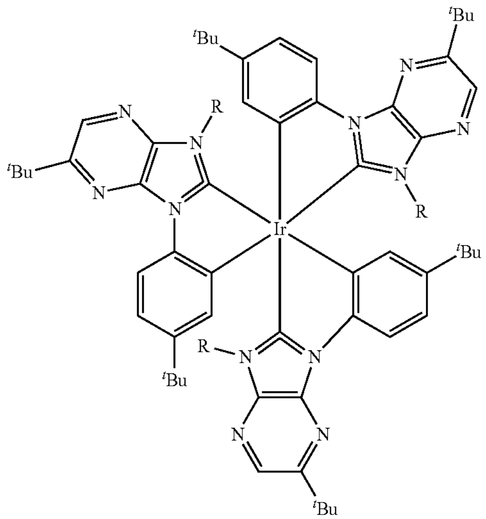
R = $C_6H_5$ -continued
11-fac
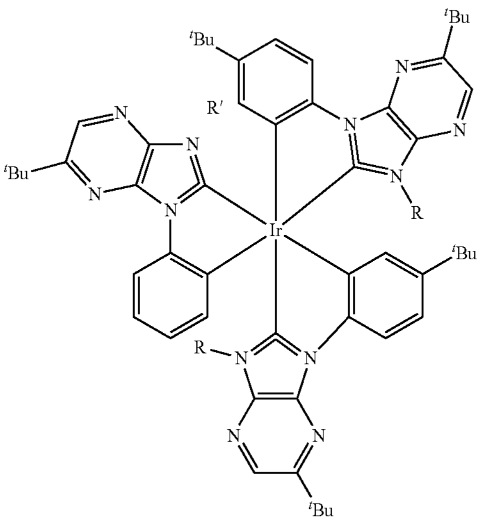
R = $C_6H_5$;
R′ = p-$C_6H_4$-$^t$Bu
12-fac
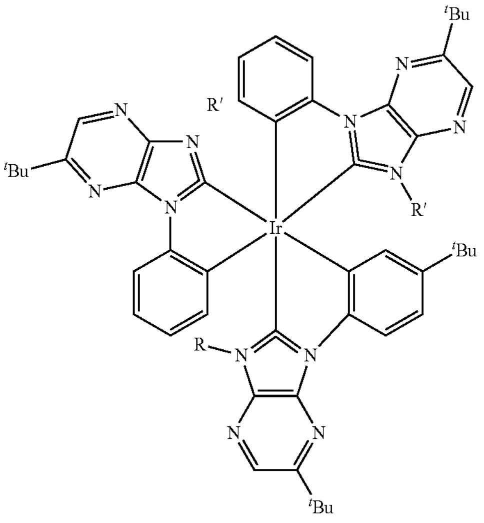
R = $C_6H_5$;
R′ = p-$C_6H_4$-$^t$Bu
-continued
13-fac
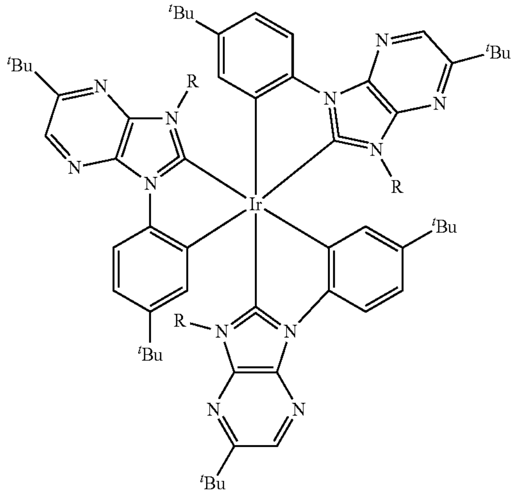
R = $C_6H_5$
14-fac
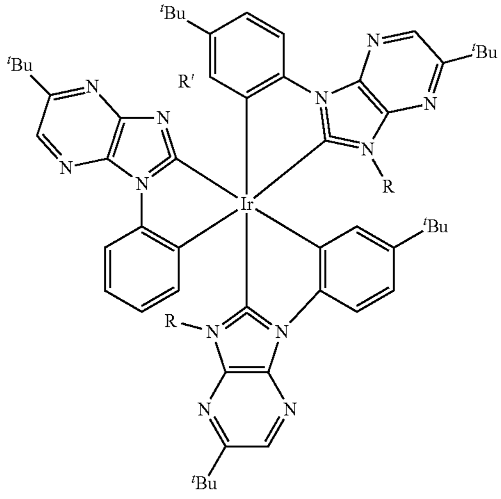
R = $C_6H_5$;
R′ = p-$C_6H_4$-$^t$Bu -continued
15-fac
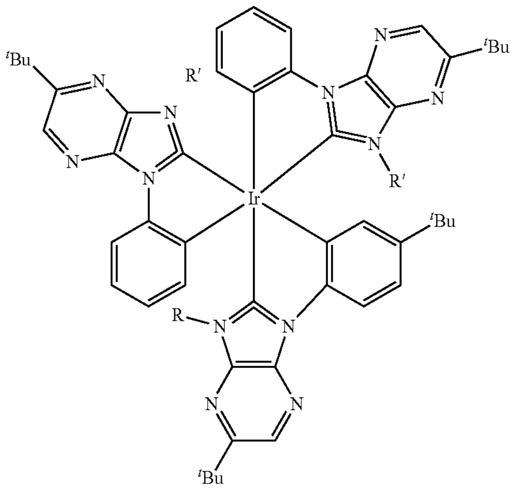
R = $C_6H_5$;
R′ = p-$C_6H_4$-$^t$Bu
16-fac
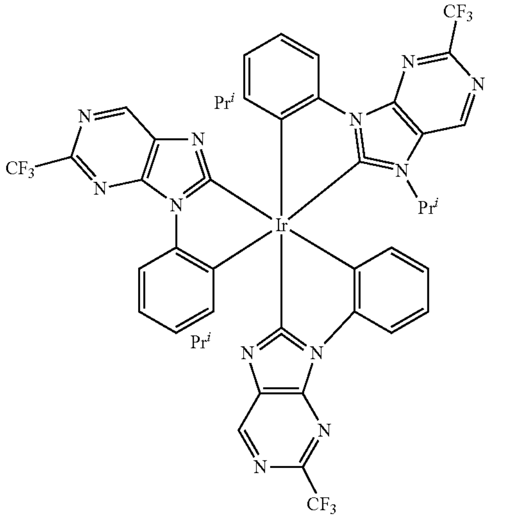
16-mer
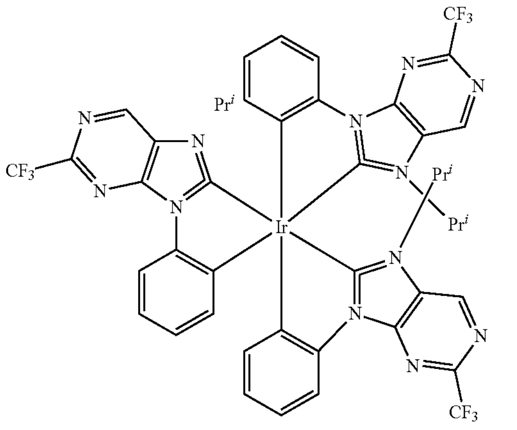
-continued
17-fac
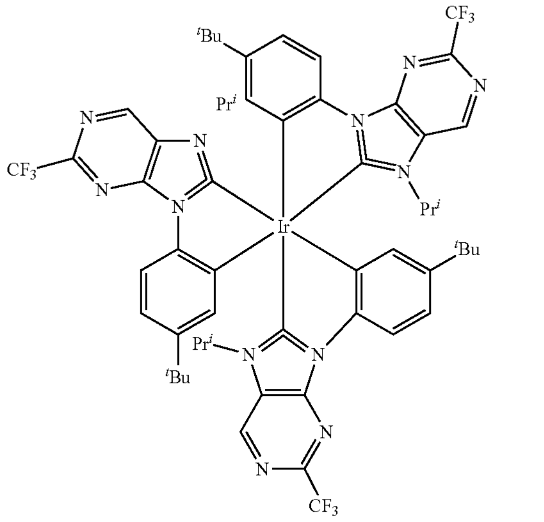
17-mer
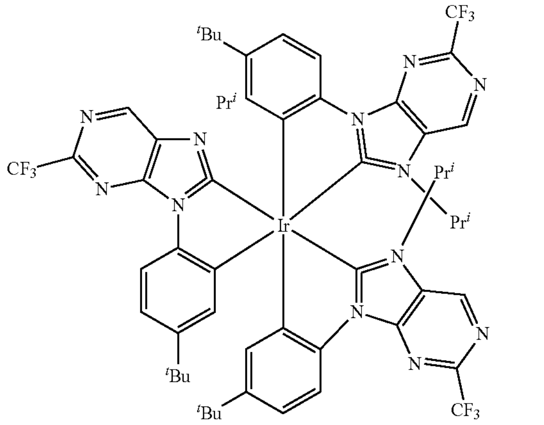
18-fac
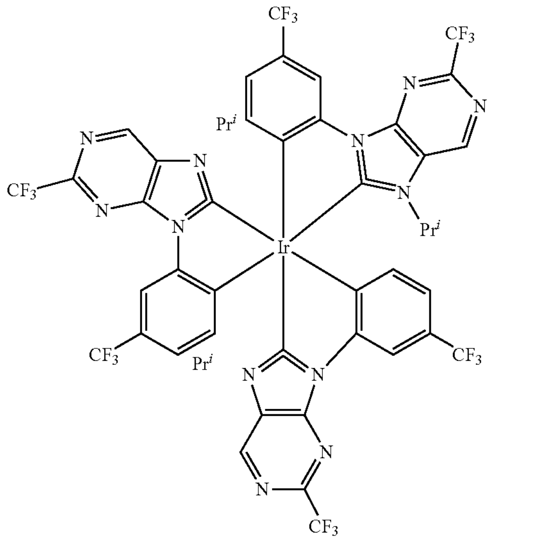

-continued
18-mer
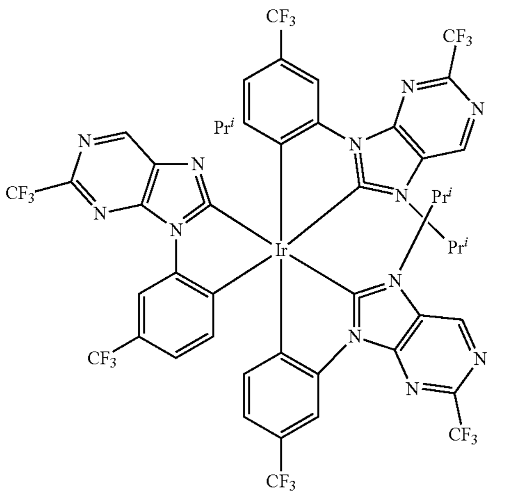
19-fac
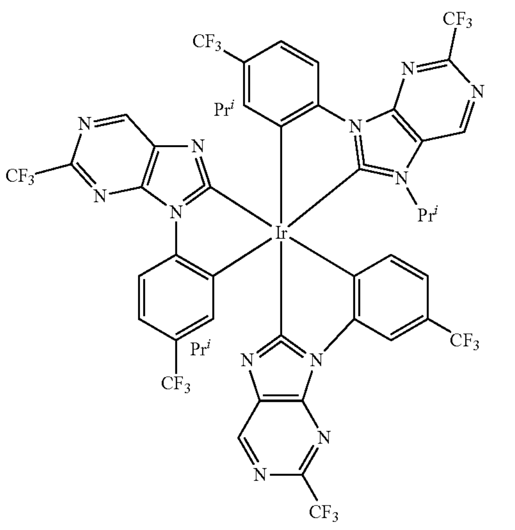
19-mer
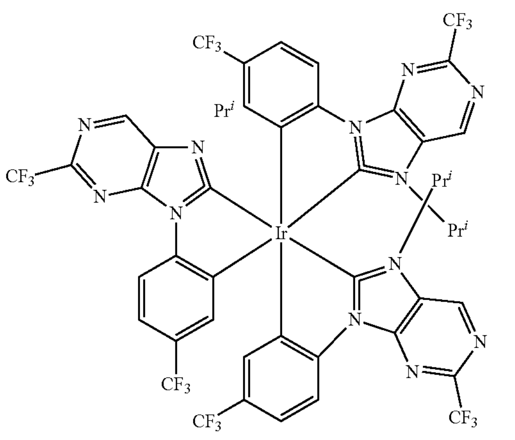
-continued
20-fac
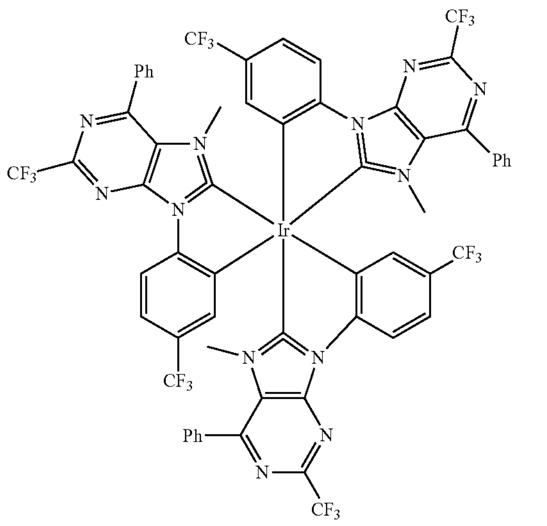
20-mer
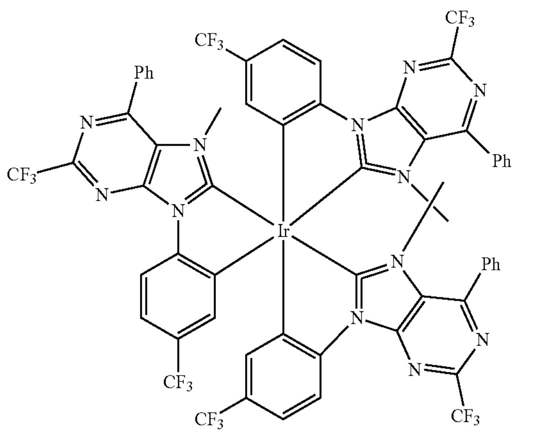
21-fac
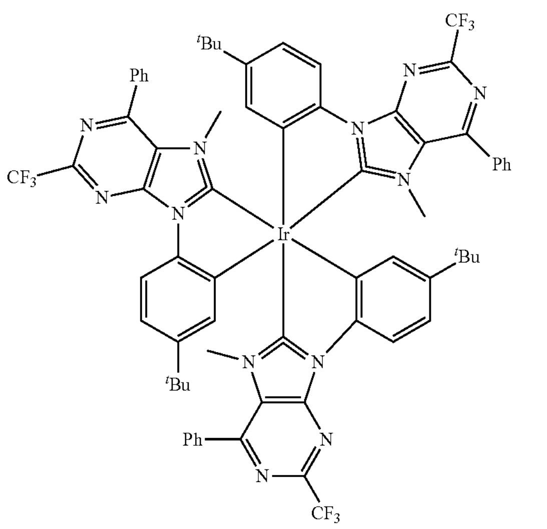

-continued
21-mer
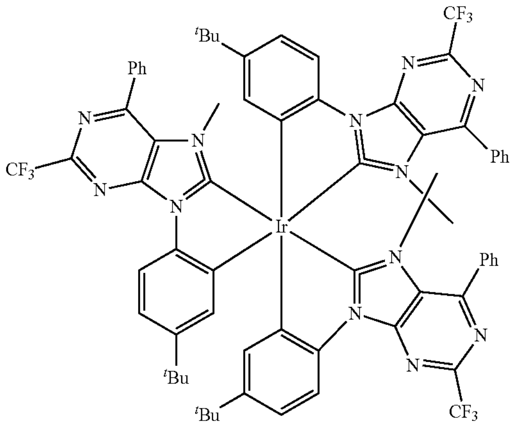
22-fac
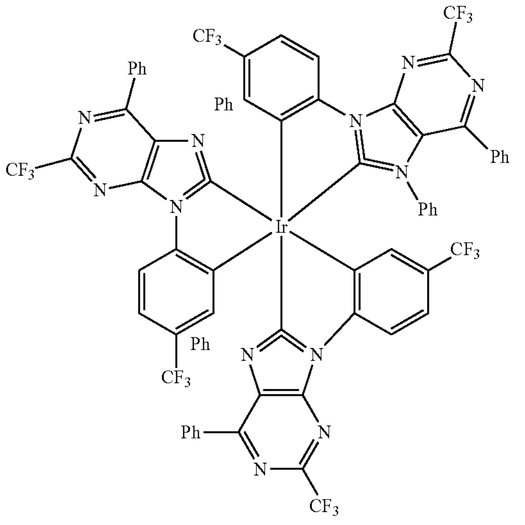
22-mer
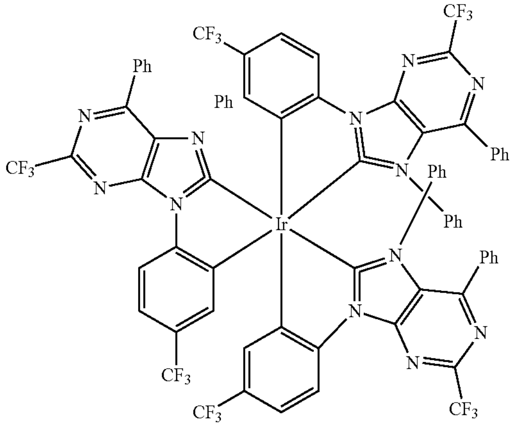
-continued
23-fac
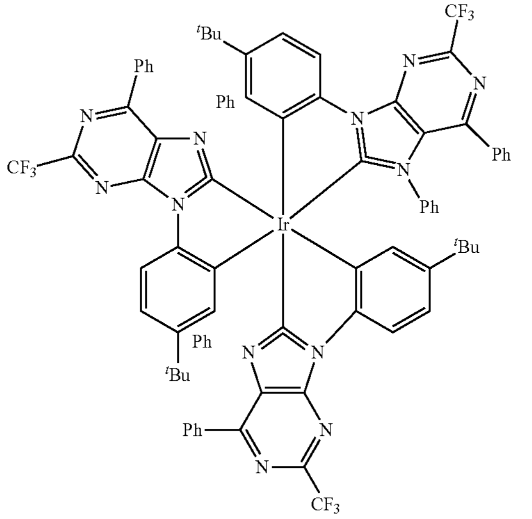
23-mer
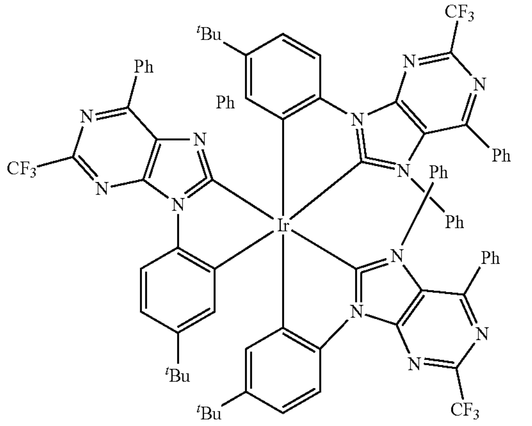
24-fac
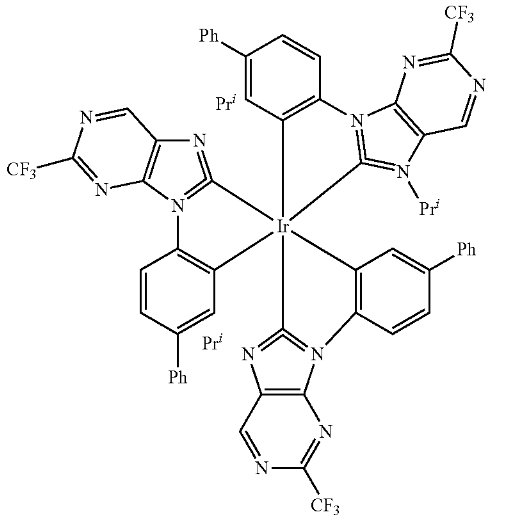

24-mer
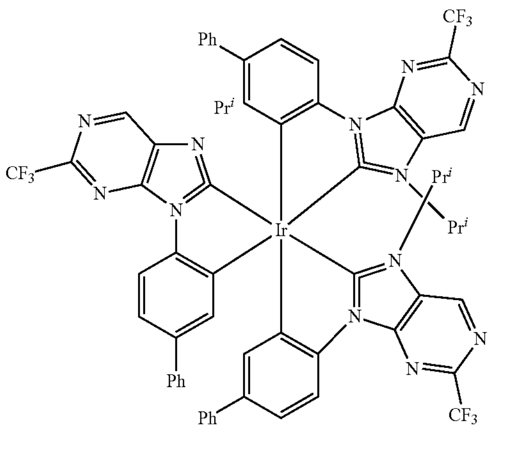
25-fac
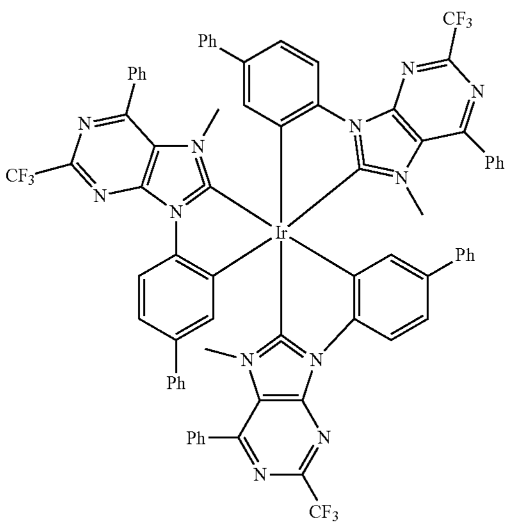
25-mer
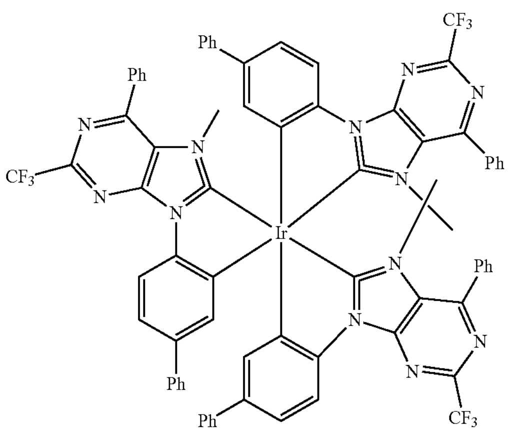
26-fac
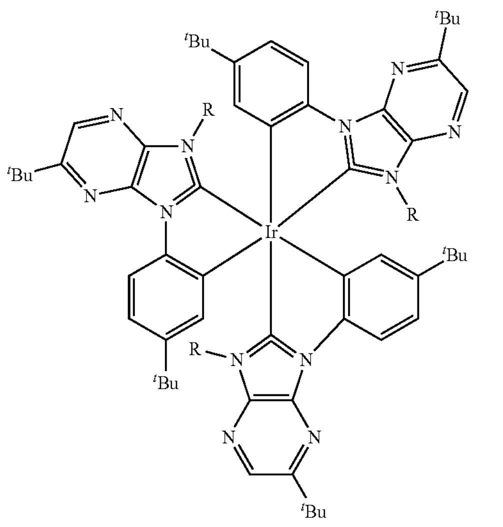
R = 1,1′-biphenyl
27-fac
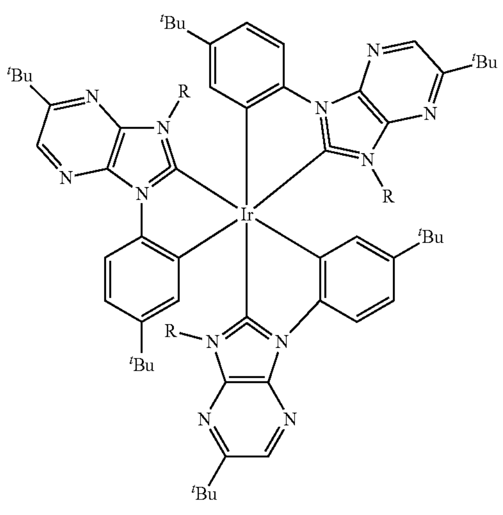
R = 1,1′-biphenyl -continued
28-fac
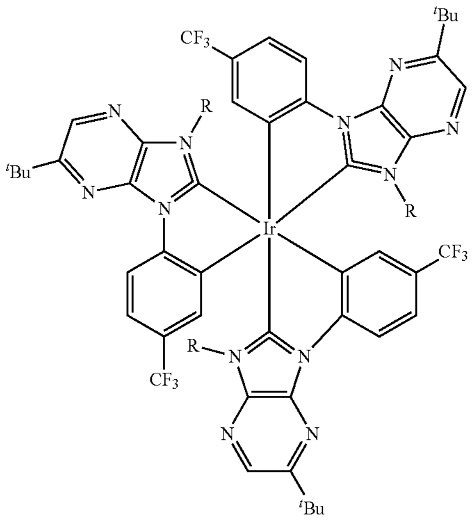
R = 1,1′-biphenyl
29-fac
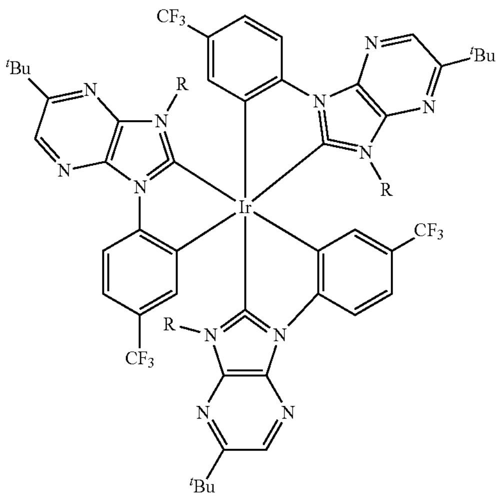
R = 1,1′-biphenyl
30-fac
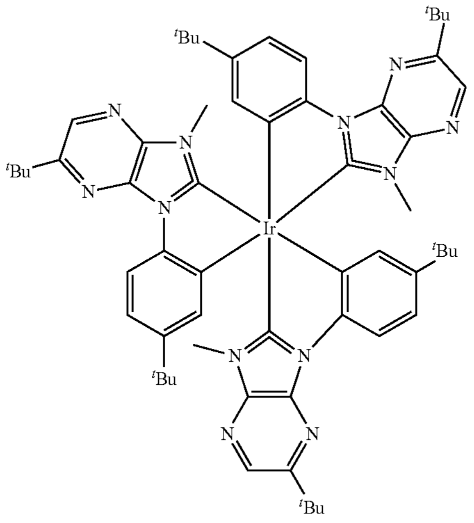
-continued
31-fac
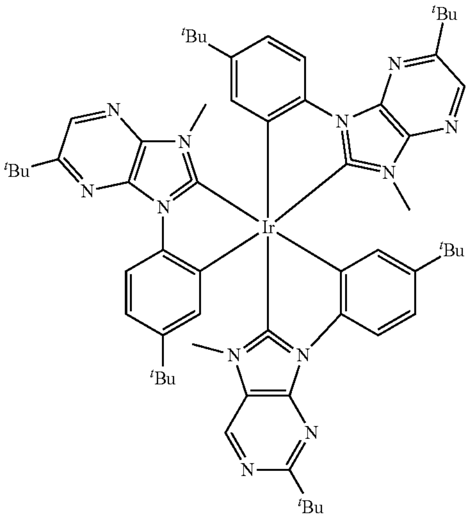
32-fac
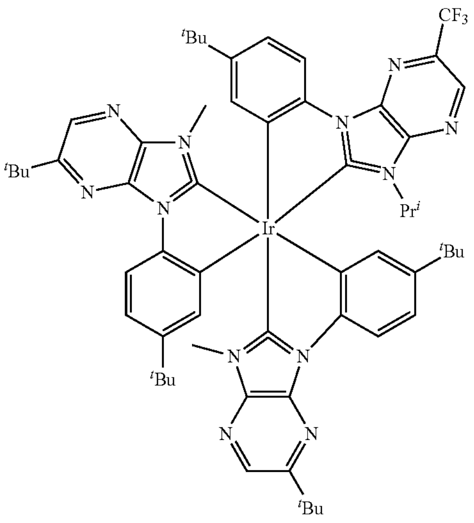
33-fac
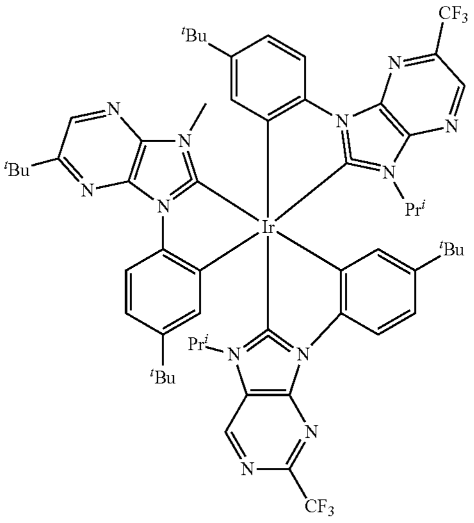

-continued
34-fac
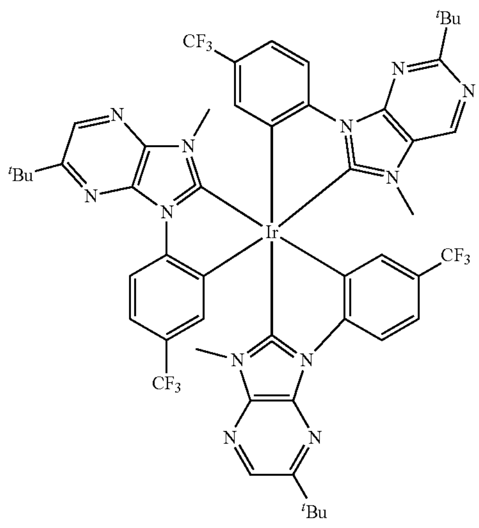
35-fac
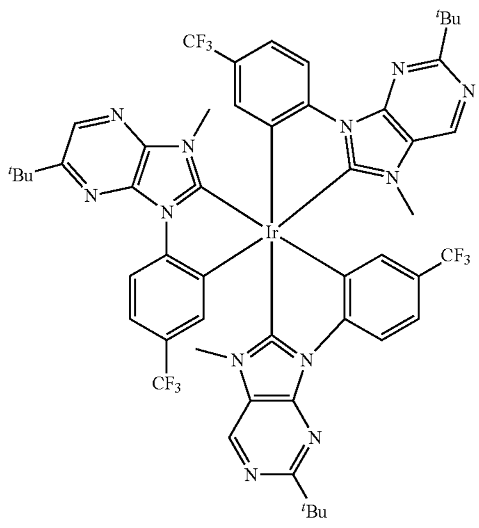
36-fac
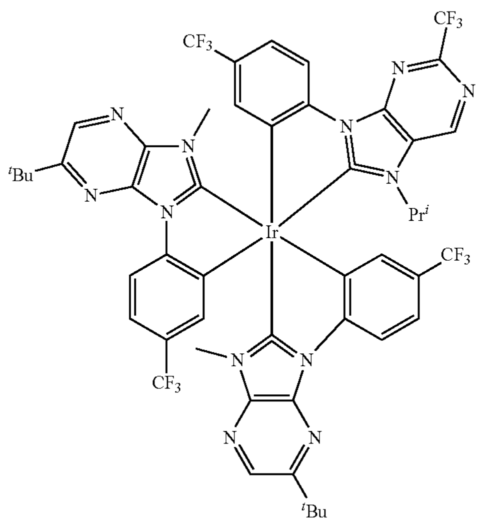
-continued
37-fac
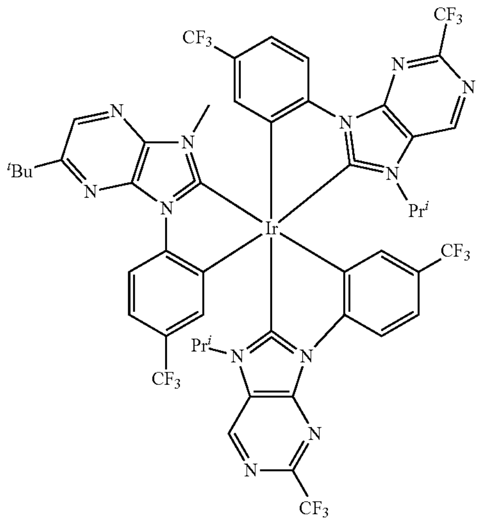
38-fac
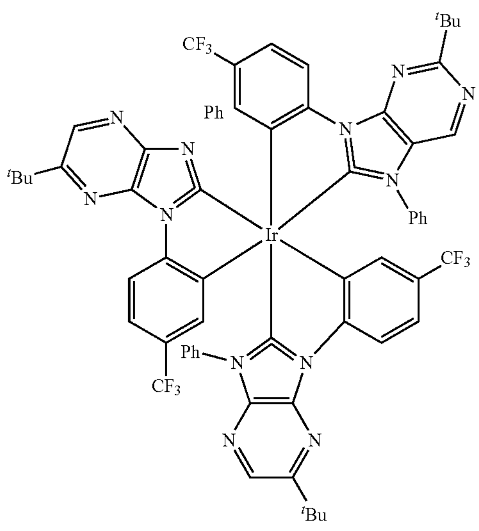
39-fac
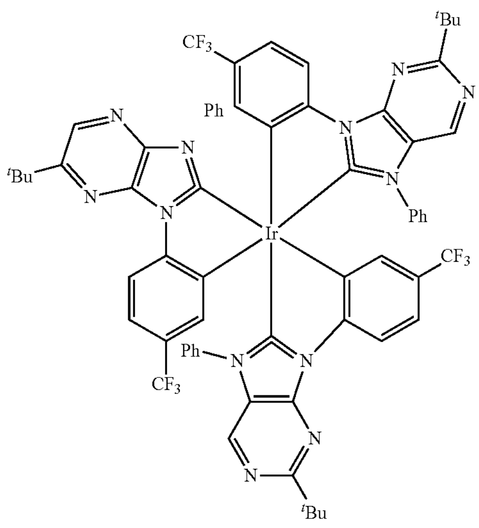

-continued
40-fac
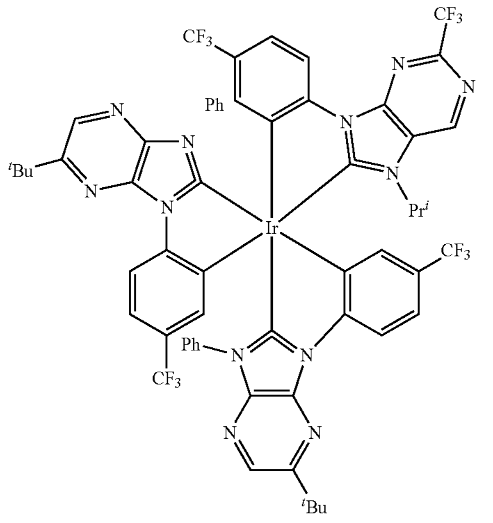
41-fac
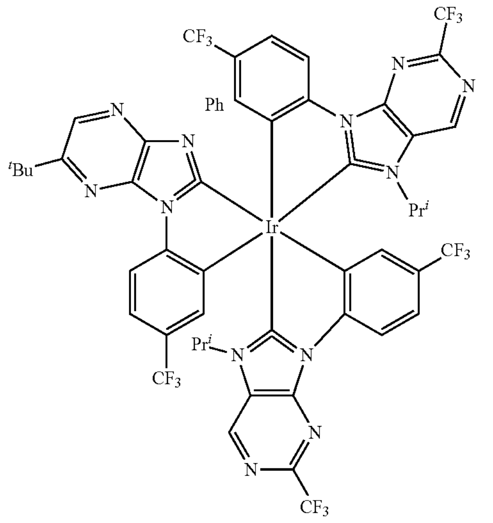
42-mer
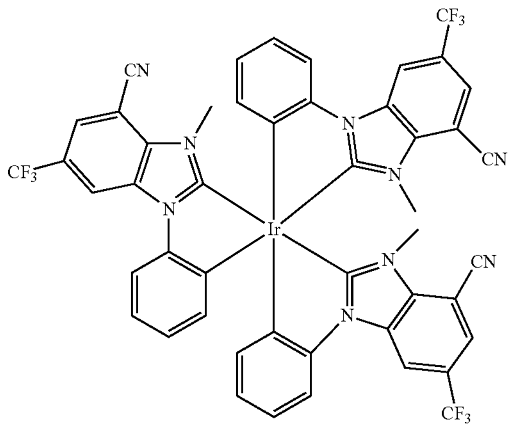
-continued
42-fac
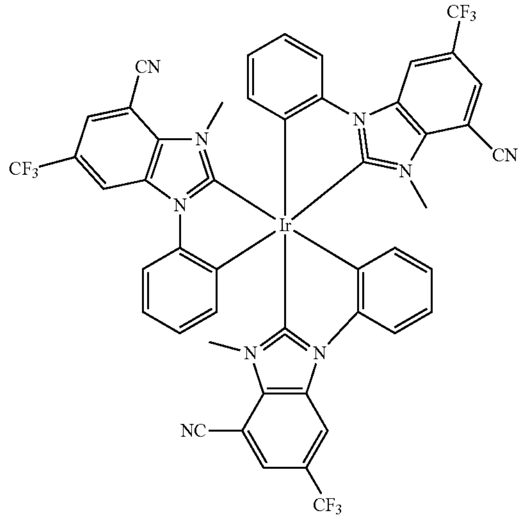
43-mer
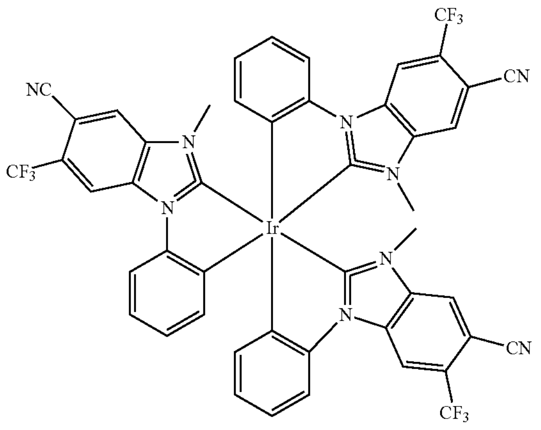
43-fac
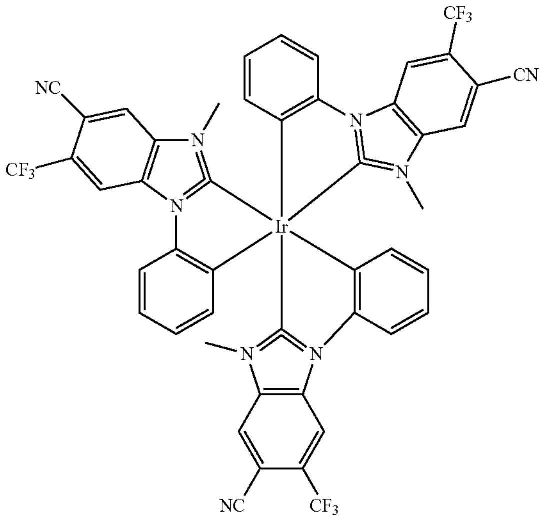

44-mer
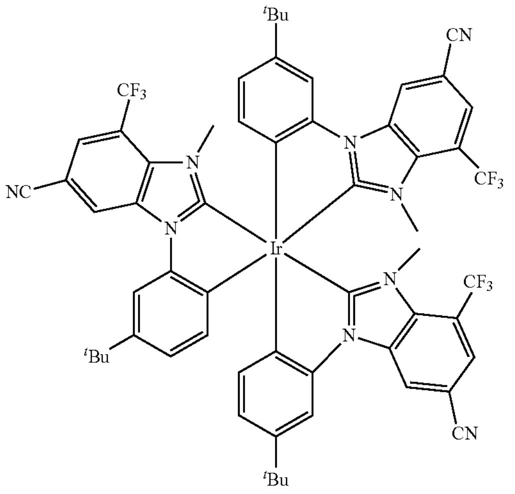
44-fac
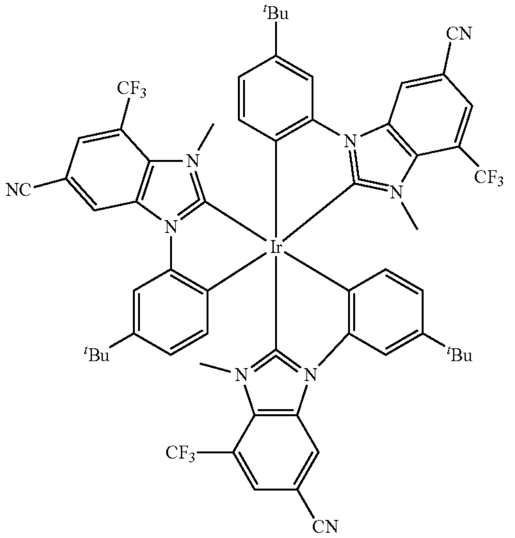
45-fac
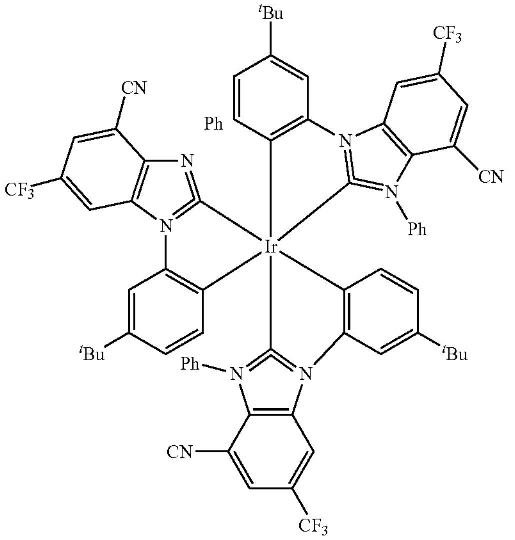
46-fac
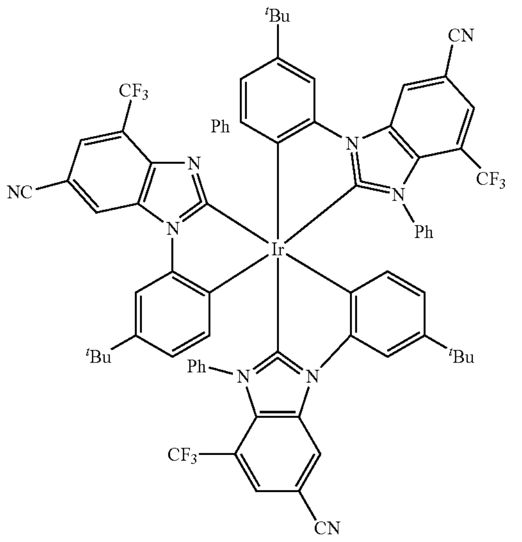
47-fac
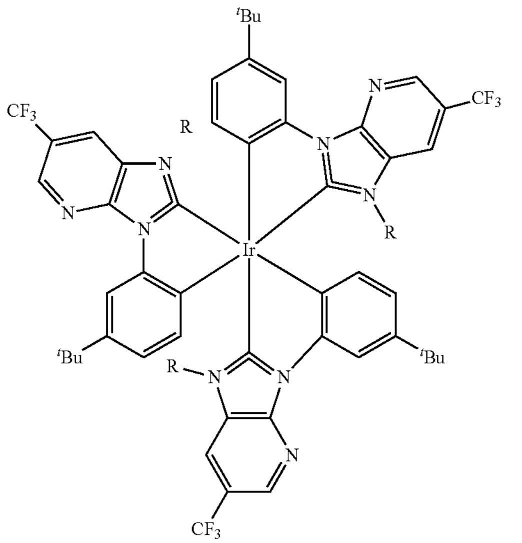
R = $C_6H_5$;

-continued
48-fac
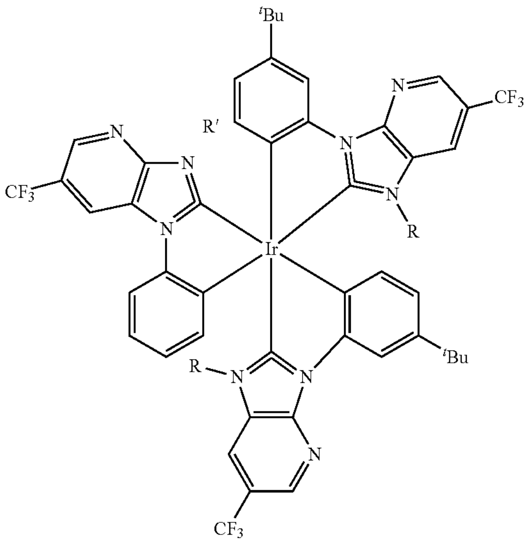
R = $C_6H_5$;
R′ = m-$C_6H_4{}^t$Bu
49-fac
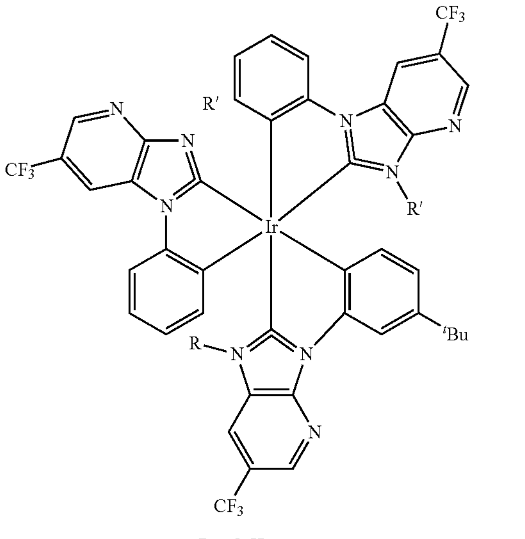
R = $C_6H_5$;
R′ = m-$C_6H_4{}^t$Bu
-continued
50-fac
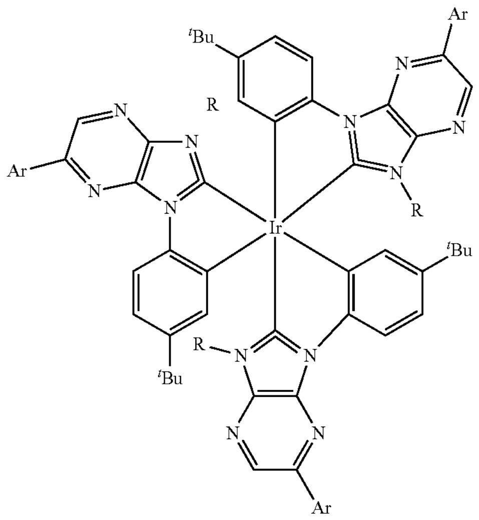
Ar = 2,6-$C_8H_3Me_2$
R = $C_6H_5$;
51-fac
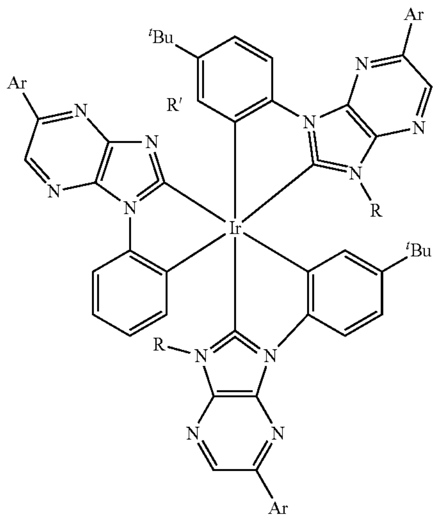
Ar = 2,6-$C_8H_3Me_2$
R = $C_6H_5$;
R′ = p-$C_6H_4{}^t$Bu -continued
52-fac
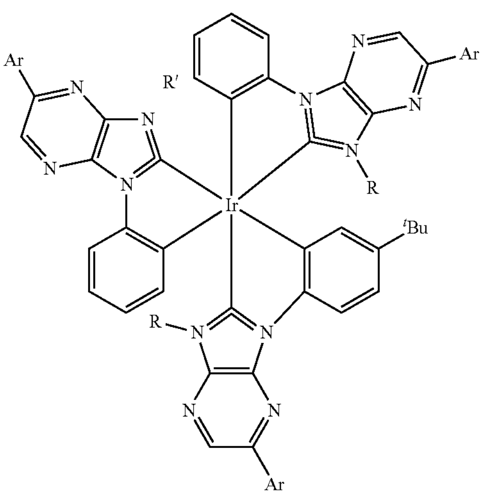
$Ar = 2,6\text{-}C_8H_3Me_2$
$R = C_6H_5$;
$R' = p\text{-}C_8H_4{}^tBu$
53-fac
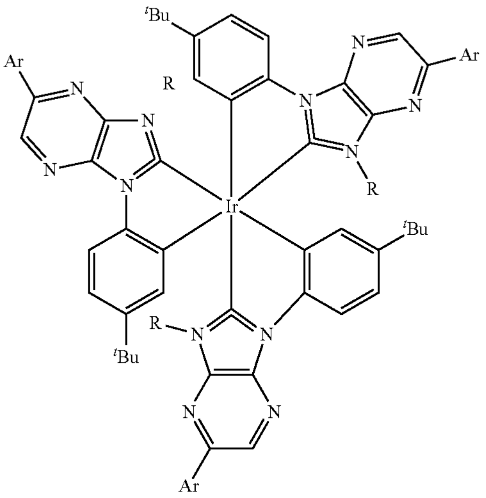
$Ar = 2,6\text{-}C_8H_3Me_2$
$R = C_6H_5$;
-continued
54-fac
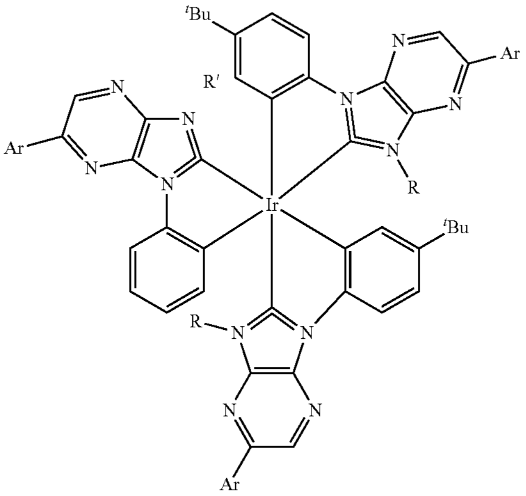
$Ar = 2,6\text{-}C_8H_3Me_2$
$R = C_6H_5$;
$R' = p\text{-}C_6H_4{}^tBu$
55-fac
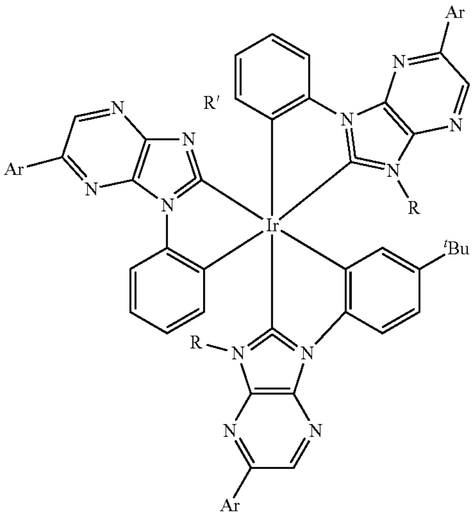
$Ar = 2,6\text{-}C_8H_3Me_2$
$R = C_6H_5$;
$R' = p\text{-}C_6H_4{}^tBu$ -continued
56-fac
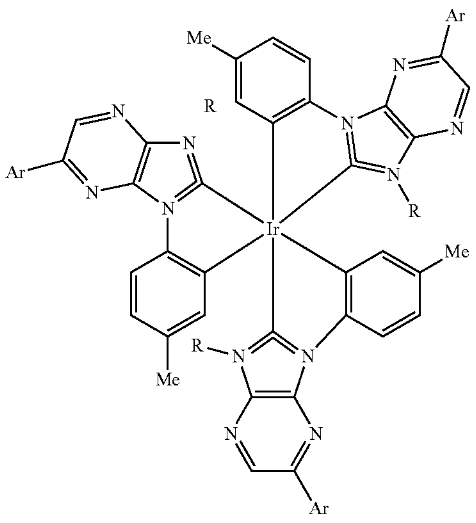
Ar = 2,6-$C_8H_3Me_2$
R = $C_6H_5$;
57-fac
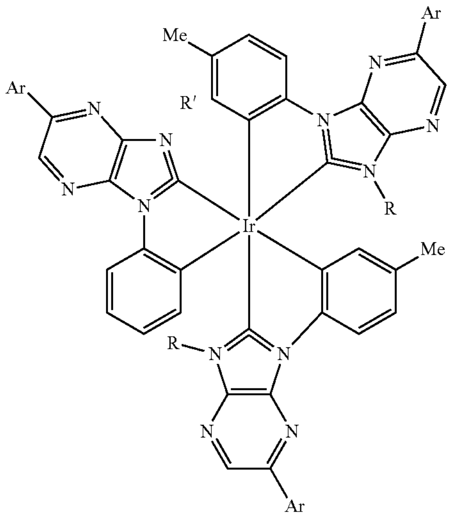
Ar = 2,6-$C_8H_3Me_2$
R = $C_6H_5$;
R′ = p-$C_6H_4Me$
-continued
58-fac
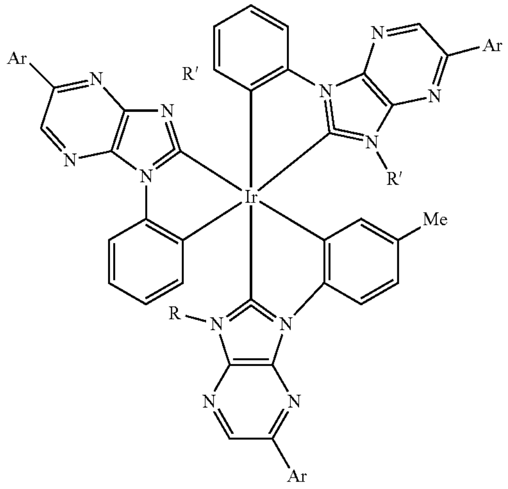
Ar = 2,6-$C_8H_3Me_2$
R = $C_6H_5$;
R′ = p-$C_6H_4Me$
59-fac
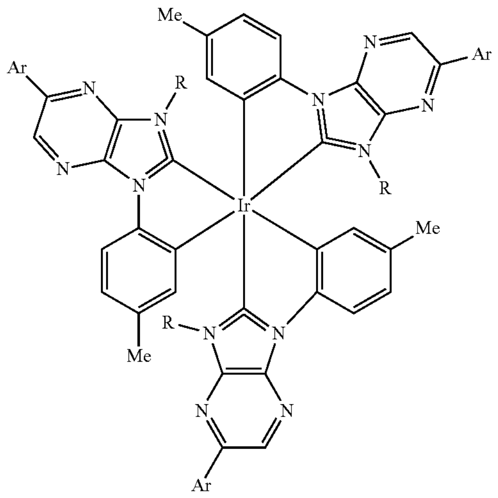
Ar = 2,6-$C_8H_3Me_2$
R = $C_6H_5$;

-continued
60-fac
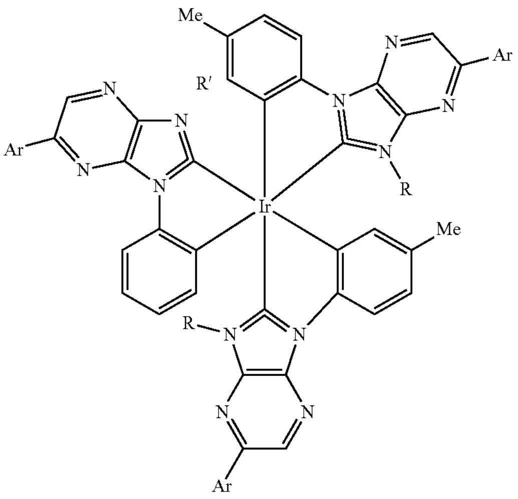
Ar = 2,6-$C_8H_3Me_2$
R = $C_6H_5$;
R′ = p-$C_6H_4Me$
62-fac
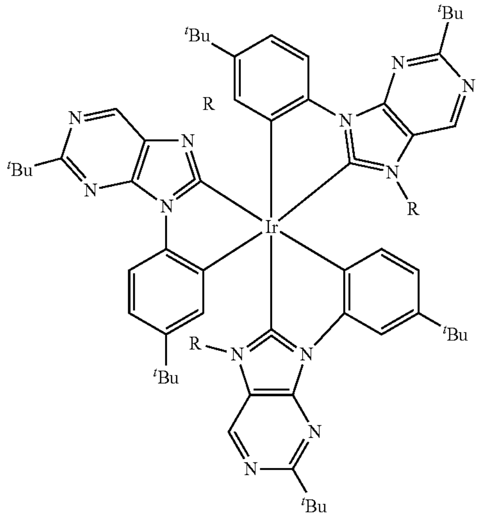
R = $C_6H_5$;
61-fac
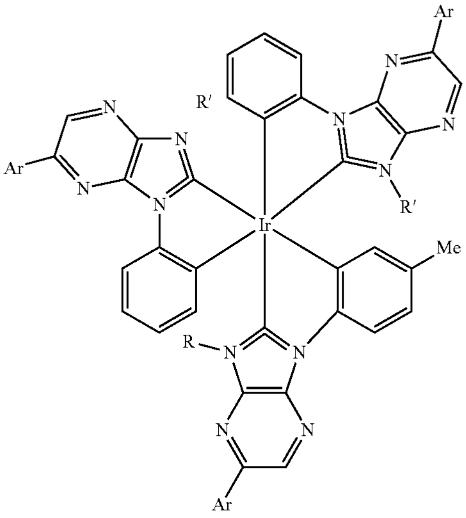
Ar = 2,6-$C_8H_3Me_2$
R = $C_6H_5$;
R′ = p-$C_6H_4Me$
63-fac
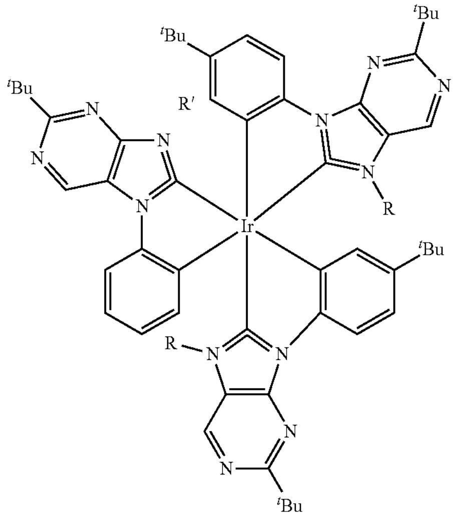
R = $C_6H_5$;
R′ = p-$C_6H_4{}^tBu$ -continued
64-fac
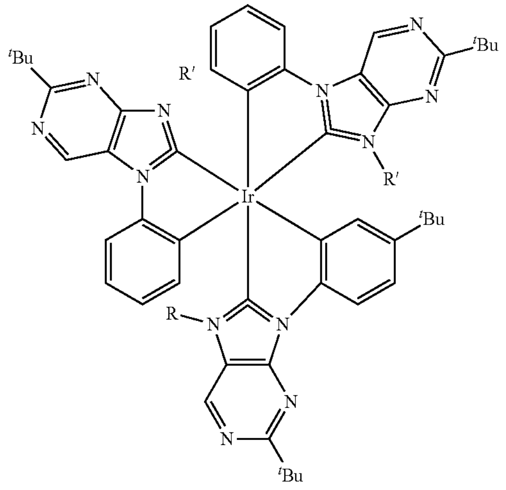
R = $C_6H_5$;
R′ = p-$C_6H_4{}^t$Bu
65-fac
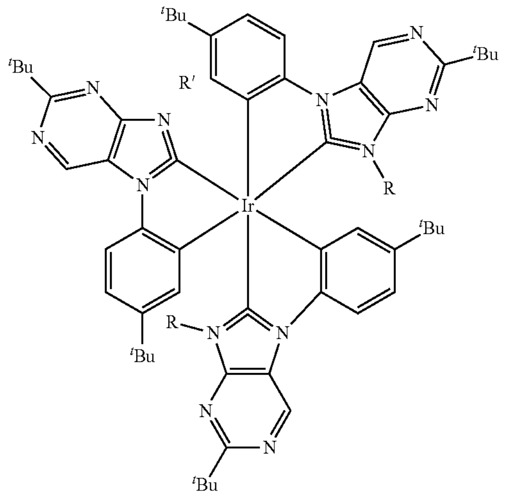
R = $C_6H_5$;
-continued
66-fac
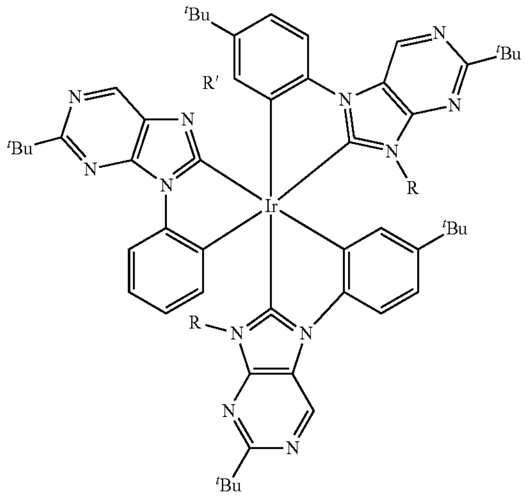
R = $C_6H_5$;
R′ = p-$C_6H_4{}^t$Bu
67-fac
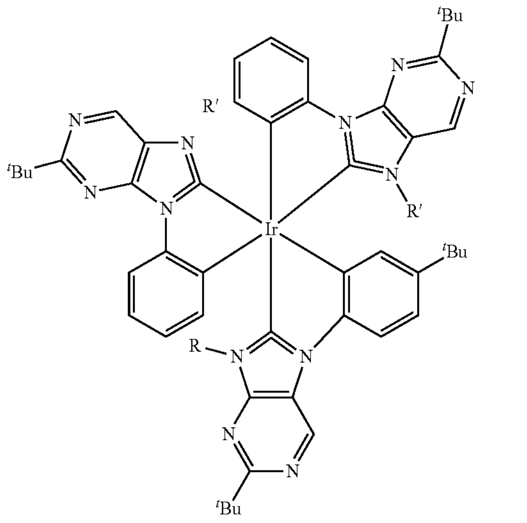
R = $C_6H_5$;
R′ = p-$C_6H_4{}^t$Bu -continued
68-fac
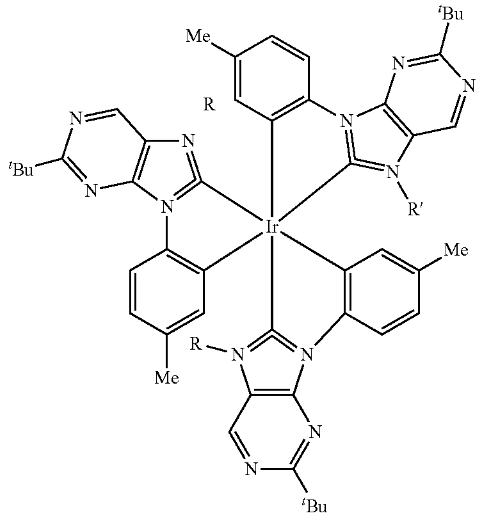
R = $C_6H_5$;
69-fac
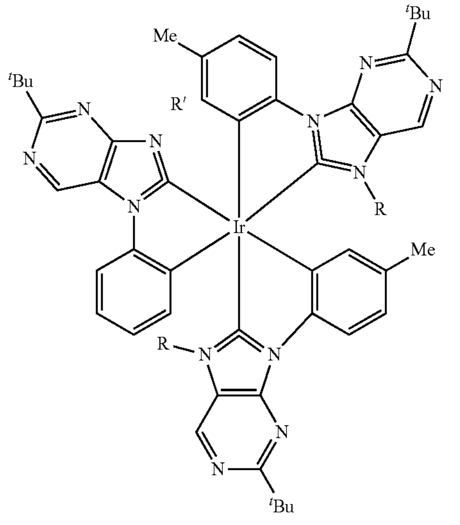
R = $C_6H_5$;
R′ = p-$C_6H_4Me$
70-fac
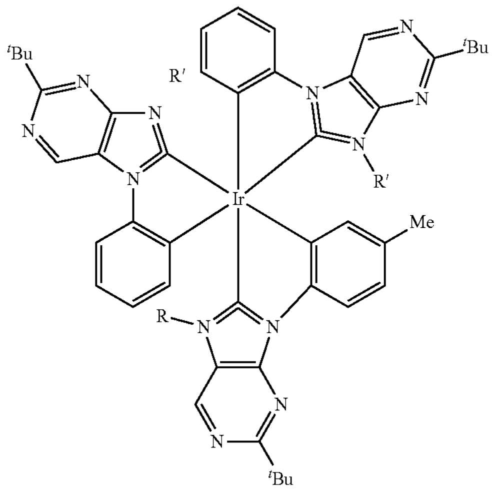
R = $C_6H_5$;
R′ = p-$C_6H_4Me$
71-fac
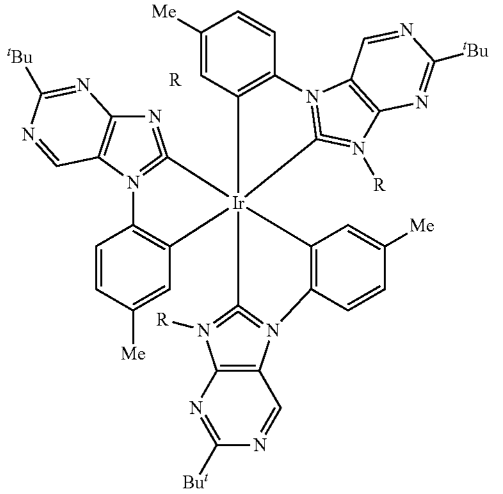
R = $C_6H_5$;

72-fac
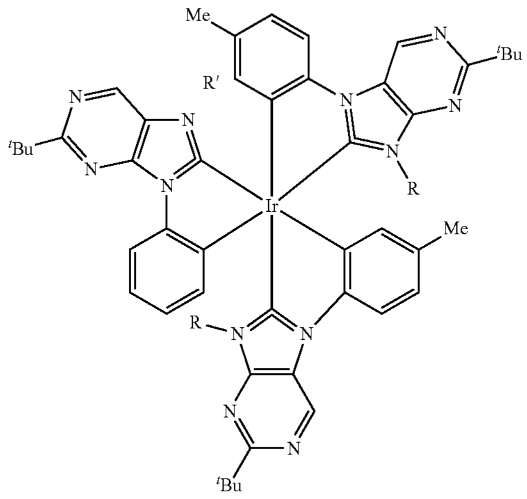
R = $C_6H_5$;
R′ = p-$C_6H_4Me$
73-fac
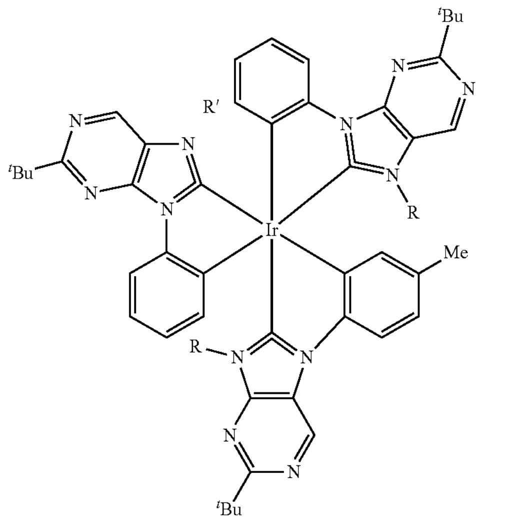
R = $C_6H_5$;
R′ = p-$C_6H_4Me$
74-fac
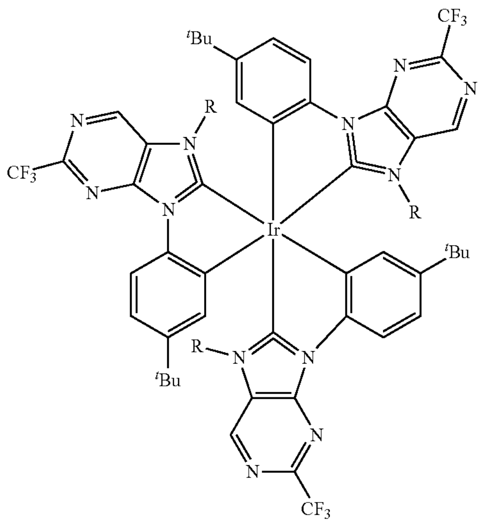
R = $C_6H_5$;
75-fac
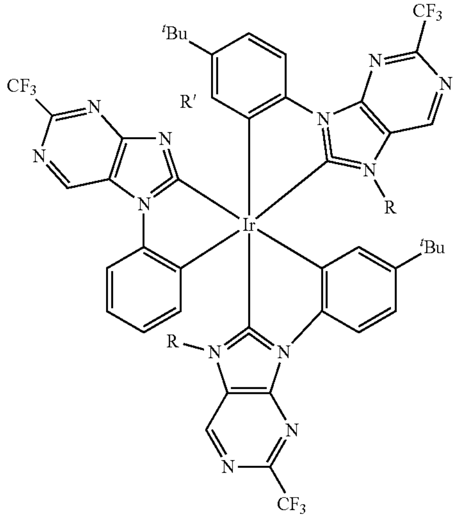
R = $C_6H_5$;
R′ = p-$C_6H_4{}^tBu$ -continued
76-fac
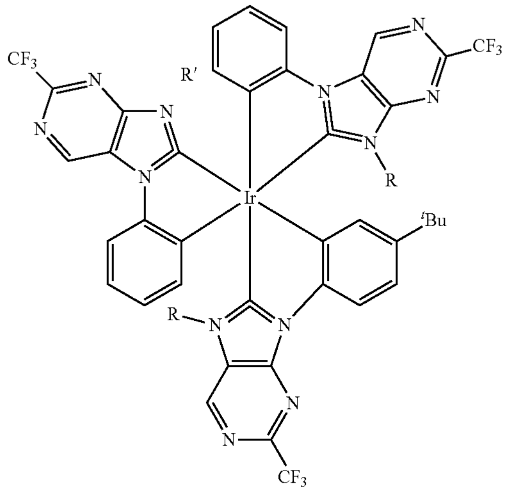
R = $C_6H_5$;
R′ = p-$C_6H_4{}^tBu$
77-fac
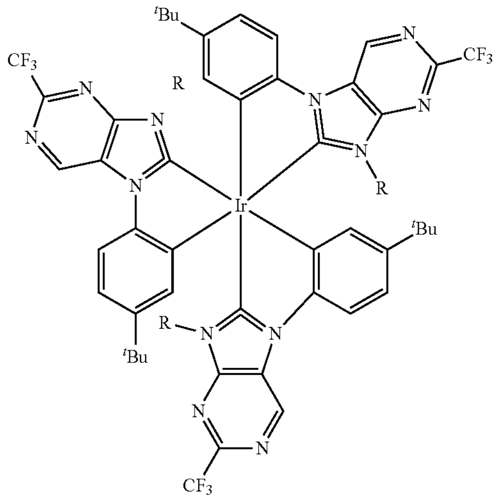
R = $C_6H_5$;
-continued
78-fac
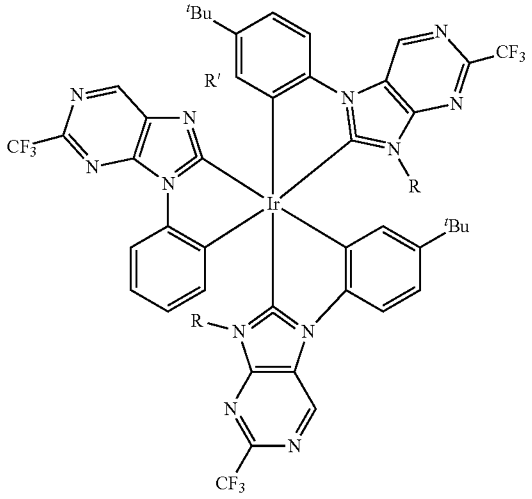
R = $C_6H_5$;
R′ = p-$C_6H_4{}^tBu$
79-fac
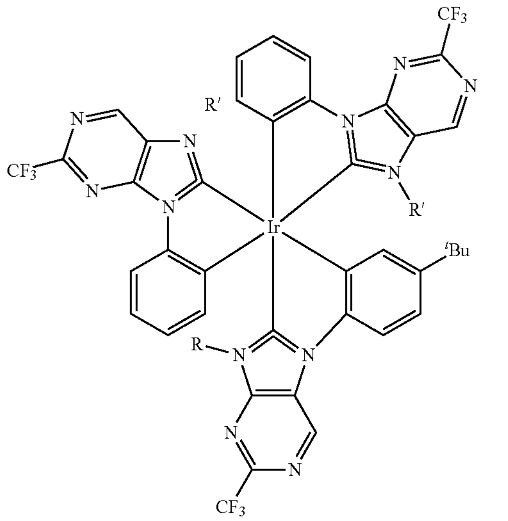
R = $C_6H_5$;
R′ = p-$C_6H_4{}^tBu$ -continued
80-fac
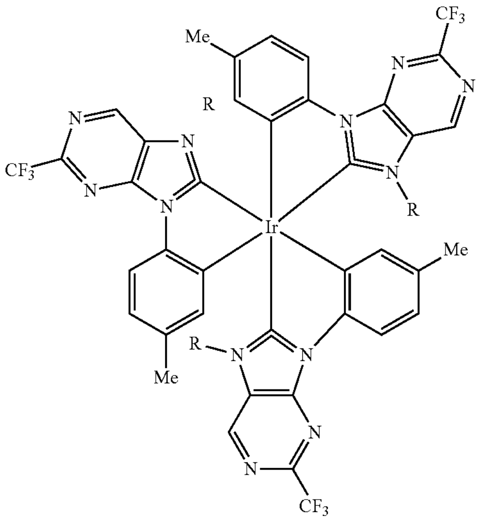
R = $C_6H_5$;
81-fac
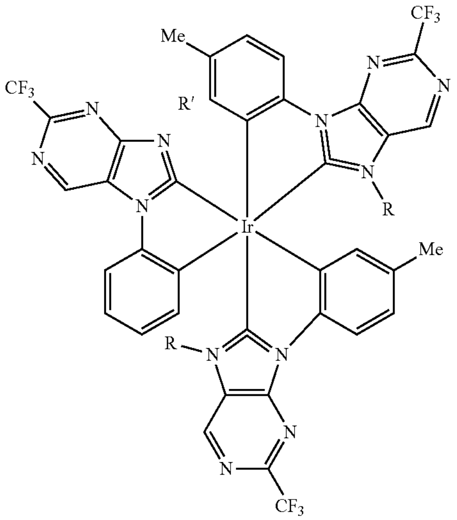
R = $C_6H_5$;
R′ = p-$C_6H_4Me$
-continued
82-fac
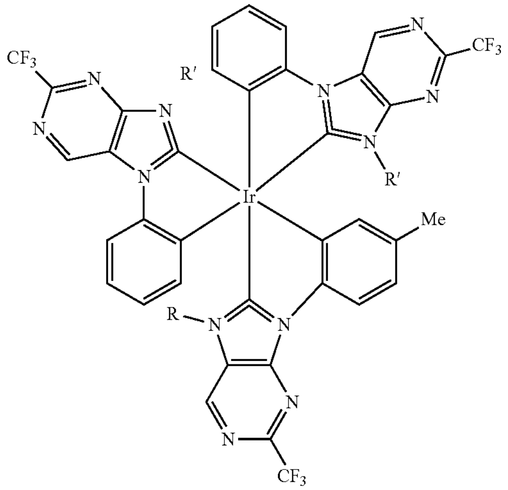
R = $C_6H_5$;
R′ = p-$C_6H_4Me$
83-fac
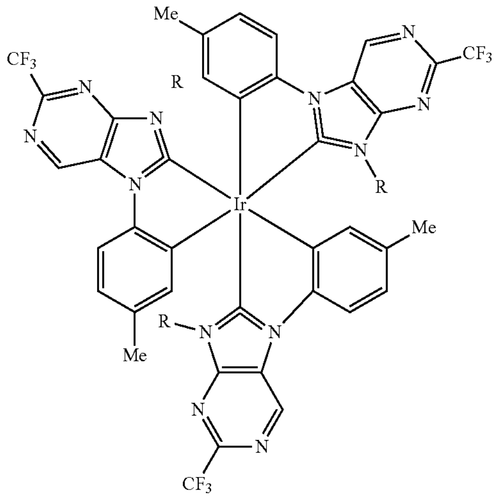
R = $C_6H_5$;

-continued
84-fac
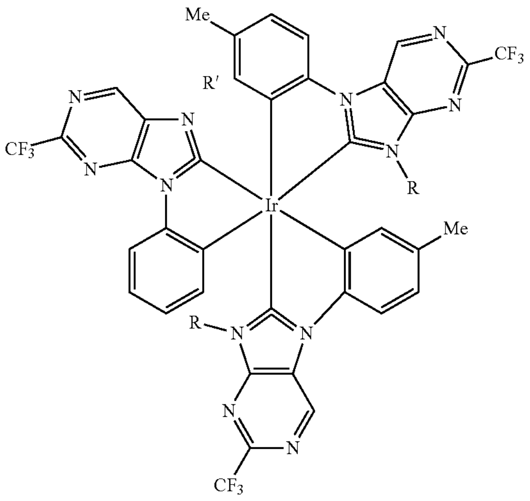
R = $C_6H_5$;
R' = p-$C_6H_4Me$
85-fac
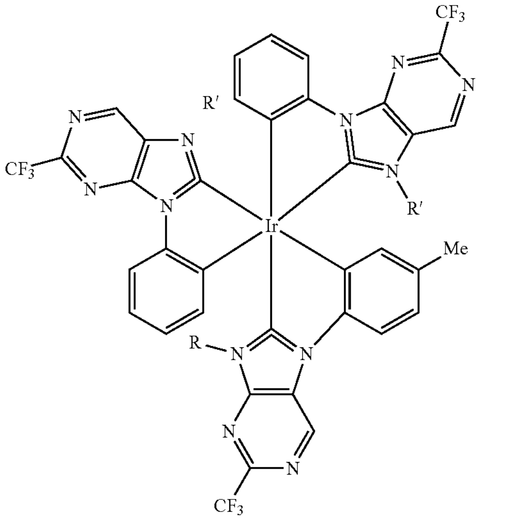
R = $C_6H_5$;
R' = p-$C_6H_4Me$
-continued
86-fac
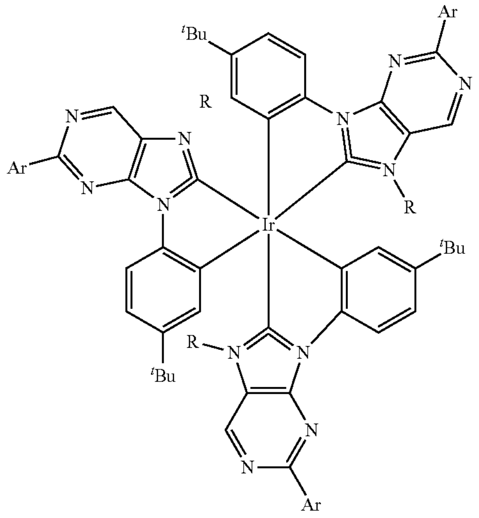
Ar = 2,6-$C_6H_3Me_2$
R = $C_6H_5$;
87-fac
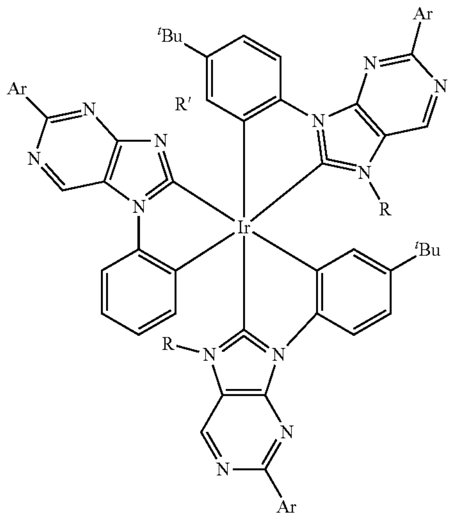
Ar = 2,6-$C_6H_3Me_2$
R = $C_6H_5$;
R' = p-$C_6H_4{}^tBu$ -continued
88-fac
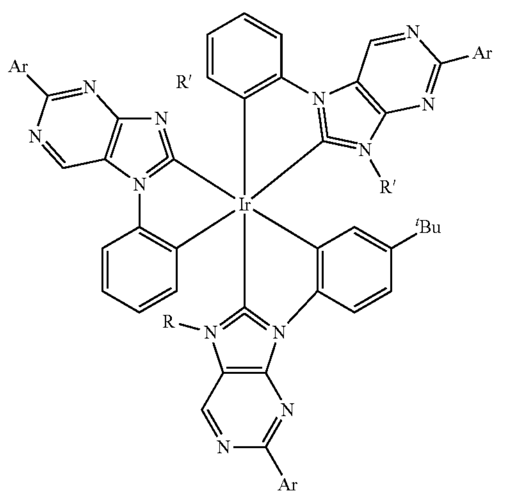
Ar = 2,6-$C_6H_3Me_2$
R = $C_6H_5$;
R′ = p-$C_6H_4{}^tBu$
89-fac
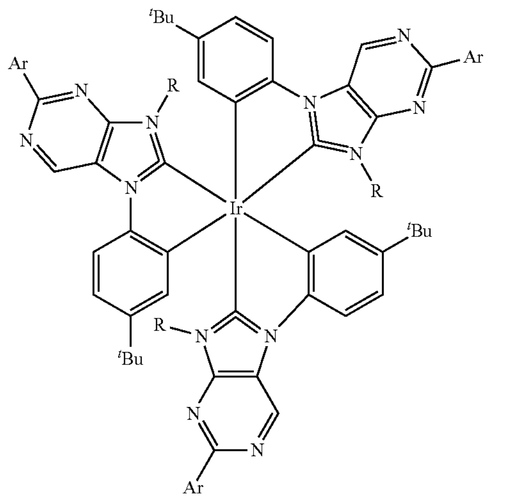
Ar = 2,6-$C_6H_3Me_2$
R = $C_6H_5$;
-continued
90-fac
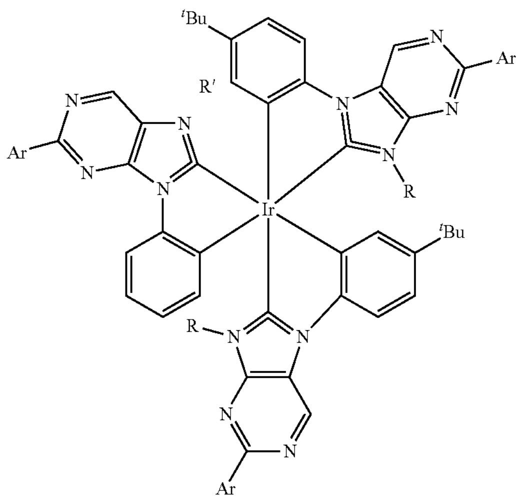
Ar = 2,6-$C_6H_3Me_2$
R = $C_6H_5$;
R′ = p-$C_6H_4$-$^tBu$
91-fac
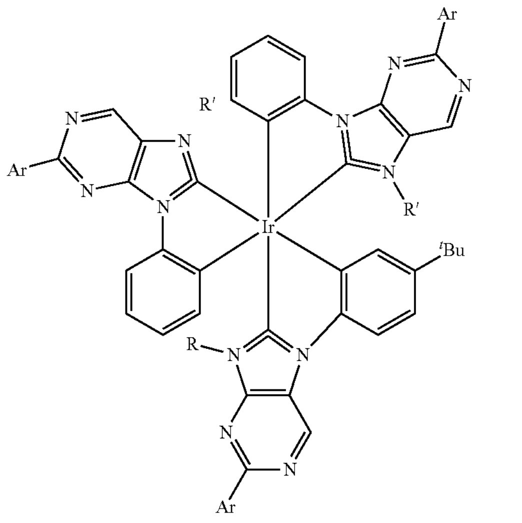
Ar = 2,6-$C_6H_3Me_2$
R = $C_6H_5$;
R′ = p-$C_6H_4$-$^tBu$ 92-fac
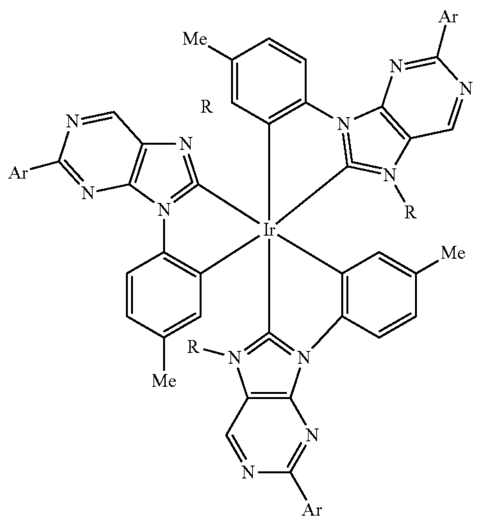
Ar = 2,6-$C_6H_3Me_2$
R = $C_6H_5$;
93-fac
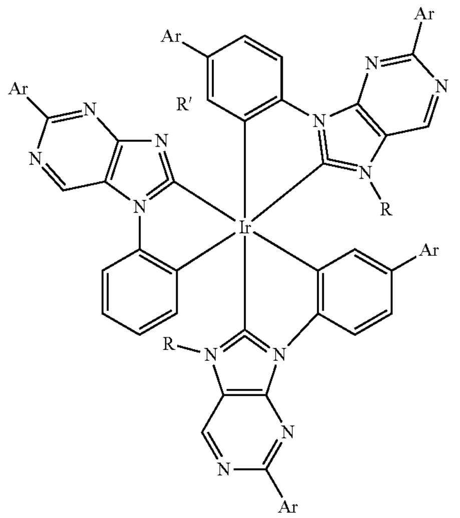
Ar = 2,6-$C_6H_3Me_2$
R = $C_6H_5$;
R′ = p-$C_6H_4Me$
94-fac
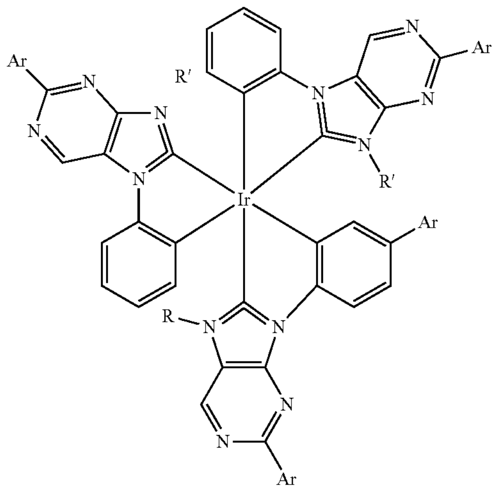
Ar = 2,6-$C_6H_3Me_2$
R = $C_6H_5$;
R′ = p-$C_6H_4Me$
95-fac
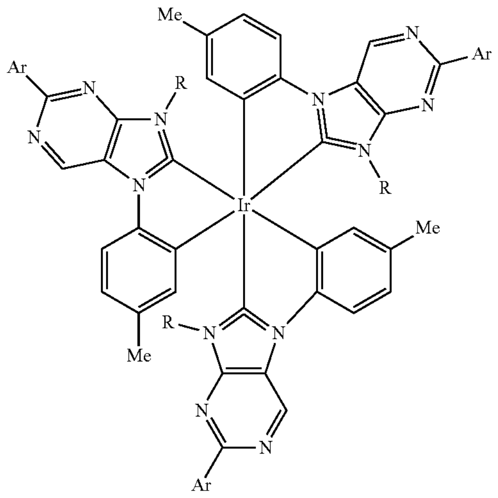
Ar = 2,6-$C_6H_3Me_2$
R = $C_6H_5$;

96-fac
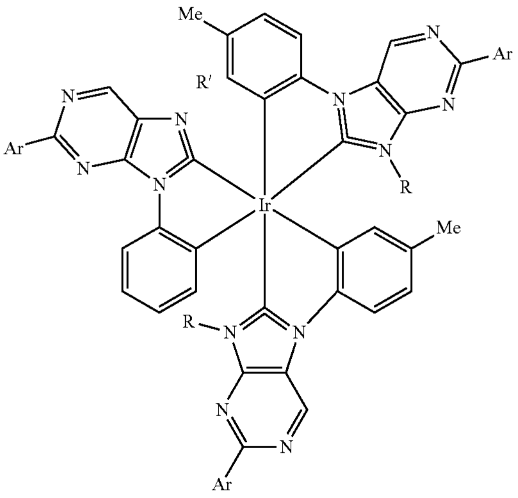
Ar = 2,6-$C_6H_3Me_2$
R = $C_6H_5$;
R′ = p-$C_6H_4Me$
97-fac
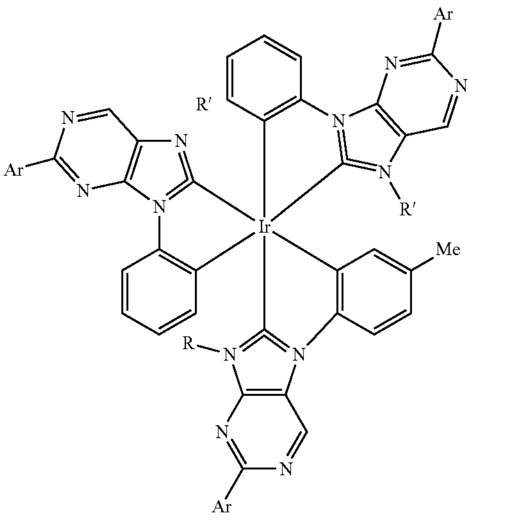
Ar = 2,6-$C_6H_3Me_2$
R = $C_6H_5$;
R′ = p-$C_6H_4Me$
98-fac
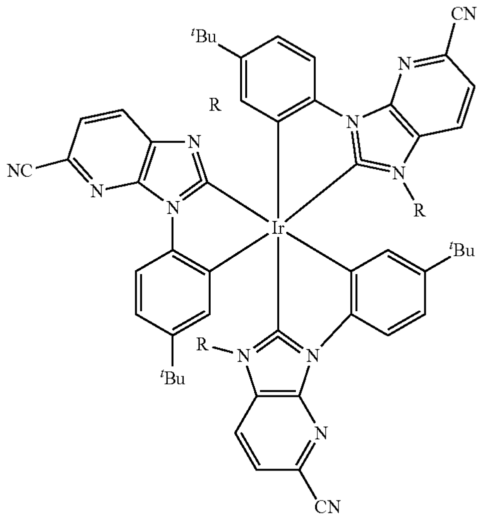
R = $C_6H_5$;
99-fac
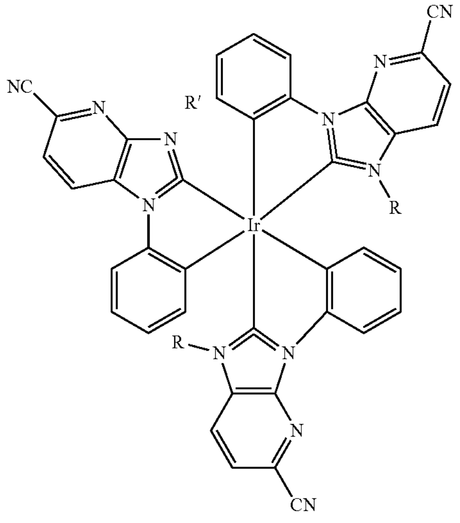
R = p-$C_6H_4{}^tBu$ -continued
100-mer
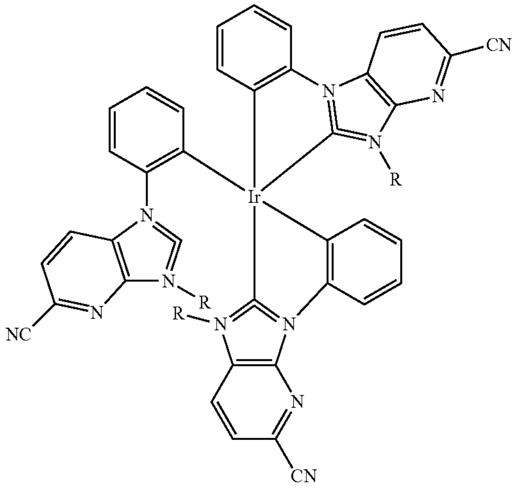
R = p-$C_6H_4{}^tBu$;
101-fac
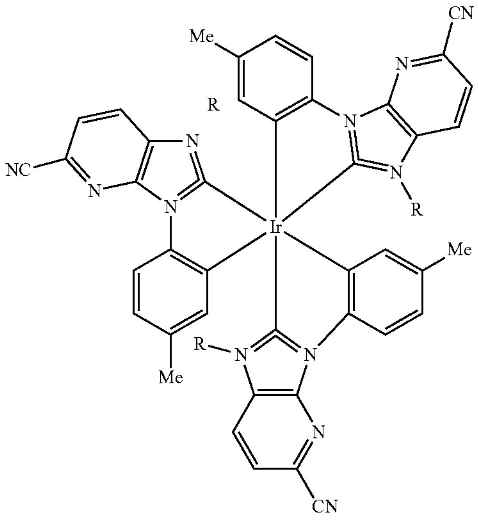
R = $C_6H_5$;
-continued
102-fac
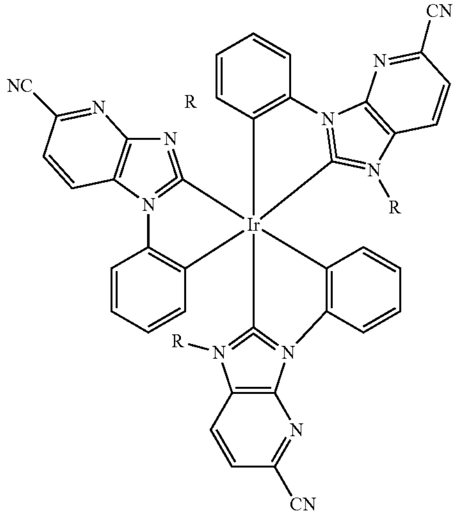
R = p-$C_6H_4Me$;
103-mer
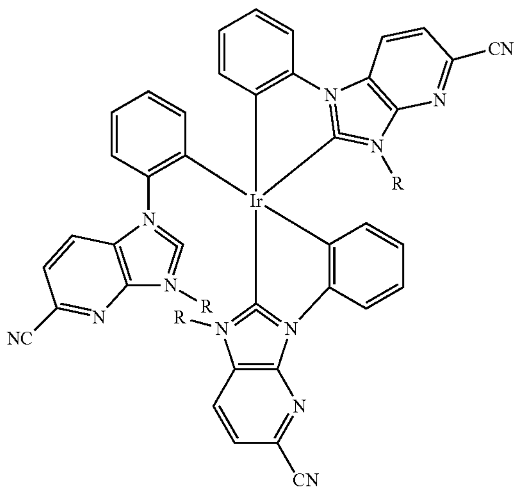
R = p-$C_6H_4Me$;

-continued
104-fac
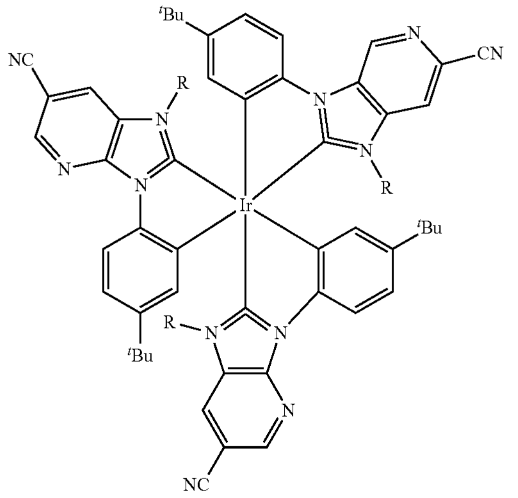
R = $C_6H_5$;
106-fac
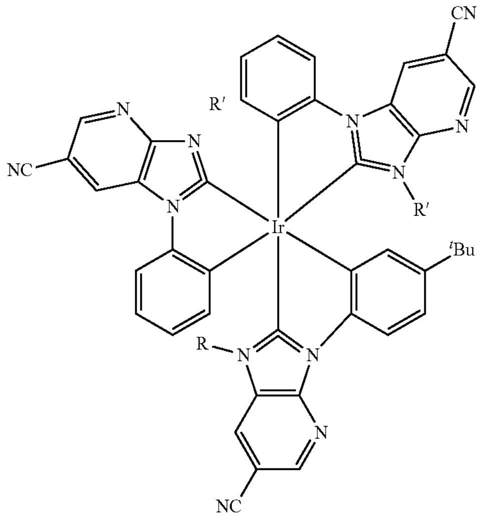
R = $C_6H_5$;
R′ = p-$C_6H_4{}^t$Bu
105-fac
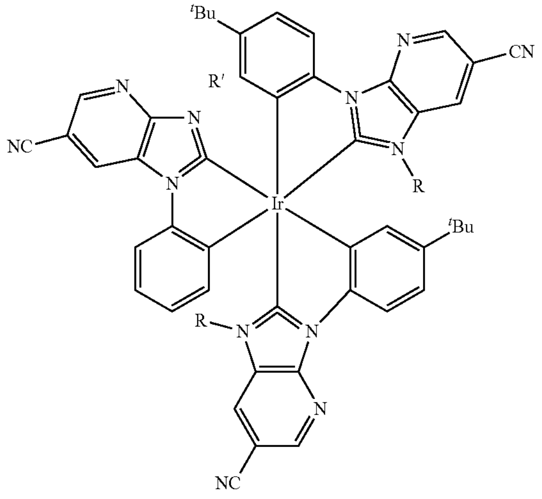
R = $C_6H_5$;
R′ = p-$C_6H_4{}^t$Bu
107-fac
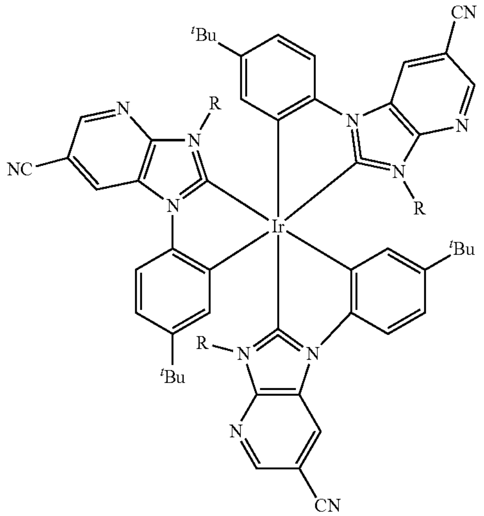
R = $C_6H_5$;

-continued
108-fac
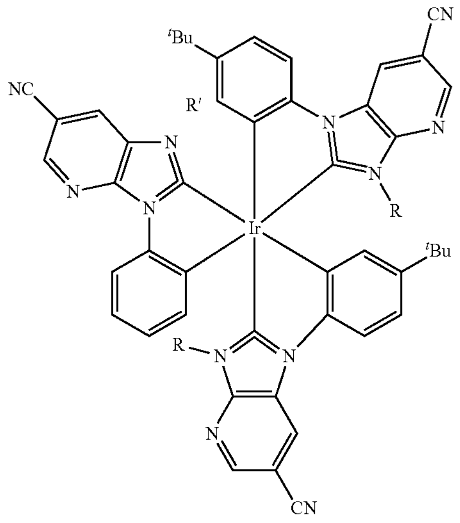
R = $C_6H_5$;
R′ = p-$C_6H_4{}^tBu$
109-fac
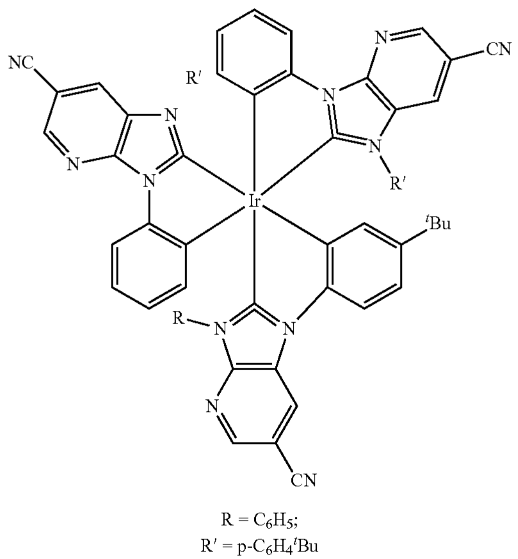
R = $C_6H_5$;
R′ = p-$C_6H_4{}^tBu$
-continued
110-fac
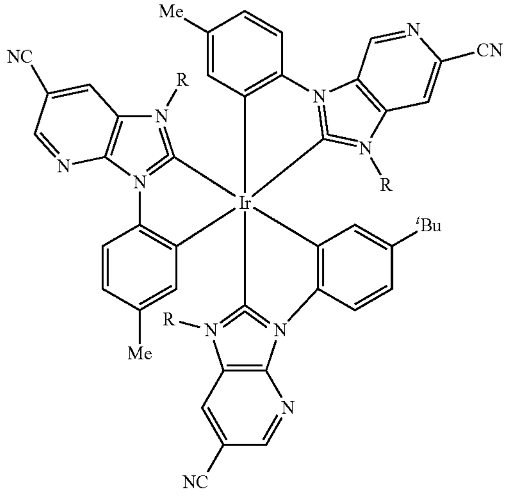
R = $C_6H_5$;
111-fac
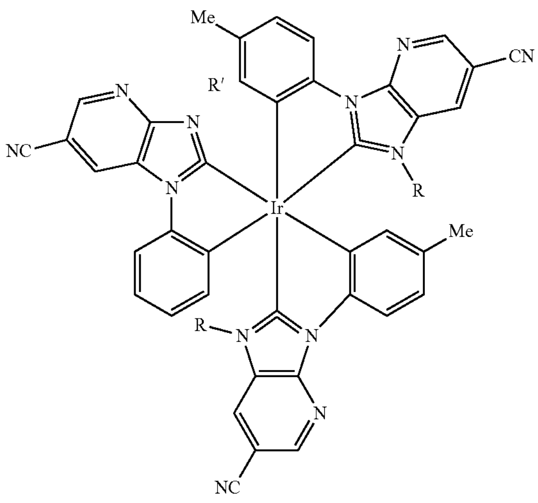
R = $C_6H_5$;
R′ = p-$C_6H_4Me$ -continued
112-fac
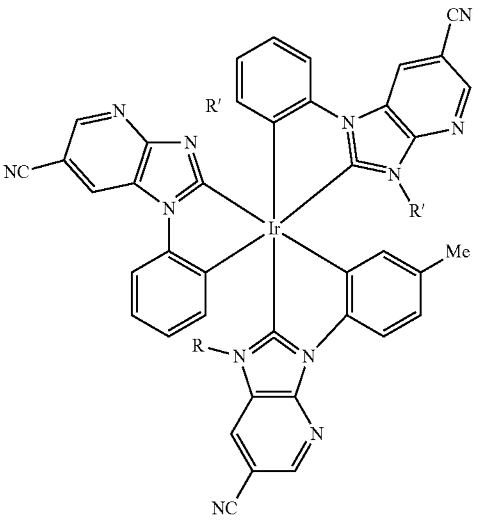
R = $C_6H_5$;
R′ = p-$C_6H_4$Me
113-fac
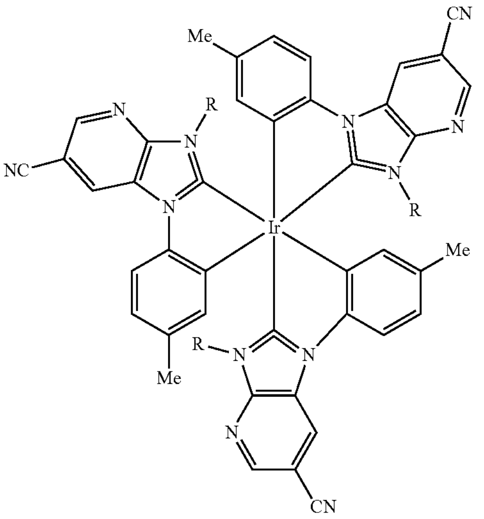
R = $C_6H_5$;
-continued
114-fac
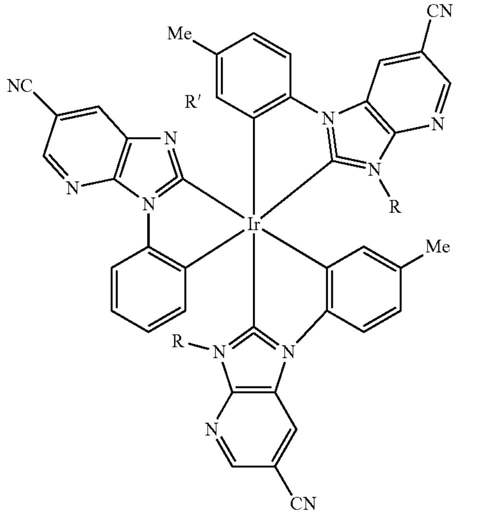
R = $C_6H_5$;
R′ = p-$C_6H_4$Me
115-fac
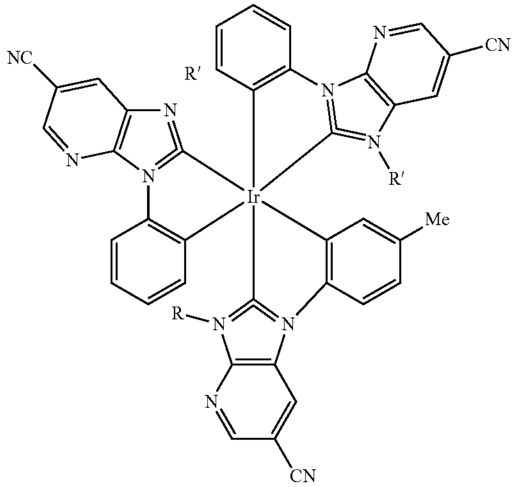
R = $C_6H_5$;
R′ = p-$C_6H_4$Me -continued 116-fac

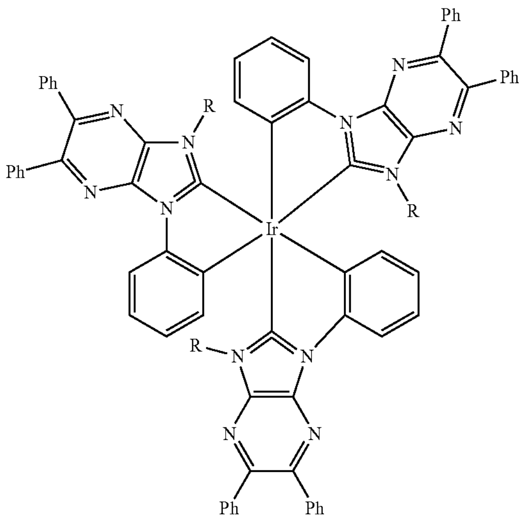

R = $C_6H_5$;

117-fac

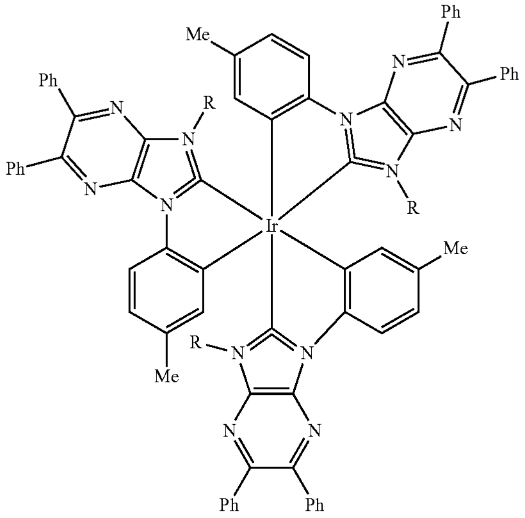

R = p-$C_6H_4Me$

-continued 118-fac

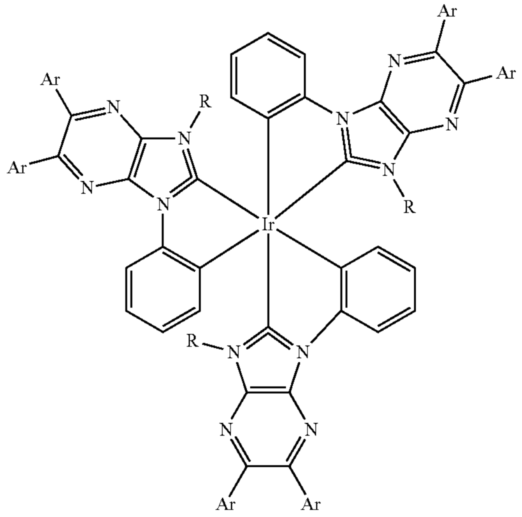

Ar = p-$C_6H_4Me$
R = $C_6H_5$

As shown above, some of the preferred chelates are based on functional (7,9-dihydro-8H-purin-8-ylidene), (1,3-dihydro-2H-imidazo[4,5-b]pyrazin-2-ylidene) and (1,3-dihydro-2H-imidazo[4,5-b]pyridin-2-ylidene), which differ in the relative number and position of nitrogen atoms, to which the electron negative nitrogen can lower the LUMO of the ligand-centered π-orbital. Some of the preferred chelates are based on benzoimidazolylidene entities substituted with multiple electron withdrawing cyano and trifluoromethyl groups, which differ in the relative position of the cyano and trifluoromethyl groups that can lower the LUMO of both free ligands and associated metal complexes. These preferred chelates are also capable of realizing the required blue-emission and shortened radiative lifetimes.

Due to the difficulty in design of carbene chelates and Ir(III) emitters, only the preparation (1,3-dihydro-2H-imidazo[4,5-b]pyrazin-2-ylidene) chelates with symmetrically arranged N-substituted aryl groups on the imidazolylidene coordination unit has been reported. As a result, if substituents $R_3$ and $R_4$ in Formula (II) on the pyrazinyl fragment were different, i.e. $R_3 \neq R_4$, it will unavoidably produce a mixture of inseparable isomers upon formation of Ir(III) phosphors, giving unpredicted and inferior properties on material processing. This is expected for this class of carbene chelates bearing two identical N-aryl groups, due to the dynamic equilibration and poor regioselectivity for the aryl cyclometalation during syntheses.

The method of preparing the metal complex in the present invention comprises the steps of: forming a chelating agent from a reagent selected from the group consisting of: a pyrimidone-based reagent, a pyrimidineamine-based reagent, a pyrimidinediol-based reagent, and a pyrazinecarbonitrile-based reagent, and mixing the chelating agent and a metal reagent to form the metal complex. "Chelating agent" and "pro-chelate" may be used interchangeably herein to refer to the compound that react with the metal ion to form a complex, preferably a charge neutral complex. "Metal reagent" as used herein refers to the material which provides the metal ion required for formation of the complex.

The metal reagent may be $IrCl_3(tht)_3$. The step of mixing the chelating agent and the metal reagent comprises heating the chelating agent, the iridium reagent, and a promoter (e.g. sodium acetate or potassium acetate) in a high boiling hydrocarbon solvent to reflux. As will be appreciated by those skilled in the art, "promoter" as used herein refers to a substance added to a catalyst to improve its performance in a reaction. The promoter may have little or no catalytic effect.

The chelating agent may be a 9H-purin-7-ium derivative, a $CF_3$-substituted 9H-purin-7-ium derivative, an imidazo[4,5-b]pyrazin-3-ium or an imidazo[4,5-b]pyridin-3-ium derivative.

In the embodiment where the chelating agent is a 9H-purin-7-ium derivative, the pyrimidone-based reagent is 2-pyrimidone or 2-(tert-butyl)pyrimidin-4(3H)-one. Also, the step of forming the chelating agent comprises the step of: forming an $N^4$-phenylpyrimidine-4,5-diamine derivative from the pyrimidone-based reagent. The step of forming the $N^4$-phenylpyrimidine-4,5-diamine derivative includes the steps of: conducting nitrosation and subsequent chlorination of the pyrimidone-based reagent to form a chloro-nitro-primidone derivative, substituting the chloro group of the chloro-nitro-primidone derivative with aniline and performing reduction of the nitro group to form the $N^4$-phenylpyrimidine-4,5-diamine derivative. The step of forming the chelating agent may further include the steps of performing cyclization of the $N^4$-phenylpyrimidine-4,5-diamine derivative and treating with a triflating agent or an iodonium reagent to form the 9H-purin-7-ium derivative. The triflating agent may be methyl triflate or ethyl triflate, while the iodonium reagent may be diphenyliodonium and relevant functional derivatives.

In contrast to the typical synthetic protocol that involved the in-situ generation of silver-carbene intermediate, the reaction condition in this embodiment required no such expensive silver salt and, hence, is very cost effective, together with another advantage of having improved product yields.

In the embodiment where the chelating agent is a $CF_3$-substituted 9H-purin-7-ium derivative, the pyrimidineamine-based reagent is a 2-(trifluoromethyl)pyrimidin-5-amine derivative. Also, the step of forming the chelating agent comprises: conducting bromination of the pyrimidineamine-based reagent to form a bromo-2-(trifluoromethyl)pyrimidin-5-amine derivative, treating the bromo-2-(trifluoromethyl)pyrimidin-5-amine derivative with aniline to form a $N^4$-phenyl-2-(trifluoromethyl)pyrimidine-4,5-diamine derivative, and performing cyclization of the $N^4$-phenyl-2-(trifluoromethyl)pyrimidine-4,5-diamine derivative to form the $CF_3$-substituted 9H-purin-7-ium derivative.

In another embodiment where the chelating agent is a $CF_3$-substituted 9H-purin-7-ium derivative or a $CF_3$-substituted imidazo[4,5-b]pyridin-3-ium derivative, the pyrimidinediol reagent is a 2-(trifluoromethyl)pyrimidin-4, 6-diol derivative. The step of forming the chelating agent comprises: conducting nitration and subsequent chlorination of the pyrimidinediol-based reagent to form a chloro-nitro-2-(trifluoromethyl)pyrimidine derivative, substituting the chloro group of the chloro-nitro-2-(trifluoromethyl)pyrimidine derivative with aniline and conducting reduction of the nitro group of the chloro-nitro-2-(trifluoromethyl)pyrimidine derivative, to form a phenyl-2-(trifluoromethyl)pyrimidine-4,5-diamine derivative, and performing cyclization of the phenyl-2-(trifluoromethyl)pyrimidine-4,5-diamine derivative and subsequent N-methylation to form the $CF_3$-substituted 9H-purin-7-ium derivative.

In the embodiment where the chelating agent is a cyano-substituted imidazo[4,5-b]pyridin-3-ium derivative. The step of forming the chelating reagent comprises: conducting a single bromo-to-aniline substitution in forming a functional N-phenylpyridin-2-amine derivative. Next, concurrent reduction of nitro group and cyclization yielded a bromo-substituted 3-phenyl-3H-imidazo[4,5-b]pyridine derivative. Substitution of bromo group with cyano entity, followed by addition of an aryl group gave formation of cyano-substituted imidazo[4,5-b]pyridin-3-ium derivative.

In the embodiment where the chelating agent is an imidazo[4,5-b]pyrazin-3-ium derivative, the pyrazinecarbonitrile-based reagent is pyrazinecarbonitrile or tert-butylpyrazinecarbonitrile. Also, the step of forming the chelating agent comprises: performing Hofmann rearrangement of the pyrazinecarbonitrile-based reagent to form an amino-pyrazinecarbonitrile derivative, conducting bromination of the amino-pyrazinecarbonitrile derivative to form a bromo-amino-pyrazinecarbonitrile derivative, treating the bromo-amino-pyrazinecarbonitrile derivative with an orthoesther to form a formimidate derivative, performing condensation of the formimidate derivative with aniline to form a formamidine derivative, and conducting cyclization of the formamidine derivative and treatment with a triflating agent or iodonium reagent such as diphenyliodonium salt to form the respective imidazo[4,5-b]pyrazin-3-ium derivative. Similar to the above embodiment, the triflating agent may be methyl triflate or ethyl triflate, while diphenyliodonium reagent can be either the symmetric or asymmetric derivatives.

This embodiment is different from the typical preparation method of the imidazo[4,5-b]pyrazin-3-ium derivative, as shown in Scheme 1, which employs commercially available 3-chloropyrazin-2-amine as the starting material. After that, the sequential treatment with aniline at 110° C. for 24 hours (i), formic acid at 100° C. for 24 hours (ii), and methyl iodide and tetrahydrofuran at 65° C. (iii) afforded the demanded 1-methyl-3-phenyl-1H-imidazo[4,5-b]pyrazin-1-ium iodide (5), which is contaminated with a by-product from possible methylation at the pyrazinyl N-atom.

An alternative typical preparation method is as follows. The symmetrically-arranged 1,3-diphenyl-1H-imidazo[4,5-b]pyrazin-1-ium (6) or ethoxy-imidazopyrazine derivative (7) can be prepared from treatment of 2,3-dichloropyrazine with aniline at 110° C. for 24 hours (iv) in affording the N,N'-diphenylpyrazine-2,3-diamine, followed by reaction with triethyl orthoformate in the presence of ammonium iodide at RT for 12 hours (v) or with triethyl orthoformate in the presence of hydrogen chloride at 100° C. for 24 hours (vi), thereby forming an imidazolium fragment, to which the products are dependent to the catalyst and reaction temperature employed. However, unlike the method in the embodiment, these earlier approaches are only suitable in synthesizing symmetrically arranged pyrazine derivatives, but cannot afford the asymmetrically-arranged imidazo[4,5-b]pyrazin-3-ium derivatives discussed above. As the result, the synthesis using this asymmetric pro-chelate such as 6-(t-butyl)-1,3-diphenyl-1H-imidazo[4,5-b]pyrazin-3-ium (8) with $[Ir(COD)(\mu\text{-}Cl)]_2$ and xylene under reflux for 5 hours (i) can only afford a statistically distributed mixture of isomeric Ir(III) emitters $[Ir(cb)_3]$, as shown in Scheme 2. The mixed products are expected to dexterously hamper the processability and reproducibility of the as-synthesized materials.

Scheme 1

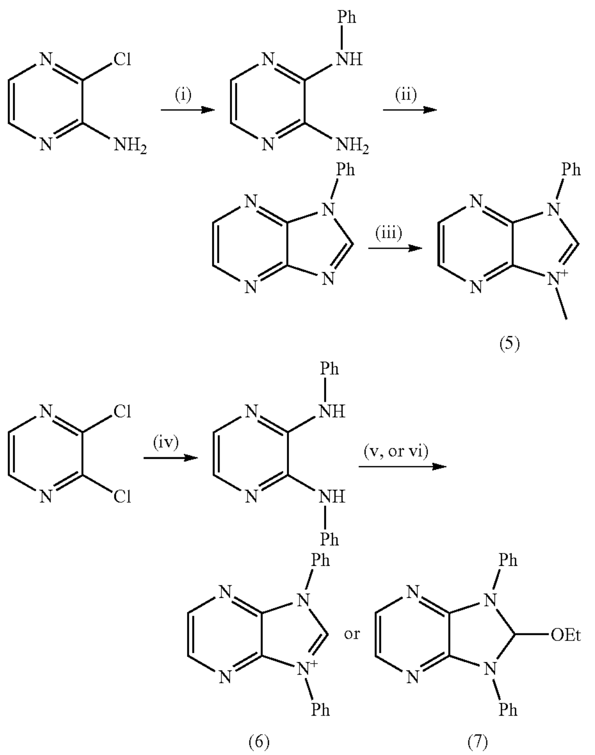

(5)

(6) or (7)

Scheme 2

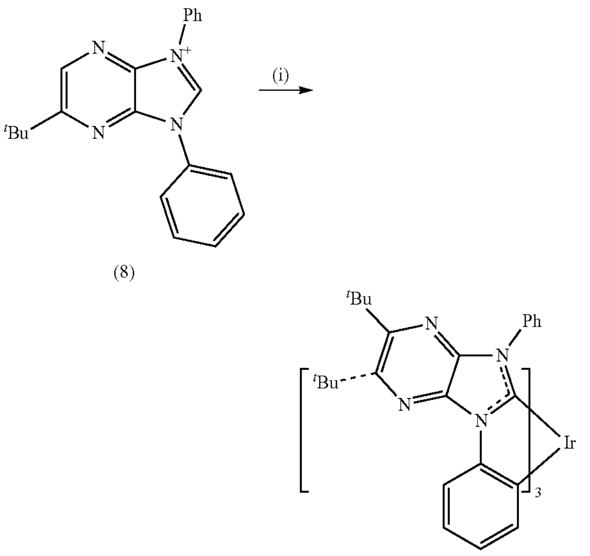

(8)

The metal complexes in the present invention may be used in a light emitting device, preferably an organic electronic device, for example, organic light-emitting diodes (OLED), light-emitting electrochemical cells (LEEC) and organic field-effect transistors (OFET). Preferably, the metal complex is used in an OLED, such as a phosphorescent OLED (PHOLED). Despite of the above-mentioned difficulty in producing the mixed Ir(III) phosphors with $R_3$ being tert-butyl and $R_4$ being H, from which the as-prepared OLED devices can still exhibit quite impressive photophysical performances. Therefore, the pure emitters (i.e. those without isomeric derivatives) in the present invention are expected to exhibit even better performance characteristics.

As known to those skilled in the art, OLEDs are considered as efficient and sustainable light sources and have already been used in both the display and lighting applications. It is usually a light-emitting diode (LED) in which the emissive electroluminescent layer is a film of organic compound which emits light in response to an electric current. This layer of organic semiconductor is usually situated between two electrodes. Generally, at least one of these electrodes is transparent. The metal complex may be present in any desired layer, preferably in the emissive electroluminescent layer (light-emitting layer), of the OLED as an emitter material. The emissive layer may emit light with a wavelength in the range of 420-565 nm, preferably in the range of 420-490 nm.

The metal complex may be used in the light-emitting layer without further additional components, or the metal complex may be comprised in the light-emitting layer with one or more further components. The light-emitting layer may further comprise one or more host (matrix) materials. This host material may be a polymer, for example poly(N-vinylcarbazole). The host material may, alternatively, be a small molecule with enlarged HOMO/LUMO energy gap and relatively greater triplet energy gap or tertiary aromatic amines, for example tris(4-carbazoyl-9-ylphenyl)amine (TCTA). The host material may also be a dibenzofuran-based material with relatively large triple energy gap, such as 2,8-bis(diphenylphosphino oxide) dibenzofuran (PPF). Suitable host materials are carbazole derivatives, for example 4,4'-bis(carbazol-9-yl)-2,2'-dimethylbiphenyl (CDBP), 4,4'-bis(carbazol-9-yl)biphenyl (CBP), 1,3-bis(N-carbazolyl)benzene (mCP), 3,3'-di(9H-carbazol-9-yl)-1,1'-biphenyl (mCBP), diphenyl[4-(triphenylsilyl)phenyl]phosphine oxide (TSPO1), and 1-(4-(dibenzo[b,d]thiophen-4-yl)-2,5-dimethylphenyl)-1H-phenanthro[9,10-d]imidazole (txI).

In addition, the present invention may beneficially avoid the need to include a dye as it provides a blue emission. However, in alternative embodiments, a fluorescent dye may be present in the light-emitting layer of an OLED to alter the emission colour of the emitter material.

In the preferred embodiment, the OLED is constructed with the following layers which are arranged in the following order: an anode layer, a hole-injection layer (optional), a hole-transporting layer (optional), an electron-blocking layer (optional), an exciton-blocking layer (optional), a light-emitting layer (including the metal complex), a hole-blocking layer (optional), an electron-transporting layer (optional), an electron-injection layer (optional), and a cathode layer.

In general, the different layers in the OLED, if present, have the following thicknesses:

anode layer: 50 to 500 nm, preferably 100 to 200 nm;

hole-injection layer (optional): 1 to 50 nm, preferably 5 to 10 nm;

hole-transporting layer (optional): 5 to 100 nm, preferably 10 to 80 nm;

electron-blocking layer (optional): 1 to 50 nm, preferably 5 to 10 nm;

exciton-blocking layer (optional): 1 to 50 nm, preferably 5 to 10 nm;

light-emitting layer: 1 to 100 nm, preferably 5 to 60 nm;

hole-blocking layer (optional): 1 to 50 nm, preferably 5 to 10 nm;

electron-transporting layer (optional): 5 to 100 nm, preferably 20 to 60 nm;

electron-injection layer (optional): 1 to 20 nm, preferably 1 to 5 nm;

cathode layer: 20 to 1000 nm, preferably 30 to 500 nm.

The OLED may be comprised in a device, for example, stationary visual display units, such as visual display units of wearable or head-mounted devices, computers, televisions, visual display units in printers, kitchen appliances, advertising panels, information panels and illuminations; mobile visual display units such as visual display units in smartphones, cell-phones, tablet computers, laptops, digital cameras, MP3-players, vehicles, keyboards and destination displays on buses and trains; illumination units; units in items of clothing; units in handbags, units in accessories, units in furniture and units in wallpaper.

The photophysical properties of the preferred Ir(III)-based emitters are shown in Table 1, which reveals high photoluminescence quantum yields up to 97%, emission peak max. located in the region of 420-565 nm, and radiative lifetime lower than 2.4 microseconds. These photophysical parameters indicate the possible direction in achieving efficient and robust blue phosphors and respective PHOLEDs.

Notably, although the PL peak max. ($\lambda_{max}$) of 540 nm and 501 nm for complexes 44-mer and 44-fac are shown to be shifted further to the lower energy region, which may be less desired for true-blue OLED devices, this may be due to tolerances occurred during the recording of the photophysical data in a polar solvent, dichloromethane. Correction in certain blue-shifting is expected to occur upon recording the emission in a non-polar solvent such as methylcyclohexane or in co-deposited solid-state matrix such as PMMA. In case the correction is not sufficient for the desired emission, correction by lowering the HOMO energy level of the Ir(III) complexes using molecular engineering, e.g. by introduction of an electron deficient trifluoromethyl group at the N-phenyl cyclometalate would be desirable.

TABLE 1

Photophysical data of the tris-bidentate Ir(III) complexes in degassed toluene solution.

| Complex | $\lambda_{max}$ (nm) | FWHM[c] ($cm^{-1}$) | $\Phi$[d][e] (%) | $\tau_{obs}$[e] (μs) | $\tau_{rad}$[e] (μs) | $k_r$ ($10^6 s^{-1}$) | $k_{nr}$ ($10^6 s^{-1}$) |
|---|---|---|---|---|---|---|---|
| 1-fac | 423[a] | 3290 | 43 | 0.52 | 1.2 | 0.83 | 1.096 |
| 1-mer | 483[a] | 4110 | 75 | 0.77 | 1.0 | 1.0 | 0.325 |
| 2-fac | 436[a] | 3350 | 62 | 0.66 | 1.1 | 0.91 | 0.576 |
| 2-mer | 496[a] | 3990 | 92 | 0.89 | 0.97 | 1.0 | 0.09 |
| 3-fac | 447[a] | 3254 | 73 | 1.25 | 1.71 | 0.58 | 0.216 |
| 4-fac | 422[a] | 3850 | 39 | 0.49 | 1.26 | 0.79 | 1.245 |
| 5-fac | 468[a] | 3246 | 97 | 0.72 | 0.74 | 1.35 | 0.042 |
| 5-mer | 526[a] | 3253 | 81 | 0.92 | 1.14 | 0.88 | 0.207 |
| 6-fac | 508[a] | 3605 | 71 | 0.76 | 1.07 | 0.93 | 0.382 |
| 6-mer | 561[a] | 3493 | 66 | 0.81 | 1.23 | 0.81 | 0.420 |
| 7-fac | 466[a] | 3309 | 74 | 1.64 | 2.21 | 0.45 | 0.159 |
| 7-mer | 518[a] | 3736 | 46 | 0.42 | 0.92 | 1.08 | 1.286 |
| 8-fac | 485[a] | 3334 | 58 | 0.96 | 1.65 | 0.61 | 0.438 |
| 8-mer | 532[a] | 3613 | 45 | 0.19 | 0.42 | 2.4 | 2.895 |
| 9-fac | 483[a] | 3278 | 53 | 0.70 | 1.31 | 0.76 | 0.671 |
| 9-mer | 518[a] | 3870 | 48 | 0.25 | 0.53 | 1.89 | 2.080 |
| 10-fac | 468[a] | 2702 | 80 | 0.72 | 090 | 1.1 | 0.278 |
| 11-fac | 468[a] | 2752 | 75 | 0.68 | 0.91 | 1.1 | 0.368 |
| 12-fac | 464[a] | 2540 | 83 | 0.53 | 0.64 | 1.6 | 0.321 |
| 42-mer | 511[a] | 3668 | 95 | 0.98 | 1.04 | 0.96 | 0.051 |
| 42-fac | 467[a] | 2913 | 88 | 1.21 | 1.38 | 0.73 | 0.099 |
| 43-mer | 479[a] | 3934 | 96 | 0.79 | 0.82 | 1.22 | 0.051 |
| 43-fac | 435[a] | 2937 | 88 | 1.05 | 1.19 | 0.84 | 0.114 |
| 44-mer | 540[b] | 3535 | 81 | 0.35 | 0.43 | 2.31 | 0.543 |
| 44-fac | 501[b] | 3674 | 93 | 0.89 | 0.96 | 1.05 | 0.079 |
| 47-fac | 452[a] | 3449 | 88 | 0.69 | 0.78 | 1.28 | 0.174 |
| 48-fac | 447[a] | 3371 | 84 | 0.78 | 0.93 | 1.08 | 0.205 |
| 49-fac | 443[a] | 3233 | 83 | 0.82 | 0.99 | 1.01 | 0.207 |
| 99-fac | 468[a] | 2915 | 92 | 1.41 | 1.53 | 0.652 | 0.057 |
| 100-mer | 467[a] | 2647 | 86 | 2.35 | 2.73 | 0.366 | 0.060 |
| 104-fac | 446[a] | 2825 | 94 | 0.88 | 0.94 | 1.07 | 0.068 |
| 105-fac | 461[a] | 2767 | 89 | 1.15 | 1.29 | 0.77 | 0.095 |

[a]Recorded at a concentration of $10^{-5}$M in toluene at RT.

[b]Recorded at a concentration of $10^{-5}$M in dichloromethane at RT.

[c]Full width at half maximum.

[d]Coumarin 102 (C102) in methanol (quantum yield (Q.Y.) = 87% and $\lambda_{max}$ = 480 nm) were employed as standard.

[e]Recorded in degassed toluene at a concentration of $10^{-5}$M at RT.

As discussed above, Ir(C^C:)$_3$ complexes are promising materials for fabrication of robust and efficient blue PHOLEDs. The introduction of pyrimidine and pyrazine appendages, or the strongly electron-withdrawing cyano and/or trifluoromethyl substituent at the chelating carbene fragments increase the strength of Ir—$C_{carbene}$ dative bonding and shifts the emission from purple to true blue. In addition, the lone pair electron on the N atoms in the as-synthesized Ir(III) emitters may cause severe instability. Therefore, in the preferred embodiments, one or more tert-butyl substituents at the nearby or adjacent position were introduced to protect these N atoms from detrimental exposure to environment which would otherwise cause the unwanted decomposition. The tert-butyl substituent as $R_3$ or $R_4$, together with other structural features, are found to be capable to improve their chemical stability and to allow fine-tuning of their photophysical properties of the as-prepared Ir(III) metal phosphors. Further, substitution of the tert-butyl substituent with an electron-withdrawing $CF_3$ appendage offers a more stabilized π*-orbital, thus offering the further red shifting of emission wavelength and improved photophysical properties of the Ir(III) complex.

It is notable that the majority of the chelates in the preferred embodiments are carbene entities with two structurally distinctive N-aryl substituents, for giving the desired steric and electronic properties. They are incorporated into the carbene chelates for achieving better regioselectivity during syntheses and improved chemical, physical and thermal stabilities to the as-prepared Ir(III) phosphors. Therefore, it is believed that these emitters can be synthesized in a controlled manner and are much suitable in serving as more durable blue emitters for fabrication of OLED devices. These employed N-aryl groups possess different electronic and steric characters. For example, one aryl group is phenyl, while the other is selected from 4-tert-butylphenyl, 5-tert-butylphenyl, 4-tolyl and 4-(2,6-dimethylphenyl)phenyl. These differences will offer a high regioselectivity in formation of structurally distinctive Ir(III) complexes, which can be easily separated using routine processes. It is believed that the electron-rich aryl group reacts relatively faster with the Ir(III) metal center in affording the cyclometalated entity, i.e., the so-called kinetic controlled process, while the electron-deficient aryl group is relatively less reactive, thus forming a more stable cyclometalated entity, i.e., affording the thermodynamically more stable product. Hence, upon employment of these two competing properties, it becomes possible to synthesize the desired blue emissive Ir(III) phosphors with improved emission efficiency and better chemical stability.

Hereinafter, the present invention is described more specifically by way of examples, but the present invention is not limited thereto.

In the following examples, unless stated otherwise, commercially available reagents were used without further purification. All solvents were dried and degassed before used, and all reactions were conducted under $N_2$ and monitored using pre-coated TLC plates (0.20 nm with fluorescent indicator F254). $^1H$ and $^{19}F$ NMR spectra were measured with Bruker Avance III HD 300 MHz NMR or Bruker Avance III 400 MHz NMR instrument. Elemental analysis was carried out on an Elemental Micro Carbon-Hydrogen-Nitrogen Analyzer (Elementar VARIO Micro Cube). Mass spectra were recorded on Applied Biosystems 4800 Plus MALDI TOF/TOF Analyzer (ABI) using 2,5-dihydroxybenzoic acid as the matrix substance. The single crystal X-ray structural analyses were conducted using phi and omega scans mode (APEX3) on a Bruker D8 Venture Photon II diffractometer with microfocus X-ray sources at 233 K. UV-Vis spectra were recorded on a HITACHI UH-4150 spectrophotometer. The steady-state emission spectra were measured with Edinburgh FS 920. Both wavelength-dependent excitation and emission responses of the fluorimeter were calibrated.

The lifetime studies were performed by a time-correlated single photon counting system (TCSPC) with a femtosecond, mode-locked Ti-Sapphire laser that was tuned to 720 nm, followed by the second-harmonic generation (360 nm) via a BBO crystal. The excitation source was then changed into vertical polarization using a half-wave plate. Lastly, a linear polarizer was set as 54.7 degree deviated from the vertical polarization plane in between the sample cell and PMT detector to avoid any emission anisotropy. Spectral grade solvents (Merck) were used as received.

To determine the photoluminescence quantum yield in solution, samples were degassed using at least three freeze-pump-thaw cycles. The solution quantum yields are calculated using the standard sample which has a known quantum yield, according to the following equation:

$$\Phi = \Phi_R \frac{I}{I_R} \frac{A_R}{A} \frac{\eta^2}{\eta_R^2} \quad \text{Equation 1}$$

where Φ is the quantum yield, the subscript R refers to the reference compound of known quantum yield, I is the integrated fluorescence intensity and η is the refractive index of the solvent. A is the absorbance at the excitation wavelength with the value of absorbance around 0.1. The Φ value of studied complexes in PMMA thin film was measured by an integrated sphere.

The radiative lifetimes ($\tau_{rad}$), radiative rate constant ($k_r$) and non-radiative rate constant ($k_{nr}$) of the metal complexes were calculated using the following equations:

$$\tau_{rad}=\tau_{obs}/\Phi \quad \text{Equation 2}$$

$$k_r=\Phi/\tau_{obs} \quad \text{Equation 3}$$

$$k_{nr}=(1-\Phi)/\tau_{obs} \quad \text{Equation 4}$$

Example 1—Purin-8-ylidene-based Ir(III) Metal Complexes 1-mer, 1-fac, 2-mer and 2-fac

Synthesis of tert-butyl-substituted 9H-purin-7-ium pro-chelates (1tBuH$_2$ and 2tBuH$_2$)

Scheme 3

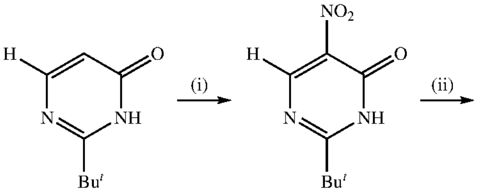

L1

L2

-continued

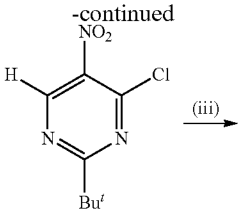

L3

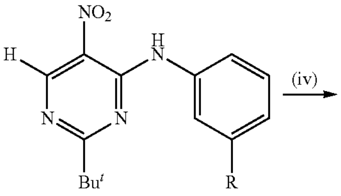

L4a: R = H
L4b: R = $Bu^t$

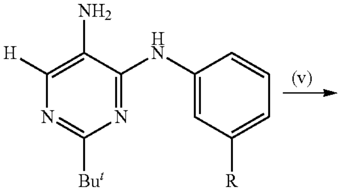

L5a: R = H
L5b: R = $Bu^t$

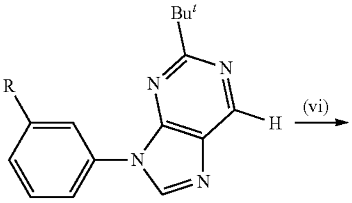

L6a: R = H
L6b: R = $Bu^t$

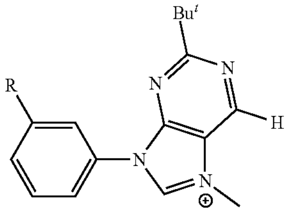

$1tBuH_2$: R = H
$2tBuH_2$: R = $Bu^t$

The functional 9H-purin-7-ium chelates were synthesized using a multi-step protocol, as shown in Scheme 3. Firstly, the key starting material, 2-(tert-butyl)pyrimidin-4(3H)-one (L1), was prepared from condensation of pivalamidine hydrochloride and the in-situ generated sodium salt of ethyl formylacetate.

Conversion of L1 to 2-(tert-butyl)-5-nitropyrimidin-4 (3H)-one (L2) and next to 2-(tert-butyl)-4-chloro-5-nitropyrimidine (L3) were achieved by treatment $KNO_3$ in concentrated sulfuric acid (i), followed by chlorination using phosphorus oxychloride under reflux for 3 hours (ii).

Substitution of the chloro group with aniline and 3-(tert-butyl)aniline was conducted by refluxing ethylene glycol for 12 hours (iii), which gave formation of 2-(tert-butyl)-5-nitro-N-phenylpyrimidin-4-amine (L4a) and 2-(tert-butyl)-N-(3-(tert-butyl)phenyl)-5-nitropyrimidin-4-amine (L4b) in high yields.

Reduction of the nitro substituent was performed with treatment of excessive $SnCl_2.2H_2O$ in methanol solution at RT for 3 hours (iv), giving isolation of 2-(tert-butyl)-$N^4$-phenylpyrimidine-4,5-diamine (L5a) and 2-(tert-butyl)-$N^4$-(3-(tert-butyl)phenyl)pyrimidine-4,5-diamine (L5b), after the routine work-up.

After that, cyclization with formic acid at 120° C. for 12 hours (v) afforded the respective 2-(tert-butyl)-9-phenyl-9H-purine (L6a) and 2-(tert-butyl)-9-(3-(tert-butyl)phenyl)-9H-purine (L6b) in high yields.

Finally, treatment with methyl trifluoromethanesulfonate with toluene at RT for 2 hours (vi) provided the pro-chelates 2-(tert-butyl)-9-phenyl-7-methyl-9H-purin-7-ium ($1tBuH_2$) and 2-(tert-butyl)-9-(3-(tert-butyl)phenyl)-7-methyl-9H-purin-7-ium ($2tBuH_2$), both of which can be employed for the subsequent coordination reaction with iridium metal reagent without further purification.

Synthesis of purin-8-ylidene-based Ir(III) Metal Complexes (1-mer and 1-fac, 2-mer and 2-fac)

A respective mixture of $1tBuH_2$ (1.0 g, 2.4 mmol) and $2tBuH_2$ (1.0 g, 2.4 mmol), $IrCl_3(tht)_3$ (0.39 g, 0.7 mmol) and a promoter (sodium acetate (0.57 g, 6.9 mmol)) in degassed tert-butylbenzene (15 mL) was refluxed overnight under $N_2$. After that, the solvent was removed under vacuum. The residue was dissolved in 100 mL of $CH_2Cl_2$, washed with water, dried over anhydrous $Na_2SO_4$ and then evaporated to dryness. This gave a mixture of f- and m-stereoisomers. The reaction mixture was then purified by column chromatography using petroleum ether/ethyl acetate (4/1, v/v) as eluent to give respective isomeric products, namely: 1-mer (0.4 g, 59%) and 1-fac (0.16 g, 23%), 2-mer (0.4 g, 57%) and 2-fac (0.2 g, 29%). The Ir complexes are provided with 2-(tert-butyl)-7-methyl-9-phenyl-7,9-dihydro-8H-purin-8-ylidene and 2-(tert-butyl)-9-(3-(tert-butyl)phenyl)-7-methyl-7,9-dihydro-8H-purin-8-ylidene coordination entities, respectively. All complexes were further purified by temperature gradient vacuum sublimation.

The combined yields of Ir(III) carbene complexes can go up to as high as about 80% and, after chromatographic separation, m-isomers are found to be approximately two-time in excess than that of corresponding f-counterparts.

Isomerization

Additional f-isomers can be obtained using acid-catalyzed isomerization process. mer-to-fac isomerization was effectively conducted in a mixture of ethyl acetate and trifluoroacetic acid, to which formation of excessive f-substituted derivatives, i.e., both 1-fac and 2-fac, were isolated as main products.

The detail of the isomerization is provided as follows. To a 100 mL sealed tube was added trifluoroacetic acid (4.9 mL, 1M in $H_2O$), ethyl acetate (53 mL), and 1-mer (0.5 g, 0.51 mmol) and 2-mer (0.5 g, 0.43 mmol), respectively. The tube was then filled with $N_2$ and heated at 70° C. for 15 hours. The reaction mixture was cooled to RT and was quenched with 100 mL of water and extracted several times with ethyl acetate. The solvent was removed and the residue was purified by silica gel column chromatography using petroleum ether/ethyl acetate (4/1, v/v) as eluent to give respective isomeric products: 1-mer (0.15 g, 30%) and 1-fac (0.35 g, 70%), 2-mer (0.20 g, 40%) and 2-fac (0.30 g, 60%).

Spectroscopic and Structural Analysis

The structures of each of 1-mer, 1-fac, 2-mer and 2-fac were verified by $^1H$ NMR spectroscopy and MALDI-TOF mass spectrometry, optionally by $^{13}C$ NMR as well. It was expected that the m- and f-isomers possess three distinctive and identical chelates around the Ir(III) metal atom. Hence, the overall pattern and total number of $^{1}H$ NMR signals would be particularly useful in providing the initial structural information.

Selected spectroscopic data for 1-mer is provided as follows: MS (MALDI-TOF, $^{193}Ir$): m/z 989.5334 $[M+H]^+$; $^{1}H$ NMR (400 MHz, acetone-$d_6$) δ 8.94-8.67 (m, 6H), 7.17-6.97 (m, 4H), 6.93-6.84 (m, 1H), 6.76-6.56 (m, 4H), 3.51 (s, 3H), 3.50 (s, 3H), 3.34 (s, 3H), 1.53 (s, 9H), 1.52 (s, 9H), 1.51 (s, 9H).

Selected spectroscopic data for 1-fac is provided as follows: MS (MALDI-TOF, $^{193}Ir$): m/z 989.5133 $[M+H]^+$; $^{1}H$ NMR (400 MHz, acetone-$d_6$) δ 8.82 (d, J=7.4 Hz, 6H), 7.06 (t, J=7.6 Hz, 3H), 6.68 (t, J=7.3 Hz, 3H), 6.68 (t, J=7.3 Hz, 3H), 3.58 (s, 9H), 1.51 (s, 27H). $^{13}C$ NMR (101 MHz, $CDCl_3$) δ 193.68, 172.24, 150.80, 146.63, 145.24, 136.35, 135.52, 125.98, 125.32, 122.13, 115.24, 39.72, 34.26, 30.08.

Selected spectroscopic data for 2-mer is provided as follows: MS (MALDI-TOF, $^{193}Ir$): m/z 1157.7310 $[M+H]^+$; $^{1}H$ NMR (400 MHz, acetone-$d_6$) δ 9.15-8.95 (m, 3H), 8.85 (d, J=5.8 Hz, 2H), 8.79 (s, 1H), 6.91 (d, J=7.6 Hz, 1H), 6.85-6.81 (m, 2H), 6.76 (d, J=7.6 Hz, 2H), 6.58 (d, J=7.7 Hz, 1H), 3.53 (s, 3H), 3.50 (s, 3H), 3.33 (s, 3H), 1.54 (s, 27H), 1.35 (s, 9H), 1.34 (s, 9H), 1.33 (s, 9H).

Selected spectroscopic data for 2-fac is provided as follows: MS (MALDI-TOF, $^{193}Ir$): m/z 1157.7418 $[M+H]^+$; $^{1}H$ NMR (400 MHz, acetone-$d_6$) δ 9.03 (s, 3H), 8.80 (s, 3H), 6.75 (d, J=7.8 Hz, 3H), 6.46 (d, J=7.7 Hz, 3H), 3.59 (s, 9H), 1.54 (s, 27H), 1.36 (s, 27H). $^{13}C$ NMR (101 MHz, $CDCl_3$) δ 194.00, 171.89, 150.70, 146.61, 144.96, 140.95, 135.24, 125.41, 122.97, 112.69, 39.65, 34.43, 34.30, 31.68, 30.07.

Figure 3:
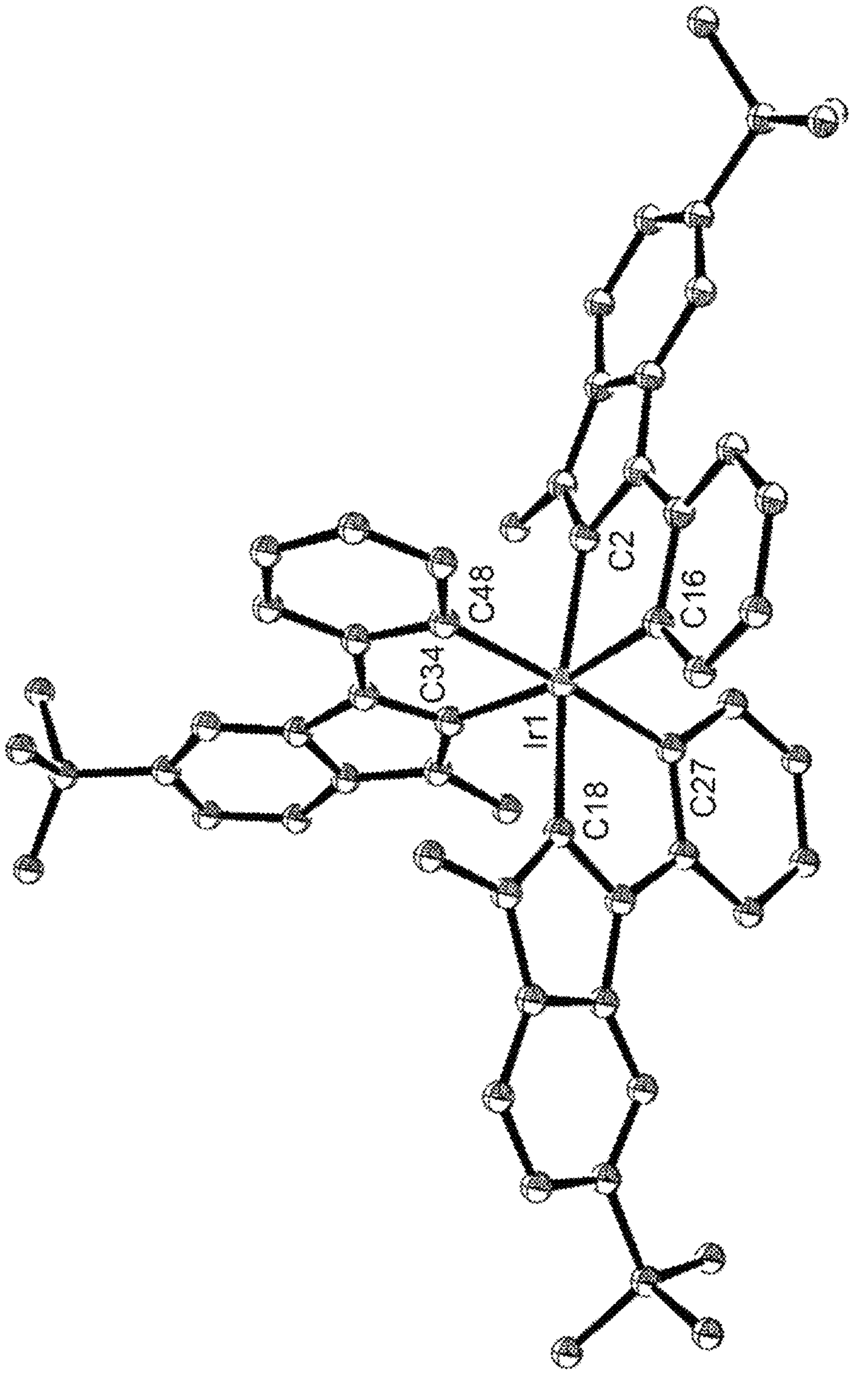
FIG. 3 shows the crystal structural drawing of 1-mer.

Single-crystal X-ray structural analysis was carried out for 1-mer to provide confirmation of the identity of chelates and gross coordination arrangement of these Ir(III) complexes. Ir(III) complex 1-mer existed as two crystallographically distinctive, but structurally identical molecules in the unit cells. FIG. 3 depicts only one of these molecules, to which the Ir(III) atom resides at the center of a slightly distorted octahedral arrangement. FIG. 3 is shown with thermal ellipsoids shown at 30% probability level, with selected bond lengths (Å) of Ir1-C32=2.020(3), Ir1-C48=2.021(3), Ir1-C34=2.092(3), Ir1-C2=2.112(3), Ir1-C16=2.125(3) and Ir1-C18=2.128(3), and selected trans-C—Ir—C bond angles (°) of C32-Ir1-C48=176.45(12), C34-Ir1-C16=168.42(13) and C2-Ir1-C18=172.12(12). Hydrogen atoms are omitted for clarity. The single crystal of 1-mer suitable for X-ray diffraction study was obtained via the slow diffusion of methanol into a saturated $CH_2Cl_2$ solution at RT.

Selected crystal data of 1-mer is provided as follows: CCDC deposition number: 2122409. $C_{48}H_{51}IrN_{12}$; M=988.20; monoclinic; space group=P $2_1/c$; a=27.660(5) Å, b=14.723(2) Å, c=29.679(6) Å; β=106.049(8)°; V=11615(4) $Å^3$; Z=8; $\rho_{calcd}$=1.130 mg·m$^{-3}$; F(000)=4000, crystal size=0.37×0.11×0.03 $mm^3$; λ(Mo—$K_\alpha$)=0.71073 Å; T=243 K; μ=4.740 $mm^{-1}$; 223695 reflections collected, 23507 independent reflections ($R_{int}$=0.0987), max. and min. transmission=0.501 and 0.745, data/restraints/parameters=23507/834/1318, GOF=1.088, final $R_1[I>2\sigma(I)]$=0.0388 and $wR_2$(all data)=0.1076.

As shown, all six Ir—C distances are different, but the unique trans-Ir—C distance (Ir1-C34=2.092(3) Å) is found to be notably shorter than the corresponding trans-Ir—C distance of phenyl cyclometalates (Ir1-C16=2.125(3) Å), which are in accordance with the metric features of many known homoleptic Ir(III) carbene cyclometalates. They can be also understood in terms of the enhanced bonding interaction between the metal $d_\pi$-orbital and empty $\pi^*$-orbital of 9H-purin-7-ium fragments.

Photophysical Analysis

Figure 4:
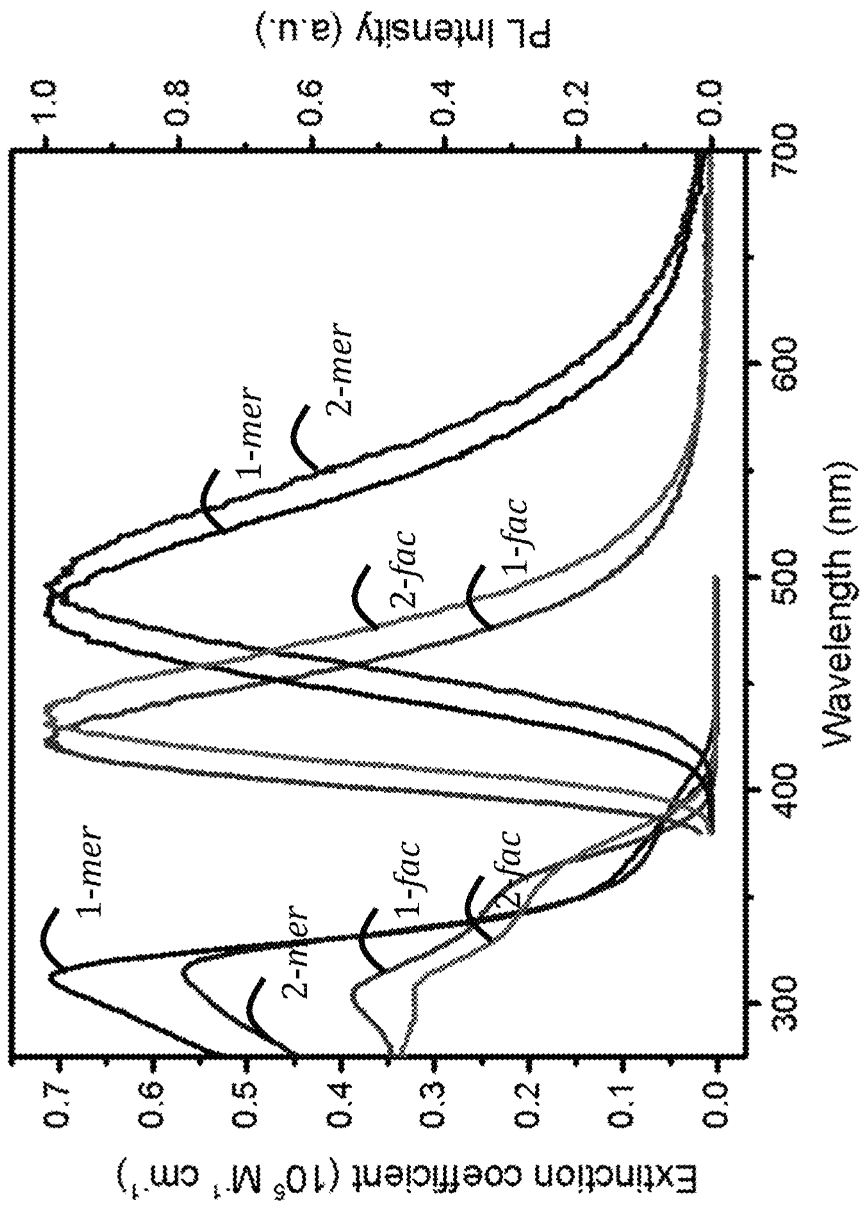
FIG. 4 shows the UV-Vis absorption and photoluminescence spectra of different purin-8-ylidene-based Ir(III) metal complexes in toluene at room temperature (RT)

FIG. 4 depicts the UV-Vis absorption of the above tris-bidentate Ir(III) complexes in degassed toluene at RT. As shown, the absorption bands with wavelengths below 340 nm are attributed to the ligand centered as well as inter-ligand $\pi\pi^*$ transitions, among which the mer-isomers showed a much larger extinction coefficient in comparison to their fac-counterparts. Further, at the longer wavelength region, the mer-isomers exhibited the relatively less intense and more red-shifted metal-to-ligand charge transfer (MLCT) absorption peaks vs. the respective fac-isomers. Without wishing to be bound by theories, this spectral pattern is believed to be related to the asymmetric arrangement of all coordinated carbene chelates and, to be universal to the relevant existing Ir(III) carbene complexes.

Also shown in FIG. 4 is their emission spectra which were measured in degassed toluene solution at RT. As shown in FIG. 4 and Table 2, both mer-isomers exhibited structureless emission profile with onset at about 410-420 nm and relatively more red-shifted peak max. at 483 nm and 496 nm, respectively. Further, the corresponding fac-isomers showed a much blue-shifted emission onset at about 380-390 nm, peak max. at 423 nm and 436 nm, and a significantly reduced full width at half maximum (FWHM) of 62 nm and 77 nm in comparison to the mer-isomers with identical carbene chelates (of about 100 nm). Moreover, those with 3-(tert-butyl)phenyl cyclometalate entities (i.e. both 2tBu derivatives) have showed more red-shifted peak wavelength in comparison with the parent 1tBu complexes with a phenyl substituent, which is a result of greater electron density at the Ir(III) metal center and more notably MLCT transition character.

The photoluminescence quantum yields (PLQYs; Φ) were measured. Particularly, the m-isomers were more efficient than their f-counterparts. Their radiative lifetimes ($\tau_{rad}$), radiative rate constant ($k_r$) and non-radiative rate constant ($k_{nr}$) were calculated and the data were listed in Table 2. The PLQYs span the region 43-92%, to which the smallest and the highest PLQY seems to coincide to those with the greatest and smallest emission energy, i.e. PL $\lambda_{max}$ at 423 nm and 496 nm, respectively. Those with more red-shifted emission peak also exhibited shortened radiative lifetime, which is in accordance with the greater MLCT contribution at the excited state manifold. It is believed that the abnormal large FWHM and red shifting in wavelengths of mer-isomers were due to the solvation effect imposed to the greater asymmetric molecules, i.e. mer-isomers, to which the degree of MLCT contribution is expected to be greater than that of the corresponding fac-isomers. This hypothesis can be confirmed using the photophysical data in rigid PMMA matrix (Table 3), to which the mer-isomers reveals a large blue shift in emission peak max. of 23 nm and 26 nm versus the respective fac-isomers, which exhibited the red shifted peak max. of 2 nm and 4 nm, i.e., in the opposite direction.

TABLE 2

Photophysical data of the purin-8-ylidene-based Ir(III) metal complexes at RT.

| Complex | abs $\lambda_{max}$[a] (nm) | PL $\lambda_{max}$[a] (nm) | FWHM[b] ($cm^{-1}$/nm) | $\Phi$[c][d] (%) | $\tau_{obs}$[d] (μs) | $\tau_{rad}$[d] (μs) | $k_r$ ($10^6$ $s^{-1}$) | $k_{nr}$ ($10^6$ $s^{-1}$) |
|---|---|---|---|---|---|---|---|---|
| 1-mer | 312 (9.92), 380 (1.00) | 483 | 4110/100 | 75 | 0.77 | 1.0 | 1.0 | 0.3 |
| 1-fac | 304 (5.46), 350 (3.31) | 423 | 3290/62 | 43 | 0.52 | 1.2 | 0.83 | 1.1 |
| 2-mer | 315 (7.95), 382 (0.92) | 496 | 3990/101 | 92 | 0.89 | 0.97 | 1.0 | 0.1 |
| 2-fac | 305 (4.55), 350 (2.78) | 436 | 3350/77 | 62 | 0.66 | 1.1 | 0.91 | 0.59 |

[a]Recorded at a concentration of $10^{-5}$M in toluene at RT; extinction coefficient (ε) is given in parentheses with a unit of $10^4$ $M^{-1}\cdot cm^{-1}$.
[b]Full width at half maximum.
[c]Quinine sulfate (QS) in 0.1M, sulfuric acid aqueous solution (Q.Y. = 54% and $\lambda_{max}$ = 455 nm) were employed as standard.
[d]Recorded in degassed toluene at a concentration of $10^{-5}$M at RT.

TABLE 3

Photophysical data of the purin-8-ylidene-based Ir(III) metal complexes in spin-casted PMMA thin film at RT (2 wt. %).

| Complex | PL $\lambda_{max}$[a] (nm) | FWHM[b] ($cm^{-1}$) | $\Phi$[c][d] (%) | $\tau_{obs}$[d] (μs) | $\tau_{rad}$[d] (μs) | $k_r$ ($10^6$ $s^{-1}$) | $k_{nr}$ ($10^6$ $s^{-1}$) |
|---|---|---|---|---|---|---|---|
| 1-mer | 460 | 4734 | 64 | 0.61 | 0.96 | 1.04 | 0.60 |
| 1-fac | 425 | 3958 | 60 | 0.68 | 1.13 | 0.88 | 0.59 |
| 2-mer | 470 | 4049 | 46 | 0.68 | 1.47 | 0.68 | 0.79 |
| 2-fac | 440 | 4753 | 59 | 0.66 | 1.12 | 0.89 | 0.63 |

[a]Recorded at a concentration of $10^{-5}$M in toluene at RT.
[b]Full width at half maximum.
[c]Quinine sulfate (QS) in 0.1M, sulfuric acid aqueous solution (Q.Y. = 54% and $\lambda_{max}$ = 455 nm) were employed as standard.
[d]Recorded in degassed toluene at a concentration of $10^{-5}$M at RT.

Electroluminescence Analysis

To investigate the electroluminescent (EL) properties of NHC-based Ir(III) metal phosphors, due to their relatively promising luminescent properties as discussed above, fabrication of blue OLEDs was conducted using two better emitters 2-mer and 2-fac, as the solely dopant phosphor in the emissive layer and, as triplet sensitizer to convey the excitation energy through FRET to the boron-nitrogen-based TADF emitter ν-DABNA in achieving the true blue emission with narrowed emission bandwidth.

Figure 5:
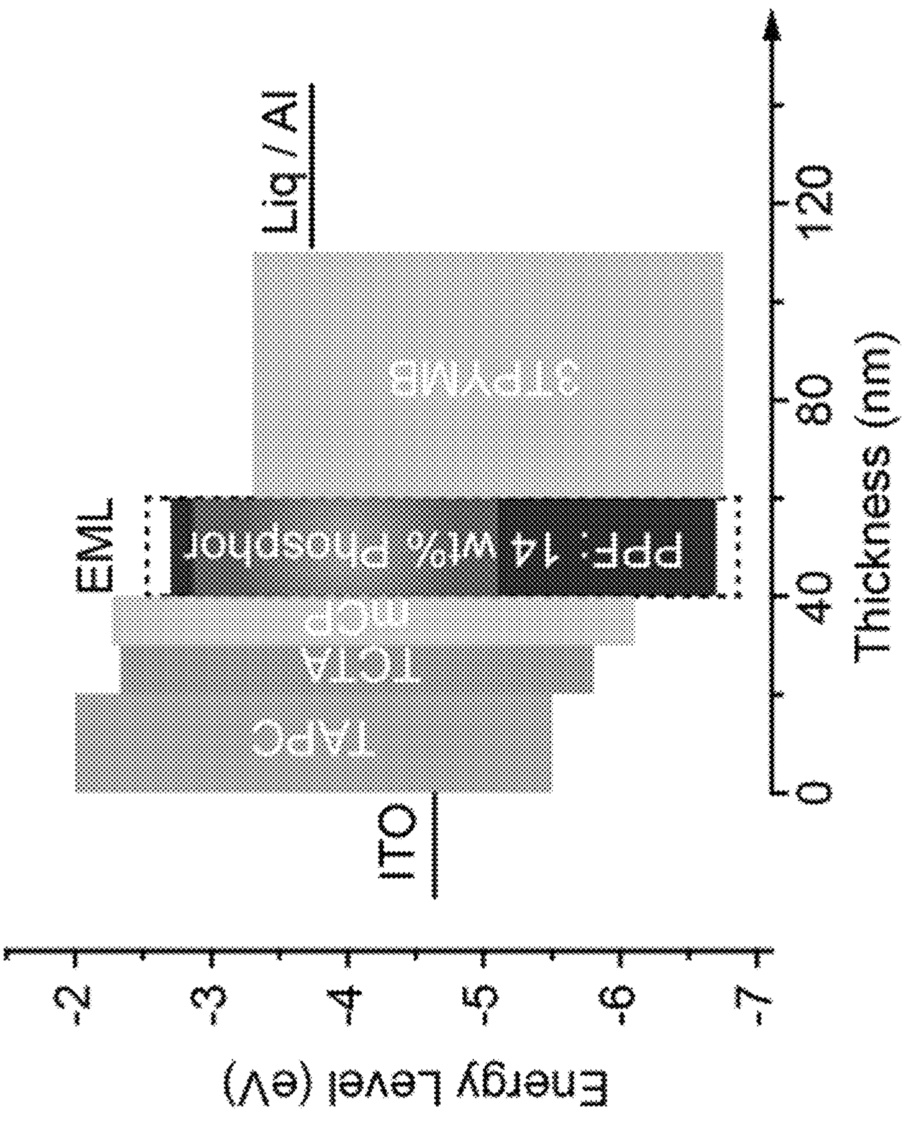
FIG. 5 is a schematic diagram of energy level alignments of OLEDs containing a purin-8-ylidene-based Ir(III) metal complex.

As shown in FIG. 5, the device structure consists of and is constructed with the following in sequential order: an indium tin oxide (ITO) electrode, 1,1-bis((di-4-tolylamino)phenyl)cyclohexane (TAPC; 20 nm), 4,4',4"-tris(54 ommercia-9-yl)-triphenylamine (TCTA; 10 nm), 1,3-di(9H-carbazol-9-yl)benzene (mCP; 10 nm), 2,8-bis(diphenylphosphino oxide) dibenzofuran (PPF): 14 wt % Ir(III) complexes (20 nm), tris(2,4,6-trimethyl-3-(54 ommerci-3-yl)phenyl)borane (3TPYMB; 40 nm), lithium fluoride (LiF; 1 nm), and an aluminum electrode. In this device, TAPC and 3TPYMB were used as hole- and electron-transporting materials, respectively. TCTA and mCP functioned as electron- and exciton-blocking materials, respectively. LiF was the electron-injection layer, and PPF served as host material for the devices.

Figure 6:
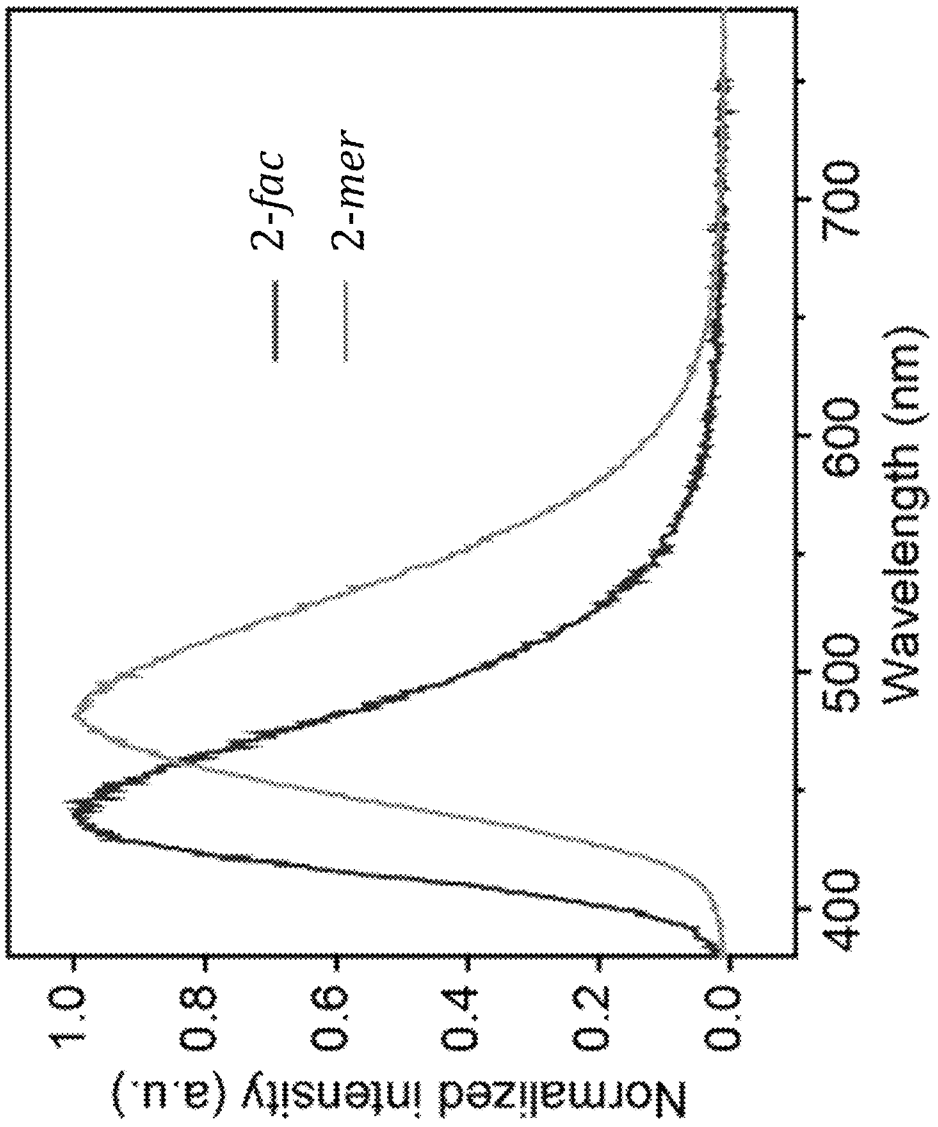
FIG. 6 shows the normalized electroluminescence spectra of a 2-mer-based OLED and a 2-fac-based OLED.
Figure 7:
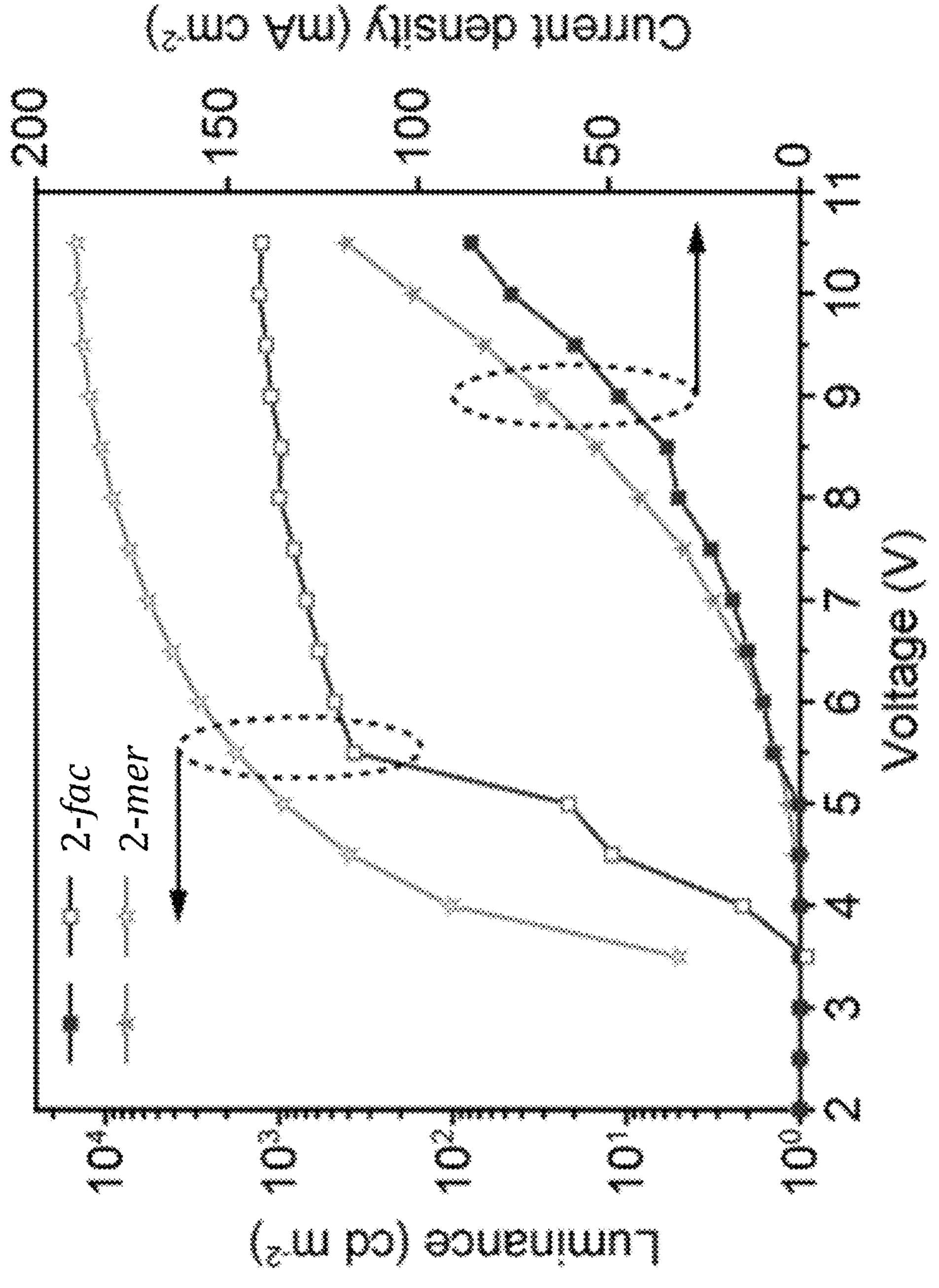
FIG. 7 is a graph showing the current density-voltage-luminance (J-V-L) characteristics of the 2-mer-based OLED and the 2-fac-based OLED.
Figure 8:
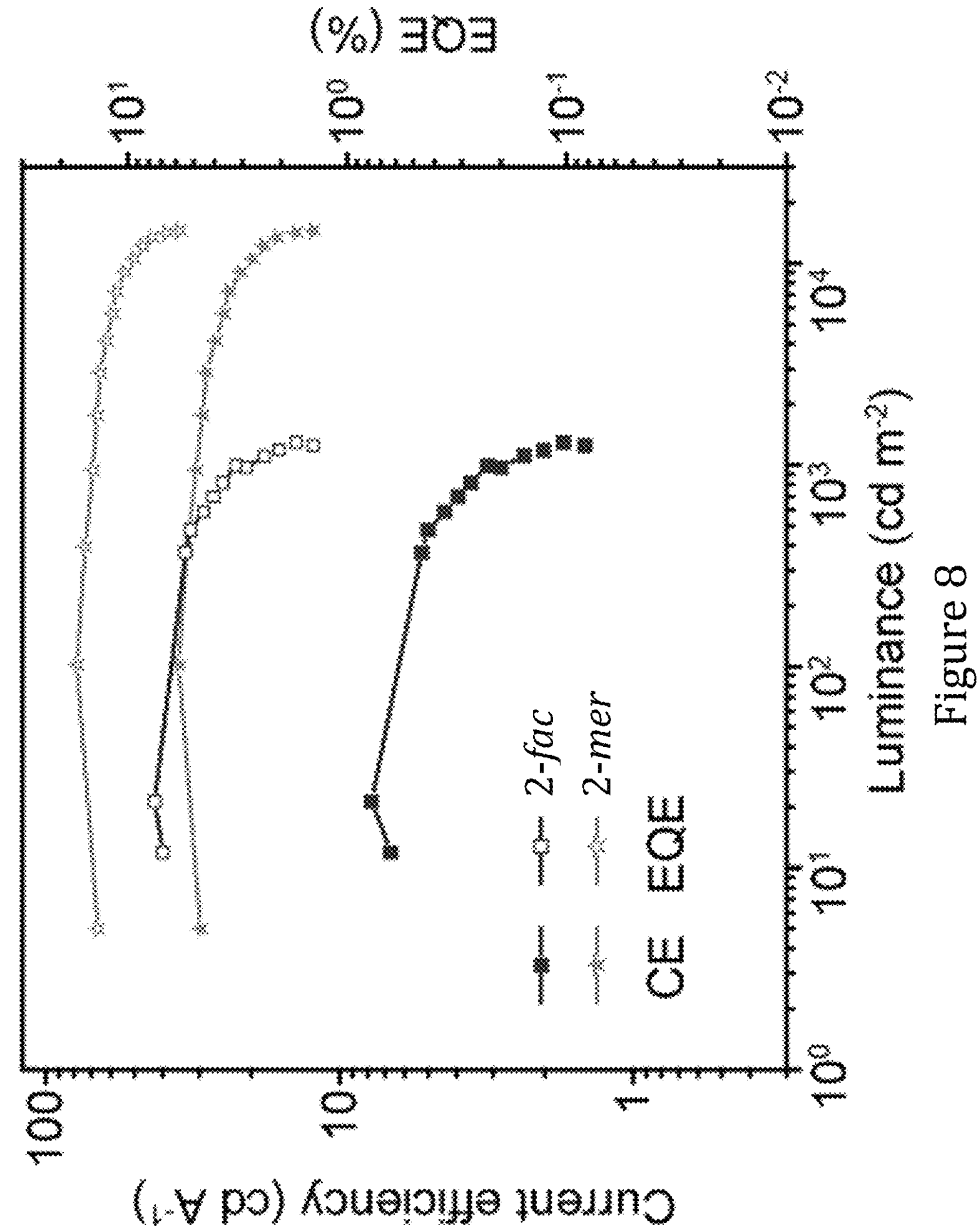
FIG. 8 is a graph showing the current density-luminance-external quantum efficiency (EQE) of the 2-mer-based OLED and the 2-fac-based OLED.

The electroluminescent characteristics and related data are shown in FIGS. 6 to 8 and Table 4.

TABLE 4

Electroluminescence data of the OLED devices.

| Sample | $V_{on}$ [V] | EL $\lambda_{max}$ [nm] | CE[a] [cd $A^{-1}$] | EQE[a] [%] | $CIE_{xy}$[b] |
|---|---|---|---|---|---|
| 2-fac | 3.6 | 440 | 7.7, 6.4, 3.1 | 7.5, 6.1, 2.8 | 0.157, 0.120 |

TABLE 4-continued

Electroluminescence data of the OLED devices.

| Sample | $V_{on}$ [V] | EL $\lambda_{max}$ [nm] | CE[a] [cd $A^{-1}$] | EQE[a] [%] | $CIE_{xy}$[b] |
|---|---|---|---|---|---|
| 2-mer | 3.5 | 482 | 35.2, 35.3, 30.2 | 17.0, 16.9, 14.2 | 0.189, 0.316 |
| 14 wt % 2-mer: 2 wt % v-DABNA | 35 | 472 | 22.4, 21.7, 15.9 | 19.6,19.0, 15.6 | 0.122, 0.161 |
| 25 wt % 2-mer: 2 wt % v-DABNA | 3.5 | 472 | 23.49, 19.7, 16.2 | 22.0,18.9, 14.9 | 0.120, 0.155 |
| 40 wt % 2-mer: 2 wt% v-DABNA | 3.5 | 472 | 22.89, 18.1, 7.8 | 21.7,17.8, 6.9 | 0.122, 0.162 |

[a]Maximum; Recorded at 100 and 1000 cd $m^{-2}$, respectively.
[b]Recorded at 100 cd $m^{-2}$ As shown in FIG. 6, the 2-fac-based device delivered true-blue emission with peaks at 440 nm and CIE coordinates of (0.157, 0.120). A fast efficiency roll-off is observed in this device (EQE from 7.5 to 2.8% at the maximum and 1000 cd $m^{-2}$), which is believed to relate to exciton leakage from 2-fac (triplet energy, ET=3.1 eV) to mCP (ET=2.91 eV) and 3TPYMB (ET=2.95 eV). EL emission of 2-mer gave a peak max. at 482 nm, which has a hypsochromic shift of 14 nm compared to its PL spectrum in toluene solution (Table 2). This is believed to be related to the greater solvation effect that induced by the MLCT character in solution and the rigid environment that restricted CT reorganization in PPF host matrix.

Moreover, only the characteristic emission bands of phosphors were observed in these OLED devices, indicating efficient energy transfer from the host material to phosphor. The current density-voltage-luminance (J-V-L) characteristics and the current density-luminance-EQE characteristics of these devices are depicted in FIGS. 7 and 8, respectively. Decent performance can be observed in 2-mer-based device with turn-on voltages of 3.5 V, maximum current efficiencies of 35.2 cd/$m^2$, and maximum EQE reached as high as 17.0%.

Hyperphosphorescent system can promote efficient energy transfer from the triplet excited states of the sensitizer to the singlet excited states of the fluorophore, giving significantly improved efficiency and operational lifetime of the fabricated device. Its working principle has been successfully applied in fabrication of a few phosphor-sensitized fluorescent and TADF-based OLED devices.

Figure 9:
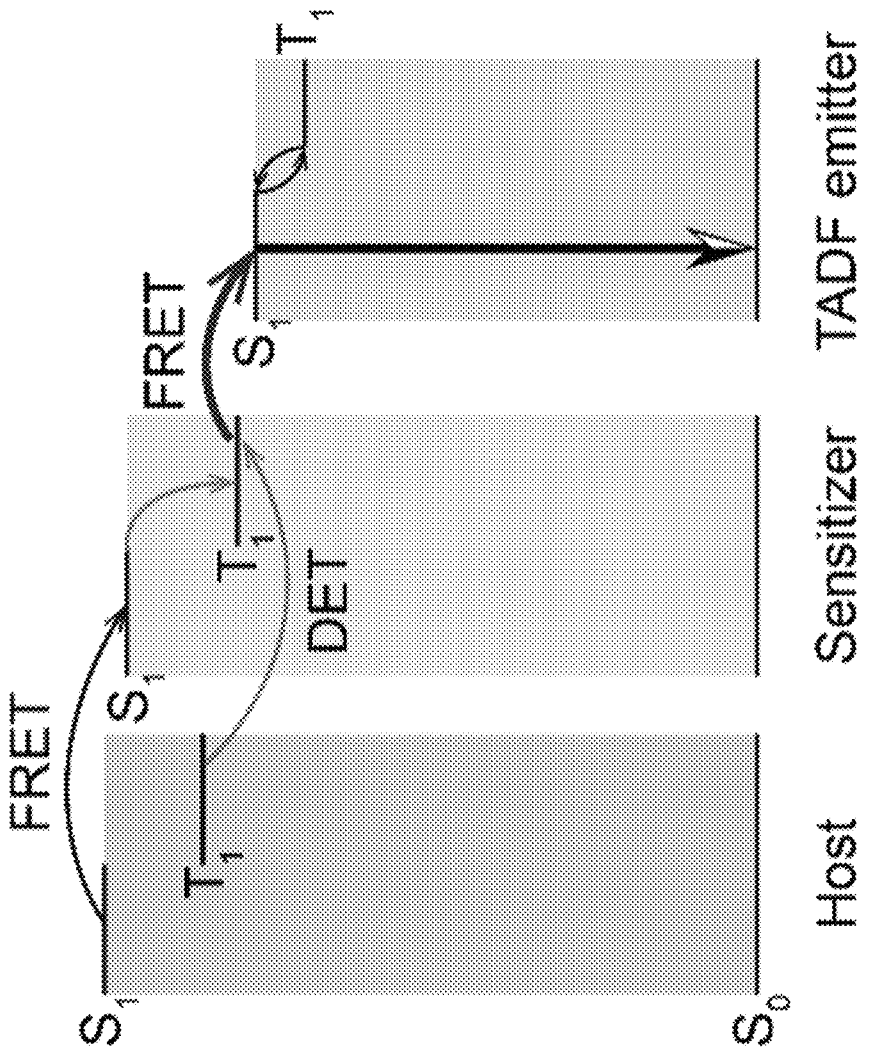
FIG. 9 is a schematic diagram of hyperphosphorescent OLED containing a purin-8-ylidene-based Ir(III) metal complex.

The energy transfer mechanism of the hyperphosphorescent OLEDs is schematically depicted in FIG. 9. In this example, ν-DABNA was selected as the terminal emitter for its high EQE, narrowed emission band, and shortened fluorescence lifetime. It is expected that Förster resonant energy transfer (FRET) from 2-mer to ν-DABNA could give efficient harvest of triplet excitons for emission because of the large overlap between the emission spectrum of 2-mer and the absorption spectrum of ν-DABNA and faster radiative transition rate of 2-mer. Moreover, the Dexter energy transfer (DET) is believed to be suppressed owing to the introduction of bulky tert-butyl groups of 2-mer in keeping the larger intermolecular separation, and lowered doping concentration of ≤2 wt % for the terminal emitter ν-DABNA.

Figure 10:
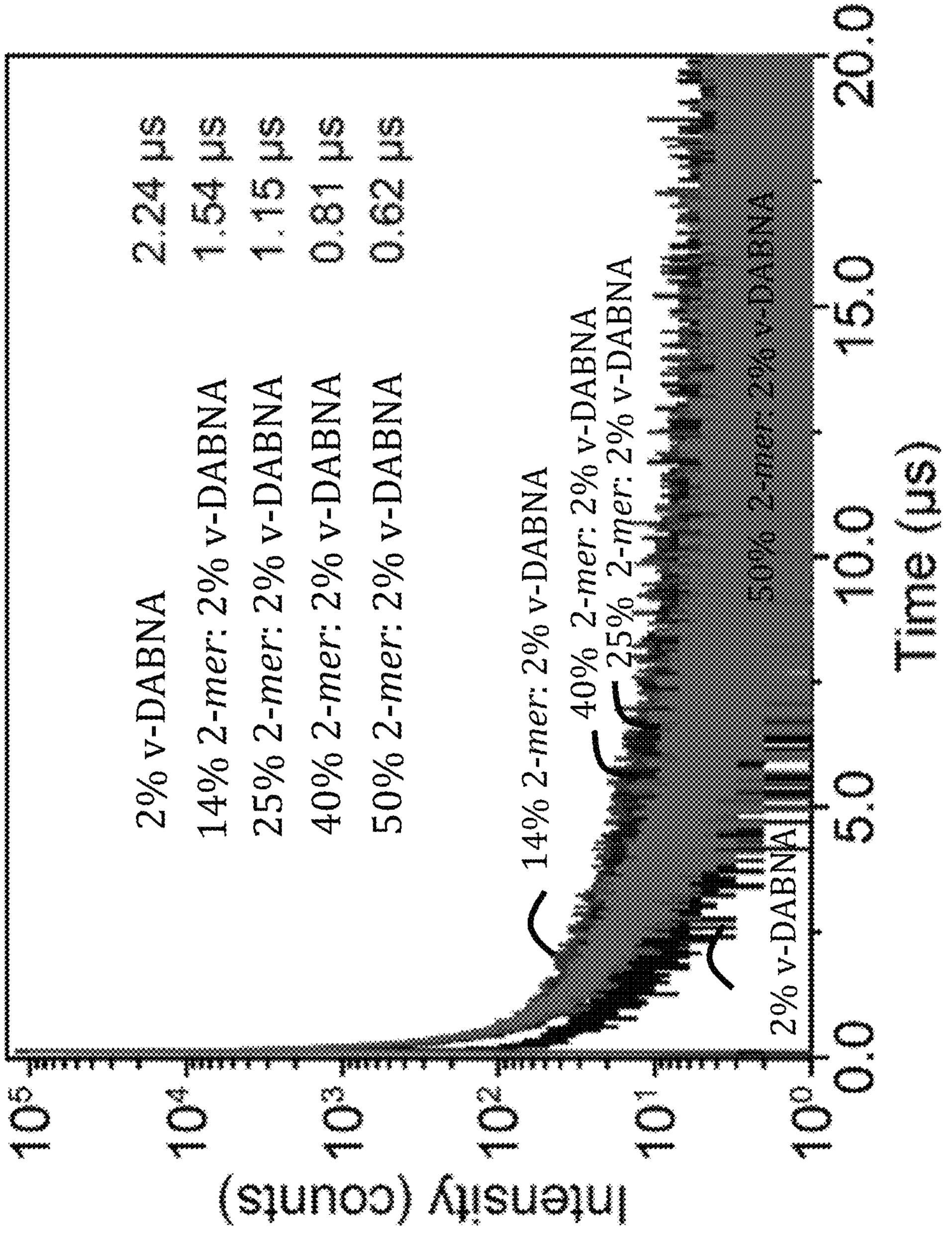
FIG. 10 shows the transient photoluminescence (PL) decay curves of the light emitting layer of an OLED with different doping contents of 2-mer.

As shown in FIG. 10, the transient decay lifetimes of ν-DABNA-based emission were notably reduced from 2.24 μs to 0.62 μs without showing any broadened emission bandwidth of the ν-DABNA-based emission, upon increasing the doping concentration of 2-mer from 14 wt % up to 50 wt %. Meanwhile, the contribution percentage of the fast (prompt) decay component with a nearly constant lifetime of about 72 ns for a range of concentration from 32% to 58%, indicating the efficient FRET from Ir(III) sensitizer 2-mer to the terminal emitter ν-DABNA.

It is expected that the decreases in the long emission lifetimes from transient decay measurement would implicate a further improvement in efficiency of doped OLED devices. Therefore, the phosphor 2-mer was employed as assistant sensitizer in fabrication of hyperphosphorescent OLED devices. The modified device architecture is similar to the above OLED architecture, consisting of: ITO/TAPC (20 nm)/TCTA (10 nm)/mCP (10 nm)/PPF: 14~40 wt % 2-mer: ν-DABNA 2 wt % (20 nm)/3TPYMB (40 nm)/LiF (1 nm)/Al.

Figure 11:
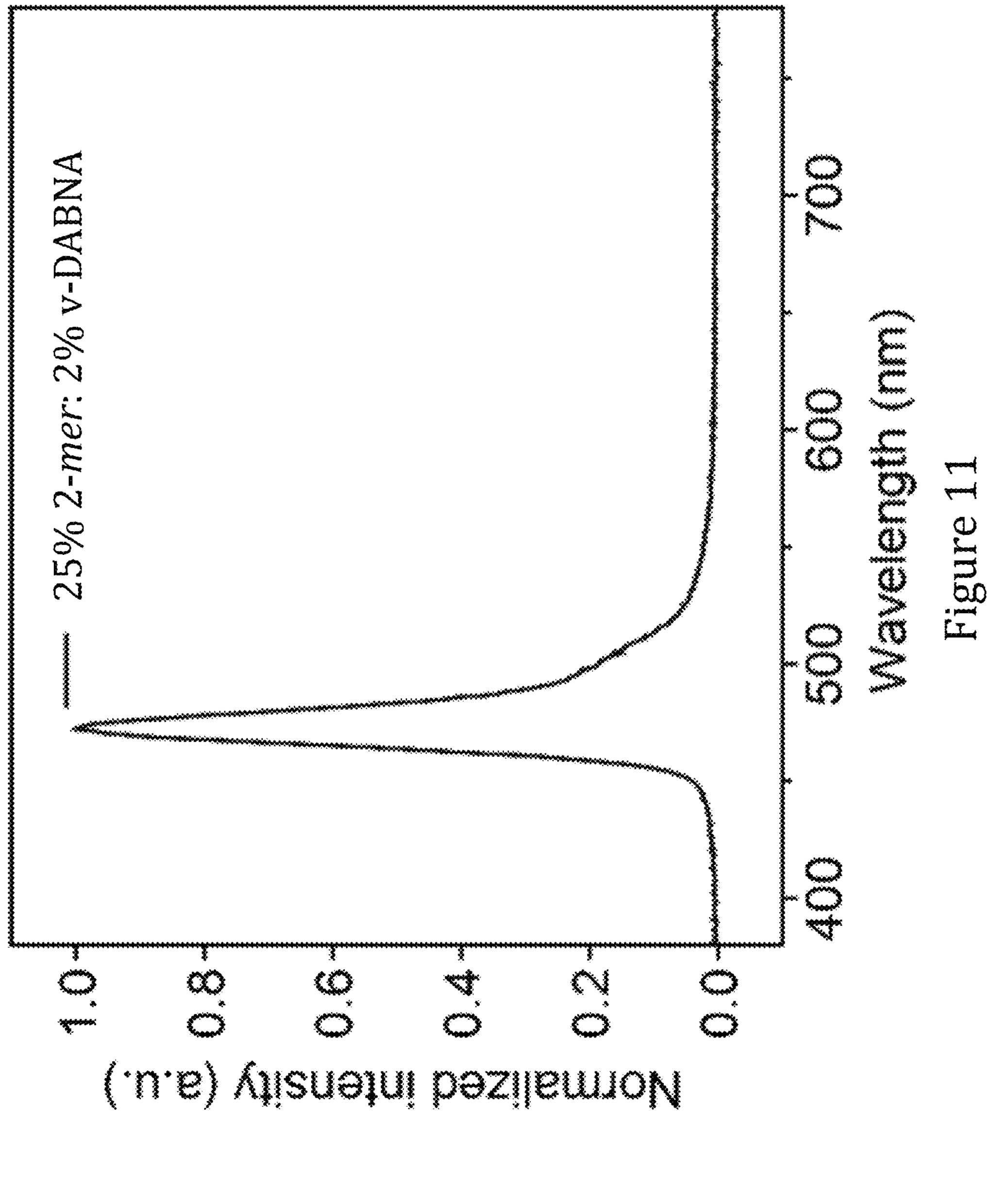
FIG. 11 shows the electroluminescent spectrum of a 2-mer-based OLED.
Figure 12:
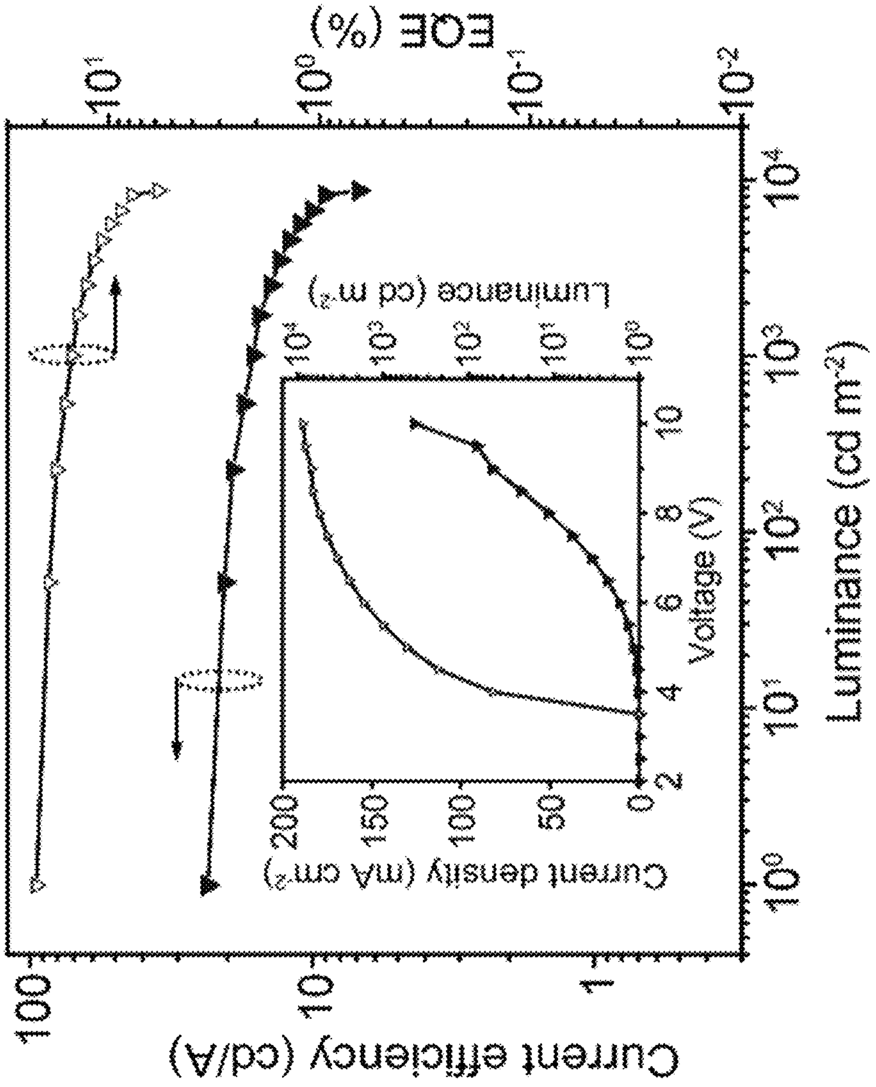
FIG. 12 is a graph showing the current density-voltage-luminance (inset) and current efficiency-luminance-EQE curves of the 2-mer-based OLED.

As can be seen from FIGS. 11 and 12, efficient energy transfer from assistant dopant 2-mer to terminal emitter ν-DABNA was confirmed by the EL spectrum, whereas only the emission of ν-DABNA was observed with a narrowed full width at half maximum (FWHM) of 21 nm for all devices. At the assistant dopant concentration of 25 wt %, both the efficient energy transfer process and excellent PL properties of ν-DABNA further push up the OLED performance to a max. EQE of 22.0%, CIE (x- and y-) coordinates of (0.122, 0.155), and a reduced efficiency roll-off, with EQE=14.9% at 1000 cd $m^{-2}$, highlighting the validity of hyperphosphorescence. Moreover, lowered device efficiencies were next obtained upon further increasing the concentration of assistant sensitizer to 40 wt %, which could be due to the triplet-triplet annihilation and triplet-polaron quenching that typically occurred at the higher doping concentration of phosphors.

Example 2—Purin-8-ylidene-based Ir(III) Metal Complexes 5-mer, 5-fac, 6-mer and 6-fac

Synthesis of $CF_3$-Substituted 9H-purin-7-ium Pro-Chelate (A4)

Scheme 4

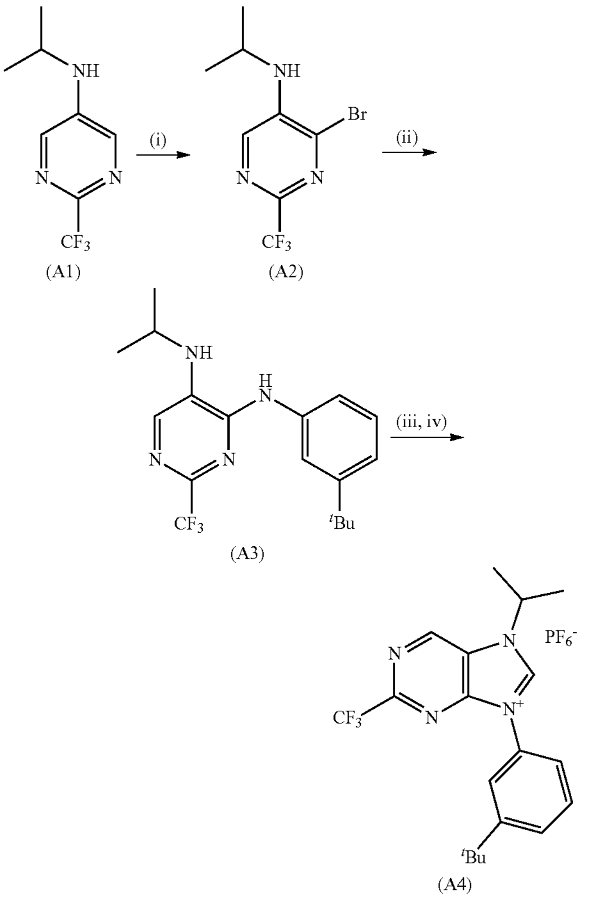

(A1) (A2) (A3) (A4)

The $CF_3$-functionalized 9H-purin-7-ium pro-chelate was synthesized using a simple synthetic protocol as depicted in Scheme 4. Firstly, N-isopropyl-2-(trifluoromethyl)pyrimidin-5-amine (A1) was prepared from treatment of commercially available 5-bromo-2-(trifluoromethyl)pyrimidine with isopropylamine upon heating.

Subsequent bromination of A1 with N-bromosuccinimide (NBS) at RT for 12 hours (i) afforded 4-bromo-N-isopropyl-2-(trifluoromethyl)pyrimidin-5-amine (A2), which was then converted to $N^4$-(3-(tert-butyl)phenyl)-$N^5$-isopropyl-2-(trifluoromethyl)pyrimidine-4,5-diamine (A3) upon treatment with 3-tert-butylaniline at RT for 12 hours (ii).

After that, condensation of A3 with formic acid at 150° C. for 12 hours (iii), followed by metathesis with an aliquot of $KPF_6$ solution and MeOH at RT (iv) yielded the $CF_3$-substituted 9H-purin-7-ium hexafluorophosphate (A4), which can be employed for subsequent reaction without further purification.

Synthesis of purin-8-ylidene-based Ir(III) Metal Complexes (5-mer)

A mixture of A4 (1.0 g, 1.97 mmol), $IrCl_3(tht)_3$ (0.32 g, 0.56 mmol) and a promoter, i.e. NaOAc (1.6 g, 5.6 mmol), in tert-butylbenzene (10 mL) was refluxed overnight under $N_2$. After that, the solvent was removed under vacuum. The residue was dissolved in 30 mL of $CH_2Cl_2$, washed with water, dried over anhydrous $Na_2SO_4$ and then evaporated to dryness. The residue was purified by column chromatography using a mixture of petroleum ether and ethyl acetate (4/1, v/v) as eluent to give tris(9-(3-(tert-butyl)phenyl)-7-isopropyl-2-(trifluoromethyl)-9H-purin-7-ium)iridium(III), 5-mer (0.43 g, 60%) as the major product. It can be further purified by recrystallization from a mixed solution of $CH_2Cl_2$ and methanol, followed by vacuum sublimation.

Synthesis of purin-8-ylidene-based Ir(III) Metal Complexes (5-fac)

To a 100 mL sealed tube was added 5-mer (0.5 g, 0.39 mmol), 4.9 mL of trifluoroacetic acid (1M in $H_2O$) and 50 mL ethyl acetate. The tube was then sealed under $N_2$ and heated at 70° C. for 48 h. After cooled to RT, the mixture was taken into excess of ethyl acetate, and washed with deionized water three times. The solvent was removed, and the residue was purified by silica gel column chromatography using a mixture of petroleum ether and ethyl acetate (4/1, v/v) as eluent to give 5-fac (0.35 g, 70%). It can be further purified by recrystallization from a mixed solution of $CH_2Cl_2$ and methanol, followed by vacuum sublimation

Synthesis of $CF_3$-Substituted 9H-purin-7-ium Pro-Chelate (B7)

Scheme 5

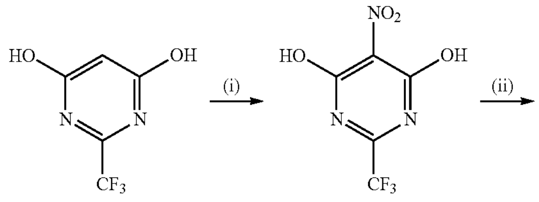

(B1) (B2)

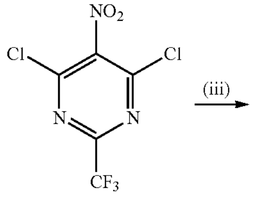

(B3)

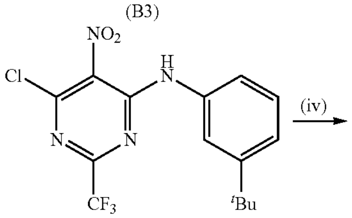

(B4)

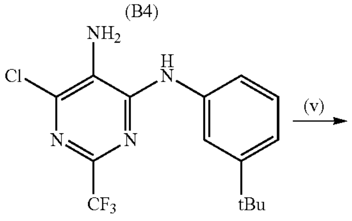

(B5)

-continued

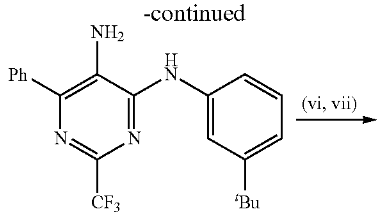

(B6)

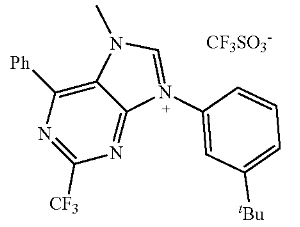

(B7)

Compared with Scheme 4, synthesis of 9H-purin-7-ium pro-chelate (B7) was relatively more complicated and required a different starting material, 2-(trifluoromethyl)pyrimidine-4,6-diol (B1), as shown in Scheme 5. After that, nitration with $HNO_3$ and $CF_3CO_2H$ at RT (i) and chlorination with $POCl_3$ and dimethylaniline at 80° C. (ii) gave sequential formation of 5-nitro-2-(trifluoromethyl)pyrimidine-4,6-diol (B2) and 4,6-dichloro-5-nitro-2-(trifluoromethyl)pyrimidine (B3) in adequate yields.

Substitution of one chloro substituent of B3 with 3-(tert-butyl)aniline was conducted at −80° C. (with THF) (iii), giving N-(3-(tert-butyl)phenyl)-6-chloro-5-nitro-2-(trifluoromethyl)pyrimidin-4-amine (B4), while reduction of the nitro group with Fe, in the presence of $NH_4Cl$, $H_2O$, THF, and MeOH at 80° C. (iv) afforded corresponding 6-chloro-2-(trifluoromethyl)pyrimidine-4,5-diamine (B5) in good yields. Then, the remaining chloro substituent of B5 was replaced with phenyl boronic acid ($PhB(OH)_2$) in the presence of $Pd(PPh_3)_4$, $Na_2CO_3$, $H_2O$ and toluene at 90° C. (v) in giving 6-phenyl-2-(trifluoromethyl)pyrimidine-4,5-diamine (B6).

Finally, cyclization of B6 with formic acid at 120° C. (vi), followed by N-methylation with $CF_3SO_3Me$ in the presence of toluene at RT (vii) afforded the $CF_3$-substituted 9H-purin-7-ium pro-chelate (B7), which is different from the pro-chelate A4 in Example 2 with a phenyl group located at the peripheral of 9H-purin-7-ium entity.

Synthesis of purin-8-ylidene-based Ir(III) Metal Complexes (6-mer and 6-fac)

A mixture of B7 (1.0 g, 1.79 mmol), $IrCl_3(tht)_3$ (0.29 g, 0.51 mmol) and a promoter, i.e. NaOAc (0.42 g, 5.1 mmol), in tert-butylbenzene (30 mL) was refluxed overnight under $N_2$. After that, the solvent was removed under vacuum. The residue was dissolved in 30 mL of $CH_2Cl_2$, washed with water, dried over anhydrous $Na_2SO_4$ and then evaporated to dryness. The residue was purified by column chromatography using a mixture of petroleum ether and ethyl acetate (4/1, v/v) as eluent, giving two light yellow Ir(III) complexes: 6-mer (0.36 g, 50%) and 6-fac (0.14 g, 20%), in an approximate ratio of 5:2. Additional 6-fac can be obtained using acid-catalyzed isomerization process. They can be further purified by recrystallization from a mixed solution of $CH_2Cl_2$ and methanol, followed by vacuum sublimation.

Spectroscopic and Structural Analysis

The structures of each of 5-mer, 5-fac, 6-mer and 6-fac were verified by $^1H$ NMR spectroscopy and MALDI-TOF mass spectrometry. It was expected that the m- and f-isomers possess three distinctive and identical chelates around the Ir(III) metal atom. Hence, the overall pattern and total number of $^1H$ NMR signals would be particularly useful in providing the initial structural information.

Selected spectroscopic data for 5-mer is provided as follows: $^1H$ NMR (400 MHz, acetone-$d_6$) δ 9.38 (s, 1H), 9.36 (s, 1H), 9.34 (s, 1H), 9.01 (d, J=1.8 Hz, 1H), 8.99 (d, J=1.9 Hz, 1H), 8.93 (d, J=2.0 Hz, 1H), 7.12 (d, J=7.7 Hz, 1H), 6.88 (d, J=1.9 Hz, 1H), 6.86 (d, J=1.9 Hz, 1H), 6.82 (d, J=7.7 Hz, 1H), 6.72 (d, J=7.8 Hz, 1H), 6.63 (d, J=7.8 Hz, 1H), 4.93-4.86 (m, 1H), 4.81-4.74 (m, 1H), 4.71-4.64 (m, 1H), 1.90 (d, J=7.0 Hz, 3H), 1.54 (d, J=7.0 Hz, 3H), 1.45 (d, J=7.0 Hz, 3H), 1.35 (s, 9H), 1.34 (s, 18H), 0.99 (d, J=7.0 Hz, 3H), 0.87 (d, J=6.9 Hz, 3H), 0.81 (d, J=7.0 Hz, 3H). $^{19}F$ NMR (376 MHz, acetone-$d_6$) δ −69.47 (s, 3F), −69.54 (s, 3F), −69.61 (s, 3F). MALDI-TOF-MS $[M+H]^+$: calculated: ($C_{54}H_{53}F_9IrN_{11}$) 1219.40; found: 1219.30.

Selected spectroscopic data for 5-fac is provided as follows: $^1H$ NMR (400 MHz, acetone-$d_6$) δ 9.35 (s, 3H), 8.94 (d, J=1.8 Hz, 3H), 6.77 (dd, J=1.8 Hz, J=7.8 Hz, 3H), 6.36 (d, J=7.8 Hz, 3H), 4.85-4.78 (m, 3H), 1.83 (d, J=7.1 Hz, 9H), 1.33 (s, 27H), 0.98 (d, J=6.9 Hz, 9H). $^{19}F$ NMR (376 MHz, acetone-$d_6$) δ −69.50 (s, 9F). MALDI-TOF-MS $[M+H]^+$: calculated: ($C_{54}H_{53}F_9IrN_{11}$) 1219.40; found: 1218.52.

Selected spectroscopic data for 6-mer is provided as follows: $^1H$ NMR (400 MHz, acetone-$d_6$) δ 8.98 (d, J=1.9 Hz, 1H), 8.95 (d, J=1.9 Hz, 1H), 8.93 (d, J=1.9 Hz, 1H), 7.73-7.71 (m, 2H), 7.63-7.61 (m, 2H), 7.59-7.46 (m, 11H), 6.91 (d, J=7.6 Hz, 1H), 6.84-6.80 (m, 2H), 6.75-6.72 (m, 2H), 6.69 (d, J=7.7 Hz, 1H), 3.36 (s, 3H), 3.24 (s, 3H), 3.06 (s, 3H), 1.33 (s, 9H), 1.29 (s, 9H), 1.25 (s, 9H). $^{19}F$ NMR (376 MHz, acetone-$d_6$) δ −69.38 (s, 3F), −69.45 (s, 3F), −69.50 (s, 3F). MALDI-TOF-MS $[M+H]^+$: calculated: ($C_{69}H_{60}F_9IrN_{12}$) 1420.45; found: 1419.44.

Selected spectroscopic data for 6-fac is provided as follows: $^1H$ NMR (400 MHz, acetone-$d_6$) δ 8.97 (s, 3H), 7.58-7.45 (m, 15H), 6.84-6.82 (d, J=8.0 Hz, 3H), 6.39-6.37 (d, J=8.0 Hz, 3H), 3.36 (s, 9H), 1.36 (s, 27H). $^{19}F$ NMR (376 MHz, acetone-$d_6$) δ −69.43 (s, 9F). MALDI-TOF-MS $[M+H]^+$: calculated: ($C_{69}H_{60}F_9IrN_{12}$) 1420.45; found: 1419.49.

The above structural characterization reveals a single and three distinctive set of the t-butyl and $CF_3$ resonance signals for the f- and m-isomers, respectively. Despite of the lowered synthetic yield, the f-derivative can be obtained in high yields using the acid-dependent isomerization well known in the art, while the unreacted m-isomers can be recovered for a second attempt. Due to their optimal emission wavelength in the blue spectral region and narrow bandwidth, their f-isomers are believed to be more advantageous for OLED fabrication in comparison to its m-isomer, 5-mer and 6-mer, to which the peak max. has already moved to 526 nm and 561 nm in solution state, as will be discussed below.

Figure 13:
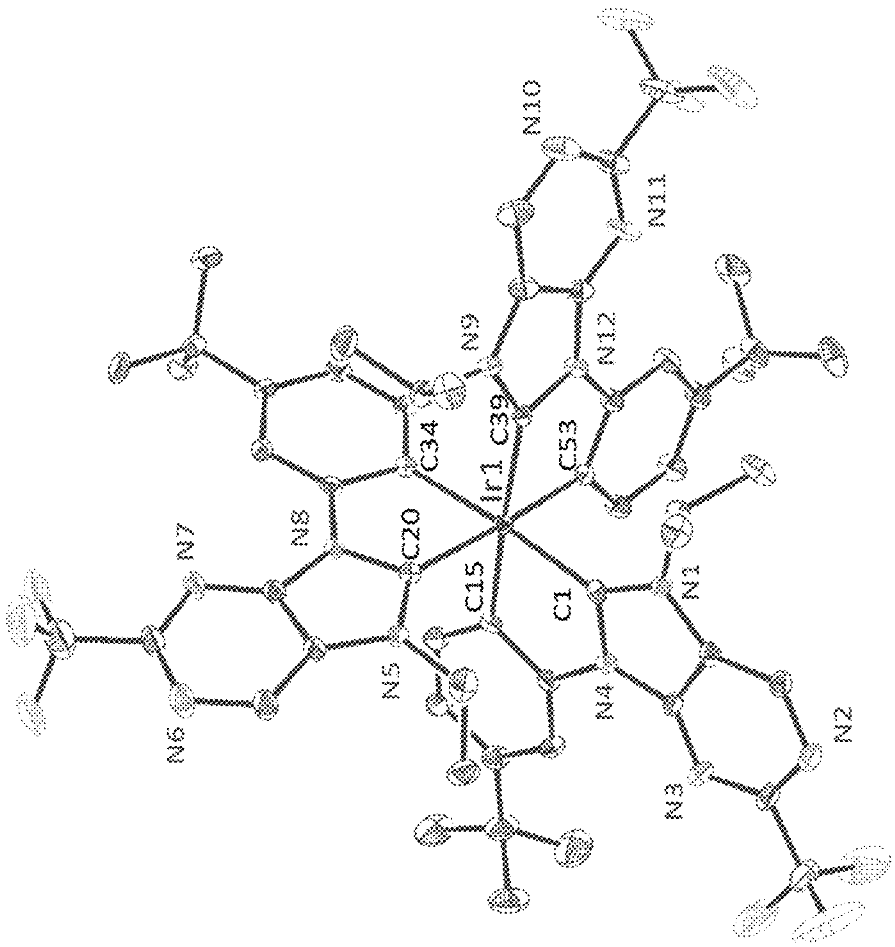
FIG. 13 shows the crystal structural drawing of 5-fac.

Single-crystal X-ray structural analysis was carried out for 5-fac to provide confirmation of the identity of chelates and gross coordination arrangement of these Ir(III) complexes. FIG. 13 is shown with thermal ellipsoids shown at 30% probability level, with selected bond lengths (Å) of Ir1-C1=2.019(5), Ir1-C20=2.031(4), Ir1-C39=2.027(4), Ir1-C15=2.088(4), Ir1-C34=2.093(4), Ir1-C53=2.090(4), and selected bond angles (°) of C1-Ir1-C15=78.33(17), C20-Ir1-C34=77.83(16) and C39-Ir1-C53=78.45(16). Hydrogen atoms are omitted for clarity. The single crystals of 5-fac suitable for X-ray diffraction study were obtained from via the slow diffusion of methanol into a saturated $CH_2Cl_2$ solution at RT.

As shown, the molecular structure of 5-fac reveals a slightly distorted octahedral arrangement. Due to the lack of C3 symmetry in crystal lattices, all six Ir—C distances are slightly different, among which the facially arranged carbenic Ir—C distances (Ir1-C1=2.019(5), Ir1-C20=2.031(4) and Ir1-C39=2.027(4) Å) are found to be notably shorter than the corresponding trans-Ir—C distance of phenyl cyclometalates (Ir1-C15=2.088(4), Ir1-C34=2.093(4) and Ir1-C53=2.090(4) Å). This metric data suggests that the Ir—$C_{(carbene)}$ bond strength is notably greater than that of Ir—$C_{(phenyl)}$ groups, which is in accordance with other structurally characterized homoleptic Ir(III) complexes with electron deficient carbene entities.

Photophysical Analysis

Figure 14:
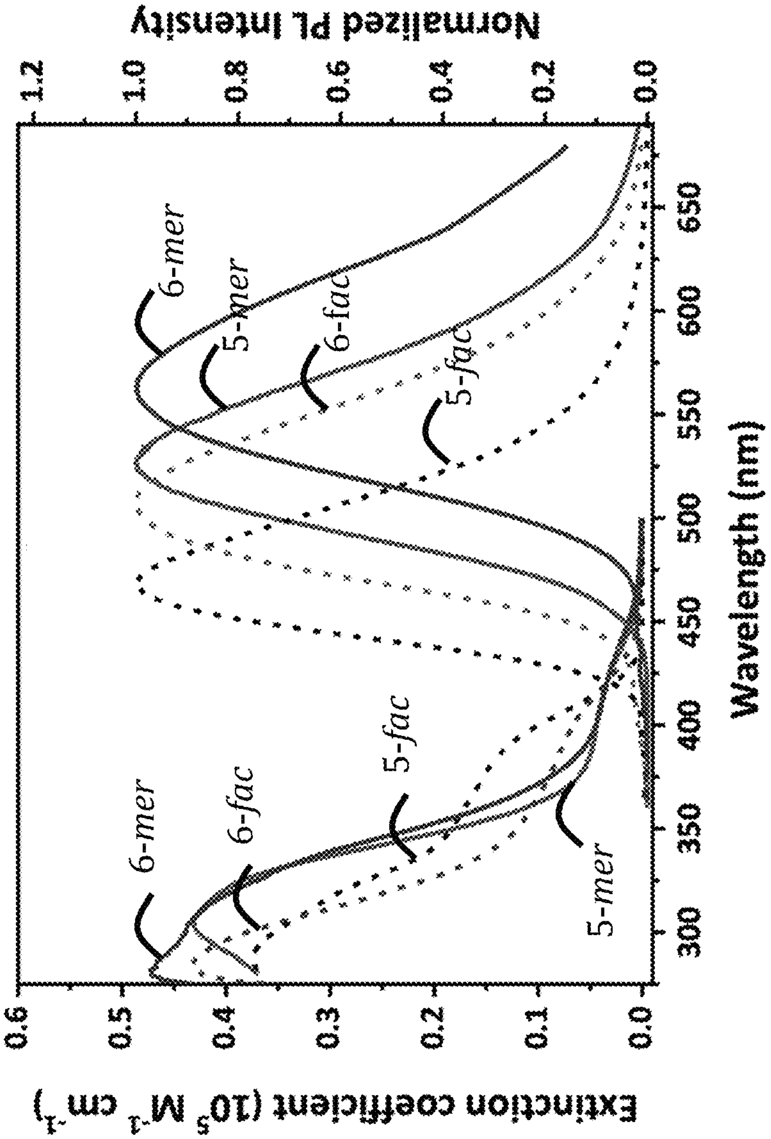
FIG. 14 shows the UV-Vis absorption and photoluminescence spectra of different purin-8-ylidene-based Ir(III) metal complexes in toluene at RT.

FIG. 14 depicts the UV-Vis absorption spectra of the above purin-8-ylidene Ir(III) complexes in toluene at RT, while Table 5 summarizes the corresponding metric parameters. As can be seen, 5-mer and 6-mer exhibited relatively intense ππ* absorption band in the high energy region between 280 nm-340 nm, and the absorption extinction coefficient (ε) turned much smaller while moved into the lowered energy region. The corresponding lower energy absorption band at 408 nm and 428 nm can be assigned to the metal-to-ligand charge transfer (MLCT) absorption. Alternatively, the respective f-isomer showed a slightly less intensive absorption band at higher energy region of 310 nm-350 nm and, upon further moving to lower energy region, the corresponding MLCT absorption band occurred at 383 nm and 397 nm and retained a relatively higher extinction coefficient (ε) in comparison to the m-counterparts. This spectral pattern may be related to the asymmetric arrangement of f-isomers and is universal to all relevant existing homoleptic Ir(III) carbene complexes.

TABLE 5

Photophysical data of the purin-8-ylidene-based Ir(III) metal complexes at RT.

| Complex | abs $\lambda_{max}$[a] (nm) | PL $\lambda_{max}$[a] (nm) | FWHM[b] ($cm^{-1}$) | Φ[c][d] (%) | $\tau_{obs}$[d] (μs) | $\tau_{rad}$[d] (μs) | $k_r$ ($10^6\ s^{-1}$) | $k_{nr}$ ($10^6\ s^{-1}$) |
|---|---|---|---|---|---|---|---|---|
| 5-mer | 304 (4.3), 408 (0.4) | 526 | 3253 | 81 | 0.92 | 1.14 | 0.88 | 0.21 |
| 5-fac | 287 (3.7), 383 (1.4) | 468 | 3246 | 97 | 0.72 | 0.74 | 1.35 | 0.04 |
| 6-mer | 280 (4.7), 428 (0.3) | 561 | 3493 | 66 | 0.81 | 1.23 | 0.81 | 0.42 |
| 6-fac | 284 (4.3), 397 (0.7) | 508 | 3605 | 71 | 0.76 | 1.07 | 0.93 | 0.38 |

[a]Recorded at a concentration of $10^{-5}$M in degassed toluene at RT; extinction coefficient (ε) is given in parentheses with a unit of $10^4 M^{-1} \cdot cm^{-1}$.

[b]Full width at half maximum.

[c]Coumarin 102 (C102) in methanol (Q.Y. = 87% and $\lambda_{max}$ = 480 nm) were employed as standard.

[d]Observed lifetime as calculated from transient PL spectra.

Furthermore, as depicted in FIG. 14, both f-isomers showed the relatively blue-shifted emission peak max. at 468 nm and 508 nm. The corresponding m-isomers exhibited more red-shifted emission with peak max. at 526 nm and 561 nm, respectively. Moreover, the introduction of phenyl substituent, with slightly greater electron withdrawing character and greater π-conjugation, are responsible to the red shifting as observed in both 6-mer and 6-fac vs. the 5-mer and 5-fac derivatives. Also, both the f-isomers possess a slightly higher emission quantum yield and faster radiative rate constant ($k_r$) in comparison to their m-counterparts. Concomitantly, both the 6-mer and 6-fac derivatives, possess a systematically lowered quantum yield, reduced radiative rate constant, and increased non-radiative constant vs. those of 5-mer and 5-fac, highlighting the influence of the phenyl appendage.

Their emission spectra were recorded in PMMA thin film at a doping concentration of 2 wt % for making comparison to those observed in degassed toluene solution. As indicated in Table 6, except for 5-fac, which exhibited a slight red shifting from 468 nm to 474 nm, all other samples showed a notable blue shifting, giving structureless emission with peak max. at 509 nm, 530 nm and 490 nm for 5-mer, 6-mer and 6-fac, respectively. Hence, the associated f- and m-isomers can be considered to possess the genuine blue and sky-blue emission, respectively.

TABLE 6

Summarized photo physical data of the Ir(III) complexes in PMMA thin films.

| Complex | PL $\lambda_{max}$[(a)] (nm) | FWHM[(b)] ($m^{-1}$/nm) | $\tau_{obs}$[(a)] [μs] |
|---|---|---|---|
| 5-mer | 509 | 3868/102 | 0.72 |
| 5-fac | 474 | 3452/80 | 0.69 |
| 6-mer | 530 | 3811/111 | 0.65 |
| 6-fac | 490 | 3907/96 | 0.42 |

[(a)]Measured in PMMA thin films at 2 wt % at RT.

[(b)]FWHM: full width at half maxima of PL emission peak max. in both $cm^{-1}$ and nm.

Example 3—Imidazo[4,5-b]pyrazin-2-ylidene-based Ir(III) Metal Complexes

Synthesis of imidazo[4,5-b]pyrazin-3-ium Pro-Chelates (timpz$H_2$·OTf, t2impz$H_2$·OTf, t2empz$H_2$·OTf, and t2phmpz$H_2$·OTf)

Scheme 6

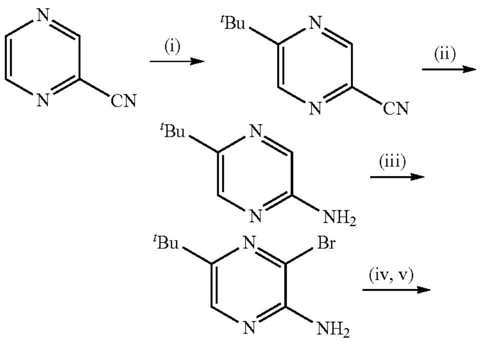

-continued

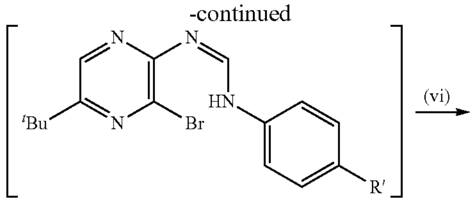

(C1), R′ = H
(C2), R′ = ᵗBu

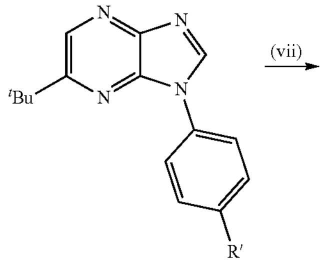

(C3), R′ = H
(C4), R′ = ᵗBu

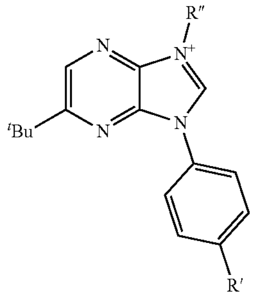

timpz$H_2$•OTf, R′ = H, R″ = Me
t2impz$H_2$•OTf, R′ = ᵗBu, R″ = Me
t2empz$H_2$•OTf, R′ = ᵗBu, R″ = Et
t2phmpz$H_2$•OTf, R′ = ᵗBu, R″ = Ph In Scheme 6, the reaction starts from commercially available pyrazinecarbonitrile, to which the tert-butyl group was introduced utilizing Minisci alkylation, in presence of both silver triflate and pivalic acid, as well as $(NH_4)_2S_2O_6$ at 80° C. (i). After that, the cyano group was converted to an amino group using a mixture of sodium hypochlorite and sodium hydroxide solution by way of Hofman rearrangement at 80° C. (ii).

Bromination was next performed using N-bromosuccinimide at 0° C. (iii) in giving 3-bromo-5-(tert-butyl)pyrazin-2-amine. After that, the formamidine derivatives (C1) and (C2) were obtained by treatment of 3-bromo-5-(tert-butyl) pyrazin-2-amine with triethyl orthoformate at 140° C. in presence of catalytic amount of concentrated HCl (iv), followed by condensation of respective formimidate intermediate with aniline or 4-tert-butyl aniline at 140° C. (v).

The formamidine was next cyclized in presence of 1,8-diazabicyclo[5.4.0]undec-7-ene and CuI catalyst at 120° C. to afford the 1-aryl-imidazo[4,5-b]pyrazine (C3) and (C4) in adequate yields (vi).

In the final step, the N-alkylation was performed using alkyl trifluoromethanesulfonate and methyl triflate or ethyl triflate at RT (vii) to give imidazo[4,5-b]pyrazin-3-ium derivatives, timpzH2·OTf, t2impzH2·OTf, and t2empzH2·OTf. This N-alkylation reaction is expected to occur at either the imidazolyl or pyrazinyl nitrogen sites and to afford a mixture of inseparable products. This isomeric mixture was directly employed for the subsequent coordination reaction with iridium metal reagent without further purification.

Alternatively, the N-arylation of 6-(tert-butyl)-1-aryl-1H-imidazo[4,5-b]pyrazine was performed using diphenyliodonium triflate in DMF solution of (4) at 100° C. in the presence of $Cu(AcO)_2$ to give the imidazo[4,5-b]pyrazin-3-ium derivative, t2phmpz$H_2$·OTf.

Synthesis of imidazo[4,5-b]pyrazin-2-ylidene-based Ir(III) Metal Complexes (7-mer, 7-fac, 8-mer, 8-fac, 9-mer, and 9-fac)

A respective degassed tert-butylbenzene (20 mL) solution of timpz$H_2$·OTf (0.416 g, 1 mmol), t2impz$H_2$·OTf (0.416 g, 1 mmol), and t2empz$H_2$·OTf (0.416 g, 1 mmol), NaOAc (0.33 g, 4 mmol) and m-trichloridotris(tetrahydrothiophene-$\kappa^S$)iridium(III) (m-$IrCl_3(tht)_3$, 0.113 g, 0.2 mmol) was refluxed for 12 hours. After removal of solvent, the residue was taken into $CH_2Cl_2$ solution. The organic phase was washed with deionized water and separated and concentrated to dryness. This gave a mixture of f- and m-stereoisomers. The residue was further purified by column chromatography eluting with n-hexane/EA (6/1, v/v), followed by recrystallization to obtain a yellow solid 7-mer (25 mg, 13%) and a light-yellow solid of 7-fac (83 mg, 42%), a yellow solid 8-mer (70 mg, 35%) and a light-yellow solid of 8-fac (20 mg, 10%), a yellow solid 9-mer (172 mg, 66%) and a light-yellow solid of 9-fac (13 mg, 5%), respectively.

Synthesis of imidazo[4,5-b]pyrazin-2-ylidene-based Ir(III) Metal Complexes (10-fac, 11-fac, and 12-fac)

A degassed tert-butylbenzene (10 mL) solution of t2phmpz$H_2$·OTf (0.33 g, 0.61 mmol), NaOAc (0.08 g, 1 mmol) and m-trichloridotris(tetrahydrothiophene-$\kappa^S$) iridium(III) (m-$IrCl_3(tht)_3$, 0.112 g, 0.2 mmol) was refluxed for 12 hours. After removal of solvent, the residue was taken into $CH_2Cl_2$ solution. The organic phase was washed with deionized water and separated and concentrated to dryness. This gave a mixture of three f-stereoisomers. The residue was further purified by column chromatography eluting with n-hexane/EA (3/1, v/v), followed by recrystallization to obtain a yellow solid 10-fac (30 mg, 11%), a yellow solid 11-fac (54 mg, 20%) and a light-yellow solid 12-fac (81 mg, 30%), respectively. Sequential conversion from 10-fac to 11-fac and, finally to 12-fac can be achieved by heating a 1,2,4-trichlorobenzene solution of either 10-fac or 11-fac in presence of p-toluenesulfonic acid and NaOAc (or potassium acetate) as catalyst.

Notably, their synthetic yields were affected by the employed imidazo[4,5-b]pyrazin-3-ium pro-chelates, among which t2empz$H_2$·OTf gave the highest overall yields of 71% (i.e., as a mixture of m- and f-isomers) in reference to other chelates. Moreover, the relative yield of f-isomers was found to decrease upon introduction of tert-butylphenyl and N-ethyl substituent to the imidazo[4,5-b]pyrazin-2-ylidene fragments. Despite of this difficulty, the acid-sensitive isomerization can be applied for effective conversion of m-isomers to their f-counterparts.

In these carbene complexes, both m- and f-isomers depicted decomposition and isomerization reactions above 330° C. during sublimation, making thermal deposition an infeasible method for OLED fabrication. This behavior is akin to the known poor stability for the homoleptic carbene emitter with dimethylfluorenyl cyclometalate, which is a common issue of blue phosphors for OLEDs.

In sharp contrast, three imidazo[4,5-b]pyrazin-2-ylidene-based Ir(III) metal complexes (10-fac, 11-fac, and 12-fac) are much more durable under all experimental conditions. Particularly, 12-fac can be heated to over 200° C. for over 2 days and showed no sign of decomposition. This class of derivatives should be highly suitable to serve as the desired OLED emitters with elongated operational lifetime.

Spectroscopic and Structural Analysis

The structures of each of 7-mer, 7-fac, 8-mer, 8-fac, 9-mer, 9-fac were verified by $^1$H NMR spectroscopy and MALDI-TOF mass spectrometry.

Selected spectroscopic data for 7-mer is provided as follows: MS (MALDI-TOF, $^{193}$Ir): m/z 988.50586 [$M^+$]; $^1$H NMR (400 MHz, $CDCl_3$, 296 K): δ 8.77 (d, J=7.8 Hz, 1H), 8.74 (d, J=7.8 Hz, 1H), 8.70 (d, J=7.8 Hz, 1H), 8.36 (s, 1H), 8.35 (s, 1H), 8.29 (s, 1H), 7.14-7.03 (m, 3H), 6.99-6.94 (m, 2H), 6.83 (t, J=7.2 Hz, 1H), 6.79 (t, J=7.2 Hz, 1H), 6.76 (t, J=7.2 Hz, 1H), 6.66 (d, J=7.2 Hz, 1H), 3.39 (s, 3H), 3.39 (s, 3H), 3.28 (s, 3H), 1.54 (s, 9H), 1.54 (s, 9H), 1.53 (s, 9H). Anal. Calcd. for $C_{48}H_{51}IrN_{12}$: C, 58.34; H, 5.20; N, 17.01. Found: C, 58.30; H, 5.21; N, 17.03.

Selected spectroscopic data for 7-fac is provided as follows: MS (MALDI-TOF, $^{193}$Ir): m/z 989.46875 [$M+H^+$]; $^1$H NMR (400 MHz, $CDCl_3$, 296 K): δ 8.75 (d, J=7.6 Hz, 3H), 8.30 (s, 3H), 7.16 (td, J=7.6, 1.2 Hz, 3H), 6.84 (td, J=7.6, 1.2 Hz, 3H), 6.62 (d, J=7.6 Hz, 3H), 3.43 (s, 9H), 1.54 (s, 27H). Anal. Calcd. for $C_{48}H_{51}IrN_{12}$: C, 58.34; H, 5.20; N, 17.01. Found: C, 58.36; H, 5.18; N, 16.98.

Selected spectroscopic data for 8-mer is provided as follows: MS (MALDI-TOF, $^{193}$Ir): m/z 1157.62402 [$M+H^+$]; $^1$H NMR (400 MHz, $CDCl_3$, 296 K): δ 8.64 (d, J=8.0 Hz, 1H), 8.63 (d, J=8.0 Hz, 1H), 8.53 (d, J=8.0 Hz, 1H), 8.33 (s, 1H), 8.32 (s, 1H), 8.28 (s, 1H), 7.15-7.08 (m, 4H), 6.93 (d, J=2.0 Hz, 1H), 6.72 (d, J=2.0 Hz, 1H), 3.50 (s, 3H), 3.33 (s, 3H), 3.28 (s, 3H), 1.53 (s, 9H), 1.52 (s, 9H), 1.51 (s, 9H), 1.12 (s, 9H), 1.12 (s, 9H), 1.11 (s, 9H). Anal. Calcd. for $C_{60}H_{75}IrN_{12}$: C, 62.31; H, 6.54; N, 14.53. Found: C, 62.25; H, 6.60; N, 14.54.

Selected spectroscopic data for 8-fac is provided as follows: MS (MALDI-TOF, $^{193}$Ir): m/z 1157.70337 [$M+H^+$]; $^1$H NMR (400 MHz, $CDCl_3$, 296 K): δ 8.59 (d, J=8.2 Hz, 3H), 8.27 (s, 3H), 7.16 (dd, J=8.2, 2.2 Hz, 3H), 6.61 (d, J=2.2 Hz, 3H), 3.47 (s, 9H), 1.52 (s, 27H), 1.08 (s, 27H). Anal. Calcd. for $C_{60}H_{73}IrN_{12}$: C, 62.31; H, 6.54; N, 14.53. Found: C, 62.28; H, 6.58; N, 14.50.

Selected spectroscopic data for 9-mer is provided as follows: MS (MALDI-TOF, $^{193}$Ir): m/z 1198.62219 [$M^+$]; $^1$H NMR (400 MHz, $CDCl_3$, 296 K): δ 8.61 (d, J=8.2 Hz, 2H), 8.53 (d, J=8.2 Hz, 1H), 8.34 (s, 1H), 8.32 (s, 1H), 8.26 (s, 1H), 7.11 (dd, J=8.2, 2.0 Hz, 1H), 7.07 (dd, J=8.2, 2.0 Hz, 1H), 7.05 (dd, J=8.2, 2.0 Hz, 1H), 7.02 (d, J=2.0 Hz, 1H), 6.91 (d, J=2.0 Hz, 1H), 6.65 (d, J=2.0 Hz, 1H), 4.09-3.84 (m, 5H), 3.61 (dq, J=13.2, 7.2 Hz, 1H), 1.53 (s, 18H), 1.51 (s, 9H), 1.09 (s, 9H), 1.08 (s, 9H), 1.07 (s, 9H), 0.97 (t, J=7.2 Hz, 6H), 0.85 (t, J=7.2 Hz, 3H). Anal. Calcd. for $C_{63}H_{81}IrN_{12}$: C, 63.13; H, 6.81; N, 14.02. Found: C, 63.08; H, 6.83; N, 13.99.

Selected spectroscopic data for 9-fac is provided as follows: MS (MALDI-TOF, $^{193}$Ir): m/z 1198.68213 [$M^+$]; $^1$H NMR (400 MHz, $CDCl_3$, 296 K): δ 8.57 (d, J=8.2 Hz, 3H), 8.26 (s, 3H), 7.11 (dd, J=8.2, 2.0 Hz, 3H), 6.57 (d, J=2.0 Hz, 3H), 4.14 (dq, J=14.0, 7.2 Hz, 3H), 3.93 (dq, J=14.0, 7.2 Hz, 3H), 1.52 (s, 27H), 1.06 (s, 27H), 0.86 (t, J=7.2 Hz, 9H). Anal. Calcd. for $C_{63}H_{81}IrN_{12}$: C, 63.13; H, 6.81; N, 14.02. Found: C, 63.11; H, 6.85; N, 13.97.

Selected spectroscopic data for 10-fac is provided as follows: MS (MALDI-TOF, $^{193}Ir$): m/z 1343.63631 [$M+H^+$]; $^1H$ NMR (400 MHz, $CDCl_3$) δ 8.67 (d, J=8.2 Hz, 3H), 8.11 (s, 3H), 7.19 (dd, J=8.4, 2.0 Hz, 3H), 6.80 (t, J=7.2 Hz, 3H), 6.76 (d, J=2.0 Hz, 3H), 6.60 (br, 6H), 1.57 (s, 27H), 1.13 (s, 27H). Anal. Calcd. for $C_{75}H_{81}IrN_{12}$: C, 67.09; H, 6.08; N, 12.52. Found: C, 67.11; H, 6.05; N, 12.48.

Selected spectroscopic data for 11-fac is provided as follows: MS (MALDI-TOF, $^{193}Ir$): m/z 1343.63521 [$M+H^+$]; $^1H$ NMR (400 MHz, $CDCl_3$, 296 K) δ 8.80 (d, J=8.4 Hz, 1H), 8.73 (d, J=7.6 Hz, 1H), 8.57 (d, J=8.4 Hz, 1H), 8.38 (s, 1H), 8.11 (s, 1H), 8.05 (s, 1H), 7.23 (dd, J=8.0, 2.4 Hz, 1H), 7.17 (td, J=8.0, 1.6 Hz, 1H), 7.11 (dd, J=8.0, 2.4 Hz, 1H), 6.84 (td, J=7.2, 0.8 Hz, 1H), 6.81-6.67 (m, 6H), 6.56 (d, J=2.0 Hz, 1H), 6.33 (s, 4H), 1.55 (s, 9H), 1.52 (s, 9H), 1.38 (s, 9H), 1.12 (s, 9H), 1.05 (s, 9H), 1.00 (s, 9H). Anal. Calcd. for $C_{75}H_{81}IrN_{12}$: C, 67.09; H, 6.08; N, 12.52. Found: C, 67.09; H, 6.10; N, 12.49.

Selected spectroscopic data for 12-fac is provided as follows: MS (MALDI-TOF, $^{193}Ir$): m/z 1343.63331 [$M+H^+$]; $^1H$ NMR (400 MHz, $CDCl_3$, 296 K) δ 8.90 (d, J=8.0 Hz, 1H), 8.69 (d, J=8.0 Hz, 1H), 8.67 (d, J=8.0 Hz, 1H), 8.42 (s, 1H), 8.34 (s, 1H), 8.07 (s, 1H), 7.23 (t, J=7.2 Hz, 1H), 7.19-7.11 (m, 2H), 6.88 (t, J=7.2 Hz, 1H), 6.82-6.77 (m, 2H), 6.70 (t, J=7.2 Hz, 1H), 6.65-6.61 (m, 2H), 6.44 (br, 2H), 6.17 (br, 4H), 1.52 (s, 9H), 1.38 (s, 9H), 1.26 (s, 9H), 1.06 (s, 9H), 1.01 (s, 9H), 1.00 (s, 9H). Anal. Calcd. for $C_{75}H_{81}IrN_{12}$: C, 67.09; H, 6.08; N, 12.52. Found: C, 67.10; H, 6.11; N, 12.55.

Figure 15:
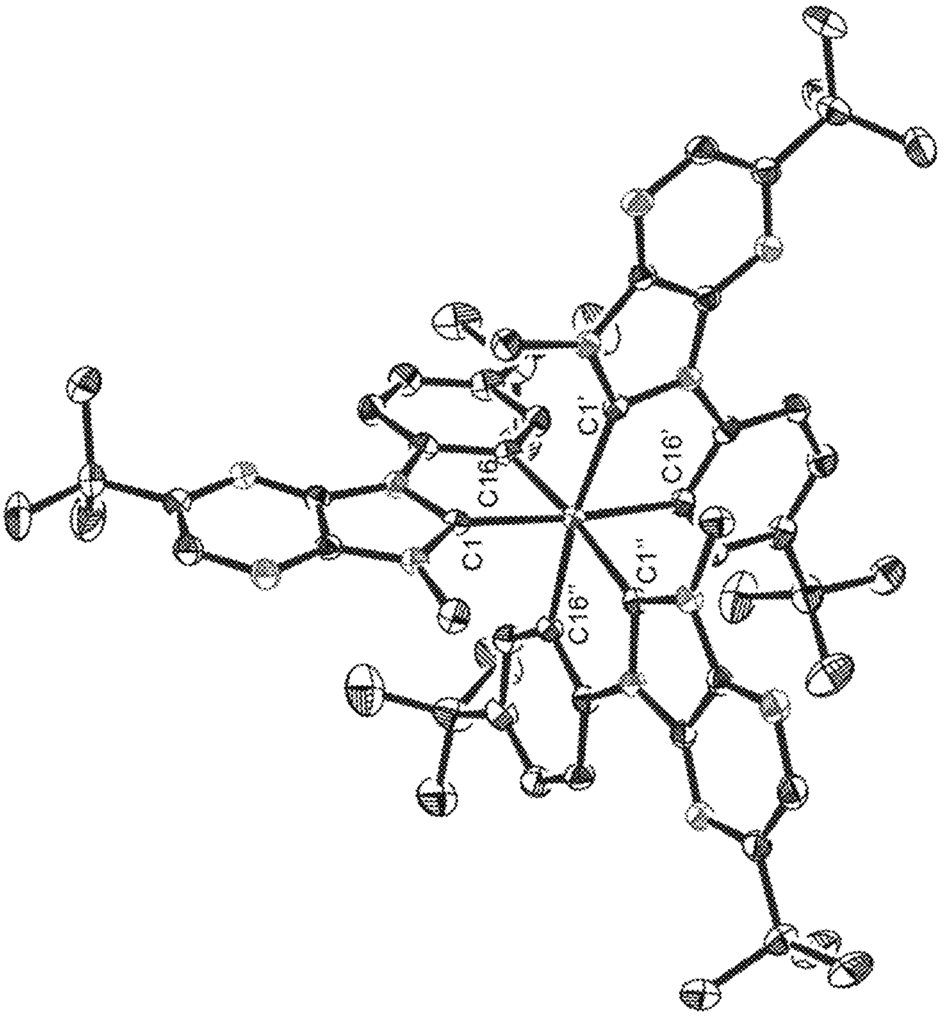
FIG. 15 shows the crystal structural drawing of 8-fac.

Single-crystal X-ray structural analysis was carried out for 8-fac to provide confirmation of the identity of chelates and gross coordination arrangement of these Ir(III) complexes. The structure of 8-fac is shown in FIG. 15, wherein thermal ellipsoids are shown at 30% probability level, with selected bond lengths (Å) being Ir—C(1)=2.0145(18) and Ir—C(16)=2.0892(19), selected bond angles (°) being C(1)-Ir—C(16)=78.23(7), and hydrogen atoms are omitted for clarity. The single crystal of 8-fac suitable for X-ray diffraction study was obtained via the slow diffusion of methanol into a saturated $CH_2Cl_2$ solution at RT. It crystallized in a trigonal crystal system with space group P-3c1 and, as expected, all three carbene cyclometalates have identical Ir—C(carbene) distance of 2.0145(18) Å and Ir—C(phenyl) distance of 2.0892(19) Å. Its Ir—C(carbene) distance is notably shorter, confirming the increased t-accepting character, particularly in comparison to that of electron deficient triazolylidene fragment.

Photophysical Analysis

Figure 16:
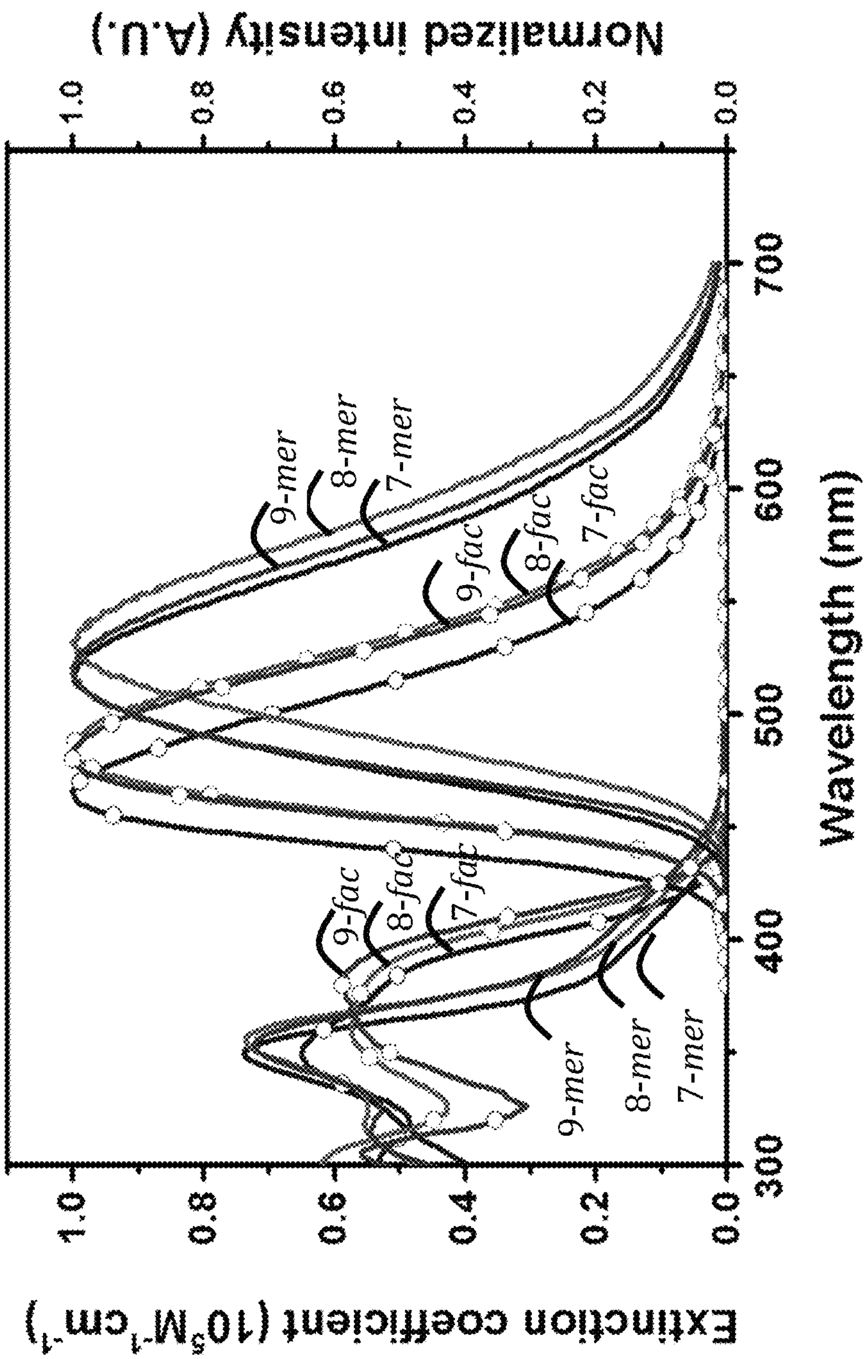
FIG. 16 shows the UV-Vis absorption and photoluminescence spectra of different imidazo[4,5-b]pyrazin-2-ylidene-based Ir(III) metal complexes in toluene at RT.

FIG. 16 depicts the UV-Vis absorption and emission spectra of the above Ir(III) imidazo[4,5-b]pyrazin-2-ylidene complexes in degassed toluene at RT. Table 7 shows the corresponding numerical data. As shown, all Ir(III) complexes exhibited intense absorption bands in 320-370 nm, which can be ascribed to ligand-centered (LC) ππ* and/or inter-ligand charge transfer transitions. For m-isomer, the weak absorption bands at 380 nm and onward, with lower absorption extinction coefficient, are attributed to a metal-to-ligand charge transfer (MLCT) transition. Notably, all f-isomers present relatively more intense absorption spanning the region 350-400 nm, to which the higher absorption extinction coefficient could be due to the co-existence of three symmetrically arranged carbene cyclometalates.

TABLE 7

Photophysical data of the tris-bidentate Ir(III) carbene complexes at RT.

| Complex | abs $\lambda_{max}$[a] (nm) | em $\lambda_{max}$[a] (nm) | FWHM[b] (nm) | Φ[c] (%) | $\tau_{obs}$ (μs) | $\tau_{rad}$ (μs) | $k_r$ ($10^6\ s^{-1}$) | $k_{nr}$ ($10^6\ s^{-1}$) |
|---|---|---|---|---|---|---|---|---|
| 7-mer | 350 (0.74) | 518 | 103 | 46 | 0.424 | 0.922 | 1.08 | 1.27 |
| 7-fac | 350 (0.65), 380 (0.52) | 466 | 75 | 74 | 1.635 | 2.21 | 0.453 | 0.159 |
| 8-mer | 318 (0.55), 356 (0.74) | 532 | 104 | 45 | 0.187 | 0.415 | 2.4 | 2.9 |
| 8-fac | 362 (0.58) | 485 | 81 | 58 | 0.958 | 1.65 | 0.605 | 0.438 |
| 9-mer | 314 (0.55), 354 (0.72) | 518 | 107 | 48 | 0.253 | 0.53 | 1.89 | 2.05 |
| 9-fac | 306 (0.56), 380 (0.59) | 483 | 79 | 53 | 0.696 | 1.31 | 0.761 | 0.675 |

[a]Recorded at a concentration of $10^{-5}$M in degassed toluene at RT; extinction coefficient (ε) is given in parentheses with a unit of $10^5 M^{-1} \cdot cm^{-1}$.

[b]Full width at half maximum.

[c]Coumarin 153 (C153) in ethanol (Q.Y. = 58% and $\lambda_{max}$ = 530 nm) and Coumarin 102 (C102) in methanol (Q.Y. = 87% and $\lambda_{max}$ = 480 nm) were employed as standard.

For the photoluminescence, all Ir(III) complexes displayed structureless profiles with relatively broadened FWHM of 75-107 nm, showing the dominated MLCT contribution. However, m- and f-isomers possessed distinctive emission properties, particularly the emission wavelengths. This is evident by the occurrence of peak max. at 518 nm, 532 nm, and 518 nm for 7-mer, 8-mer, and 9-mer, respectively. In the meantime, their f-isomers displayed a hypochromic shifted peak max. at 466 nm, 485 nm, and 483 nm, respectively. The difference in emission peak max. between m- and f-isomers has been rationalized by the greater degree of MLCT contribution in m-isomers that is induced by possible ligand-to-ligand charge transfer processes.

Moreover, introduction of tert-butylphenyl cyclometalates induced a more red-shifted emission wavelength, comparing the spectral profiles of 7-mer and 8-mer. The variation in emission of the f-isomers, i.e., 7-fac and 8-fac, was consistent with this trend, as the electron-donating ability of tert-butyl substituent would increase the electron density at the Ir(III) metal center and, hence, result in a much reduced MLCT transition energy gap.

Upon replacing N-methyl group of 8-mer with N-ethyl group in giving 9-mer, the emission is blue-shifted from 532 nm to 518 nm. Since both methyl and ethyl substituents possess similar electronic properties, this change in peak wavelength is believed to be related to the solvatochromism, exerted by the less polar N-ethyl substituents. This hypothesis is confirmed by a small variation in emission wavelength between the respective f-isomers, i.e., 8-fac (485 nm) and 9-fac (483 nm), as a result of inherently reduced MLCT contribution.

The photoluminescence quantum yields (PLQYs) were also measured. Particularly, the f-isomers were more efficient than their m-counterparts. Their radiative lifetimes, radiative and non-radiative rate constants were calculated and the data were listed in Table 7. Notably, the radiative lifetimes (and radiative rate constants) of all m-isomers were found to be shorter (and smaller) than their f-isomers, which may be attributed to the lowered emission energy and greater MLCT contribution at the excited states. Furthermore, the Ir(III) complexes bearing tert-butylphenyl cyclometalates, i.e., 8-mer and 8-fac and 9-mer and 9-fac, showed both the greater radiative and non-radiative rate constants, which can be due to the higher electron donating character and solution fluxionality of the additional tert-butyl appendages. Most importantly, the blue emission and higher PLQY of the f-isomers make them better candidates for fabrication of blue OLEDs.

Electroluminescence Analysis

To investigate the electroluminescent (EL) properties of NHC-based Ir(III) metal phosphors, solution-processed OLEDs were fabricated using the following architecture: an indium tin oxide (ITO) electrode, poly(3,4-ethylenedioxythiophene): polystyrenesulfonic acid (PEDOT:PSS; 50 nm), the combination of Ir(III) complexes and BCzBN doped in 1,3-di(9H-carbazol-9-yl)benzene (mCP) (30 nm)/bis[2-(diphenylphosphino)phenyl]ether oxide (DPEPO; 10 nm), 1,3,5-tri(3-pyridyl-3-phenyl)benzene (TmPyPB; 50 nm), 8-hydroxyquinolinolato-lithium (Liq; 1 nm), and an aluminum electrode (100 nm). In these devices, PEDOT:PSS and Liq were served as hole- and electron-injection layers, respectively. TmPyPB was employed as an electron-transporting material, and DPEPO was used as the hole-blocking layer. mCP served as the host material for the devices. The chemical structures of the materials are shown below.

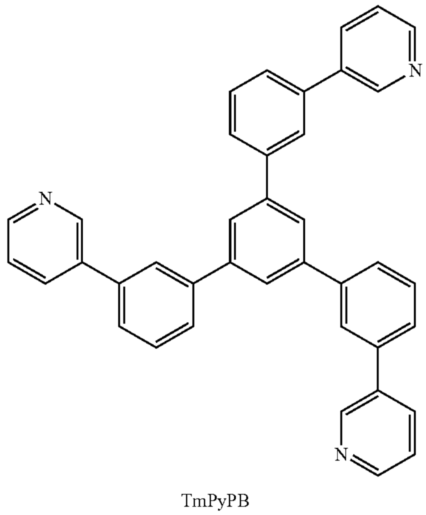

TmPyPB

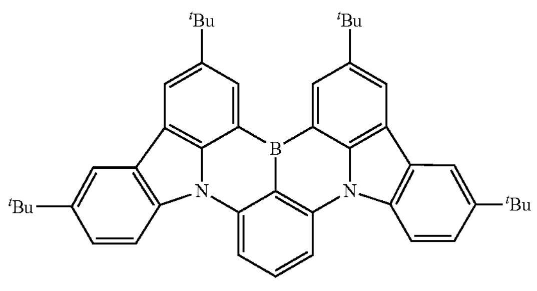

BCzBN

-continued

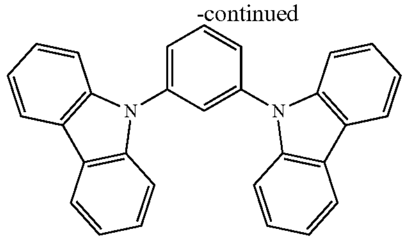

mCP

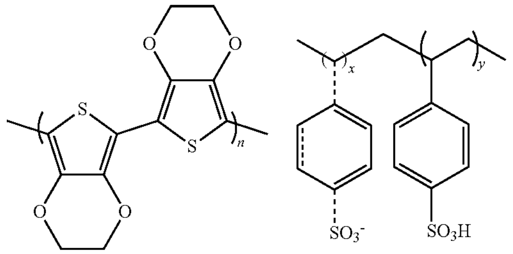

PEDOT:PSS

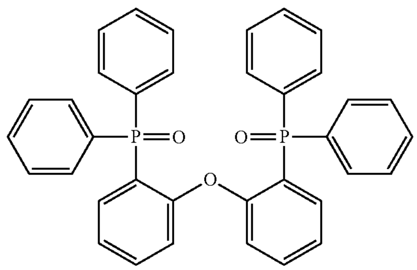

DPEPO

Figure 17:
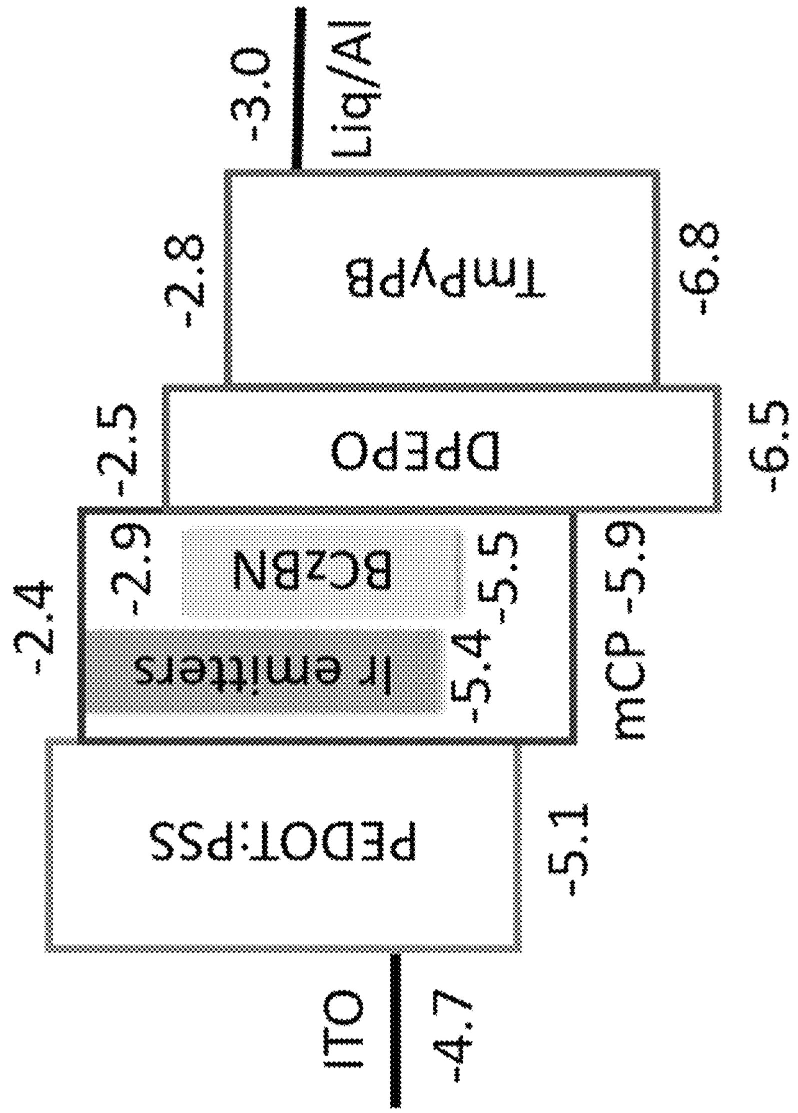
FIG. 17 is a schematic diagram of energy level alignments of the solution-processed OLED containing an imidazo[4,5-b]pyrazin-2-ylidene-based Ir(III) metal complex.
Figure 18:
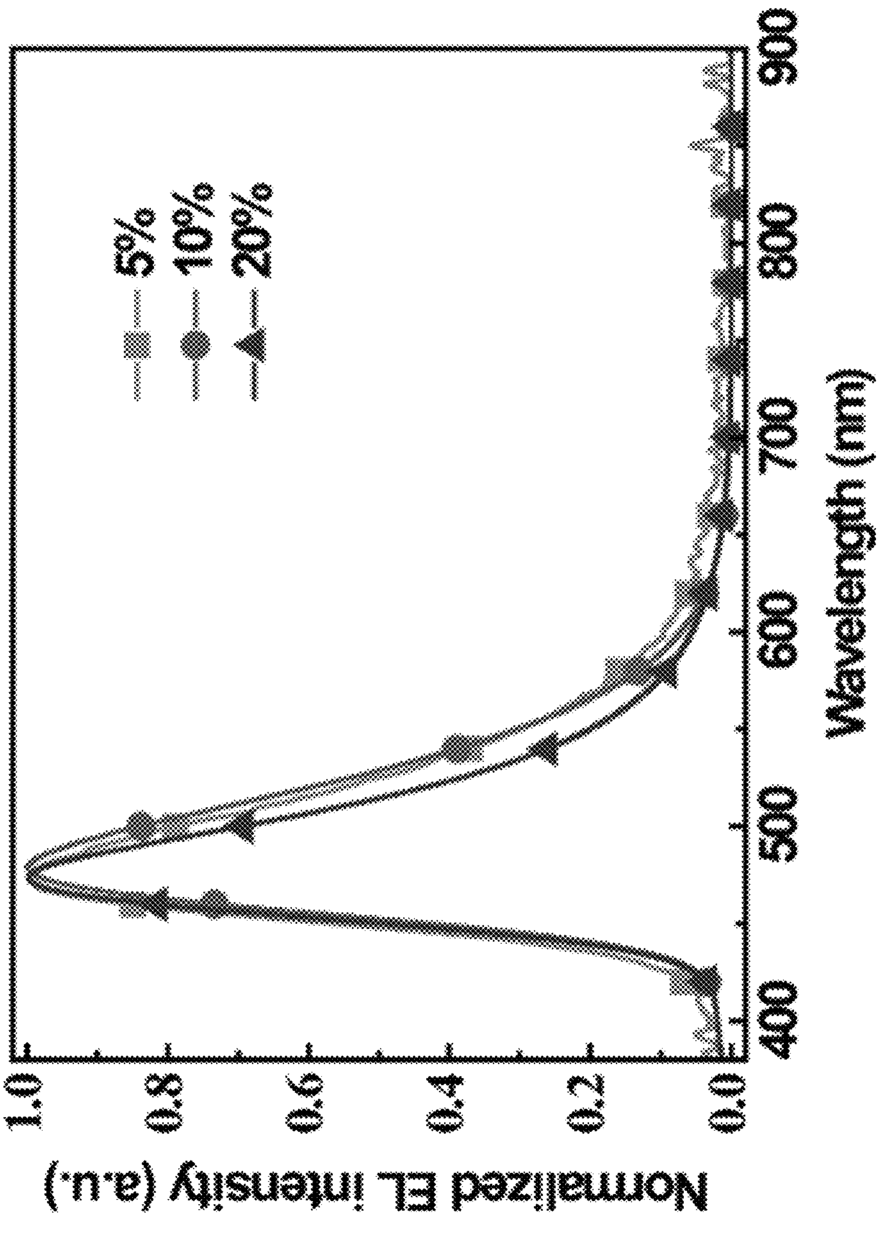
FIG. 18 shows the normalized electroluminescent spectra of a 9-fac-based OLED at different doping levels.
Figure 19A:
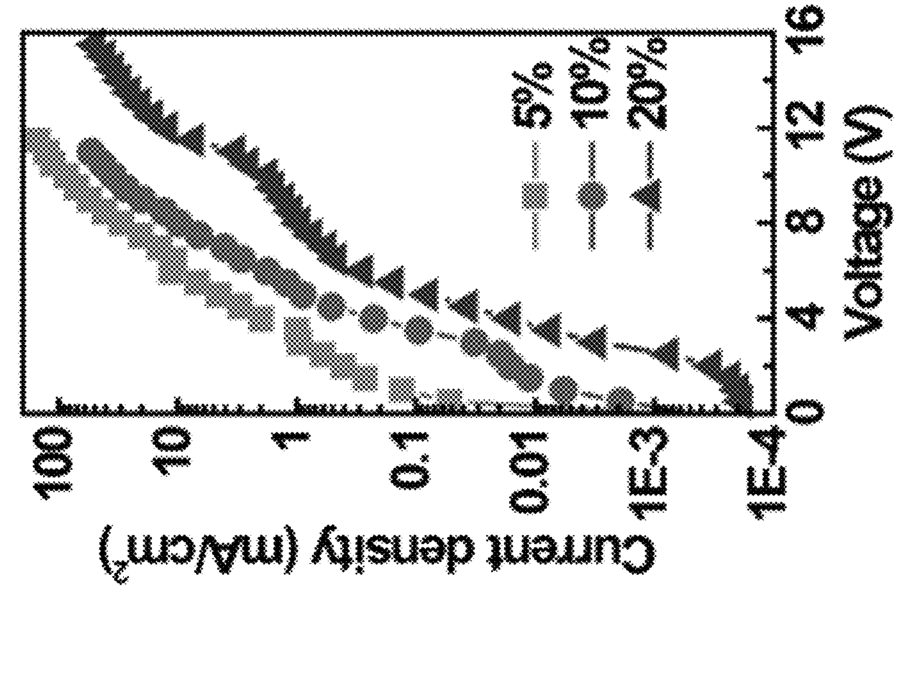
FIG. 19A is a graph showing the current density against the applied voltage of the 9-fac-based OLED at different doping levels.
Figure 19B:
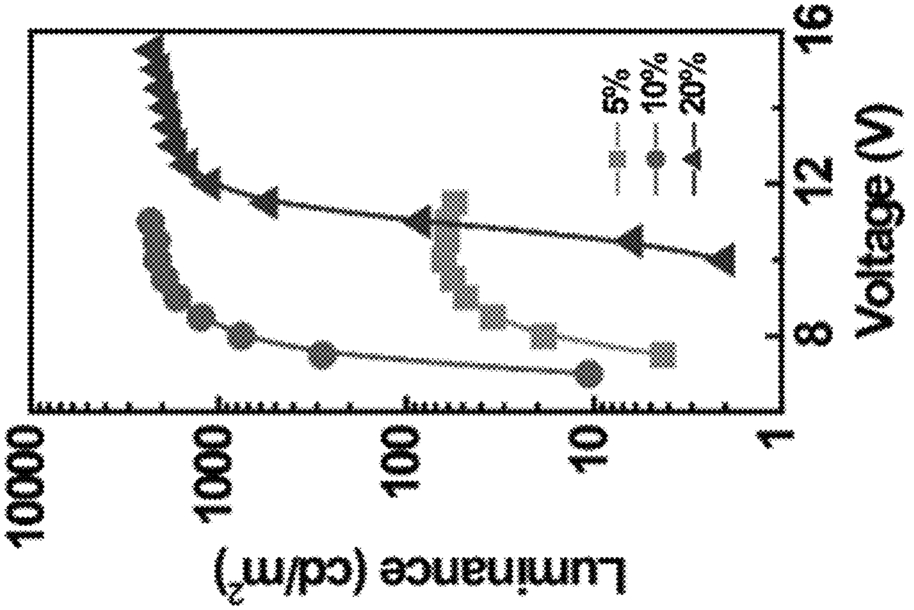
FIG. 19B is a graph showing the luminance against the applied voltage of the 9-fac-based OLED at different doping levels.
Figure 20A:
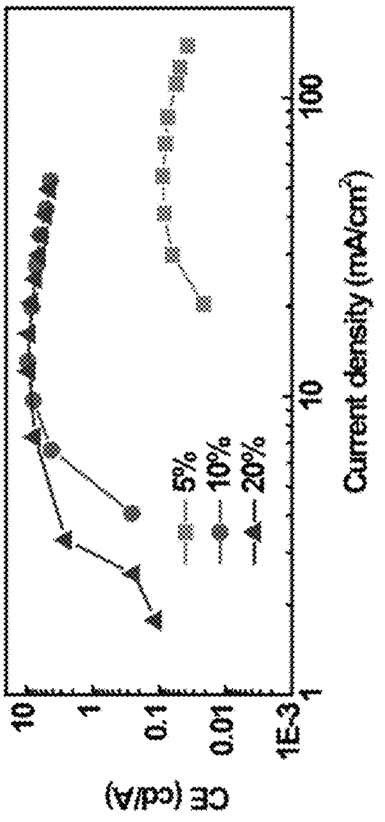
FIG. 20A is a graph showing the current efficiency against the applied current density of the 9-fac-based OLED at different doping levels.
Figure 20B:
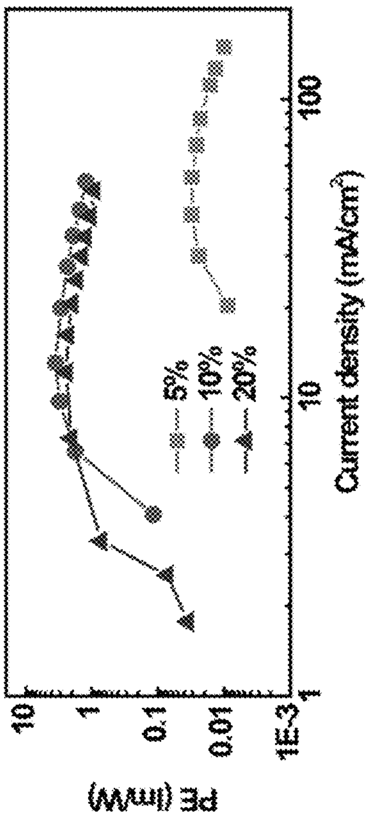
FIG. 20B is a graph showing the power efficiency against the applied current density of the 9-fac-based OLED at different doping levels.
Figure 20C:
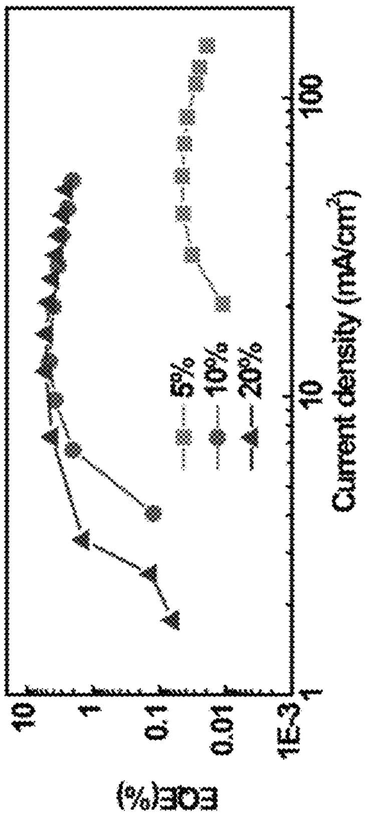
FIG. 20C is a graph showing the external quantum efficiency against the applied current density of the 9-fac-based OLED at different doping levels.
Figure 21:
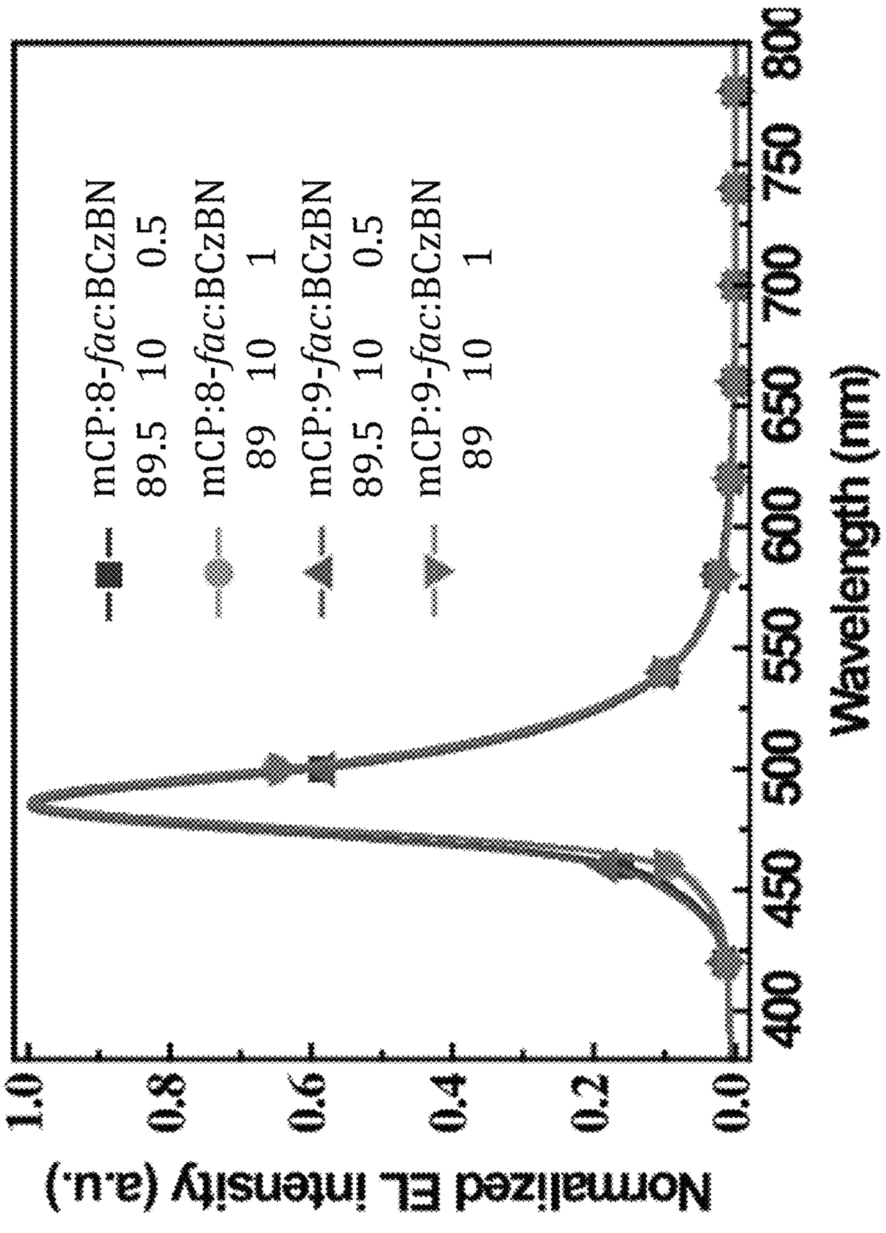
FIG. 21 shows the normalized electroluminescent spectra of the OLEDs based on the sensitizers 8-fac and 9-fac and the narrow bandwidth emitter BCzBN.
Figures 22A, 22B:
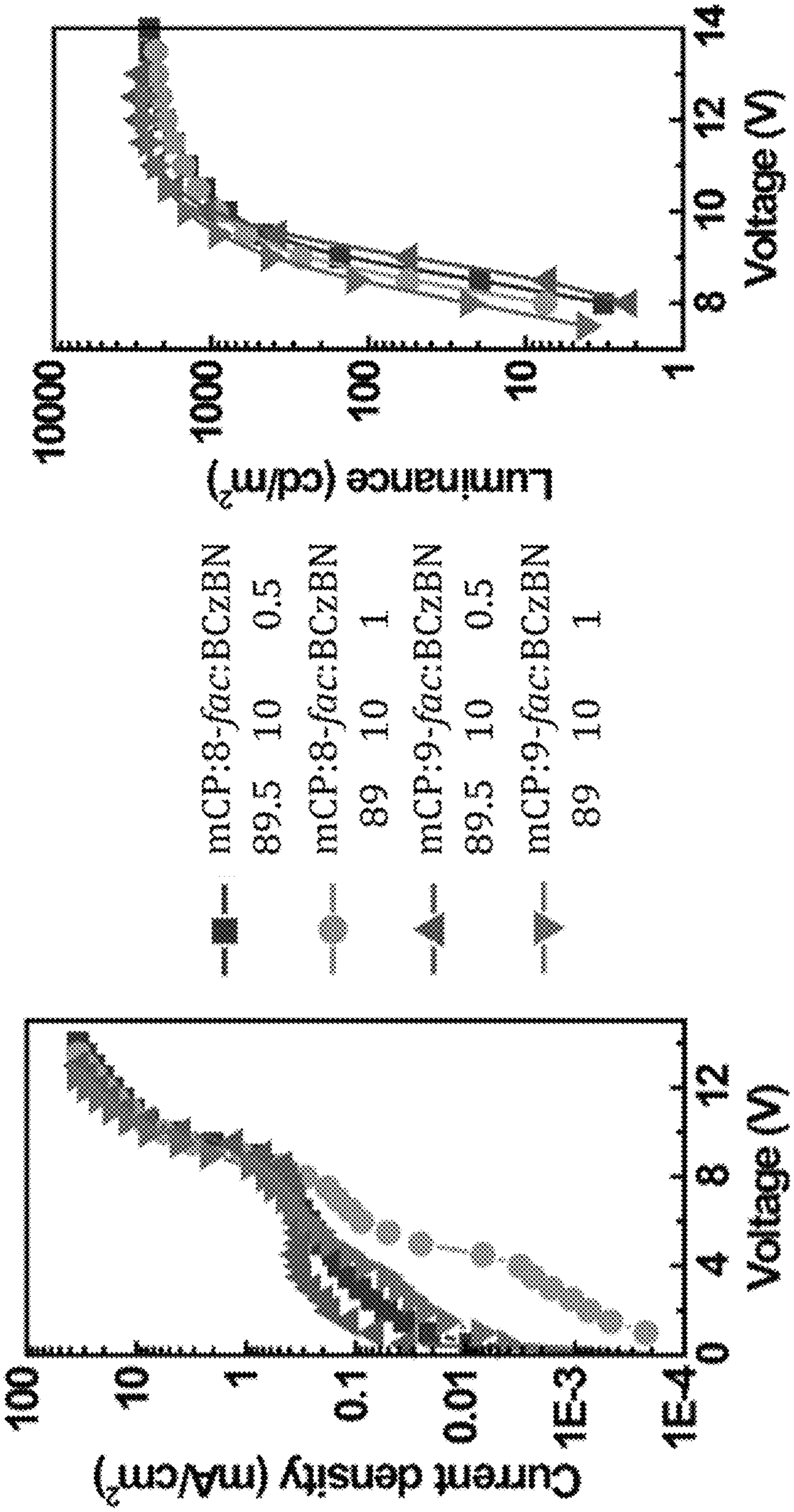
FIG. 22A is a graph showing the current density against the applied voltage of the OLEDs based on the sensitizers 8-fac and 9-fac and the narrow bandwidth emitter BCzBN.
FIG. 22B is a graph showing the luminance against the applied voltage of the OLEDs based on the sensitizers 8-fac and 9-fac and the narrow bandwidth emitter BCzBN.
Figures 23A, 23B, 23C:
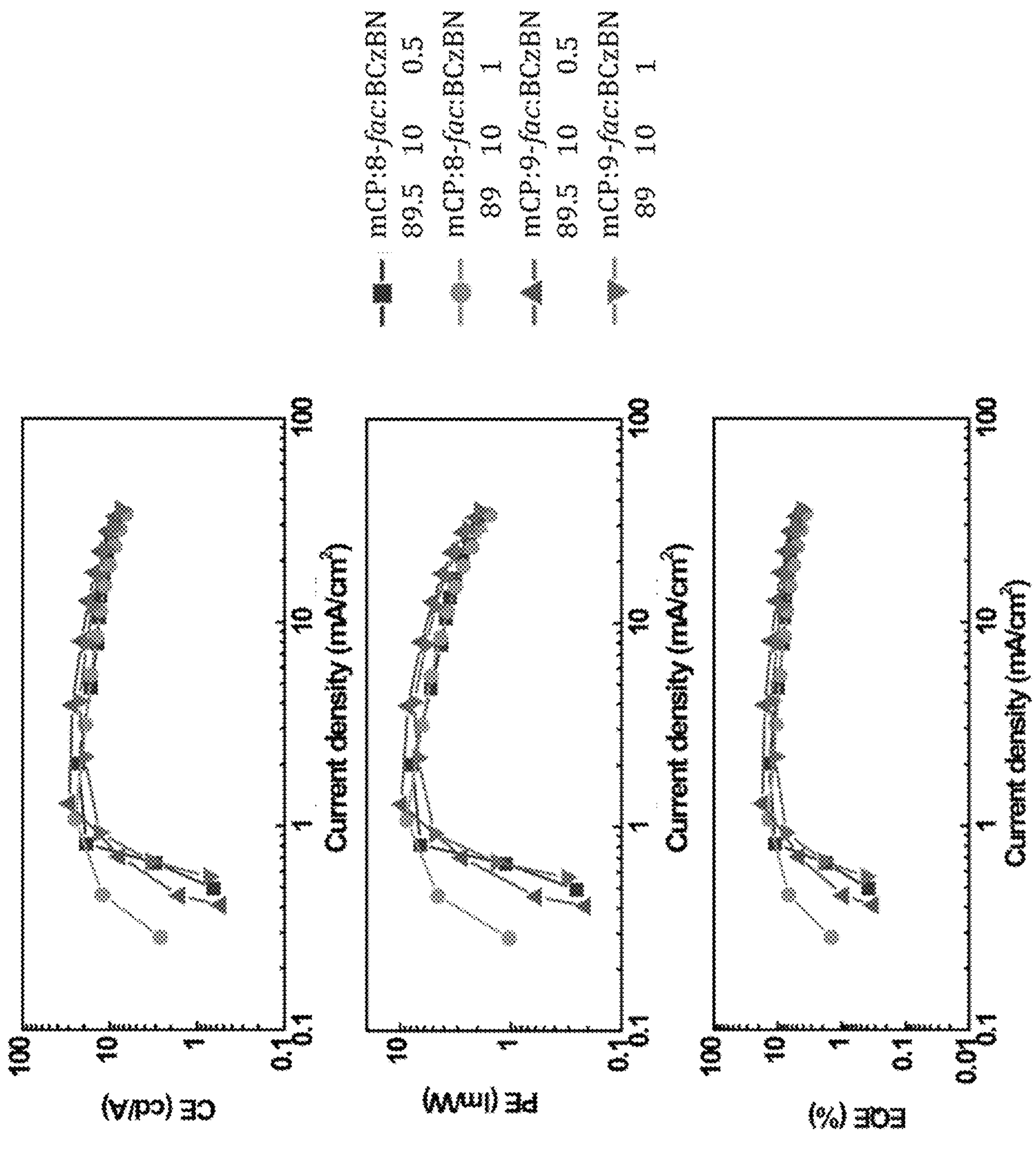
FIG. 23A is a graph showing the current efficiency against the applied current density of the OLEDs based on the sensitizers 8-fac and 9-fac and the narrow bandwidth emitter BCzBN.
FIG. 23B is a graph showing the power efficiency against the applied current density of the OLEDs based on the sensitizers 8-fac and 9-fac and the narrow bandwidth emitter BCzBN.
FIG. 23C is a graph showing the external quantum efficiency against the applied current density of the OLEDs based on the sensitizers 8-fac and 9-fac and the narrow bandwidth emitter BCzBN.

The energy levels of the employed materials were schematically depicted in FIG. 17. Among these Ir(III) emitters, 9-fac presented good solubility in majority of organic solvents and exhibited moderate emission properties. Hence, 9-fac was selected to evaluate the electroluminescent (EL) properties. As shown in FIG. 18, the 9-fac-based devices presented a sky-blue emission with the peak wavelength located between 474-480 nm at doping concentration of 5-20 wt %. The small fluctuation in the EL spectral profiles exemplified the suppressed intermolecular interaction due to the presence of bulky tert-butyl groups.

Relatively poor performances were observed at a low doping concentration of 5 wt %. The poor device performances can be ascribed to the carrier leakage or imbalanced carriers in the emissive layers. To improve the device performances, OLEDs with higher doping levels at 10 and 20 wt % were fabricated. The electroluminescent characteristics and corresponding data are shown in FIGS. 18 to 20C and Table 8. The performances were dramatically increased at a doping concentration of 20 wt %, giving a respectable maximum external quantum efficiency (EQE) of 5.1%, and high luminance (L) over 2000 cd $m^{-2}$.

TABLE 8

Performances of the solution-processed phosphorescent OLED devices.

| Guest | Concentration (%) | EL $\lambda_{max}$ (nm) | Maximum efficiency CE (cd/A) | PE (lm/W) | EQE (%) | L (cd $m^{-2}$) |
|---|---|---|---|---|---|---|
| 9-fac | 5 | 474 | 0.08 | 0.05 | 0.05 | 63 |
| 9-fac | 10 | 480 | 9.5 | 3.5 | 4.6 | 2294 |
| 9-fac | 20 | 474 | 9.1 | 2.4 | 5.1 | 2229 |

To maximize the application potential of these phosphors, the solution processed hyper-OLEDs (hyperphosphorescence) were designed. This is based on an understanding that the Ir(III) phosphors with the shortened radiative lifetime can sensitize the multi-resonance thermally activated delayed fluorescence (MR-TADF) emitter such as BCzBN with the unfavorably long delayed lifetime 50 μs. In view of the overall EL performances recorded in aforementioned binary devices, 10 wt % doping level was selected to achieve optimal carrier balance and Förster resonance energy transfer (FRET).

As depicted in FIGS. 21 to 23C and Table 9, narrowband emission with a full width at half maximum (FWHM) of 32 nm was successfully obtained. Meanwhile, regardless of the chosen sensitizer (8-fac or 9-fac), a sky-blue narrowband emission was observed, peaking at 485 nm, confirming the efficient energy transfer from the Ir(III) assistant sensitizer to the MR-TADF terminal emitter BCzBN. More impressively, the champion device was successfully achieved using 10 wt % of 9-fac and 0.5 wt % of BCzBN doped in the common host material mCP, giving a sky-blue emission with maximum EQE and luminance of 17.4% and 2978 cd $m^{-2}$, respectively, which are superior to the binary devices consisting of only the TADF host and BCzBN emitter with the red-shifted EL peak max. at around 490 nm. This result also provides a supplement to the reports on hyper-OLEDs using vacuum deposited phosphorescent sensitizer and blue emissive terminal emitter.

TABLE 9

Performances of solution-processed OLED devices with common host material mCP.

| Guest | Concentration (%) | EL $\lambda_{max}$ (nm) | FWHM (nm) | Maximum efficiency CE (cd/A) | PE (lm/W) | EQE (%) | L (cd $m^{-2}$) |
|---|---|---|---|---|---|---|---|
| 8-fac:BCzBN | 10:0.5 | 485 | 32 | 23.2 | 7.7 | 13.7 | 2476 |
| 8-fac:BCzBN | 10:1 | 485 | 32 | 24.8 | 8.7 | 13.8 | 243 |
| 9-fac:BCzBN | 10:0.5 | 485 | 32 | 29.2 | 9.7 | 17.4 | 2978 |
| 9-fac:BCzBN | 10:1 | 485 | 32 | 22.6 | 7.5 | 12.6 | 2702 |

Example 4—Cyano- and trifluoromethyl-substituted benzo[d]imidazol-2-ylidene-based Ir(III) Metal Complexes

Synthesis of cyano- and trifluoromethyl-substituted benzo[d]imidazol-3-ium Pro-Chelates ($mfcpH_2$·OTf, $ofcpH_2$·OTf, and 5-$mfcpH_2$·OTf)

Scheme 7

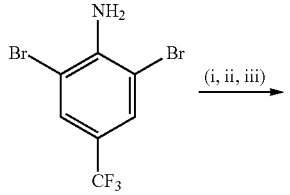

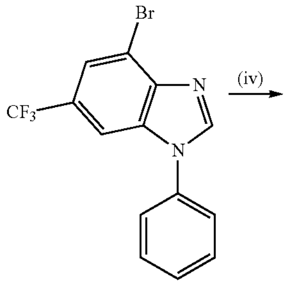

(D1)

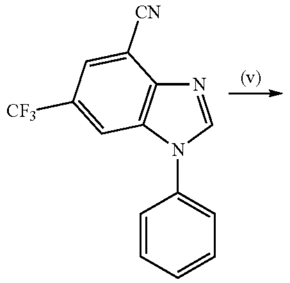

(D2)

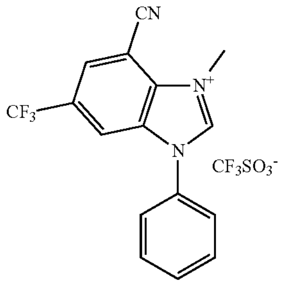

$mfcpH_2$•OTf

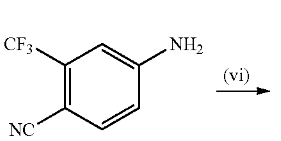

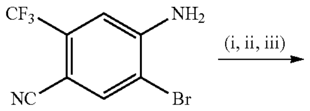

(D3)

-continued

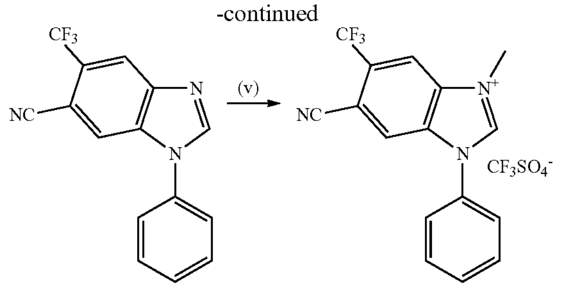

(D4) $ofcpH_2$•OTf

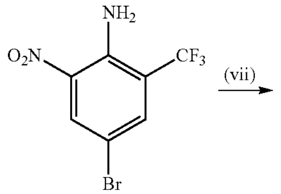

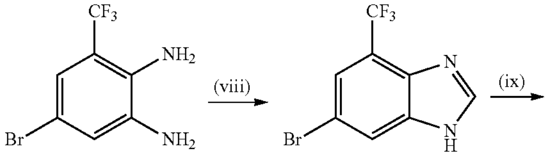

(D5) (D6)

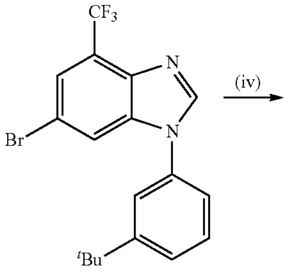

(D7)

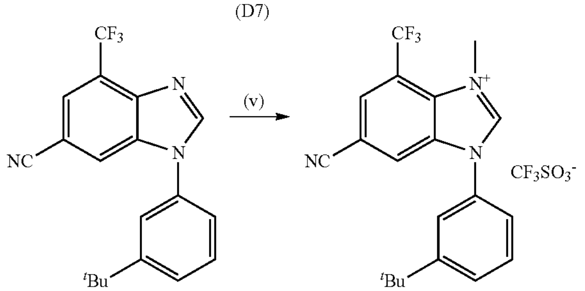

(D8) 5-$mfcpH_2$•OTf

As shown in Scheme 7, for pro-chelate $mfcpH_2$·OTf, the key starting material is compound (D1), which was synthesized from commercially available 2,6-dibromo-4-(trifluoromethyl)aniline with triethyl orthoformate at 120° C. in presence of catalytic amount of glacial acetic acid (i), followed by condensation with aniline at 140° C. (ii) and treatment with 1,8-diazabicyclo[5.4.0]undec-7-enein (DBU), copper iodide, and dimethyl sulfoxide (DMSO) at 150° C. (iii) in a one-pot procedure. Then, the cyano group of (D2) was introduced using a catalytic nucleophilic substitution with zinc cyanide ($Zn(CN)_2$), which was catalyzed by $Pd(PPh_3)_4$ in DMF solution at 120° C. (iv). In the final step, the N-alkylation was performed using methyl trifluoromethanesulfonate ($CF_3SO_3CH_3$) in toluene at RT to give $mfcpH_2$·OTf (v).

Preparation of $ofcpH_2$·OTf required an intermediate compound (D3), e.g., 4-amino-5-bromo-2-(trifluoromethyl)benzonitrile, which was synthesized from commercially available 4-amino-2-(trifluoromethyl)benzonitrile via simple bromination using NBS and $CH_2Cl_2$ at 0° C. (vi). After then, a three-steps reaction in one pot with triethyl orthoformate at 120° C. in presence of catalytic amount of glacial acetic acid (i), followed by condensation with aniline at 140° C. (ii) and treatment with 1,8-diazabicyclo[5.4.0]undec-7-enein (DBU), copper iodide, and dimethyl sulfoxide (DMSO) at 150° C. (iii) afforded compound (D4). Similar to the preparation of mfcp$H_2$·OTf, the N-alkylation was performed using methyl trifluoromethanesulfonate ($CF_3SO_3CH_3$) in toluene at RT (v) to give ofcpH2·OTf.

5-mfcp$H_2$·OTf was synthesized via a distinctively different procedure. Briefly, 4-bromo-2-nitro-6-(trifluoromethyl) aniline was reduced to (D5) in the presence of iron powder and $NH_4Cl$ solid in a solution of THF/MeOH/$H_2O$ (1/1/2, v/v/v) at 70° C. (vii). After then, cyclization of D5 with formic acid under reflux for 4 hours (viii) afforded the functional benzoimidazole compound (D6), Subsequent C—N coupling reaction with (3-(tert-butyl)phenyl)boronic acid in presence of $Cu(OAC)_2·H_2O$ in acetonitrile at RT for 24 hours (ix) produced intermediate (D7). This was followed by a nucleophilic substitution with copper(I) cyanide, which was catalyzed by $Pd(PPh_3)_4$ in DMF solution at 120° C. (iv) in giving the benzimidazole derivative (D8). Similar to the above, the N-alkylation was performed using methyl trifluoromethanesulfonate ($CF_3SO_3CH_3$) in toluene at RT (v) to give 5-mfcp$H_2$·OTf.

The anticipated imidazolylidene pro-chelates mfcp$H_2$·OTf, ofcp$H_2$·OTf, and 5-mfcp$H_2$·OTf were achieved with yields as high as 96%.

Syntheses of cyano- and trifluoromethyl-substituted benzo[d]imidazol-2-ylidene-based Ir(III) Metal Complexes (42-mer, 42-fac, 43-mer, 43-fac, 44-mer, and 44-fac)

A respective degassed tert-butylbenzene (50 mL) solution of mfcp$H_2$·OTf (1.35 g, 3.0 mmol), ofcp$H_2$·OTf (1.35 g, 3.0 mmol) and 5-mfcp$H_2$·OTf (1.12 g, 3.26 mmol), m-trichloridotris(tetrahydrothiophene-κ$^S$)iridium(III) ($IrCl_3(tht)_3$, 0.51 g, 0.9 mmol), and sodium acetate (1.48 g, 18 mmol) was heated at reflux overnight under $N_2$. After then, the solvent was removed under vacuum. The residue was then dissolved in $CH_2Cl_2$ (150 mL), washed with brine, dried over anhydrous $Na_2SO_4$ and, then, evaporated to dryness. This gave a mixture of f- and m-stereoisomers. The crude product was further purified by column chromatography using petroleum ether/ethyl acetate (4/1, v/v) as eluent to give chartreuse yellow solid 42-mer (585 mg, 59.5%) and colorless solid 42-fac (248 ng, 25.2%), yellow solid 43-mer (550 ng, 50.5%) and colorless solid 43-fac (140 mg, 12.8%), yellow solid 44-mer (120 mg, 28.9%) and light-yellow solid 44-fac (70 mg, 16.9%), respectively.

Spectroscopic and Structural Analysis

The structures of each of 42-mer, 42-fac, 43-mer, 43-fac, 44-mer, and 44-fac were verified by $^1$H NMR spectroscopy and MALDI-TOF mass spectrometry.

Selected spectroscopic data for 42-mer is provided as follows: MS (MALDI-TOF, $^{193}$Ir): m/z 1094.33801 [M+H$^+$], calcd. for $C_{48}H_{27}F_9IrN_9$: 1093.18749; $^1$H NMR (400 MHz, acetone-d$_6$) δ 8.99 (s, 1H), 8.97 (s, 1H), 8.92 (s, 1H), 8.12 (m, 6H), 7.03 (m, 4H), 6.82 (d, J=7.2 Hz, 1H), 6.76-6.64 (m, 4H), 3.88 (s, 3H), 3.83 (s, 3H), 3.65 (s, 3H); $^{19}$F NMR (376 MHz, acetone-d$_6$) δ −61.37 (s, 3F), −61.38 (s, 3F), −61.41 (s, 3F). Anal. Calcd. for $C_{48}H_{27}F_9IrN_9$: C, 52.75; H, 2.49; N, 11.53. Found: C, 52.64; H, 2.46; N, 11.52.

Selected spectroscopic data for 42-fac is provided as follows: MS (MALDI-TOF, $^{193}$Ir): m/z 1094.27173 [M+H$^+$], calcd. for $C_{48}H_{27}F_9IrN_9$: 1093.18749; $^1$H NMR (400 MHz, acetone-d$_6$) δ 8.93 (s, 3H), 8.13 (d, J=8.0 Hz, 3H), 8.09 (s, 3H), 7.07 (t, J=7.2 Hz, 3H), 6.66 (t, J=7.2 Hz, 3H), 6.52 (d, J=6.4 Hz, 3H), 3.93 (s, 9H); $^{19}$F NMR (376 MHz, acetone-d$_6$) δ −61.39 (s, 9F). Anal. Calcd. for $C_{48}H_{27}F_9IrN_9$: C, 52.75; H, 2.49; N, 11.53. Found: C, 52.62; H, 2.75; N, 11.53.

Selected spectroscopic data for 43-mer is provided as follows: MS (MALDI-TOF, $^{193}$Ir): m/z 1094.34900 [M+H$^+$], calcd. for $C_{48}H_{27}F_9IrN_9$: 1093.18749; $^1$H NMR (400 MHz, acetone-d$_6$) δ 9.12 (s, 2H), 9.07 (s, 1H), 8.23 (d, J=4.4 Hz, 1H), 8.21 (d, J=4.4 Hz, 1H), 8.17-8.14 (m, 3H), 8.09 (s, 1H), 7.09-6.98 (m, 3H), 6.96 (dd, J=7.2, 1.2 Hz, 1H), 6.87 (dd, J=7.2, 1.2 Hz, 1H), 6.74-6.63 (m, 4H), 3.61 (s, 3H), 3.58 (s, 3H), 3.43 (s, 3H); $^{19}$F NMR (376 MHz, acetone-d$_6$) δ −60.88 (s, 3F), −60.90 (s, 6F). Anal. Calcd. for $C_{48}H_{27}F_9IrN_9$: C, 52.75; H, 2.49; N, 11.53. Found: C, 52.23; H, 2.66; N, 11.48.

Selected spectroscopic data for 43-fac is provided as follows: MS (MALDI-TOF, $^{193}$Ir): m/z 1094.34473 [M+H$^+$], calculated for $C_{48}H_{27}F_9IrN_9$: 1093.18749; $^1$H NMR (400 MHz, acetone-d$_6$) δ 9.09 (s, 3H), 8.21 (d, J=8.0 Hz, 3H), 8.08 (s, 3H), 7.07 (t, J=7.6 Hz, 3H), 6.67 (t, J=7.6 Hz, 3H), 6.57 (d, J=7.2 Hz, 3H), 3.66 (s, 9H); $^{19}$F NMR (376 MHz, acetone-d$_6$) δ −60.89 (s, 9F). Anal. Calcd. for $C_{48}H_{27}F_9IrN_9$: C, 52.75; H, 2.49; N, 11.53. Found: C, 52.60; H, 2.95; N, 11.38.

Selected spectroscopic data for 44-mer is provided as follows: MS (MALDI-TOF, $^{193}$Ir): m/z 1262.39253 [M+H$^+$], calculated for $C_{60}H_{52}F_9IrN_9$: 1262.37530; $^1$H NMR (400 MHz, $CD_2Cl_2$) δ/ppm 8.69 (d, J=5.1 Hz, 2H), 8.61 (s, 1H), 7.98-7.89 (m, 3H), 7.85-7.74 (m, 3H), 6.81 (t, J=7.3 Hz, 3H), 6.60 (d, J=7.7 Hz, 1H), 6.53 (d, J=7.7 Hz, 1H), 6.31 (d, J=7.7 Hz, 1H), 3.56 (s, 3H), 3.55 (s, 3H), 3.39 (s, 3H), 1.35 (s, 9H), 1.33 (s, 9H), 1.30 (s, 9H). $^{19}$F NMR (376 MHz, $CD_2Cl_2$) δ/ppm −53.89 (s, 3F), −53.93 (s, 3F), −54.10 (s, 3F). Anal. Calcd for $C_{60}H_{51}F_9IrN_9$: C, 57.13; H, 4.08; N, 9.99. Found: C, 57.19; H, 4.10; N, 10.01.

Selected spectroscopic data for 44-fac is provided as follows: MS (MALDI-TOF, $^{193}$Ir): m/z 1262.388532 [M+H$^+$], calculated for $C_{60}H_{52}F_9IrN_9$: 1262.37530; $^1$H NMR (400 MHz, $CD_2Cl_2$) δ/ppm 8.67 (s, 3H), 7.91 (s, 3H), 7.80 (d, J=1.6 Hz, 3H), 6.79 (dd, J=7.9, 1.6 Hz, 3H), 6.17 (d, J=7.9 Hz, 3H), 3.60 (s, 9H), 1.33 (s, 27H). $^{19}$F NMR (376 MHz, $CD_2Cl_2$) δ/ppm −54.04 (s, 9F). Anal. Calcd. for $C_{60}H_{51}F_9IrN_9$: C, 57.13; H, 4.08; N, 9.99. Found: C, 57.16; H, 4.07; N, 10.06.

Figure 24:
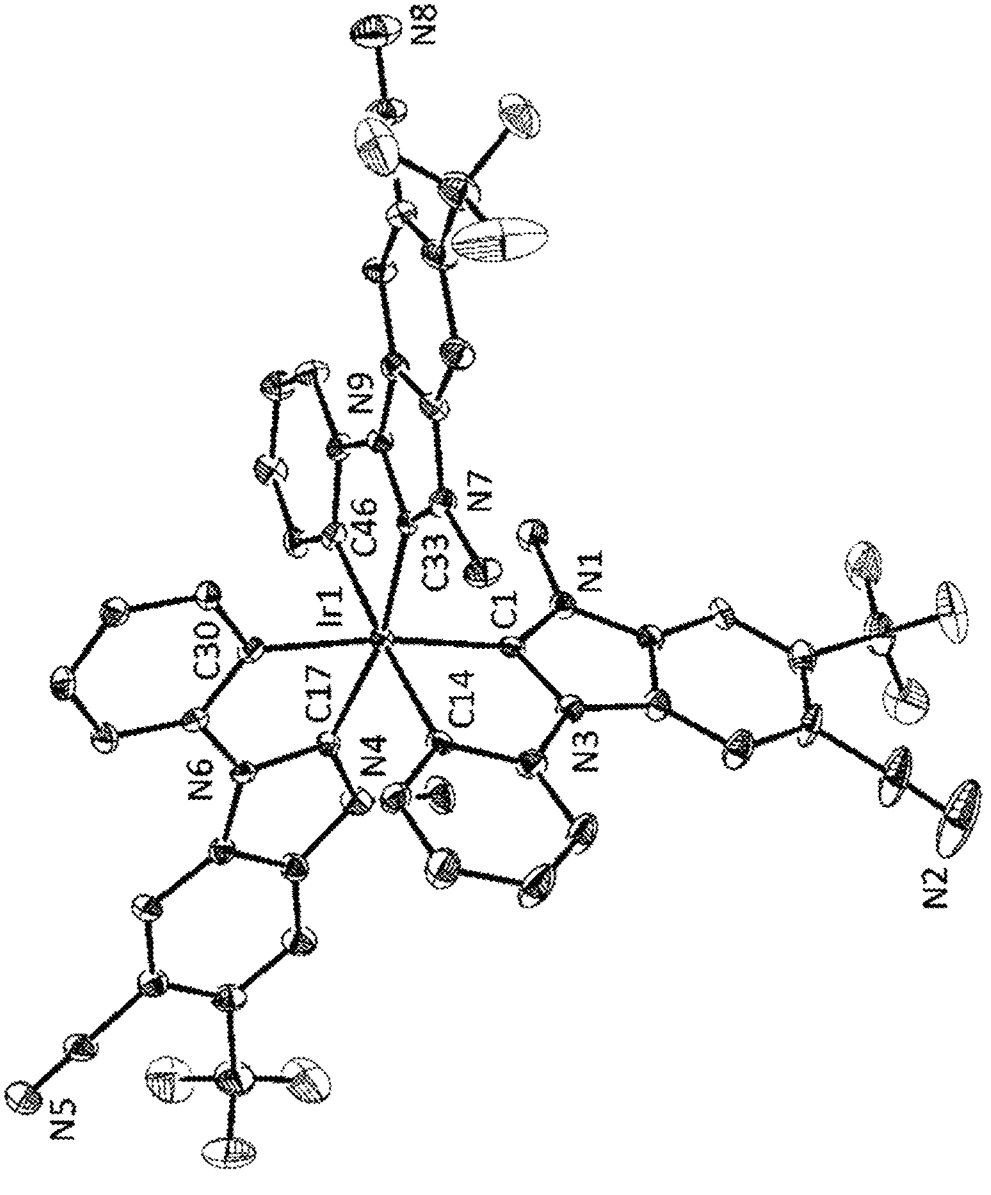
FIG. 24 shows the crystal structural drawing of 43-mer.

Single-crystal X-ray structural analysis was carried out for 43-mer to provide confirmation of the identity of chelates and gross coordination arrangement of these Ir(III) complexes. The structure of 43-mer is shown in FIG. 24, wherein thermal ellipsoids are shown at 30% probability level, with selected bond lengths (Å) being Ir—C(1)=2.038(6), Ir—C(14)=2.101(6), Ir—C(17)=2.014(6), Ir—C(30)=2.080(6), Ir—C(33)=2.038(6), Ir—C(46)=2.095(6), selected bond angles (°) being C(1)-Ir—C(30)=170.8(2), C(14)-Ir—C(46)=177.0(2), C(17)-Ir—C(33)=166.9(2), and hydrogen atoms are omitted for clarity. The single crystal of 43-mer suitable for X-ray diffraction study was obtained via the slow diffusion of hexane into a saturated acetone solution at RT.

Selected crystal data of 43-mer is provided as follows: CCDC deposition number: 2160348. $C_{52.5}H_{36}F_9IrN_9O_{1.5}$; M=1180.10; triclinic; space group=P-1; a=11.3289(4) Å, b=14.1299(5) Å, c=16.2541(7) Å; α=76.8930(10)°; β=85.3850(10)°; γ=82.9610(10)°; V=2511.28(17) Å$^3$; Z=2;

$\rho_{Calcd}$=1.561 mg·m$^{-3}$; F(000)=1168.0, crystal size=0.32×0.09×0.03 mm$^3$; λ(Mo—K$_\alpha$)=0.71073 Å; T=213(2) K; μ=2.741 mm$^{-1}$; 85173 reflections collected, 31281 independent reflections ($R_{int}$=0.0858), max. and min. transmission=0.449 and 0.745, data/restraints/parameters=10257/89/701, GOF=1.024, final $R_1$[I>2σ(I)]=0.0487 and w$R_2$(all data)=0.1110.

Figure 25:
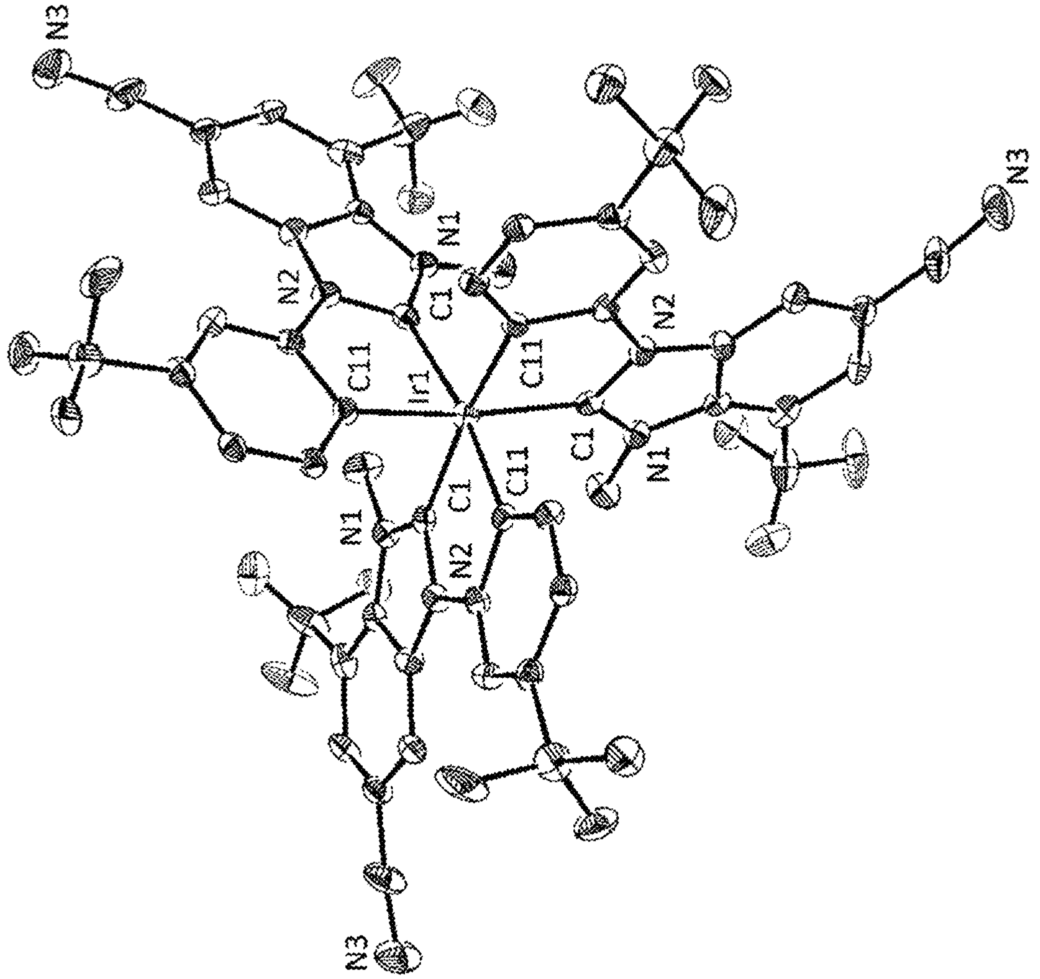
FIG. 25 shows the crystal structural drawing of 44-fac.

Another single-crystal X-ray structural analysis was carried out for 44-fac as shown in FIG. 25. Thermal ellipsoids are shown at 30% probability level, with selected bond lengths (Å) being Ir1-C(1)=2.059(4), Ir1-C(11)=2.091(4). The single crystal of 44-fac suitable for X-ray diffraction study was obtained via the vaporation of saturated dichlormethane solution at RT.

Selected crystal data of 44-fac is provided as follows: CCDC deposition number: 2171206. $C_{60}H_{51}F_9IrN_9$; M=1261.29; trigonal; space group=P31c; a=18.4552(5) Å, b=18.4552(5) Å, c=26.0118(7) Å; V=7672.5(5) Å$^3$; Z=4; $\rho_{Calcd}$=1.092 mg·m$^{-3}$; F(000)=2528, crystal size=0.25×0.07×0.04 mm$^3$; λ(Cu—K$_\alpha$)=1.54178 Å; T=213(2) K; μ=3.851 mm$^{-1}$; 95971 reflections collected, 10100 independent reflections ($R_{int}$=0.0437), max. and min. transmission=0.493 and 0.754, data/restraints/parameters=10100/355/550, GOF=1.031, final $R_1$[I>2σ(I)]=0.0267 and w$R_2$(all data)=0.0718.

Example 5—Trifluoromethyl-substituted imidazo[4,5-b]pyridin-2-ylidene-based Ir(III) Metal Complexes

Synthesis of $CF_3$-substituted imidazo[4,5-b]pyridin-3-ium Pro-Chelate (E4)

Scheme 8

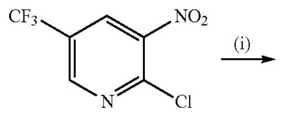

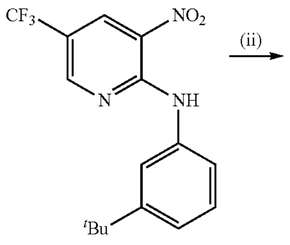

(E1)

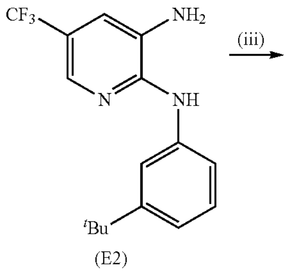

(E2)

-continued

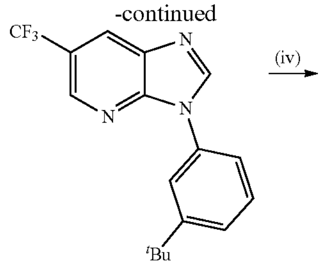

(E3)

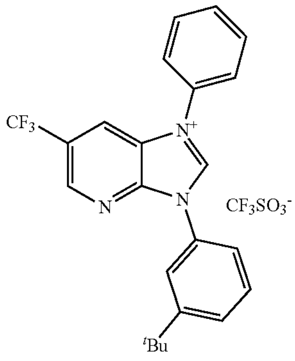

(E4)

As shown in Scheme 8, base promoted substitution of commercially available 2-chloro-3-nitro-5-(trifluoromethyl)pyridine with 3-(tert-butyl)aniline, triethylamine, and isopropanol under reflux for 24 hours (i) afforded key intermediate E1. This was reduced to compound E2 using fine powder of iron in the presence of ammonium chloride ($NH_4Cl$) and THF/MeOH/$H_2O$ (1/1/2, v/v/v) at 70° C. for 12 hours (ii). After then, cyclization of E2 with formic acid under reflux afforded the functional benzoimidazole compound E3 (iii), which underwent direct aryl quaternization using Ph-Mes-iodonium(III) salts ((PhI$^+$Mes)($CF_3SO_3^-$), Mes=mesityl) in presence of $Cu_2O$ as catalyst and in DMF at 100° C. for 8 hours, in giving the 3-(3-(tert-butyl)phenyl)-1-phenyl-6-(trifluoromethyl)-3H-imidazo[4,5-b]pyridin-1-ium pro-chelate E4 (iv).

Synthesis of trifluoromethyl-substituted imidazo[4,5-b]pyridin-2-ylidene-based Ir(III) Metal Complexes (47-fac, 48-fac and 49-fac)

Facially coordinated ir(III) complexes 47-fac, 48-fac and 49-fac were synthesized by treatment of E4 with mer-trichloridotris-(tetrahydro-thiophene-κ$^S$)iridium(III), mer-$IrCl_3(THT)_3$ in refluxing tert-butylbenzene solution and with the presence of sodium acetate for 24 hours. The mixture was separated using silica gel column chromography eluting with a mixture of hexane and $CH_2Cl_2$ (3/1, v/v), yield: 33%, 36% and 8% for 47-fac, 48-fac and 49-fac, respectively. No mer-isomer was observed under this reaction condition.

Isomerization

Additional f-isomers can be obtained using the following isomerization process. A mixture of 47-fac (100 mg, 0.073 mmol) and TsOH·$H_2O$ (3 mg, 0.015 mmol) in 10 mL o-dichlorobenzene was placed into a 25 mL flask and heated at 180° C. for 24 h. The solution gradually turned from light yellow to light grey during heating. After cooled to RT, the solvent was removed and the residue was redissolved in ethyl acetate. The solution was washed with water (20 mL), dried over anhydrous $Na_2SO_4$ and then concentrated. The residue was further purified by silica gel column and eluted with n-hexane/$CH_2Cl_2$ (3/1, v/v) to afford a mixture of 30% 47-fac, 34% 48-fac and 7.0% 49-fac, respectively. Heating of 48-fac with TsOH·$H_2O$ in refluxing o-dichlorobenzene afforded a similar proportion of the isomeric products.

Spectroscopic and Structural Analysis

The structures of 47-fac, 48-fac and 49-fac were verified by $^1$H and $^{19}$F NMR spectroscopy and MALDI-TOF mass spectrometry.

Selected spectroscopic data for 47-fac is provided as follows: MS (MALDI-TOF, $^{193}$Ir): m/z 1375.46423 [$M^+$], calcd. for $C_{69}H_{57}F_9IrN_9$: 1375.42225; $^1$H NMR (400 MHz, $CDCl_3$) 9.00 (s, 3H), 8.72 (s, 3H), 7.35 (t, J=7.5 Hz, 3H), 6.92-6.79 (m, 9H), 6.60 (d, J=7.8 Hz, 3H), 6.52 (d, J=7.8 Hz, 3H), 6.41-6.28 (m, 6H), 1.38 (s, 27H); $^{19}$F NMR (376 MHz, $CDCl_3$) δ −60.29 (s, 9F). Anal. Calcd. for $C_{69}H_{57}F_9IrN_9$: C, 60.25; H, 4.18; N, 9.17. Found: C, 60.30; H, 4.16; N, 9.13.

Selected spectroscopic data for 48-fac is provided as follows: MS (MALDI-TOF, $^{193}$Ir): m/z 1375.47468 [$M^+$], calcd. for $C_{69}H_{57}F_9IrN_9$: 1375.42225; $^1$H NMR (400 MHz, $CDCl_3$) 9.08 (br, 1H), 8.93 (br, 1H), 8.76 (br, 2H), 8.56 (br, 1H), 8.41 (br, 1H), 8.38 (s, 1H), 7.74 (br, 1H), 7.52 (br, 1H), 7.33 (t, J=8.0 Hz, 1H), 7.16 (m, 2H), 7.00 (br, 1H), 6.84 (m, 9H), 6.33 (m, 8H); $^{19}$F NMR (376 MHz, $CDCl_3$) δ −60.11 (br, 3F), −60.30 (br, 3F), −60.35 (s, 3F). Anal. Calcd. for $C_{69}H_{57}F_9IrN_9$: C, 60.25; H, 4.18; N, 9.17. Found: C, 60.29; H, 4.19; N, 9.15.

Selected spectroscopic data for 49-fac is provided as follows: MS (MALDI-TOF, $^{193}$Ir): MS (MALDI-TOF, $^{193}$Ir): m/z 1375.44962 [$M^+$], calcd. for $C_{69}H_{57}F_9IrN_9$: 1375.42225; $^1$H NMR (400 MHz, $CDCl_3$) δ 9.10 (br, 1H), 8.75 (br, 1H), 8.56 (br, 1H), 8.40 (br, 1H), 8.16 (br, 1H), 7.88 (br, 2H), 7.75 (br, 2H), 7.52 (br, 2H), 7.43 (br, 2H), 7.31 (br, 1H), 6.81 (m, 10H), 6.37 (m, 6H), 1.38 (br, 9H), 1.31 (s, 9H), 1.04 (br, 9H); $^{19}$F NMR (376 MHz, $CDCl_3$) δ −60.00 (br, 3F), −60.11 (br, 3F), −60.38 (s, 3F). Anal. Calcd. for $C_{69}H_{57}F_9IrN_9$: C, 60.25; H, 4.18; N, 9.17. Found: C, 60.19; H, 4.20; N, 9.23.

Figure 26:
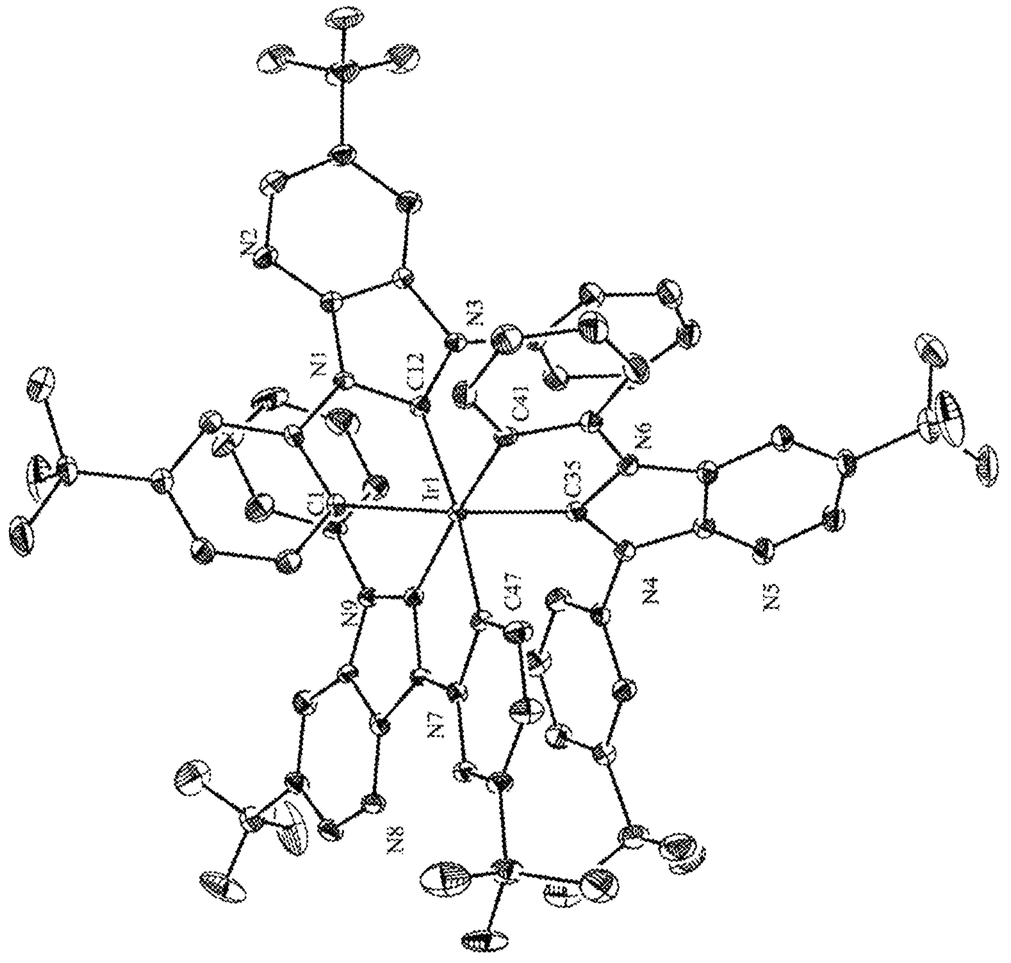
FIG. 26 shows the crystal structural drawing of 48-fac.

Single-crystal X-ray structural analysis was carried out for 48-fac to provide confirmation of the identity of chelates and gross coordination arrangement of these Ir(III) complexes. FIG. 26 is shown with thermal ellipsoids shown at 30% probability level, to which there are two t-butylphenyl cyclometalates together with a single cyclometalating phenyl group, with one Ir—C distance being substantially longer than to other two, i.e., Ir—C1=2.106(4), Ir—C41=2.086(5) and Ir—C47=2.087(4) Å. The single crystal of 48-fac suitable for X-ray diffraction study was obtained via slow diffusion of hexane into a saturated $CH_2Cl_2$ solution at RT.

Selected crystal data of 48-fac is provided as follows: $C_{69}H_{57}F_9IrN_9 \cdot C_3H_6O.0.5 \times CH_2Cl_2$; M=1261.29; monoclinic; space group=C2/c; a=52.2937(14) Å, b=12.9766(3) Å, c=19.5372(6) Å; β=103.731(1)°, V=12878.9(6) Å$^3$; Z=8; $\rho_{calcd}$=1.051 mg·m$^{-3}$; F(000)=5876, crystal size=0.25×0.07×0.04 mm$^3$; λ(Mo—$K_\alpha$)=0.71073 Å; T=193(2) K; μ=2.173 mm$^{-1}$; 74461 reflections collected, 13174 independent reflections ($R_{int}$=0.0837), ratio max. and min. transmission=0.831, data/restraints/parameters=13174/434/968, GOF=1.001, final $R_1$[I>2σ(I)]=0.0400 and $wR_2$(all data)=0.1071.

Example 6—Cyano-substituted imidazo[4,5-b]pyridin-2-ylidene-based Ir(III) Metal Complexes

Synthesis of cyano-substituted imidazo[4,5-b]pyridin-3-ium Pro-Chelate (F4)

Scheme 9

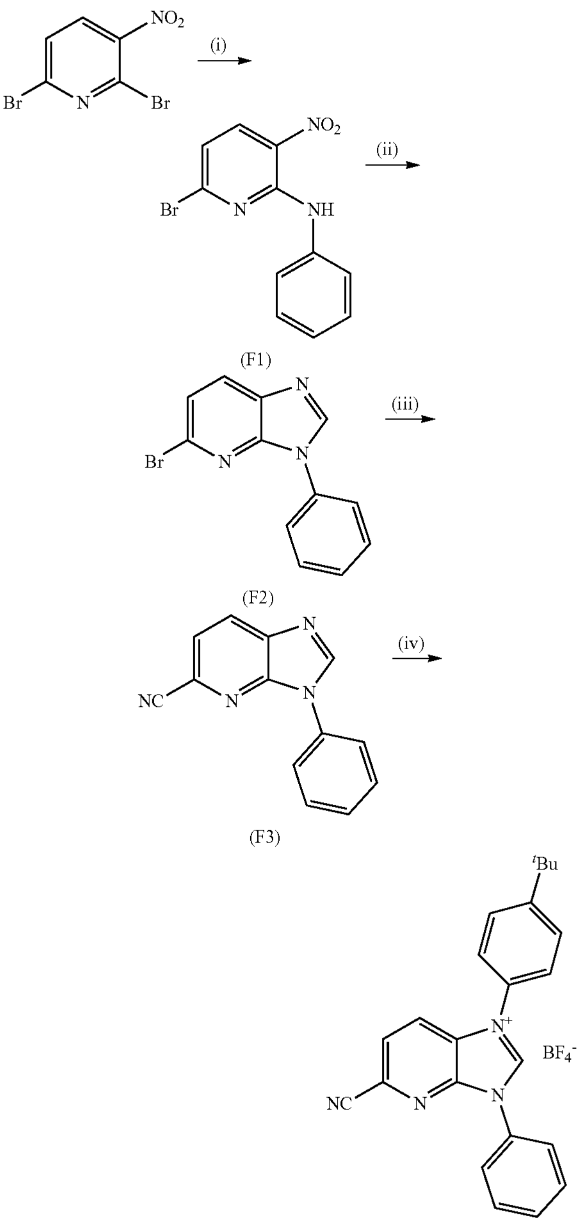

(F1)

(F2)

(F3)

(F4)

As shown in Scheme 9, substitution of commercially available 2,6-dibromo-3-nitropyridine with aniline in isopropanol at RT for 12 hours afforded key intermediate, which is a functional N-phenylpyridin-2-amine derivative F1 (i). It was reduced and cyclized with formic acid in the presence of fine iron powder to form a bromo-substituted 3-phenyl-3H-imidazo[4,5-b]pyridine derivative F2 (ii). After then, F2 was converted to F3 using $Zn(CN)_2$ in DMF and with $Pd(PPh_3)_4$ at 120° C. for 12 h (iii), which underwent quaternization using iodonium(III) reagent ((4-$^t$Bu$C_6H_4I^+$Mes)($BF_4^-$), Mes=mesityl) in presence of $Cu_2O$ and in DMF at 100° C. for 8 hours to yield 1-(4-(tert-butyl)phenyl)-5-cyano-3-phenyl-3H-imidazo[4,5-b]pyridin-1-ium (F4) (iv).

Synthesis of cyano-substituted imidazo[4,5-b]pyridin-2-ylidene-based Ir(III) Metal Complexes (99-fac and 100-mer)

1-(4-(tert-butyl)phenyl)-5-cyano-3-phenyl-3H-imidazo[4,5-b]pyridin-1-ium tetrafluoroborate (F4, 3.00 g, 6.81 mmol), sodium acetate (1.86 g, 22.7 mmol) and mer-$IrCl_3$(tht)$_3$ (1.28 g, 2.27 mmol) were dissolved in o-dichlorobenzene (80 mL) in a 100 mL flask. The mixture was refluxed for 24 hours with vigorous stirring. After removal of solvent under vacuum, the residue was taken into $CH_2Cl_2$ and washed with deionized water. The organic phase was separated and concentrated and, the residue was further purified by column chromatography with a mixture of n-hexane, ethyl acetate and $CH_2Cl_2$ (4/1/1, v/v/v) to afford 99-fac ($R_f$=0.50) and 100-fac ($R_f$=0.40) in sequence. Recrystallization with a mixture of $CH_2Cl_2$ and methanol attained a yellow solid of 99-fac (781 mg, 27.6%) and greenish-yellow solid of 100-mer (880 mg, 31.1%), respectively.

Spectroscopic and Structural Analysis

The structures of 99-fac and 100-mer were verified by $^1H$ NMR spectroscopy and MALDI-TOF mass spectrometry.

Selected spectroscopic data for 99-fac is provided as follows: MS (MALDI-TOF, $^{193}Ir$): m/z 1246.44584 [$M^+$], calcd. for $C_{69}H_{57}IrN_{12}$: 1246.49653; $^1H$ NMR (400 MHz, $CDCl_3$) δ 8.94 (d, J=7.9 Hz, 1H), 8.84 (d, J=7.9 Hz, 1H), 8.41 (d, J=8.3 Hz, 1H), 7.66 (t, J=8.6 Hz, 2H), 7.48 (dd, J=8.3, 2.1 Hz, 1H), 7.43-7.35 (m, 3H), 7.26-7.16 (m, 3H), 7.12 (dd, J=8.3, 2.2 Hz, 1H), 6.94-6.84 (m, 2H), 6.84-6.76 (m, 3H), 6.75 (dd, J=8.3, 2.3 Hz, 1H), 6.69-6.64 (m, 1H), 6.61 (d, J=2.3 Hz, 1H), 6.55-6.36 (m, 3H), 6.34-6.09 (m, 6H), 1.01 (s, 18H), 1.01 (s, 9H). Anal. Calcd. for $C_{69}H_{57}IrN_{12}$: C, 66.49; H, 4.61; N, 13.48. Found: C, 66.50; H, 4.60; N, 13.52.

Selected spectroscopic data for 100-mer is provided as follows: MS (MALDI-TOF, $^{193}Ir$): m/z 1246.44584 [$M^+$], calcd. for $C_{69}H_{57}IrN_{12}$: 1246.58364; $^1H$ NMR (400 MHz, $CDCl_3$) δ 8.89 (dd, J=7.9, 0.8 Hz, 3H), 7.40-7.35 (m, 6H), 7.20 (td, J=7.9, 1.4 Hz, 3H), 6.83 (td, J=7.3, 1.1 Hz, 3H), 6.76 (d, J=8.1 Hz, 3H), 6.57 (dd, J=7.3, 1.2 Hz, 3H), 6.46 (dd, J=8.3, 2.1 Hz, 3H), 6.30 (dd, J=8.3, 2.3 Hz, 3H), 6.24 (dd, J=8.3, 2.3 Hz, 3H), 1.02 (s, 27H). Anal. Calcd. for $C_{69}H_{57}IrN_{12}$: C, 66.49; H, 4.61; N, 13.48. Found: C, 66.51; H, 4.63; N, 13.50.

Synthesis of cyano-substituted imidazo[4,5-b]pyridin-3-ium Pro-Chelate (G4)

Scheme 10

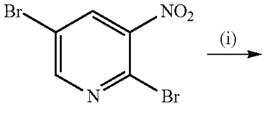

-continued

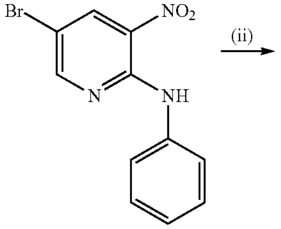

(G1)

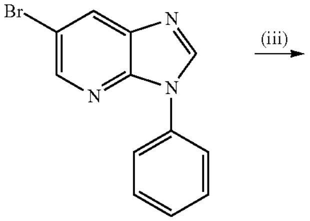

(G2)

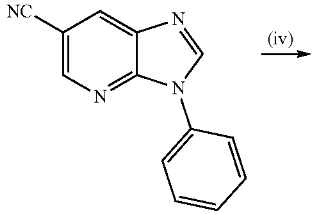

(G3)

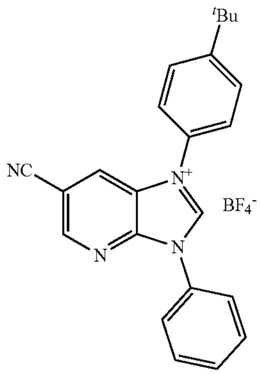

(G4)

As shown in Scheme 10, reaction of 2,5-dibromo-3-nitropyridine with aniline in a mixed solution of isopropanol and THF at reflux afforded intermediate G1 (i). It was reduced and cyclized to afford G2 in presence of both fine iron powder and formic acid (ii). After then, G2 was substituted with $Zn(CN)_2$ using $Pd(PPh_3)_4$ as catalyst in DMA at 160° C. to afford G3 (iii), which reacted with iodonium(III) salt ((4-$^t$Bu$C_6H_4I^+$Mes)($BF_4^-$), Mes=mesityl) in presence of $Cu_2O$ and in DMF at 100° C. for 8 hours to afford 1-(4-(tert-butyl)phenyl)-6-cyano-3-phenyl-3H-imidazo[4,5-b]pyridin-1-ium (G4) (iv).

Synthesis of cyano-substituted imidazo[4,5-b]pyridin-2-ylidene-based Ir(III) Metal Complex (104-fac and 105-fac)

6-cyano-1-(4-(tert-butyl)phenyl)-3-phenyl-3H-imidazo[4,5-b]pyridin-1-ium trifluoromethanesulfonate (3.00 g, 5.97 mmol), NaOAc (1.63 g, 19.90 mmol), mer-$IrCl_3$(tht)$_3$ (1.12 g, 1.99 mmol) and o-dichlorobenzene (80 mL) were added in a 100 mL flask. The mixture was refluxed for 24 hours with vigorous stirring. After removal of solvent under vacuum, the residue was taken into $CH_2Cl_2$ and washed with deionized water. The organic phase was separated and concentrated and, the residue was further purified by column chromatography with a mixture of n-hexane, ethyl acetate and $CH_2Cl_2$ (3/1/1, v/v/v) to afford 104-fac ($R_f$=0.40) and 105-fac ($R_f$=0.30) in sequence. Recrystallization in $CH_2Cl_2$ and methanol attained a yellow 104-fac (900 mg, 36.3%) and yellow 105-fac (700 mg, 28.2%), respectively.

Spectroscopic and Structural Analysis

The structures of 104-fac and 105-fac were verified by $^1H$ NMR spectroscopy and MALDI-TOF mass spectrometry.

Selected spectroscopic data for 104-fac is provided as follows: MS (MALDI-TOF, $^{193}Ir$): m/z 1246.46432 [$M^+$], calcd. for $C_{69}H_{57}IrN_{12}$: 1246.49653; $^1H$ NMR (400 MHz, $CDCl_3$) δ 8.91 (d, J=7.4 Hz, 3H), 8.67 (d, J=1.8 Hz, 3H), 7.41 (dd, J=8.4, 2.1 Hz, 3H), 7.22-7.16 (m, 3H), 6.89 (d, J=1.8 Hz, 3H), 6.84 (td, J=7.4, 0.9 Hz, 3H), 6.59 (dd, J=7.4, 1.0 Hz, 3H), 6.43 (dd, J=8.4, 2.1 Hz, 3H), 6.29 (dd, J=8.3, 2.3 Hz, 3H), 6.22 (dd, J=8.3, 2.3 Hz, 3H), 1.06 (s, 27H). Anal. Calcd. for $C_{69}H_{57}IrN_{12}$: C, 66.49; H, 4.61; N, 13.48. Found: C, 66.51; H, 4.62; N, 13.50.

Selected spectroscopic data for 105-fac is provided as follows: MS (MALDI-TOF, $^{193}Ir$): m/z 1246.44329 [$M^+$], calcd. for $C_{69}H_{57}IrN_{12}$: 1246.49653; $^1H$ NMR (400 MHz, $CDCl_3$) δ 8.95 (d, J=7.9 Hz, 1H), 8.82 (d, J=7.9 Hz, 1H), 8.69 (d, J=1.7 Hz, 1H), 8.64 (d, J=1.7 Hz, 1H), 8.58 (d, J=1.4 Hz, 1H), 8.34 (d, J=1.4 Hz, 1H), 7.63 (d, J=8.2 Hz, 1H), 7.52 (dd, J=8.2, 2.0 Hz, 1H), 7.41 (dd, J=8.4, 2.0 Hz, 1H), 7.26-7.11 (m, 5H), 7.07 (d, J=1.7 Hz, 1H), 6.96 (d, J=1.7 Hz, 1H), 6.91-6.75 (m, 4H), 6.66 (d, J=7.3 Hz, 1H), 6.61 (d, J=2.1 Hz, 1H), 6.50 (d, J=6.5 Hz, 2H), 6.40 (dd, J=8.4, 2.0 Hz, 1H), 6.37-6.30 (m, 2H), 6.24 (dd, J=8.4, 2.1 Hz, 2H), 6.21-6.06 (m, 2H), 1.04 (s, 9H), 1.00 (d, J=1.4 Hz, 18H). Anal. Calcd. for $C_{69}H_{57}IrN_{12}$: C, 66.49; H, 4.61; N, 13.48. Found: C, 66.53; H, 4.60; N, 13.52.

Accordingly, the present invention provides strategical approaches that afford the desired Ir(III) metal complexes bearing distinctive, functional $CF_3$-substituted 1,3-dihydro-2H-benzo[d]imidazol-2-ylidene and imidazo[4,5-b]pyridin-2-ylidene chelates with an electron withdrawing cyano group, functional 7,9-dihydro-8H-purin-8-ylidene chelates and $CF_3$-substituted 8H-purin-8-ylidene chelates, and functional 1,3-dihydro-2H-imidazo[4,5-b]pyrazin-2-ylidene chelates with cyclometalating appendages, plus a N-alkyl appendage or even an non-cyclometalating N-aryl appendage. This new design would allow only one coordination possibility for carbene chelates and, hence, effectively inhibit formation of multiple isomers. Moreover, the added tert-butyl substituent, together with other essential structural features, can offer improvement to their chemical stability and the capability of fine-tuning photophysical properties of the as-prepared Ir(III)-based carbene phosphors.

It has been demonstrated that these carbene cyclometalate emitters possess both the m- and f-coordination modes, and efficient emission in the blue-to-purple spectral region, respectively. Both class of emitters can be utilized in fabrication of both the single dopant blue phosphorescent OLED devices, and efficient hyperphosphorescent OLED devices via efficient FRET. All homoleptic Ir(III) complexes with either m- and f-modes exhibited moderate to good photoluminescence in the fluid state with emission spanning from blue to green color at RT. The Ir(III) complexes in the present invention are true-blue emitters with very high emission efficiencies and short radiative lifetimes in solution, doped PMMA matrix and selected host materials of OLED devices. Short radiative lifetime may offer the elongated device stability urgently needed for blue emitters.

It will be appreciated by persons skilled in the art that numerous variations and/or modifications may be made to the invention as shown in the specific embodiments without departing from the spirit or scope of the invention as broadly described. The described embodiments of the invention should therefore be considered in all respects as illustrative, not restrictive.

The invention claimed is:

1. A tris-bidentate iridium(III) complex comprising a first, a second, and a third bidentate ligands configured in an octahedral arrangement around the iridium(III) center, the first bidentate ligand has a structure of Formula (II):

Formula (II)

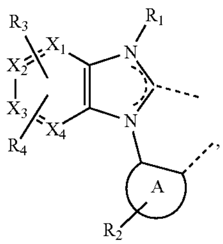

where:

A is phenyl;

wherein X1, X2, X3, X4, R1, R2, R3, and R4 are defined as follows:

when X1 is N and X2, X3, and X4 are each C, R1 is selected from the group consisting of p-methylphenyl, p-tert-butylphenyl and m-tert-butylphenyl; R2 is selected from the group consisting of hydrogen, tert-butyl and 2,6-dimethylphenyl; one of R3 and R4 is selected from the group consisting of cyano and trifluoromethyl, and the other is hydrogen; or when X4 is N and X1, X2, and X3 are each C, R1 is selected from the group consisting of p-methylphenyl, p-tert-butylphenyl and m-tert-butylphenyl; R2 is selected from the group consisting of hydrogen, tert-butyl and 2,6-dimethylphenyl; one of R3 and R4 is selected from the group consisting of cyano and trifluoromethyl, and the other is hydrogen; or when X1 and X3 are each C and X2 and X4 are each N, R1 is selected from the group consisting of p-tert-butyl phenyl and m-tert-butyl phenyl, R2 is selected from the group consisting of hydrogen, tert-butyl and 2,6-dimethylphenyl; one of R3 and R4 is selected from the group consisting of hydrogen, tert-butyl and 2,6-dimethylphenyl and the other is hydrogen; or when X1 and X3 are each N and X2 and X4 are each C, R1 is selected from the group consisting of p-tert-butylphenyl and m-tert-butylphenyl, R2 is selected from the group consisting of hydrogen, tert-butyl and 2,6-dimethylphenyl; one of R3 and R4 is selected from the group consisting of hydrogen, tert-butyl and 2,6-dimethylphenyl and the other is hydrogen; or when X1 and X4 are each N and X2 and X3 are each C, R1 is selected from the group consisting of p-tert-butylphenyl and m-tert-butylphenyl, R2 is selected from the group consisting of hydrogen, tert-butyl and 2,6-dimethylphenyl; one of R3 and R4 is selected from the group consisting of hydrogen, tert-butyl and 2,6-dimethylphenyl and the other is hydrogen.

2. The tris-bidentate iridium(III) complex according to claim 1, wherein the tris-bidentate iridium(III) complex is a homoleptic iridium(III) complex.

3. The tris-bidentate iridium(III) complex according to claim 1, wherein the tris-bidentate iridium(III) complex with either one of the second and the third bidentate ligands being identical to the first bidentate ligand.

4. The tris-bidentate iridium(III) complex according to claim 1, wherein the tris-bidentate iridium(III) complex with both of the second and the third bidentate ligands being identical to the first bidentate ligand.

5. The tris-bidentate iridium(III) complex according to claim 1, comprising a facial isomer or a meridional isomer.

6. A light emitting device comprising an emissive layer having the tris-bidentate iridium(III) complex according to claim 1.

7. The tris-bidentate iridium(III) complex according to claim 1, wherein the tris-bidentate iridium(III) complex is selected from one of the following:

48-fac

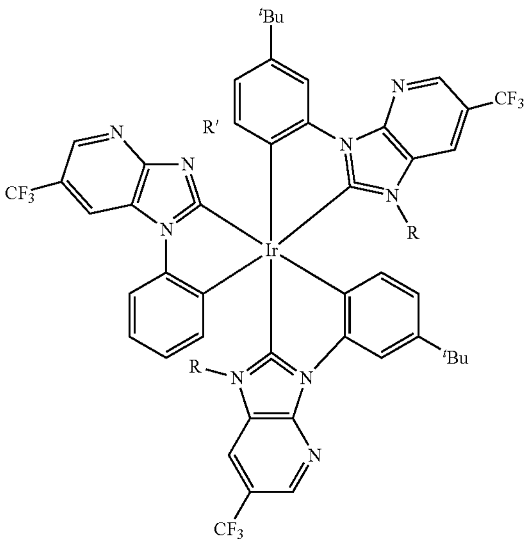

$R = C_6H_5$;
$R' = m\text{-}C_6H_4{}^{t}Bu$

-continued 49-fac

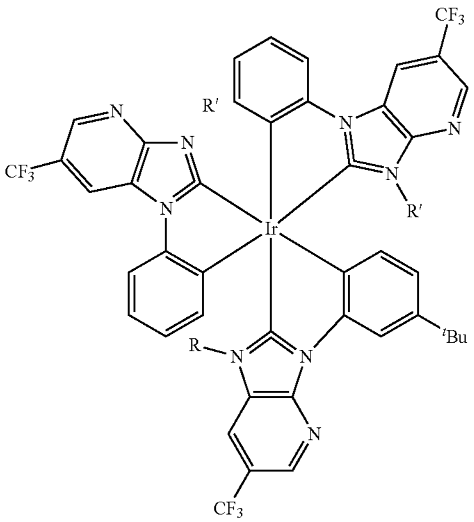

$R = C_6H_5$;
$R' = m\text{-}C_6H_4{}^{t}Bu$ 51-fac

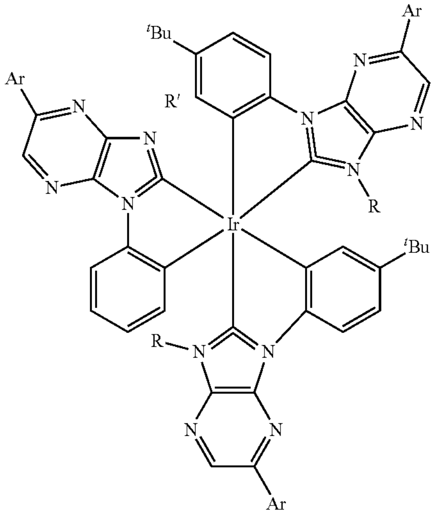

$Ar = 2,6\text{-}C_6H_3Me_2$
$R = C_6H_5$;
$R' = p\text{-}C_6H_4{}^{t}Bu$

-continued
52-fac
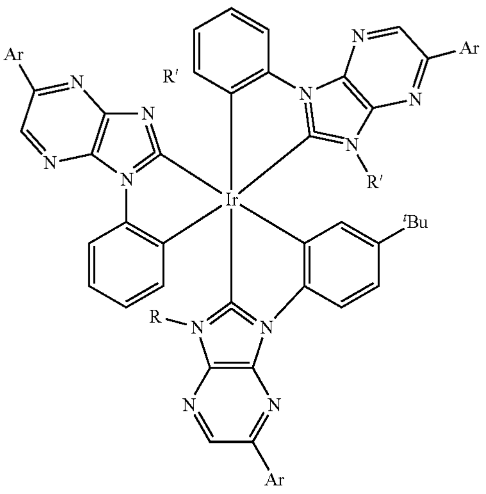
Ar = 2,6-$C_6H_3Me_2$
R = $C_6H_5$;
R′ = p-$C_6H_4{}^tBu$
55-fac
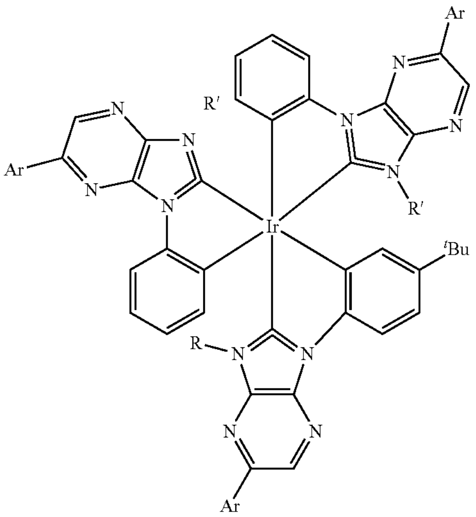
Ar = 2,6-$C_6H_3Me_2$
R = $C_6H_5$;
R′ = p-$C_6H_4{}^tBu$
54-fac
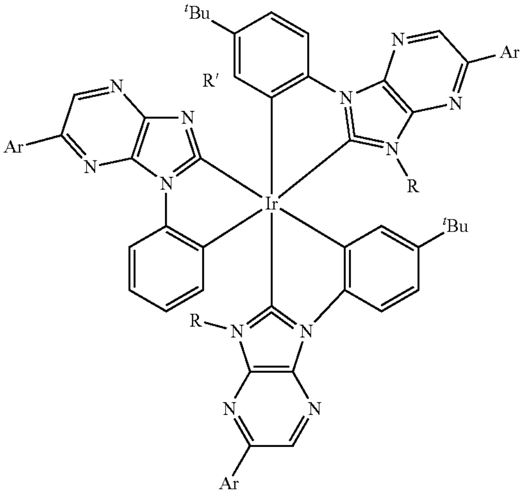
Ar = 2,6-$C_6H_3Me_2$
R = $C_6H_5$;
R′ = p-$C_6H_4{}^tBu$
87-fac
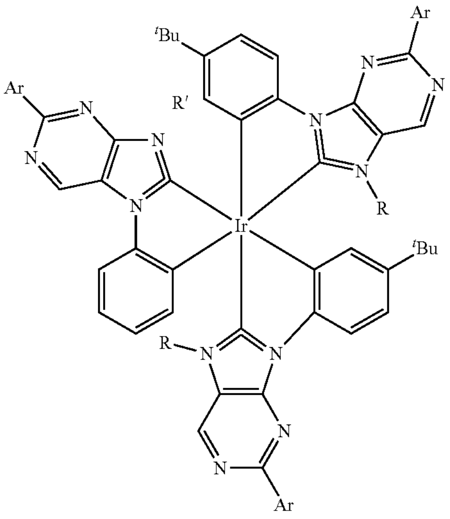
Ar = 2,6-$C_6H_3Me_2$
R = $C_6H_5$;
R′ = p-$C_6H_4{}^tBu$ 88-fac
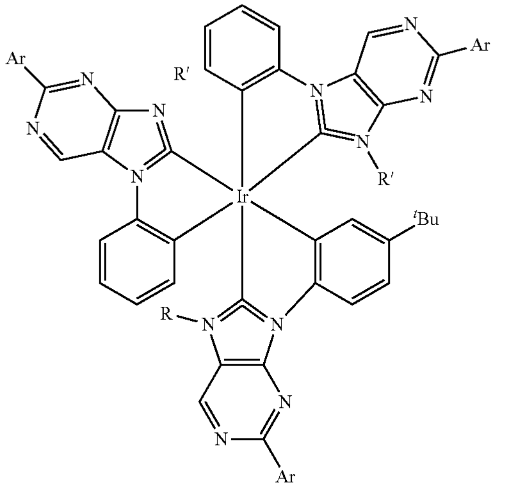
Ar = 2,6-$C_6H_3Me_2$
R = $C_6H_5$;
R′ = p-$C_6H_4{}^tBu$
90-fac
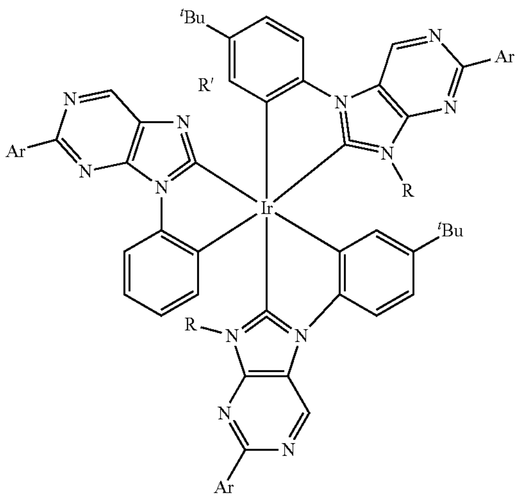
Ar = 2,6-$C_6H_3Me_2$
R = $C_6H_5$;
R′ = p-$C_6H_4$-${}^tBu$
91-fac
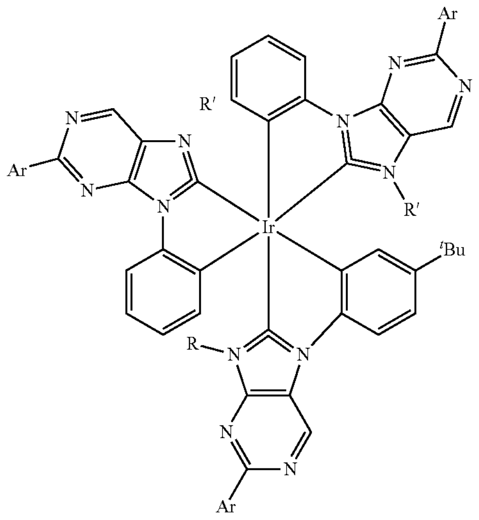
Ar = 2,6-$C_6H_3Me_2$
R = $C_6H_5$;
R′ = p-$C_6H_4$-${}^tBu$
99-fac
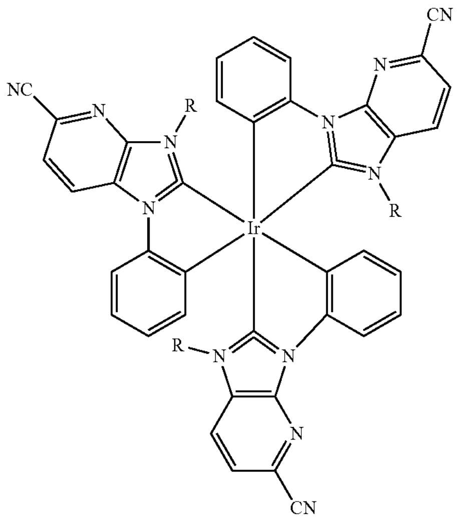
R = p-$C_6H_4{}^tBu$ -continued
100-mer
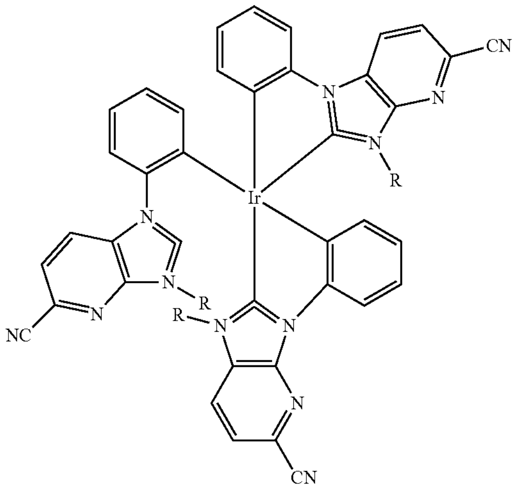
R = p-$C_6H_4{}^tBu$;
102-fac
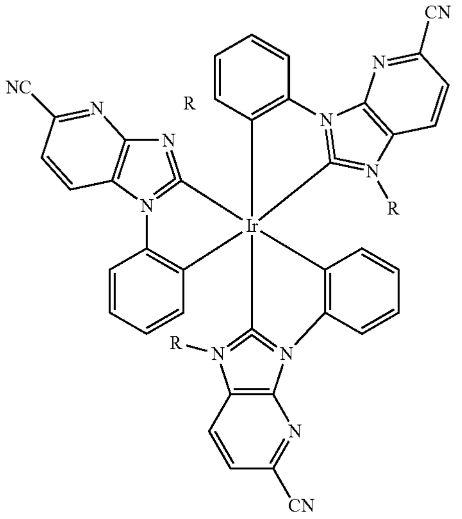
R = p-$C_6H_4Me$;
103-mer
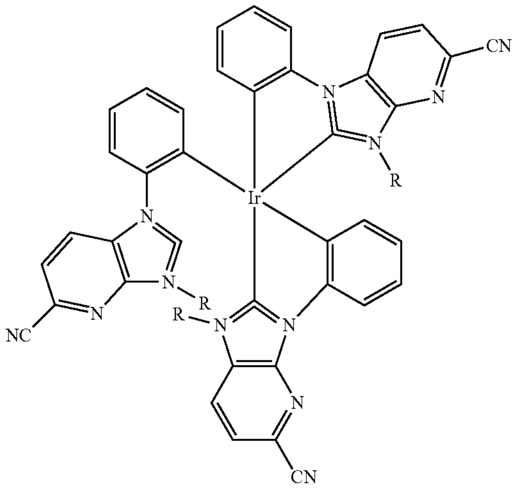
R = p-$C_6H_4Me$;
-continued
105-fac
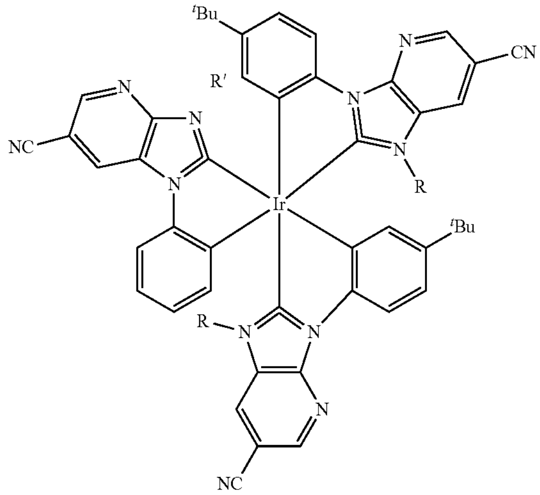
R = $C_6H_5$;
R′ = p-$C_6H_4{}^tBu$
106-fac
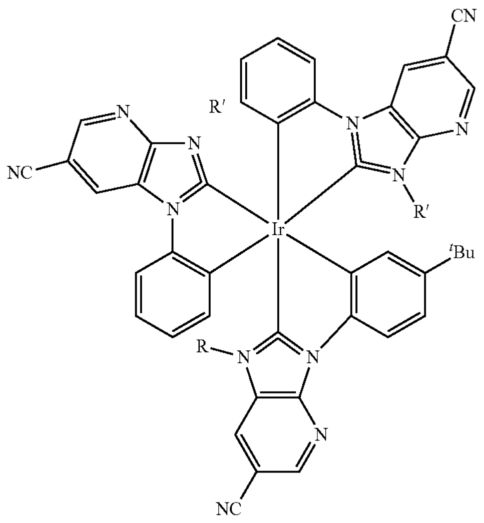
R = $C_6H_5$;
R′ = p-$C_6H_4{}^tBu$ -continued
108-fac
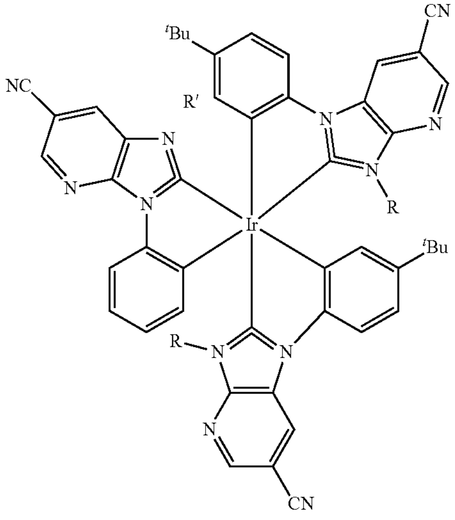
R = $C_6H_5$;
R′ = p-$C_6H_4{}^tBu$
109-fac
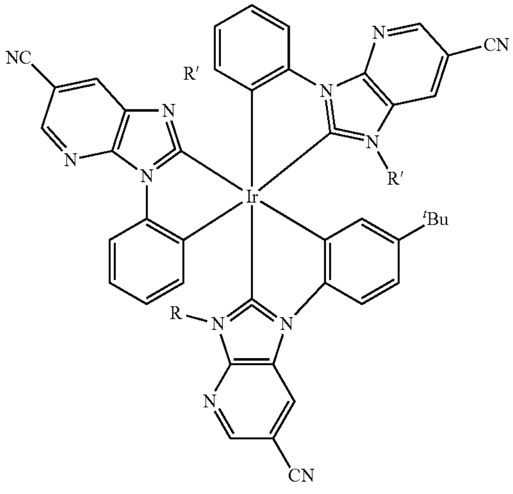
R = $C_6H_5$;
R′ = p-$C_6H_4{}^tBu$
-continued
111-fac
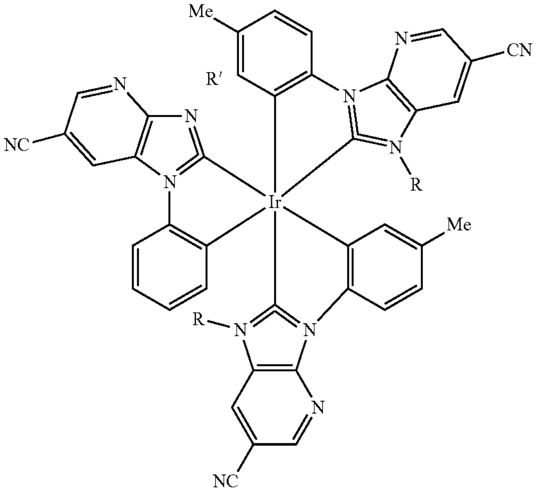
R = $C_6H_5$;
R′ = p-$C_6H_4Me$
112-fac
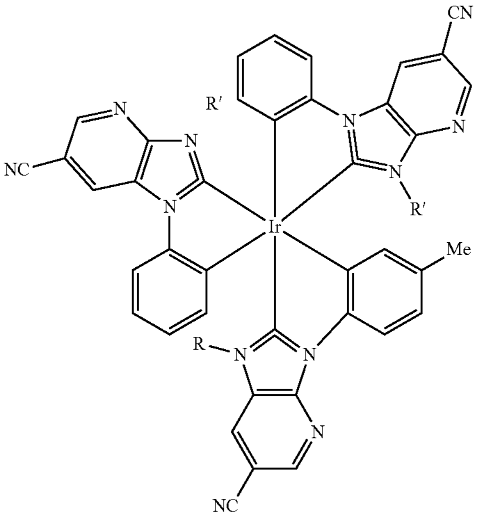
R = $C_6H_5$;
R′ = p-$C_6H_4Me$ -continued
114-fac
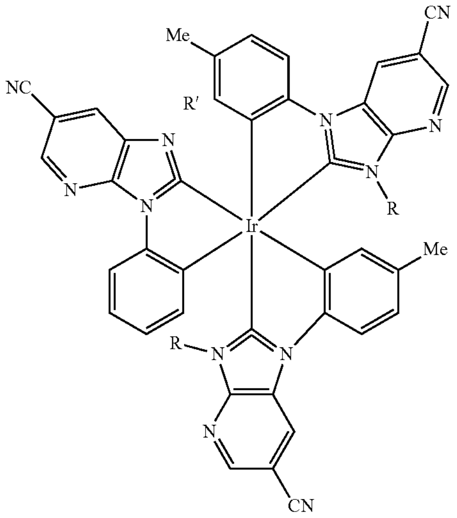
R = $C_6H_5$;
R' = p-$C_6H_4$Me
-continued
115-fac
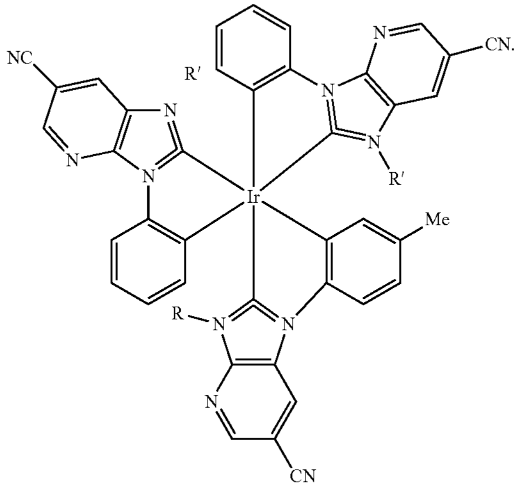
R = $C_6H_5$;
R' = p-$C_6H_4$Me
* * * * *